(12) United States Patent
Chen et al.

(10) Patent No.: US 9,604,978 B2
(45) Date of Patent: Mar. 28, 2017

(54) COMPOUNDS FOR INFLAMMATION AND IMMUNE-RELATED USES

(75) Inventors: Shoujun Chen, Bedford, MA (US);
Gary Bohnert, Wilmington, MA (US);
Jun Jiang, Norwood, MA (US);
Zhiqiang Xia, Acton, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 14/115,506

(22) PCT Filed: May 3, 2012

(86) PCT No.: PCT/US2012/036241
§ 371 (c)(1),
(2), (4) Date: Feb. 3, 2014

(87) PCT Pub. No.: WO2012/151355
PCT Pub. Date: Nov. 8, 2012

(65) Prior Publication Data
US 2014/0171446 A1  Jun. 19, 2014

Related U.S. Application Data

(60) Provisional application No. 61/481,797, filed on May 3, 2011, provisional application No. 61/506,403, filed on Jul. 11, 2011, provisional application No. 61/552,683, filed on Oct. 28, 2011, provisional application No. 61/566,870, filed on Dec. 5, 2011.

(51) Int. Cl.
| | | |
|---|---|---|
| *A61K 31/4965* | (2006.01) | |
| *C07D 401/12* | (2006.01) | |
| *C07D 417/14* | (2006.01) | |
| *A61K 31/165* | (2006.01) | |
| *A61K 31/44* | (2006.01) | |
| *A61K 31/497* | (2006.01) | |
| *C07D 401/14* | (2006.01) | |
| *C07D 405/14* | (2006.01) | |
| *C07D 413/14* | (2006.01) | |
| *C07D 213/82* | (2006.01) | |

(52) U.S. Cl.
CPC .......... *C07D 417/14* (2013.01); *A61K 31/165* (2013.01); *A61K 31/44* (2013.01); *A61K 31/497* (2013.01); *C07D 213/82* (2013.01); *C07D 401/12* (2013.01); *C07D 401/14* (2013.01); *C07D 405/14* (2013.01); *C07D 413/14* (2013.01)

(58) Field of Classification Search
CPC .................. A61K 31/4965; C07D 401/12
See application file for complete search history.

(56) References Cited

U.S. PATENT DOCUMENTS

| | | |
|---|---|---|
| 2005/0107436 A1 | 5/2005 | Xie et al. |
| 2006/0094761 A1 | 5/2006 | Haque et al. |
| 2006/0173021 A1 | 8/2006 | Sun et al. |
| 2007/0249609 A1 | 10/2007 | Chen et al. |
| 2007/0254925 A1 | 11/2007 | Vo et al. |
| 2009/0274655 A1 | 11/2009 | Grimes et al. |
| 2010/0130510 A1 | 5/2010 | Chen et al. |
| 2010/0249195 A1 | 9/2010 | Jiang et al. |

FOREIGN PATENT DOCUMENTS

| | | | |
|---|---|---|---|
| DE | 25 25 024 A1 | 12/1976 | |
| EP | 1 024 138 A1 | 8/2000 | |
| EP | 1 875 925 A1 | 1/2008 | |
| JP | 2000256358 | 9/2000 | |
| JP | 2001220390 A | 8/2001 | |
| JP | 2006514032 A | 4/2006 | |
| JP | 2006528641 | 12/2006 | |
| JP | 2008517954 A | 5/2008 | |
| JP | 2008517956 A | 5/2008 | |
| JP | 2008526866 A | 7/2008 | |
| JP | 2008528520 A | 7/2008 | |
| JP | 2009525285 A | 7/2009 | |
| JP | 2009530402 A | 8/2009 | |
| JP | 2014532656 A | 12/2014 | |
| WO | WO 2006081391 A2 * | 8/2006 | .......... A61K 31/495 |
| WO | WO 2006115140 A1 | 11/2006 | |
| WO | WO 2010/039236 A1 | 4/2010 | |
| WO | WO 2010039237 A1 | 4/2010 | |
| WO | WO 2010039238 A1 | 4/2010 | |
| WO | WO 2011038572 A1 | 4/2011 | |
| WO | WO 2013/063385 A1 | 5/2013 | |

OTHER PUBLICATIONS

Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
["Clathrate." Dictionary.com (c) 1998. Available from: < http://dictionary.reference.com/browse/clathrate >.*
Connors, K. "The Stability of Cyclodextrin Complexes in Solution." Chem. Rev. (1997), vol. 97, pp. 1325-1357.*
Extended European Search Report for EP12779736.3 mailed Sep. 25, 2014.
Debnath, Pharmacophore mapping of a series of 2,4-diamino-5-deazapteridine inhibitors of *Mycobacterium avium* complex dihydrofolate reductase. J Med Chem. Jan. 3, 2002;45(1):41-53.
Gangjee et al., Synthesis and biological evaluation of nonclassical 2,4-diamino-5-methylpyrido[2,3-d]pyrimidines with novel side chain substituents as potential inhibitors of dihydrofolate reductases. J Med Chem. Feb. 14, 1997;40(4):479-85.

(Continued)

*Primary Examiner* — Noble Jarrell
*Assistant Examiner* — John S Kenyon

(57) ABSTRACT

The invention relates to certain compounds or pharmaceutically acceptable salts, solvates, clathrates, or prodrugs thereof, that are useful as immunosuppressive agents and for treating and preventing inflammatory conditions, allergic disorders, and immune disorders.

9 Claims, No Drawings

(56) References Cited

OTHER PUBLICATIONS

Sweeney et al., Small-molecule inhibitors of store-operated calcium entry. ChemMedChem. May 2009;4(5):706-18. doi:10.1002/cmdc.200800452.
International Search Report and Written Opinion for International Application No. PCT/US2012/036241 mailed Sep. 24, 2012.
International Preliminary Report on Patentability for International Application No. PCT/US2012/036241 mailed Nov. 14, 2013.
Search Report, of May 7, 2015.
Cover, of May 7, 2015.
Office Action, of May 7, 2015.
Brown, N.J. & Roberts II, L.J. "Histamine, Bradykinin, and their Antagonists". Goodman & Gilman's The Pharmacological Basis of Therapeutics (10th ed). 2001. pp. 645-667.
Carstensen, J.T. Drug Stability: Principles & Practices. 2nd. Ed., Marcel Dekker, Inc., NY, NY. 1995. pp. 360-385.
Feske, S. et al. "A mutation in Oral 1 causes immune deficiency by abrogating CRAC channel function". Nature. vol. 441. 2006. pp. 179-185.
Hanson, G.R. "Analgesic, Antipyretic and Anti-Inflammatory Drugs". Remington: The Science and Practice of Pharmacy. (A.R. Gennaro ed. 19th ed.), vol. II. 1995. pp. 1196-1221.
Insel, P.A. "Analgesic-Antipyretic and Anti-inflammatory Agents and Drugs Employed in the Treatment of Gout". Goodman & Gilman's The Pharmacological Basis of Therapeutics. (Perry B. Molinhoff and Raymond W. Ruddori eds., 9th Ed. 1996. pp. 617-657.
Lewis, R.S. "Calcium oscillations in T-cells: mechanisms and consequences for gene expression". Biochemical Society Transactions. vol. 31, part 5. 2003. pp. 925-929.
Vig, M. et al. "CRACM1 is a Plasma Membrane Protein Essential for Store-Operated Ca2+ Entry". Science. 312. 2006. pp. 1220-1223.
Yonetoku, Y. et al. "Novel potent and selective Ca2+ release activated Ca2+ (CRAC) channel inhibitors. Part 3: Synthesis and CRAC channel inhibitory activity of 4'-[trifluoromethyl)pyrazol-1-yl]carboxanllides". Biorganic & Medicinal Chemistry, vol. 16, No. 21, 2008. pp. 9457-9466.

\* cited by examiner

COMPOUNDS FOR INFLAMMATION AND IMMUNE-RELATED USES

RELATED APPLICATIONS

This application is a national stage filing under 35 U.S.C. §371 of International Application No. PCT/US2012/036241, filed May 3, 2012, which claims the benefit of U.S. Provisional Application No. 61/481,797, filed May 3, 2011, U.S. Provisional Application No. 61/506,403, filed Jul. 11, 2011, U.S. Provisional Application No. 61/552,683, filed Oct. 28, 2011, and U.S. Provisional Application No. 61/566,870, filed Dec. 5, 2011, the entire teachings of which are incorporated herein.

FIELD OF THE INVENTION

This invention relates to biologically active chemical compounds that may be used for immunosuppression or to treat or prevent inflammatory conditions and immune disorders.

BACKGROUND OF THE INVENTION

Inflammation is a mechanism that protects mammals from invading pathogens. However, while transient inflammation is necessary to protect a mammal from infection, uncontrolled inflammation causes tissue damage and is the underlying cause of many illnesses. Inflammation is typically initiated by binding of an antigen to a T-cell antigen receptor. Antigen binding by a T-cell initiates calcium influx into the cell via calcium ion channels, such as $Ca^{2+}$-release-activated $Ca^{2+}$ channels (CRAG). Calcium ion influx in turn initiates a signaling cascade that leads to activation of these cells and an inflammatory response characterized by cytokine production.

Interleukin 2 (IL-2) is a cytokine that is secreted by T-cells in response to calcium ion influx into the cell. IL-2 modulates immunological effects on many cells of the immune system. For example, it is a potent T-cell mitogen that is required for T-cell proliferation, promoting their progression from G1 to S phase of the cell cycle; it stimulates the growth of NK cells; and it acts as a growth factor to B-cells and stimulates antibody synthesis.

IL-2, although useful in the immune response, can cause a variety of problems. IL-2 damages the blood-brain barrier and the endothelium of blood vessels in the brain. These effects may be the underlying causes of neuropsychiatric side effects observed under IL-2 therapy, e.g., fatigue, disorientation, and depression. It also alters the electrophysiological behavior of neurons.

Due to its effects on both T and B-cells, IL-2 is a major central regulator of immune responses. It plays a role in inflammatory reactions, tumor surveillance, and hematopoiesis. It also affects the production of other cytokines, inducing IL-1, TNFα, and TNF-β secretion, as well as stimulating the synthesis of IFN-γ in peripheral leukocytes.

T-cells that are unable to produce IL-2 become inactive (anergic). This renders them potentially inert to any antigenic stimulation they might receive in the future. As a result, agents which inhibit IL-2 production can be used for immunosuppression or to treat or prevent inflammation and immune disorders. This approach has been clinically validated with immunosuppressive drugs such as cyclosporin, FK506, and RS61443. Despite this proof of concept, agents that inhibit IL-2 production remain far from ideal. Among other problems, efficacy limitations and unwanted side effects (including dose-dependant nephrotoxicity and hypertension) hinder their use.

Over-production of proinflammatory cytokines other than IL-2 has also been implicated in many autoimmune diseases. For example, interleukin 5 (IL-5), a cytokine that increases the production of eosinophils, is increased in asthma. Over-production of IL-5 is associated with the accumulation of eosinophils in the asthmatic bronchial mucosa, a hall mark of allergic inflammation. Thus, patients with asthma and other inflammatory disorders involving the accumulation of eosinophils would benefit from the development of new drugs that inhibit the production of IL-5.

Interleukin 4 (IL-4) and interleukin 13 (IL-13) have been identified as mediators of the hypercontractility of smooth muscle found in inflammatory bowel disease and asthma. Thus, patients with asthma and inflammatory bowel disease would benefit from the development of new drugs that inhibit IL-4 and IL-13 production.

Granulocyte macrophage-colony stimulating factor (GM-CSF) is a regulator of maturation of granulocyte and macrophage lineage population and has been implicated as a key factor in inflammatory and autoimmune diseases. Anti-GM-CSF antibody blockade has been shown to ameliorate autoimmune disease. Thus, development of new drugs that inhibit the production of GM-CSF would be beneficial to patients with an inflammatory or autoimmune disease.

SUMMARY OF THE INVENTION

The present disclosure, in an aspect, addresses the continuing need for new drugs which overcome one or more of the shortcomings of drugs currently used for immunosuppression or in the treatment or prevention of inflammatory conditions, allergic disorders, and autoimmune disorders. Desirable properties of such drugs include efficacy against diseases or disorders that are currently untreatable or poorly treatable, new mechanism of action, oral bioavailability and/or reduced side effects. Accordingly, compounds that inhibit the activity of CRAG ion channels and inhibit the production of IL-2, IL-4, IL-5, IL-13, GM-CSF, TNFα, and IFN-γ are disclosed herein. These compounds are particularly useful for immunosuppression and/or to treat or prevent inflammatory conditions and immune disorders. The particular genus of compounds described herein are particularly advantageous in that they are believed to combine inhibition of CRAG ion channels (e.g., as measured by modulated $I_{CRAC}$ current) and cytokines including IL-2, low incidence of off-target effects, and a favorable toxicity profile.

The invention features compounds of formula (I):

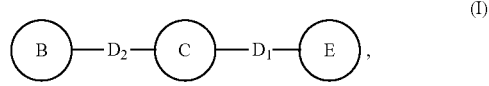

(I)

or a pharmaceutically acceptable salt, solvate, clathrate, or prodrug thereof, wherein, B is benzimidazolyl, benzodioxolyl, phenyl, pyridinyl, pyrimidinyl, pyrrolyl, furanyl, thienyl, imidazolyl, pyrazolyl, oxazolyl, or thiazolyl, each of which may be optionally substituted by halo, OH, cyano, carboxyl, optionally substituted $C_{1-6}$ alkyl, optionally substituted $C_{1-6}$ haloalkyl, optionally substituted $C_{2-6}$ alkenyl, optionally substituted C$_{3-8}$ cycloalkyl, optionally substituted C$_{1-6}$ alkoxy, optionally substituted C$_{1-6}$ haloalkoxy, optionally substituted C$_{3-8}$ cycloalkoxy, optionally substituted C$_{6-10}$ aryl, optionally substituted C$_{7-16}$ aralkyloxy, optionally substituted C$_{2-9}$ heterocyclyl (e.g., optionally substituted C$_{2-9}$ heteroaryl), optionally substituted C$_{2-9}$ (heterocyclyl)oxy, optionally substituted C$_{3-12}$ heterocyclylalkyl, optionally substituted C$_{2-9}$ (heterocyclyl)alkynyl, optionally substituted C$_{1-6}$ alkylsulfonyl, substituted C$_{1-6}$ alkylsulfonyloxy, optionally substituted C$_{1-6}$ alkylsulfamoyloxy, optionally substituted C$_{1-6}$ alkylcarbonyl, optionally substituted C$_{1-6}$ alkoxycarbonyl, or optionally substituted amino;

D$_2$ is a bond or —C(V$_1$)(V$_2$)—, wherein V$_1$ and V$_2$ are, independently, H, OH, optionally substituted C$_{1-6}$ alkyl, or optionally substituted C$_{1-6}$ alkenyl, or V$_1$ and V$_2$, with the carbon to which they are attached, combine to form optionally substituted C$_{3-8}$ cycloalkyl, or V$_1$ is absent and V$_2$ is optionally substituted C$_{1-6}$ alkylidene or optionally substituted C$_{1-6}$ alkoxyimino;

C is optionally substituted phenyl, optionally substituted pyridinyl, or optionally substituted pyrazinyl;

D$_1$ is —NH—C(O)—, —C(O)—NH—, —NHCH$_2$—, or —CH$_2$NH—; and

E is optionally substituted 4-methylpyridin-3-yl. In certain embodiments, B is not 4-phenyl imidazol-2-yl, haloalkyl substituted pyrazolyl, or amido substituted thienyl.

The invention also features compounds of formula (II):

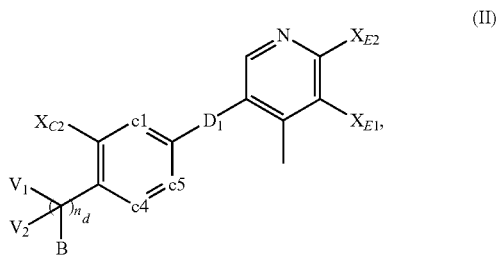

(II)

or a pharmaceutically acceptable salt, solvate, clathrate, or prodrug thereof, wherein, B is optionally substituted benzimidazolyl, optionally substituted benzodioxolyl, optionally substituted phenyl, optionally substituted pyridinyl, optionally substituted pyrimidinyl, optionally substituted pyrrolyl, optionally substituted furanyl, optionally substituted thienyl, optionally substituted imidazolyl, optionally substituted pyrazolyl, optionally substituted oxazolyl, or optionally substituted thiazolyl;

n$_d$ is an integer from 0 to 1;

V$_1$ and V$_2$ are, independently, H, OH, optionally substituted C$_{1-6}$ alkyl, or optionally substituted C$_{1-6}$ alkenyl, or V$_1$ and V$_2$, with the carbon to which they are attached, combine to form optionally substituted C$_{3-8}$ cycloalkyl, or V$_1$ is absent and V$_2$ is optionally substituted C$_{1-6}$ alkylidene or optionally substituted C$_{1-6}$ alkoxyimino;

c1, c4, and c5 are, independently, N or CH, wherein c1 and c4 are both N or both CH, and c5 is CH or wherein one of c1, c4, and c5 is N and the others are CH;

X$_{C2}$ is H or optionally substituted C$_{1-6}$ alkyl;

D$_1$ is NH—C(O)—, —C(O)—NH—, —NHCH$_2$—, or —CH$_2$NH—; and

X$_{E1}$ and X$_{E2}$ are, independently, H, halo, cyano, nitro, optionally substituted C$_{1-6}$ alkyl, or optionally substituted amino. In certain embodiments, B is not haloalkyl substituted pyrazolyl or amido substituted thienyl.

In certain embodiments, B is substituted with one or more substituents selected from the group consisting of halo, OH, cyano, carboxyl, optionally substituted C$_{1-6}$ alkyl, optionally substituted C$_{1-6}$ haloalkyl, optionally substituted C$_{2-6}$ alkenyl, optionally substituted C$_{3-8}$ cycloalkyl, optionally substituted C$_{1-6}$ alkoxy, optionally substituted C$_{1-6}$ haloalkoxy, optionally substituted C$_{3-8}$ cycloalkoxy, optionally substituted C$_{6-10}$ aryl, optionally substituted C$_{7-16}$ aralkyloxy, optionally substituted C$_{2-9}$ heterocyclyl (e.g., optionally substituted C$_{2-9}$ heteroaryl), optionally substituted C$_{2-9}$ (heterocyclyl)oxy, optionally substituted C$_{3-12}$ heterocyclylalkyl, optionally substituted C$_{2-9}$ (heterocyclyl)alkynyl, optionally substituted C$_{1-6}$ alkylsulfonyl, optionally substituted C$_{1-6}$ alkylsulfonyloxy, optionally substituted C$_{1-6}$ alkylsulfamoyloxy, optionally substituted C$_{1-6}$ alkylcarbonyl, optionally substituted C$_{1-6}$ alkoxycarbonyl, and optionally substituted amino. In particular embodiments, B is substituted with one or more substituents selected from the group consisting of halo, OH, cyano, carboxyl, optionally substituted C$_{1-6}$ alkyl, optionally substituted C$_{1-6}$ haloalkyl, optionally substituted C$_{3-8}$ cycloalkyl, optionally substituted C$_{1-6}$ alkoxy, optionally substituted C$_{3-8}$ cycloalkoxy, optionally substituted C$_{2-9}$ heterocyclyl (e.g., optionally substituted pyridinyl, optionally substituted pyrazolyl, optionally substituted thiazolyl, optionally substituted imidazolyl, optionally substituted tetrazolyl, optionally substituted pyrrolidinyl, or optionally substituted isoxazolyl), optionally substituted C$_{2-9}$ (heterocyclyl)oxy (e.g., optionally substituted (pyridinyl)oxy, optionally substituted (pyrimidinyl)oxy, optionally substituted (oxetanyl)oxy, or optionally substituted (isoxazolyl) oxy), optionally substituted C$_{1-6}$ alkylsulfamoyloxy, optionally substituted C$_{1-6}$ alkylsulfonyl, optionally substituted C$_{1-6}$ alkylsulfonyloxy, optionally substituted C$_{1-6}$ alkylcarbonyl, optionally substituted C$_{1-6}$ alkoxycarbonyl, and optionally substituted amino (e.g., C$_{1-6}$ alkylamino or C$_{2-9}$ (heterocyclyl)amino).

In certain embodiments, B is optionally substituted benzimidazolyl, optionally substituted benzodioxolyl, optionally substituted phenyl, optionally substituted pyridinyl, optionally substituted pyrazolyl, or optionally substituted thiazolyl.

In particular embodiments, B is

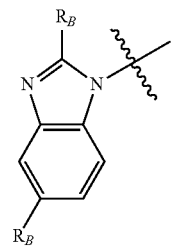

and each R$_B$ is, independently, H, optionally substituted C$_{1-6}$ alkyl, optionally substituted C$_{1-6}$ haloalkyl, or optionally substituted C$_{1-6}$ alkoxy;

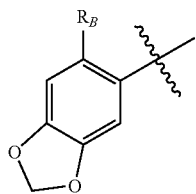

and $R_B$ is H or optionally substituted $C_{1-6}$ alkyl;

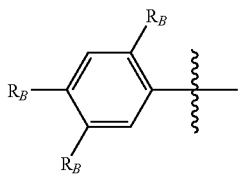

and each $R_B$ is, independently, H, halo, cyano, optionally substituted $C_{1-6}$ alkyl, optionally substituted $C_{1-6}$ haloalkyl, optionally substituted $C_{1-6}$ alkoxy, optionally substituted $C_{6-10}$ aryl, optionally substituted $C_{2-9}$ heterocyclyl (e.g., optionally substituted $C_{2-9}$ heteroaryl), optionally substituted $C_{1-6}$ alkoxycarbonyl, or optionally substituted amino;

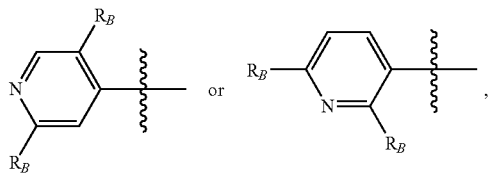

and each $R_B$ is, independently, H, halo, cyano, optionally substituted $C_{1-6}$ alkyl, optionally substituted $C_{1-6}$ haloalkyl, optionally substituted $C_{1-6}$ alkoxy, optionally substituted $C_{6-10}$ aryl, optionally substituted $C_{2-9}$ heterocyclyl (e.g., optionally substituted $C_{2-9}$ heteroaryl), optionally substituted $C_{1-6}$ alkoxycarbonyl, or optionally substituted amino;

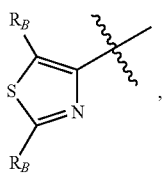

or

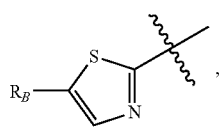

and each $R_B$ is, independently, H, optionally substituted $C_{1-6}$ alkyl, or optionally substituted $C_{2-9}$ heterocyclyl; or

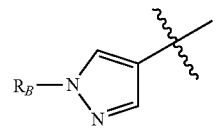

and $R_B$ is H or optionally substituted $C_{1-6}$ alkyl.

In certain embodiments of formula (II), c1 and c4 are both N, and c5 is CH. In other embodiments, each of c1, c4, and c5 is CH. In yet other embodiments, one of c1, c4, and c5 is N and the others are CH.

In certain embodiments of formula (II), $X_{C2}$ is methyl. In other embodiments, $X_{E1}$ is halo (e.g., fluoro, chloro, or bromo). In yet other embodiments, $n_d$ is 0. In some embodiments, $n_d$ is 1, and $V_1$ and $V_2$, with the carbon to which they are attached, combine to form optionally substituted cyclopropyl. In some embodiments, $n_d$ is 1, $V_1$ is absent, and $V_2$ is optionally substituted methylene, optionally substituted ethylidene, optionally substituted vinylidene, optionally substituted isopropylidene, optionally substituted allylidene, optionally substituted propylidene, optionally substituted methoxyimino, or optionally substituted ethoxyimino.

The present invention features compounds exemplified by those in Table 1, below, or a pharmaceutically acceptable salt (or the free form, where a salt is depicted), solvate, clathrate, or prodrug thereof. These compounds, featuring an optionally substituted methylnicotinic moiety, are found to have surprisingly good pharmaceutical and physico-chemical properties, e.g., in vivo exposure, oral bioavailability, and solubility.

In an embodiment, the compound includes an optionally substituted methylnicotinic moiety that is 4-methylnicotinamide, i.e.,

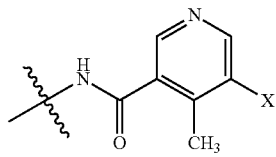

where X may be hydrogen, or in other embodiments, halo, e.g., F, lower alkyl or lower alkoxy, or cyano. In other aspects, pharmaceutical compositions including a pharmaceutically acceptable carrier and a compound of the invention are disclosed. The composition may further include one or more additional therapeutic agents, e.g., immunosuppressive agents, anti-inflammatory agents, and suitable mixtures thereof. Other additional therapeutic agents include steroids, non-steroidal anti-inflammatory agents, antihistamines, analgesics, and suitable mixtures thereof.

Compounds as disclosed herein, or a pharmaceutically acceptable salt (or the free form, where a salt is depicted), solvate, clathrate, or prodrug thereof, are particularly useful inhibiting immune cell (e.g., T-cells and/or B-cells) activation (e.g., activation in response to an antigen). In particular, these compounds or a pharmaceutically acceptable salt (or the free form, where a salt is depicted), solvate, clathrate, or prodrug thereof can inhibit the production of certain cytokines that regulate immune cell activation. For example, a compound of the invention or a pharmaceutically acceptable salt (or the free form, where a salt is depicted), solvate, clathrate, or prodrug thereof can inhibit the production of IL-2, IL-4, IL-5, IL-13, GM-CSF, TNFα, IFN-γ, or combinations thereof. Moreover, a compound of the invention or a pharmaceutically acceptable salt (or the free form, where a salt is depicted), solvate, clathrate, or prodrug thereof can modulate the activity of one or more ion channels involved in activation of immune cells, such as CRAG ion channels.

A compound of the invention or a pharmaceutically acceptable salt (or the free form, where a salt is depicted), solvate, clathrate, or prodrug thereof is particularly useful for immunosuppression or for treating or preventing inflammatory conditions, allergic disorders, and immune disorders.

The invention also encompasses pharmaceutical compositions comprising a compound of the invention (e.g., any one of compounds 1-146 in Table 1) or a pharmaceutically acceptable salt (or the free form, where a salt is depicted), solvate, clathrate, or prodrug thereof; and a pharmaceutically acceptable excipient, carrier, or vehicle. These compositions may further comprise additional agents. These compositions are useful for immunosuppression and treating or preventing inflammatory conditions, allergic disorders, and immune disorders.

The invention further encompasses methods for treating or preventing inflammatory conditions, allergic disorders, and immune disorders, comprising administering to a subject in need thereof an effective amount of a compound of the invention or a pharmaceutically acceptable salt (or the free form, where a salt is depicted), solvate, clathrate, or prodrug thereof, or a pharmaceutical composition comprising a compound of the invention or a pharmaceutically acceptable salt (or the free form, where a salt is depicted), solvate, clathrate, or prodrug thereof. These methods may also comprise administering to the subject an additional agent separately or in a combination composition with the compound of the invention or a pharmaceutically acceptable salt (or the free form, where a salt is depicted), solvate, clathrate, or prodrug thereof.

The invention further encompasses methods for suppressing the immune system of a subject, comprising administering to a subject in need thereof an effective amount of a compound of the invention or a pharmaceutically acceptable salt (or the free form, where a salt is depicted), solvate, clathrate, or prodrug thereof, or a pharmaceutical composition comprising a compound of the invention or a pharmaceutically acceptable salt (or the free form, where a salt is depicted), solvate, clathrate, or prodrug thereof. These methods may also comprise administering to the subject an additional agent separately or in a combination composition with the compound of the invention or a pharmaceutically acceptable salt (or the free form, where a salt is depicted), solvate, clathrate, or prodrug thereof.

The invention further encompasses methods for inhibiting immune cell activation, including inhibiting proliferation of T-cells and/or B-cells, in vivo or in vitro comprising administering to the cell an effective amount of a compound of the invention or a pharmaceutically acceptable salt (or the free form, where a salt is depicted), solvate, clathrate, or prodrug thereof or a pharmaceutical composition comprising a compound of the invention or a pharmaceutically acceptable salt (or the free form, where a salt is depicted), solvate, clathrate, or prodrug thereof.

The invention further encompasses methods for inhibiting cytokine production in a cell (e.g., IL-2, IL-4, IL-5, IL-13, GM-CSF, TNFα, and/or IFN-γ production) in vivo (e.g., in a subject) or in vitro comprising administering to a cell an effective amount of a compound of the invention or a pharmaceutically acceptable salt (or the free form, where a salt is depicted), solvate, clathrate, or prodrug thereof or a pharmaceutical composition comprising a compound of the invention or a pharmaceutically acceptable salt (or the free form, where a salt is depicted), solvate, clathrate, or prodrug thereof.

The invention further encompasses methods for modulating ion channel activity (e.g., CRAC) in vivo (e.g., in a subject) or in vitro comprising administering an effective amount of a compound of the invention or a pharmaceutically acceptable salt (or the free form, where a salt is depicted), solvate, clathrate, or prodrug thereof or a pharmaceutical composition comprising a compound of the invention or a pharmaceutically acceptable salt (or the free form, where a salt is depicted), solvate, clathrate, or prodrug thereof.

All of the methods of this invention may be practiced with a compound of the invention alone, or in combination with other agents, such as other immunosuppressive agents, anti-inflammatory agents, agents for the treatment of allergic disorders or agents for the treatment of immune disorders.

The invention further encompasses compounds for use in therapy; for treating a subject with an immune disorder; for treating an inflammatory condition; for suppressing the immune system; or for treating an allergic disorder.

DETAILED DESCRIPTION OF THE INVENTION

As used herein, the term "alkyl" means a saturated straight chain or branched non-cyclic hydrocarbon typically having from 1 to 10 carbon atoms, from 1 to 6 carbon atoms, or from 1 to 4 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents, such as amino, alkylamino, alkoxy, alkylthio, oxo, halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, (heterocyclyl)oxy, (heterocyclyl)amino, (heterocyclyl)thio, and the like. In addition, any carbon in the alkyl segment may be substituted with oxygen ($=$O), sulfur ($=$S), or nitrogen ($=NR^{23}$, wherein $R^{23}$ is —H, an alkyl, acetyl, or aralkyl). Lower alkyls are typically preferred for the compounds of this invention.

As used herein, the term "alkenyl" means an unsaturated straight chain or branched non-cyclic hydrocarbon with one or more double bonds and typically having from 2 to 10 carbon atoms, from 2 to 6 carbon atoms, or from 2 to 4 carbon atoms. Alkenyl groups can be optionally substituted with 1, 2, 3, or 4 substituent groups as defined herein for an alkyl group.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. Exemplary alkylene groups have 1 to 10 carbon atoms, e.g., 1 to 6 carbon atoms. In some embodiments, the alkylene can be further substituted with 1, 2, 3, or 4 substituent groups as defined herein for an alkyl group.

The term "alkylidene," as used herein, represents =CR$_1$R$_2$, where each R$_1$ and R$_2$ is, independently, H, optionally substituted C$_{1-6}$ alkyl, or optionally substituted C$_{1-6}$ alkenyl, as defined herein, or R$_1$ and R$_2$ combine to form an alkylidene. Exemplary alkylidenes include methylene (=CH$_2$), ethylidene (=CH—CH$_3$), vinylidene (=C=CH$_2$), isopropylidene (=C—(CH$_3$)$_2$), allylidene (=CH—CH=CH$_2$), and propylidene (=CH—CH$_2$—CH$_3$), where each may be further substituted with 1, 2, 3, or 4 substituent groups as defined herein for an alkyl group.

The term "alkoxy," as used herein, refers to an alkyl group that is linked to another moiety though an oxygen atom. Alkoxy groups can be substituted or unsubstituted, as with an alkyl group.

The term "alkoxycarbonyl," as used herein, represents an alkoxy group attached to the parent molecular group through an —C(O)— group. Exemplary unsubstituted alkoxycarbonyl groups are from 1 to 6 carbons. In some embodiments, the alkoxy group can be further substituted with 1, 2, 3, or 4 substituent groups as defined herein for an alkyl group.

The term "alkoxyimino," as used herein, represents an imino group, as defined herein, where R is an alkoxy group, as defined herein. Exemplary unsubstituted alkoxyimino groups are from 1 to 6 carbons, such as methoxyimino (=N—OCH$_3$) and ethoxyimino (=N—OCH$_2$CH$_3$). In some embodiments, the alkoxy group can be further substituted with 1, 2, 3, or 4 substituent groups as defined herein for an alkyl group.

The term "alkylamino," as used herein, represents an alkyl group, as defined herein, substituted by an amino group, as defined herein. The alkyl and amino each can be further substituted with 1, 2, 3, or 4 substituent groups as described herein for the respective group.

The term "alkylcarbonyl," as used herein, represents an alkyl group attached to the parent molecular group through an —C(O)— group. Exemplary unsubstituted alkylcarbonyl groups are from 1 to 6 carbons. In some embodiments, the alkyl group can be further substituted with 1, 2, 3, or 4 substituent groups as defined herein for an alkyl group.

The term "alkylsulfamoyloxy," as used herein, represents an alkyl group attached to the parent molecular group through an —NRS(O)$_2$O— group, where R is H or C$_{1-6}$ alkyl. Exemplary unsubstituted alkylsulfamoyloxy groups are from 1 to 6 carbons, such as (CH$_3$)$_2$NS(O)$_2$O—. In some embodiments, the alkyl group can be further substituted with 1, 2, 3, or 4 substituent groups as defined herein for an alkyl group.

The term "alkylsulfonyl," as used herein, represents an alkyl group attached to the parent molecular group through an —S(O)$_2$— group. Exemplary unsubstituted alkylsulfonyl groups are from 1 to 6 carbons. In some embodiments, the alkyl group can be further substituted with 1, 2, 3, or 4 substituent groups as defined herein for an alkyl group.

The term "alkylsulfonyloxy," as used herein, represents an alkyl group attached to the parent molecular group through an —S(O)$_2$O— group. Exemplary unsubstituted alkylsulfonyloxy groups are from 1 to 6 carbons, such as CH$_3$S(O)$_2$O—. In some embodiments, the alkyl group can be further substituted with 1, 2, 3, or 4 substituent groups as defined herein for an alkyl group.

The term "amino," as used herein, represents N(R$^{N1}$)$_2$, wherein each R$^{N1}$ is, independently, H, an N-protecting group, alkyl, alkenyl, alkynyl, aryl, aralkyl, cycloalkyl, alkcycloalkyl, heterocyclyl (e.g., heteroaryl), or heterocylylalkyl (e.g., heteroaralkyl). In some embodiments, the R$^{N1}$ group is optionally substituted with 1, 2, 3, or 4 substituent groups as defined herein for an alkyl group (e.g., halo). In a preferred embodiment, amino is NH$_2$, or NHR$^{N1}$, wherein R$^{N1}$ is, independently, optionally substituted alkyl, optionally substituted aryl, or optionally substituted heterocyclyl.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents, as described herein.

The term "aralkyl," as used herein, represents an aryl group, as defined herein, attached to the parent molecular group through an alkylene group. Exemplary unsubstituted aralkyl groups are from 7 to 16 carbons (e.g., benzyl).

The term "aralkyloxy," as used herein, represents an aralkyl group, as defined herein, attached to the parent molecular group through an oxygen atom. Exemplary unsubstituted aralkyloxy groups are from 7 to 16 carbons (e.g., benzyloxy).

The term "carboxyl," as used herein, means —CO$_2$H.

As used herein, the term "cycloalkyl" means a saturated, mono- or polycyclic alkyl radical typically having from 3 to 10 carbon atoms, from 3 to 8 carbon atoms, or from 3 to 7 carbon atoms. Representative cycloalkyls include cyclopropyl, cyclobutyl, cyclopentyl, cyclohexyl, cycloheptyl, cyclooctyl, cyclononyl, cyclodecyl, adamantlyl, decahydronaphthyl, octahydropentalene, bicyclo[1,1,1]pentanyl, and the like. Cycloalkyl groups can be substituted or unsubstituted, as with alkyl groups.

The term "cycloalkoxy," as used herein, represents a cycloalkyl group, as defined herein, attached to the parent molecular group through an oxygen atom. Exemplary unsubstituted cycloalkoxy groups are from 3 to 8 carbons. In some embodiment, the cycloalkyl group can be further substituted with 1, 2, 3, or 4 substituent groups as described herein.

As used herein, the term "halogen" or "halo" means —F, —Cl, —Br, or —I.

As used herein, the term "haloalkyl" means an alkyl group in which one or more —H is replaced with a halo group. Examples of haloalkyl groups include —CF$_3$, —CHF$_2$, —CH$_2$F, —CCl$_3$, —CH$_2$CH$_2$Br, —CH$_2$CH(CH$_2$CH$_2$Br) CH$_3$, —CHICH$_3$, and the like.

As used herein, the term "haloalkoxy", as used herein, refers to a haloalkyl group that is linked to another moiety though an oxygen atom. Examples of haloalkoxy groups include —OCF$_3$, —OCHF$_2$, —OCH$_2$F, —OCCl$_3$, —OCH$_2$CH$_2$Br, —OCH$_2$CH(CH$_2$CH$_2$Br)CH$_3$, —OCHICH$_3$, and the like.

The term "heteroaryl," as used herein, represents that subset of heterocyclyls, as defined herein, which are aromatic: i.e., they contain 4n+2 pi electrons within the mono- or multicyclic ring system. In some embodiments, the heteroaryl is substituted with 1, 2, 3, or 4 substituents groups as defined for a heterocyclyl group.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds.

Certain heterocyclyl groups include from 2 to 9 carbon atoms. Other such groups may include up to 12 carbon atoms. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Exemplary heterocyclyl groups include pyridinyl, pyrazolyl, thiazolyl, imidazolyl, tetrazolyl, pyrrolidinyl, isoxazolyl, pyrimidinyl, oxetanyl, benzimidazolyl, benzodioxolyl, pyrrolyl, furanyl, thienyl, imidazolyl, pyrazinyl, and oxazolyl.

The term "heterocyclylalkyl" represents a heterocyclyl group, as defined herein, attached to the parent molecular group through an alkylene group, as defined herein. Exemplary unsubstituted heterocyclylalkyl groups are from 2 to 14 or from 3 to 12 carbons. In some embodiments, the alkylene and the heterocyclyl each can be further substituted with 1, 2, 3, or 4 substituent groups as defined herein for the respective group.

The term "(heterocyclyl)alkynyl," as used herein, represents a heterocyclyl group, as defined herein, attached to the parent molecular group through a divalent alkynyl group. In some embodiments, the heterocyclyl group or the alkynyl group can be substituted with 1, 2, 3, or 4 substituent groups as defined herein for the respective group.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "imino," as used herein, represents a (NR) group, which can also be represented as =NR, where R is H, optionally substituted alkyl or optionally substituted alkoxy, as described herein.

As used herein, the terms "subject," "patient," and "animal", are used interchangeably and include, but are not limited to, a cow, monkey, horse, sheep, pig, chicken, turkey, quail, cat, dog, mouse, rat, rabbit, guinea pig, or human. The preferred subject, patient, or animal is a human.

As used herein, the term "lower" refers to a group having up to six (e.g., up to four) carbon atoms. For example, a "lower alkyl" refers to an alkyl radical having from 1 to 6 (e.g., 1 to 4) carbon atoms, and a "lower alkenyl" or "lower alkynyl" refers to an alkenyl or alkynyl radical having from 2 to 6 (e.g., 2 to 4) carbon atoms, respectively. A lower alkoxy or a lower alkylsulfanyl refers to an alkoxy or an alkylsulfanyl having from 1 to 6 (e.g., 1 to 4) carbon atoms. Lower substituents are typically preferred.

Where a particular substituent, such as an alkyl substituent, occurs multiple times in a given structure or moiety, the identity of the substituent is independent in each case and may be the same as or different from other occurrences of that substituent in the structure or moiety. Furthermore, individual substituents in the specific embodiments and exemplary compounds of this invention are preferred in combination with other such substituents in the compounds of this invention, even if such individual substituents are not expressly noted as being preferred or not expressly shown in combination with other substituents.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Suitable substituents for an alkyl, alkoxy, alkylsulfanyl, alkylamino, dialkylamino, alkylene, alkenyl, alkynyl, cycloalkyl, cycloalkenyl, cycloalkoxy, heterocyclyl, (heterocyclyl)oxy, heterocyclylalkyl, (heterocyclyl)alkynyl, aryl, aralkyl, aralkyloxy, heteroaryl, heteroaralkyl, alkylsulfonyl, alkylsulfonyloxy, alkylsulfamoyloxy, alkylcarbonyl, alkoxycarbonyl, amino, alkylidene, and alkoxyimino groups include any substituent that will form a stable compound of the invention. Examples of substituents for an alkyl, alkoxy, alkylsulfanyl, alkylamino, dialkylamino, alkylene, alkenyl, alkynyl, cycloalkyl, cycloalkenyl, cycloalkoxy, heterocyclyl, (heterocyclyl)oxy, heterocyclylalkyl, (heterocyclyl)alkynyl, aryl, aralkyl, aralkyloxy, heteroaryl, heteroaralkyl, alkylsulfonyl, alkylsulfonyloxy, alkylsulfamoyloxy, alkylcarbonyl, alkoxycarbonyl, amino, alkylidene, and alkoxyimino include an alkyl, alkoxy, alkylsulfanyl, alkylamino, dialkylamino, an alkenyl, an alkynyl, an cycloalkyl, an cycloalkenyl, an heterocyclyl, an aryl, an heteroaryl, an aralkyl, an heteroaralkyl, a haloalkyl, —C(O)NR$_{13}$R$_{14}$, —NR$_{15}$C(O)R$_{16}$, halo, —OR$_{15}$, cyano, nitro, haloalkoxy, —C(O)R$_{15}$, —NR$_{13}$R$_{14}$, —SR$_{15}$, —C(O)OR$_{15}$, —OC(O)R$_{15}$, —NR$_{15}$C(O)NR$_{13}$R$_{14}$, —OC(O)NR$_{13}$R$_{14}$, —NR$_{15}$C(O)OR$_{16}$, —S(O)$_p$R$_{15}$, or —S(O)$_p$NR$_{13}$R$_{14}$, wherein R$_{13}$ and R$_{14}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted heterocyclylalkyl, an optionally substituted aralkyl, an optionally substituted aralkyloxy, or an optionally substituted heteroaralkyl; or R$_{13}$ and R$_{14}$ taken together with the nitrogen to which they are attached form optionally substituted heterocyclyl or optionally substituted heteroaryl; R$_{15}$ and R$_{16}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted heterocyclylalkyl, an optionally substituted aralkyl, an optionally substituted aralkyloxy, or an optionally substituted heteroaralkyl; and p is an integer from 0 to 2.

In addition, alkyl, cycloalkyl, alkylene, heterocyclyl, and any saturated portion of an alkenyl, cycloalkenyl, alkynyl, aralkyl, aralkyloxy, heterocyclylalkyl, or heteroaralkyl group, may also be substituted with =O, =S, or =N—R$_{15}$, where R$_{15}$ is defined above.

When a heterocyclyl, heterocyclylalkyl, heteroaryl, or heteroaralkyl group contains a nitrogen atom, it may be substituted or unsubstituted. When a nitrogen atom in the aromatic ring of a heteroaryl group has a substituent, the nitrogen may be a quaternary nitrogen.

The compounds of the invention can comprise isotopes of the elements which are explicitly disclosed. For example, each hydrogen substituent on compounds of the invention is independently selected from $^1$H, $^2$H, and $^3$H isotopes.

Choices and combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

Unless indicated otherwise, the compounds of the invention containing reactive functional groups (such as, without limitation, carboxyl, hydroxyl, and amino moieties) also include protected derivatives thereof. "Protected derivatives" are those compounds in which a reactive site or sites are blocked with one ore more protecting groups. Suitable protecting groups for carboxyl moieties include benzyl, tert-butyl, and the like. Suitable protecting groups for amino and amido groups include acetyl, tert-butoxycarbonyl, benzyloxycarbonyl, and the like. Suitable protecting groups for hydroxy include benzyl and the like. Other suitable protecting groups are well known to those of ordinary skill in the art and include those found in T. W. Greene, *Protecting Groups in Organic Synthesis*, John Wiley & Sons, Inc. 1981, the entire teachings of which are incorporated herein by reference.

As used herein, the term "compound(s) of this invention" and similar terms refers to compounds, such as exemplified in Table I, or pharmaceutically acceptable salts thereof (or the free form, where a salt is depicted) and also include protected derivatives thereof.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, but they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that include —NO, —NO₂, —ONO, or —ONO₂ moieties. Prodrugs can typically be prepared using well-known methods, such as those described in *Burger's Medicinal Chemistry and Drug Discovery* (1995) 172-178, 949-982 (Manfred E. Wolff ed., 5$^{th}$ ed), the entire teachings of which are incorporated herein by reference.

As used herein, the term "pharmaceutically acceptable salt" is a salt formed from an acid and a basic group of one of the compounds of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound of the invention having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

When a disclosed compound is named or depicted by structure, it is to be understood that solvates (e.g., hydrates) of the compound or its pharmaceutically acceptable salts are also included. "Solvates" refer to crystalline forms wherein solvent molecules are incorporated into the crystal lattice during crystallization. Solvate may include water or non-aqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include a stoichiometric or non-stoichiometric amount of water bound by non-covalent intermolecular forces.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e., the capacity to occur in different crystalline forms). These different crystalline forms are typically known as "polymorphs." It is to be understood that when named or depicted by structure, the disclosed compounds and solvates (e.g., hydrates) also include all polymorphs thereof. As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it. In addition, one polymorph may spontaneously convert to another polymorph under certain conditions.

When a disclosed compound is named or depicted by structure, it is to be understood that clathrates ("inclusion compounds") of the compound or its pharmaceutically acceptable salts, solvates or polymorphs are also included. As used herein, the term "clathrate" means a compound of the present invention or a salt thereof in the form of a crystal lattice that contains spaces (e.g., channels) that have a guest molecule (e.g., a solvent or water) trapped within.

As used herein, the term "asthma" means a pulmonary disease, disorder or condition characterized by reversible airway obstruction, airway inflammation, and increased airway responsiveness to a variety of stimuli.

"Immunosuppression" refers to impairment of any component of the immune system resulting in decreased immune function. This impairment may be measured by any conventional means including whole blood assays of lymphocyte function, detection of lymphocyte proliferation and assessment of the expression of T-cell surface antigens. The antisheep red blood cell (SRBC) primary (IgM) antibody response assay (usually referred to as the plaque assay) is one specific method. This and other methods are described in Luster, M. I., Portier, C., Pait, D. G., White, K. L., Jr., Gennings, C., Munson, A. E., and Rosenthal, G. J. (1992). "Risk Assessment in Immunotoxicology I: Sensitivity and Predictability of Immune Tests." Fundam. Appl. Toxicol., 18, 200-210. Measuring the immune response to a T-cell dependent immunogen is another particularly useful assay (Dean, J. H., House, R. V., and Luster, M. I. (2001). "Immunotoxicology: Effects of, and Responses to, Drugs and Chemicals" in *Principles and Methods of Toxicology*: Fourth Edition (A. W. Hayes, Ed.), pp. 1415-1450, Taylor & Francis, Philadelphia, Pa.). The term "suppressing the immune system" herein refers to administering a compound or a composition of the invention to a subject to promote immunosuppression, as defined herein. The term "inhibiting immune cell activation" herein refers to decreasing cellular progression, proliferation, and/or growth of one or more immune cells or reducing the expression of one or more surface antigens on such cells upon administration of a compound or a composition of the invention, as compared to control without the compound or the composition. Exemplary cells include T-cells and B-cells.

The compounds of this invention can be used to treat subjects with immune disorders. As used herein, the term "immune disorder" and like terms means a disease, disorder or condition caused by the immune system of an animal, including autoimmune disorders. Immune disorders include those diseases, disorders or conditions that have an immune component and those that are substantially or entirely immune system-mediated. Autoimmune disorders are those wherein the animal's own immune system mistakenly attacks itself, thereby targeting the cells, tissues, and/or organs of the animal's own body. For example, the autoimmune reaction is directed against the nervous system in multiple sclerosis and the gut in Crohn's disease. In other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barré, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease, Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a compound or a composition of the invention to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "allergic disorder" means a disease, condition or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize masT-cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma, and food allergies.

The compounds of this invention can be used to prevent or to treat subjects with inflammatory conditions. As used herein, an "inflammatory condition" means a disease, disorder or condition characterized by inflammation of body tissue or having an inflammatory component. These include local inflammatory responses and systemic inflammation. Examples of such inflammatory conditions include: transplant rejection, including skin graft rejection; chronic inflammatory conditions of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory conditions of the gums, including gingivitis and periodontitis; tuberculosis; leprosy; inflammatory diseases of the kidney including uremic complications, glomerulonephritis and nephrosis; inflammatory conditions of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis); as well as various other diseases with significant inflammatory components, including preeclampsia; chronic liver failure, brain and spinal cord trauma, cancer). There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. "Treatment of an inflammatory condition" herein refers to administering a compound or a composition of the invention to a subject, who has an inflammatory condition, a symptom of such a condition or a predisposition towards such a condition, with the purpose to cure, relieve, alter, affect, or prevent the inflammatory condition, the symptom of it, or the predisposition towards it.

An "effective amount" is the quantity of compound in which a beneficial outcome is achieved when the compound is administered to a subject or alternatively, the quantity of compound that possess a desired activity in vivo or in vitro. In the case of inflammatory conditions and autoimmune disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of inflammatory condition or autoimmune disorder or the degree of immunosuppression sought. The skilled artisan will be able to determine appropriate dosages depending on these and other factors. Effective amounts of the disclosed compounds typically range between about 1 mg/m$^2$ per day and about 10 grams/m$^2$ per day, and preferably between 10 mg/m$^2$ per day and about 1 gram/m$^2$.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers and stereoisomers, that is, both the stereomerically pure form (e.g., geometrically pure, enantiomerically pure, or diastereomerically pure) and enantiomeric, diastereomeric, and geometric isomeric mixtures. In some cases, one enantiomer, diastereomer, or geometric isomer will possess superior activity or an improved toxicity or kinetic profile compared to others. In those cases, such enantiomers, diastereomers, and geometric isomers of a compound of this invention are preferred.

The term "inhibit production of IL-2" and like terms means inhibiting IL-2 synthesis (e.g., by inhibiting transcription (mRNA expression), or translation (protein expression)) and/or inhibiting IL-2 secretion in a cell that has the ability to produce and/or secrete IL-2 (e.g., T lymphocyte). Likewise, the term "inhibiting cytokine production" means inhibiting the synthesis (e.g., by inhibiting transcription, or translation) and/or inhibiting the secretion in a cell that has the ability to produce and/or secrete a cytokine (e.g., IL-4, IL-5, IL-13, GM-CSF, TNFα, or IFN-γ). As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of the invention.

Enantiomeric and diastereomeric mixtures can typically be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

When administered to a patient, e.g., to a non-human animal for veterinary use or for improvement of livestock, or to a human for clinical use, the compounds of the invention are typically administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single compound of the invention by weight of the isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

DETAILED DESCRIPTION OF THE INVENTION

The invention relates to compounds exemplified by those in Table 1, below, or pharmaceutically acceptable salts thereof (or the free form, where a salt is depicted), and pharmaceutical compositions that are particularly useful for immunosuppression or to treat or prevent inflammatory conditions, immune disorders, and allergic disorders.

Exemplary Compounds

Exemplary compounds of the invention, that have been made in accordance with the descriptions in the examples below, are depicted in Table 1 below.

TABLE 1

| Number | Structure | Compound Name | IL-2 inhibition Jurkat/PHA/ 1% FBS IC50 (nM) |
|---|---|---|---|
| 1. | 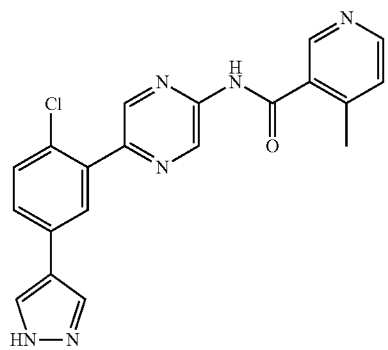 [SMILES: Cc1ccncc1C(=O)Nc1cnc(-c2cc(-c3cn[nH]c3)ccc2Cl)cn1] | N-(5-(2-chloro-5-(1H-pyrazol-4-yl)phenyl)pyrazin-2-yl)-4-methylnicotinamide | 34 |
| 2. | 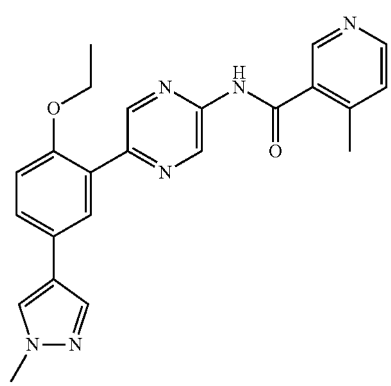 [SMILES: CCOc1ccc(-c2cnn(C)c2)cc1-c1cnc(NC(=O)c2cnccc2C)cn1] | N-(5-(2-ethoxy-5-(1-methyl-1H-pyrazol-4-yl)phenyl)pyrazin-2-yl)-4-methylnicotinamide | 51 |
| 3. | 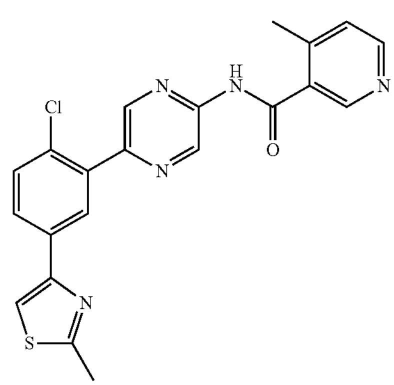 [SMILES: Cc1nc(-c2ccc(Cl)c(-c3cnc(NC(=O)c4cnccc4C)cn3)c2)cs1] | N-(5-(2-chloro-5-(2-methylthiazol-4-yl)phenyl)pyrazin-2-yl)-4-methylnicotinamide | 60 |

TABLE 1-continued

| Number | Structure | Compound Name | IL-2 inhibition Jurkat/PHA/ 1% FBS IC50 (nM) |
|---|---|---|---|
| 4. | 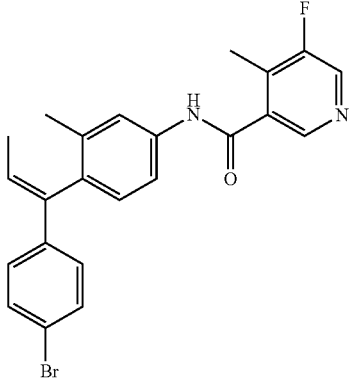 [SMILES: C/C=C(/c1ccc(Br)cc1)c1ccc(NC(=O)c2cncc(F)c2C)cc1C] | (Z)-N-(4-(1-(4-bromophenyl)prop-1-en-1-yl)-3-methylphenyl)-5-fluoro-4-methylnicotinamide | 50 |
| 5. | 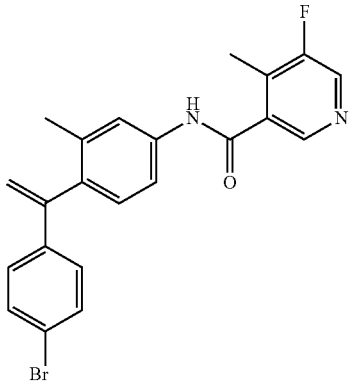 [SMILES: C=C(c1ccc(Br)cc1)c1ccc(NC(=O)c2cncc(F)c2C)cc1C] | N-(4-(1-(4-bromophenyl)vinyl)-3-methylphenyl)-5-fluoro-4-methylnicotinamide | 202 |
| 6. | 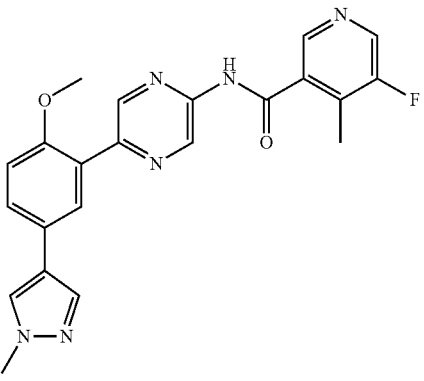 [SMILES: COc1ccc(-c2cnn(C)c2)cc1-c1cnc(NC(=O)c2cncc(F)c2C)cn1] | 5-fluoro-N-(5-(2-methoxy-5-(1-methyl-1H-pyrazol-4-yl)phenyl)pyrazin-2-yl)-4-methylnicotinamide | 20 |
| 7. | 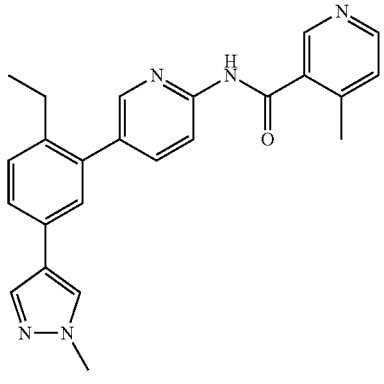 | N-(5-(2-ethyl-5-(1-methyl-1H-pyrazol-4-yl)phenyl)pyridin-2-yl)-4-methylnicotinamide | 12 |

TABLE 1-continued

| Number | Structure | Compound Name | IL-2 inhibition Jurkat/PHA/ 1% FBS IC50 (nM) |
|---|---|---|---|
| 8. | 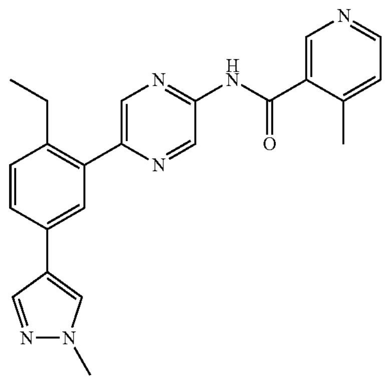 [SMILES: CCc1ccc(-c2cnn(C)c2)cc1-c1cnc(NC(=O)c2cnccc2C)cn1] | N-(5-(2-ethyl-5-(1-methyl-1H-pyrazol-4-yl)phenyl)pyrazin-2-yl)-4-methylnicotinamide | 25 |
| 9. | 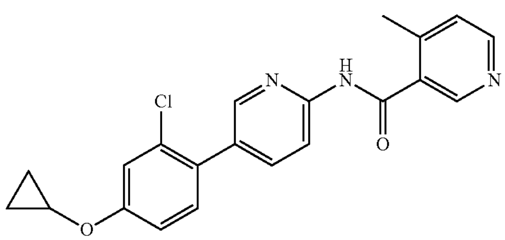 [SMILES: Cc1ccncc1C(=O)Nc1ccc(-c2ccc(OC3CC3)cc2Cl)cn1] | N-(5-(2-chloro-4-cyclopropoxyphenyl)pyridin-2-yl)-4-methylnicotinamide | 28 |
| 10. | 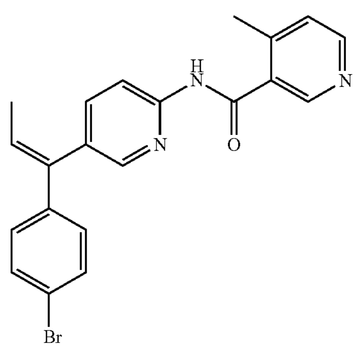 [SMILES: C/C=C(/c1ccc(Br)cc1)c1ccc(NC(=O)c2cnccc2C)nc1] | (Z)-N-(5-(1-(4-bromophenyl)prop-1-en-1-yl)pyridin-2-yl)-4-methylnicotinamide | 46 |
| 11. | 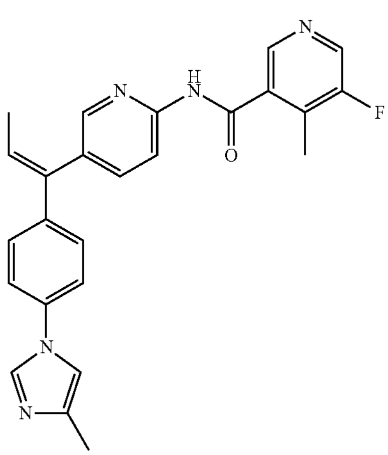 [SMILES: C/C=C(/c1ccc(-n2cnc(C)c2)cc1)c1ccc(NC(=O)c2cncc(F)c2C)nc1] | (Z)-5-fluoro-4-methyl-N-(5-(1-(4-(4-methyl-1H-imidazol-1-yl)phenyl)prop-1-en-1-yl)pyridin-2-yl)nicotinamide | 58 |

TABLE 1-continued

| Number | Structure | Compound Name | IL-2 inhibition Jurkat/PHA/ 1% FBS IC50 (nM) |
|---|---|---|---|
| 12. | 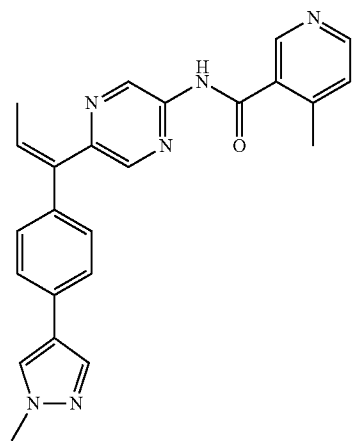 [SMILES: C/C=C(/c1ccc(-c2cnn(C)c2)cc1)c1cnc(NC(=O)c2cnccc2C)cn1] | (Z)-4-methyl-N-(5-(1-(4-(1-methyl-1H-pyrazol-4-yl)phenyl)prop-1-en-1-yl)pyrazin-2-yl)nicotinamide | 763 |
| 13. | 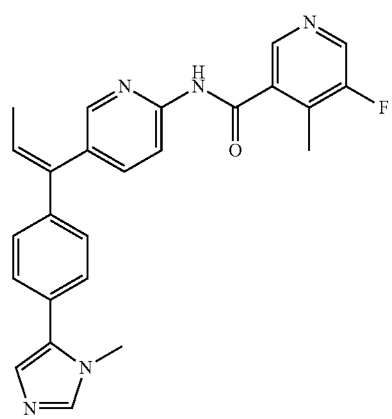 [SMILES: C/C=C(/c1ccc(-c2cncn2C)cc1)c1ccc(NC(=O)c2cncc(F)c2C)nc1] | (Z)-5-fluoro-4-methyl-N-(5-(1-(4-(1-methyl-1H-imidazol-5-yl)phenyl)prop-1-en-1-yl)pyridin-2-yl)nicotinamide | 44 |
| 14. | 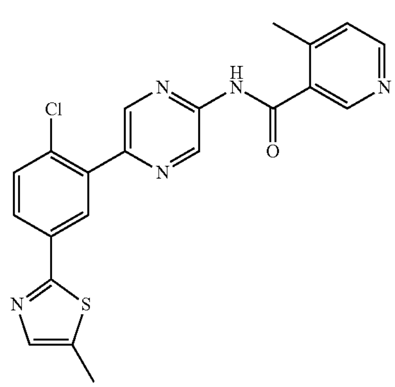 [SMILES: Cc1cnc(-c2ccc(Cl)c(-c3cnc(NC(=O)c4cnccc4C)cn3)c2)s1] | N-(5-(2-chloro-5-(5-methylthiazol-2-yl)phenyl)pyrazin-2-yl)-4-methylnicotinamide | 13 |

TABLE 1-continued

| Number | Structure | Compound Name | IL-2 inhibition Jurkat/PHA/ 1% FBS IC50 (nM) |
|---|---|---|---|
| 15. | 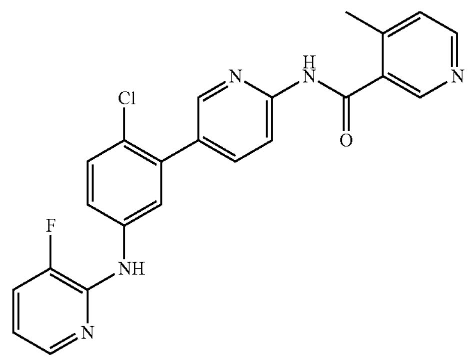 [SMILES: Cc1ccncc1C(=O)Nc1ccc(-c2cc(Nc3ncccc3F)ccc2Cl)cn1] | N-(5-(2-chloro-5-((3-fluoropyridin-2-yl)amino)phenyl)pyridin-2-yl)-4-methylnicotinamide | 104 |
| 16. | 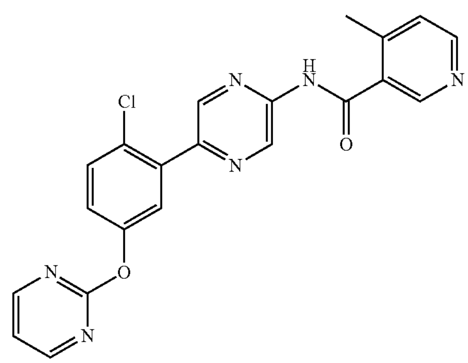 [SMILES: Cc1ccncc1C(=O)Nc1cnc(-c2cc(Oc3ncccn3)ccc2Cl)cn1] | N-(5-(2-chloro-5-(pyrimidin-2-yloxy)phenyl)pyrazin-2-yl)-4-methylnicotinamide | 46 |
| 17. | 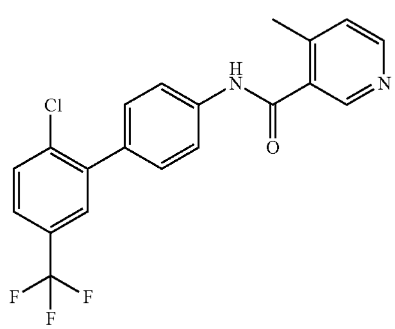 [SMILES: Cc1ccncc1C(=O)Nc1ccc(-c2cc(C(F)(F)F)ccc2Cl)cc1] | N-(2'-chloro-5'-(trifluoromethyl)-[1,1'-biphenyl]-4-yl)-4-methylnicotinamide | 12 |
| 18. | 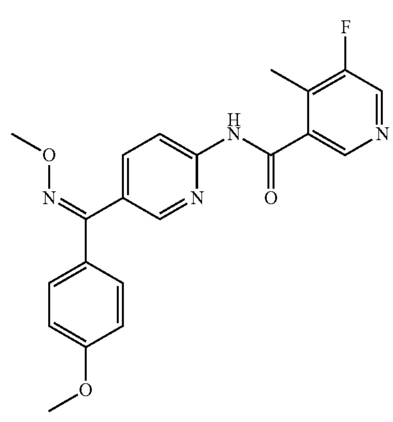 [SMILES: CO/N=C(/c1ccc(OC)cc1)c1ccc(NC(=O)c2cncc(F)c2C)nc1] | (Z)-5-fluoro-N-(5-((methoxyimino)(4-methoxyphenyl)methyl)pyridin-2-yl)-4-methylnicotinamide | 52 |

TABLE 1-continued

| Number | Structure | Compound Name | IL-2 inhibition Jurkat/PHA/ 1% FBS IC50 (nM) |
|---|---|---|---|
| 19. | 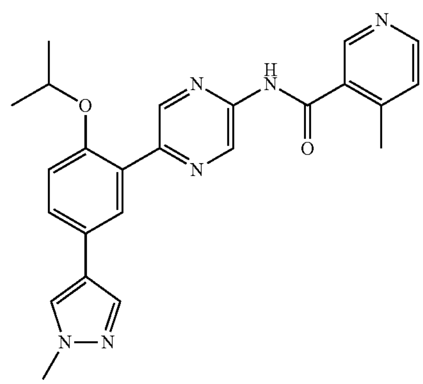 [SMILES: Cc1ccncc1C(=O)Nc1cnc(-c2cc(-c3cnn(C)c3)ccc2OC(C)C)cn1] | N-(5-(2-isopropoxy-5-(1-methyl-1H-pyrazol-4-yl)phenyl)pyrazin-2-yl)-4-methylnicotinamide | 79 |
| 20. | 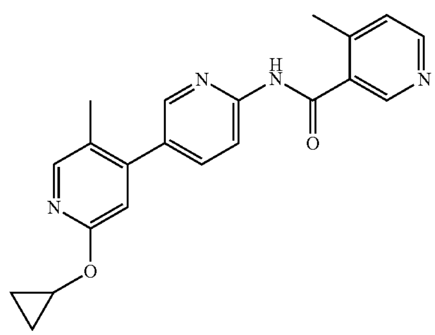 [SMILES: Cc1ccncc1C(=O)Nc1ccc(-c2cc(OC3CC3)ncc2C)cn1] | N-(2'-cyclopropoxy-5'-methyl-[3,4'-bipyridin]-6-yl)-4-methylnicotinamide | 73 |
| 21. | 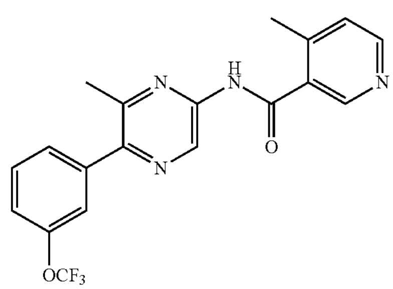 [SMILES: Cc1ccncc1C(=O)Nc1cnc(-c2cccc(OC(F)(F)F)c2)c(C)n1] | 4-methyl-N-(6-methyl-5-(3-(trifluoromethoxy)phenyl)pyrazin-2-yl)nicotinamide | 1000 |
| 22. | 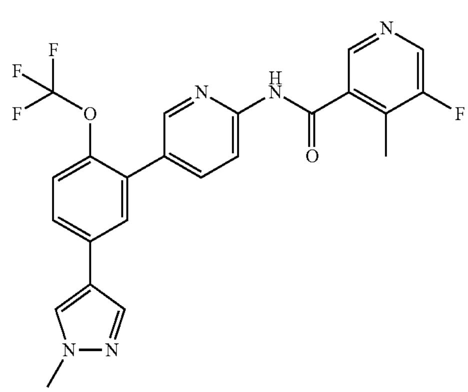 | 5-fluoro-4-methyl-N-(5-(5-(1-methyl-1H-pyrazol-4-yl)-2-(trifluoromethoxy)phenyl)pyrazin-2-yl)nicotinamide | 9 |

TABLE 1-continued
| Number | Structure | Compound Name | IL-2 inhibition Jurkat/PHA/ 1% FBS IC50 (nM) |
|---|---|---|---|
| 23. | 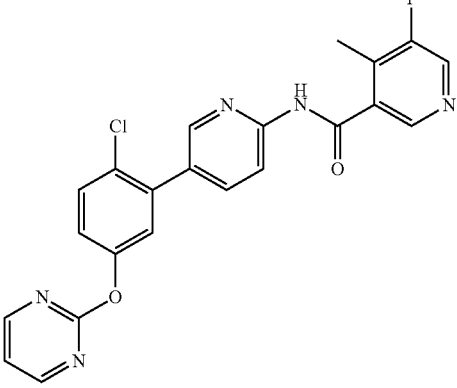 | N-(5-(2-chloro-5-(pyrimidin-2-yloxy)phenyl)pyridin-2-yl)-5-fluoro-4-methylnicotinamide | 46 |
| 24. | 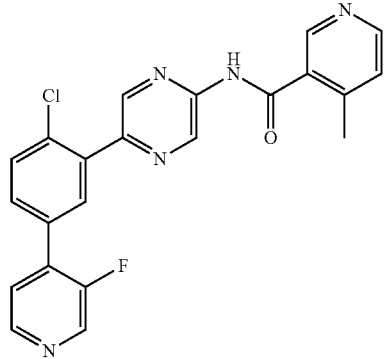 [SMILES: Cc1ccncc1C(=O)Nc1cnc(-c2cc(-c3ccncc3F)ccc2Cl)cn1] | N-(5-(2-chloro-5-(3-fluoropyridin-4-yl)phenyl)pyrazin-2-yl)-4-methylnicotinamide | 19 |
| 25. | 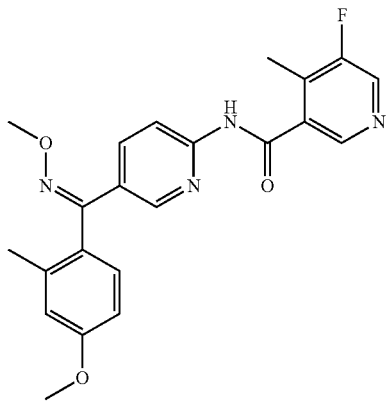 [SMILES: CO/N=C(\c1ccc(NC(=O)c2cncc(F)c2C)nc1)c1ccc(OC)cc1C] | (Z)-5-fluoro-N-(5-((4-methoxy-2-methylphenyl)(methoxyimino)methyl)pyridin-2-yl)-4-methylnicotinamide | 130 |

TABLE 1-continued

| Number | Structure | Compound Name | IL-2 inhibition Jurkat/PHA/ 1% FBS IC50 (nM) |
|---|---|---|---|
| 26. | 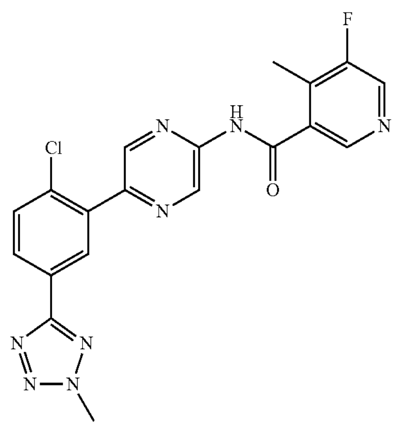 | N-(5-(2-chloro-5-(2-methyl-2H-tetrazol-5-yl)phenyl)pyrazin-2-yl)-5-fluoro-4-methylnicotinamide | 26 |
| 27. | 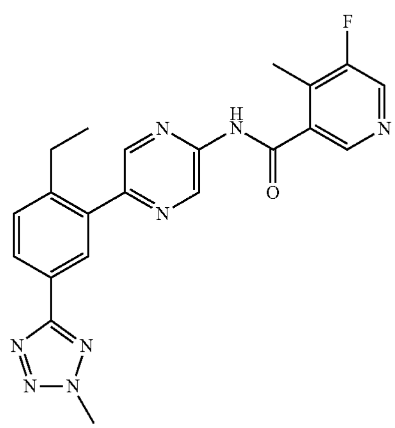 | N-(5-(2-ethyl-5-(2-methyl-2H-tetrazol-5-yl)phenyl)pyrazin-2-yl)-5-fluoro-4-methylnicotinamide | 26 |
| 28. | 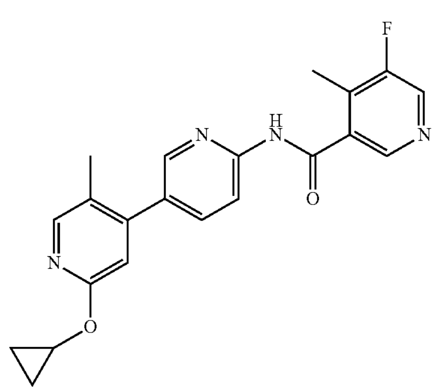 [SMILES: Cc1cnc(OC2CC2)cc1-c1ccc(NC(=O)c2cncc(F)c2C)nc1] | N-(2'-cyclopropoxy-5'-methyl-[3,4'-bipyridin]-6-yl)-5-fluoro-4-methylnicotinamide | 114 |

TABLE 1-continued

| Number | Structure | Compound Name | IL-2 inhibition Jurkat/PHA/ 1% FBS IC50 (nM) |
|---|---|---|---|
| 29. | 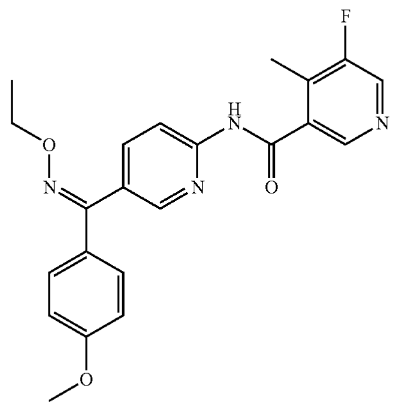 [SMILES: CCO/N=C(/c1ccc(OC)cc1)c1ccc(NC(=O)c2cncc(F)c2C)nc1] | (Z)-N-(5-((ethoxyimino)(4-methoxyphenyl)methyl)pyridin-2-yl)-5-fluoro-4-methylnicotinamide | 210 |
| 30. | 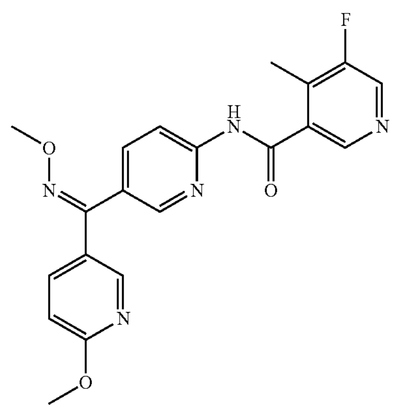 | (E)-5-fluoro-N-(5-((methoxyimino)(6-methoxypyridin-3-yl)methyl)pyridin-2-yl)-4-methylnicotinamide | 247 |
| 31. | 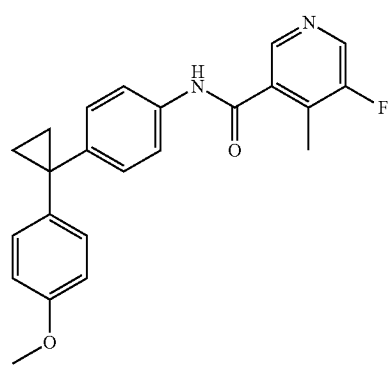 [SMILES: COc1ccc(C2(c3ccc(NC(=O)c4cncc(F)c4C)cc3)CC2)cc1] | 5-fluoro-N-(4-(1-(4-methoxyphenyl)cyclopropyl)phenyl)-4-methylnicotinamide | 104 |
| 32. | 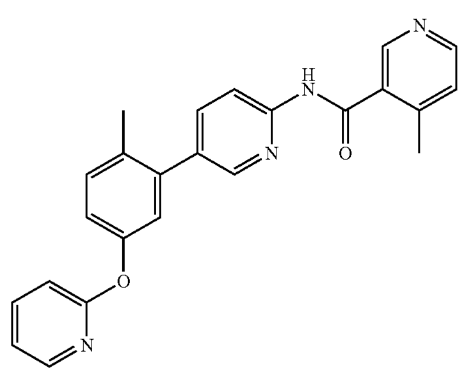 [SMILES: Cc1ccncc1C(=O)Nc1ccc(-c2cc(Oc3ccccn3)ccc2C)cn1] | 4-methyl-N-(5-(2-methyl-5-(pyridin-2-yloxy)phenyl)pyridin-2-yl)nicotinamide | 91 |

TABLE 1-continued

| Number | Structure | Compound Name | IL-2 inhibition Jurkat/PHA/ 1% FBS IC50 (nM) |
|---|---|---|---|
| 33. | 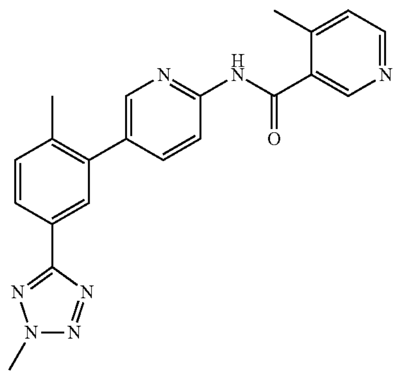 [SMILES: Cc1ccncc1C(=O)Nc1ccc(-c2cc(-c3nnn(C)n3)ccc2C)cn1] | 4-methyl-N-(5-(2-methyl-5-(2-methyl-2H-tetrazol-5-yl)phenyl)pyridin-2-yl)nicotinamide | 31 |
| 34. | 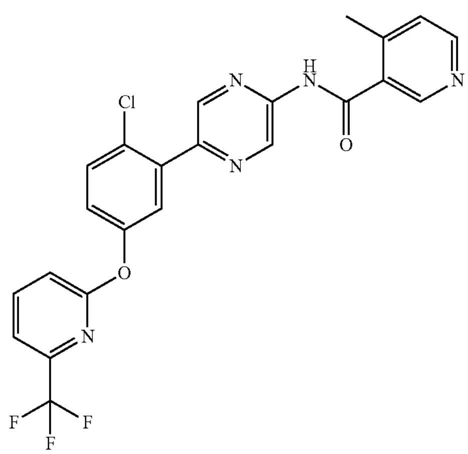 [SMILES: Cc1ccncc1C(=O)Nc1cnc(-c2cc(Oc3cccc(C(F)(F)F)n3)ccc2Cl)cn1] | N-(5-(2-chloro-5-((6-(trifluoromethyl)pyridin-2-yl)oxy)phenyl)pyrazin-2-yl)-4-methylnicotinamide | 26 |
| 35. | 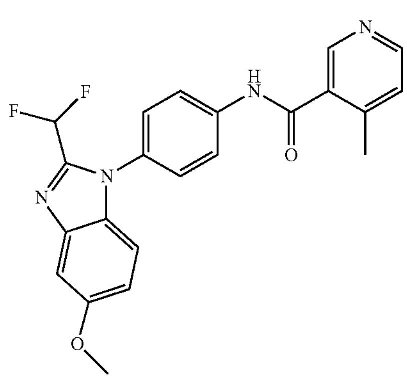 [SMILES: COc1ccc2c(c1)nc(C(F)F)n2-c1ccc(NC(=O)c2cnccc2C)cc1] | N-(4-(2-(difluoromethyl)-5-methoxy-1H-benzo[d]imidazol-1-yl)phenyl)-4-methylnicotinamide | 190 |

TABLE 1-continued

| Number | Structure | Compound Name | IL-2 inhibition Jurkat/PHA/ 1% FBS IC50 (nM) |
|---|---|---|---|
| 36. | 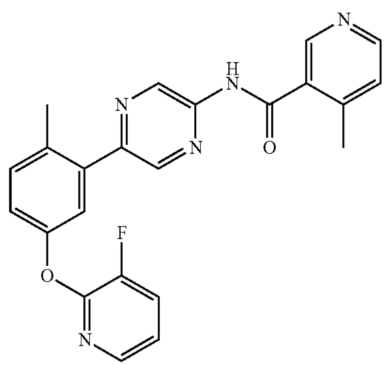 [SMILES: Cc1ccncc1C(=O)Nc1cnc(-c2cc(Oc3ncccc3F)ccc2C)cn1] | N-(5-(5-((3-fluoropyridin-2-yl)oxy)-2-methylphenyl)pyrazin-2-yl)-4-methylnicotinamide | 134 |
| 37. | 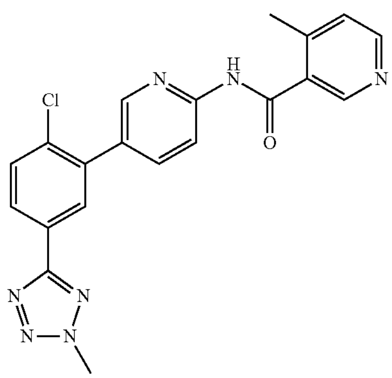 | N-(5-(2-chloro-5-(2-methyl-2H-tetrazol-5-yl)phenyl)pyridin-2-yl)-4-methylnicotinamide | 18 |
| 38. | 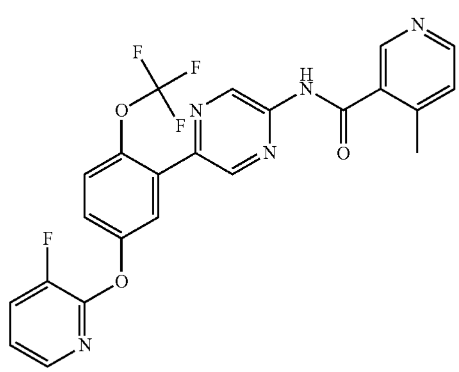 [SMILES: Cc1ccncc1C(=O)Nc1cnc(-c2cc(Oc3ncccc3F)ccc2OC(F)(F)F)cn1] | N-(5-(5-((3-fluoropyridin-2-yl)oxy)-2-(trifluoromethoxy)phenyl)pyrazin-2-yl)-4-methylnicotinamide | 79 |
| 39. | 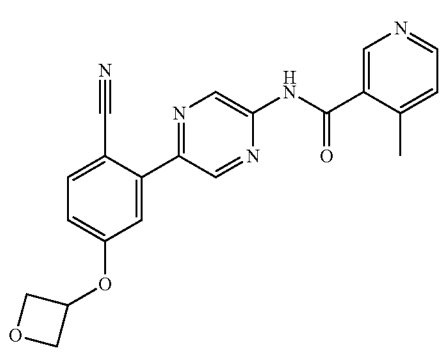 [SMILES: Cc1ccncc1C(=O)Nc1cnc(-c2cc(OC3COC3)ccc2C#N)cn1] | N-(5-(2-cyano-5-(oxetan-3-yloxy)phenyl)pyrazin-2-yl)-4-methylnicotinamide | 1000 |

TABLE 1-continued
| Number | Structure | Compound Name | IL-2 inhibition Jurkat/PHA/ 1% FBS IC50 (nM) |
|---|---|---|---|
| 40. | 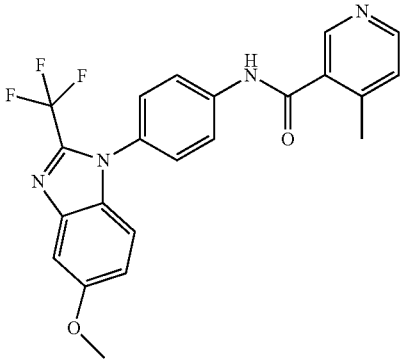 [SMILES: COc1ccc2c(c1)nc(C(F)(F)F)n2-c1ccc(NC(=O)c2cnccc2C)cc1] | N-(4-(5-methoxy-2-(trifluoromethyl)-1H-benzo[d]imidazol-1-yl)phenyl)-4-methylnicotinamide | 77 |
| 41. | 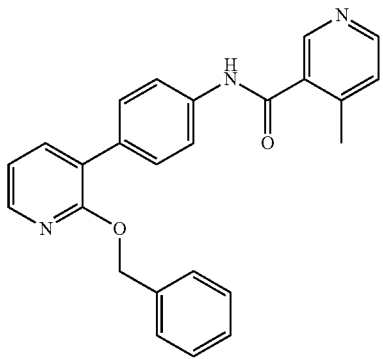 [SMILES: Cc1ccncc1C(=O)Nc1ccc(-c2cccnc2OCc2ccccc2)cc1] | N-(4-(2-(benzyloxy)pyridin-3-yl)phenyl)-4-methylnicotinamide | 1000 |
| 42. | 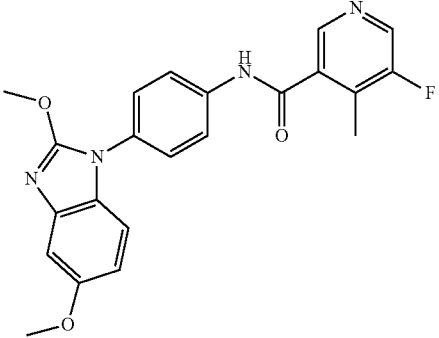 [SMILES: COc1ccc2c(c1)nc(OC)n2-c1ccc(NC(=O)c2cncc(F)c2C)cc1] | N-(4-(2,5-dimethoxy-1H-benzo[d]imidazol-1-yl)phenyl)-5-fluoro-4-methylnicotinamide | 81 |
| 43. | 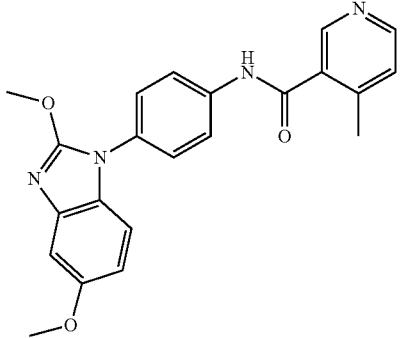 [SMILES: COc1ccc2c(c1)nc(OC)n2-c1ccc(NC(=O)c2cnccc2C)cc1] | N-(4-(2,5-dimethoxy-1H-benzo[d]imidazol-1-yl)phenyl)-4-methylnicotinamide | 352 |

TABLE 1-continued

| Number | Structure | Compound Name | IL-2 inhibition Jurkat/PHA/ 1% FBS IC50 (nM) |
|---|---|---|---|
| 44. | 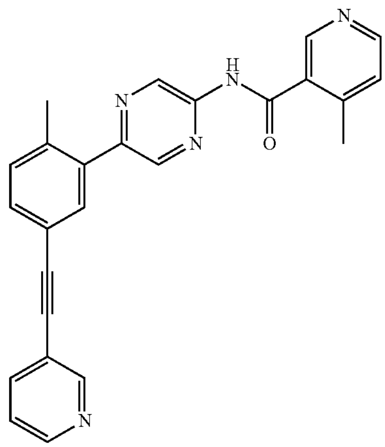 [SMILES: Cc1ccncc1C(=O)Nc1cnc(-c2cc(C#Cc3cccnc3)ccc2C)cn1] | 4-methyl-N-(5-(2-methyl-5-(pyridin-3-ylethynyl)phenyl)pyrazin-2-yl)nicotinamide | 140 |
| 45 | 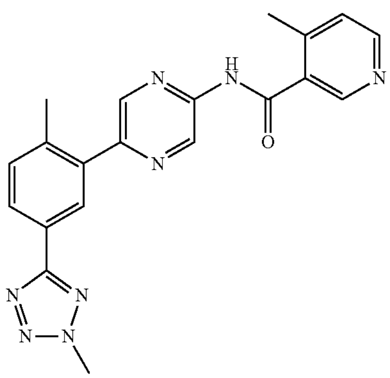 | 4-methyl-N-(5-(2-methyl-5-(2-methyl-2H-tetrazol-5-yl)phenyl)pyrazin-2-yl)nicotinamide | 80 |
| 46. | 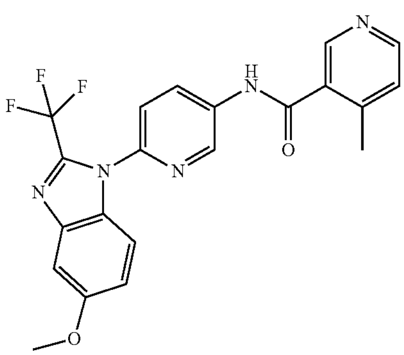 [SMILES: COc1ccc2c(c1)nc(C(F)(F)F)n2-c1ccc(NC(=O)c2cnccc2C)cn1] | N-(6-(5-methoxy-2-(trifluoromethyl)-1H-benzo[d]imidazol-1-yl)pyridin-3-yl)-4-methylnicotinamide | 156 |
| 47. | 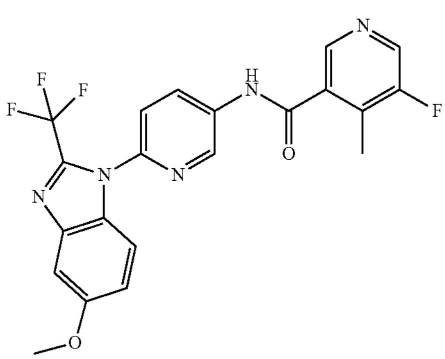 [SMILES: COc1ccc2c(c1)nc(C(F)(F)F)n2-c1ccc(NC(=O)c2cncc(F)c2C)cn1] | 5-fluoro-N-(6-(5-methoxy-2-(trifluoromethyl)-1H-benzo[d]imidazol-1-yl)pyridin-3-yl)-4-methylnicotinamide | 116 |

TABLE 1-continued

| Number | Structure | Compound Name | IL-2 inhibition Jurkat/PHA/ 1% FBS IC50 (nM) |
|---|---|---|---|
| 48. | 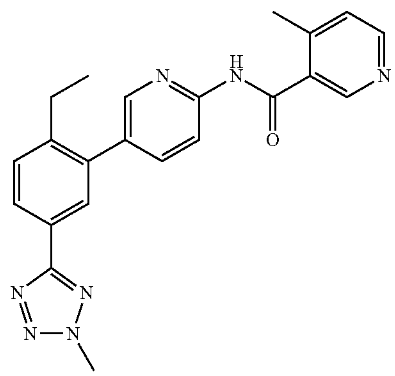 | N-(5-(2-ethyl-5-(2-methyl-2H-tetrazol-5-yl)phenyl)pyridin-2-yl)-4-methylnicotinamide | 22 |
| 49. | 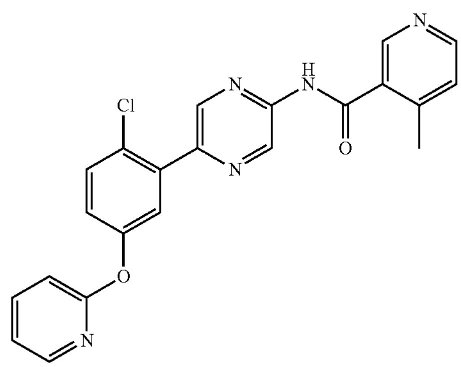 [SMILES: Cc1ccncc1C(=O)Nc1cnc(-c2cc(Oc3ccccn3)ccc2Cl)cn1] | N-(5-(2-chloro-5-(pyridin-2-yloxy)phenyl)pyrazin-2-yl)-4-methylnicotinamide | 45 |
| 50. | 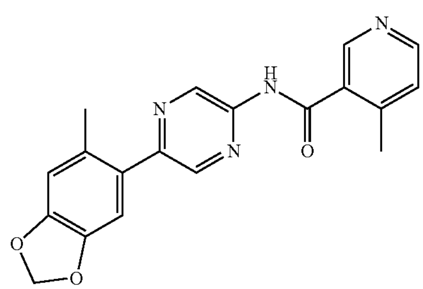 [SMILES: Cc1ccncc1C(=O)Nc1cnc(-c2cc3c(cc2C)OCO3)cn1] | 4-methyl-N-(5-(6-methylbenzo[d][1,3]dioxol-5-yl)pyrazin-2-yl)nicotinamide | 205 |
| 51. | 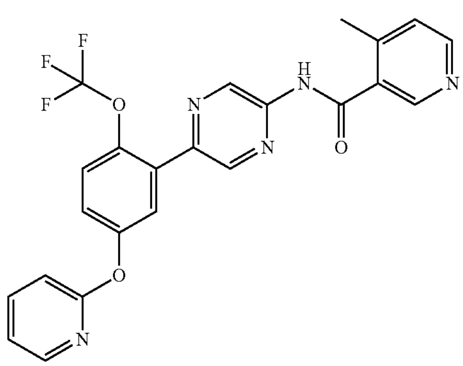 [SMILES: Cc1ccncc1C(=O)Nc1cnc(-c2cc(Oc3ccccn3)ccc2OC(F)(F)F)cn1] | 4-methyl-N-(5-(5-(pyridin-2-yloxy)-2-(trifluoromethoxy)phenyl)pyrazin-2-yl)nicotinamide | 50 |

TABLE 1-continued

| Number | Structure | Compound Name | IL-2 inhibition Jurkat/PHA/ 1% FBS IC50 (nM) |
|---|---|---|---|
| 52. | 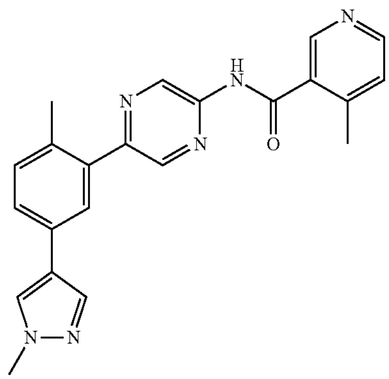 | 4-methyl-N-(5-(2-methyl-5-(1-methyl-1H-pyrazol-4-yl)phenyl)pyrazin-2-yl)nicotinamide | 44 |
| 53. | 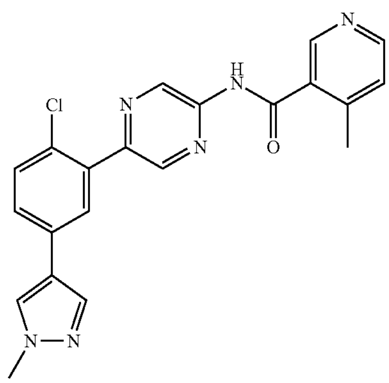 | N-(5-(2-chloro-5-(1-methyl-1H-pyrazol-4-yl)phenyl)pyrazin-2-yl)-4-methylnicotinamide | 38 |
| 54. | 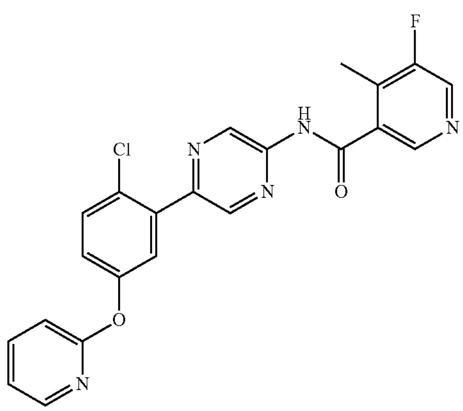 [SMILES: Cc1c(F)cncc1C(=O)Nc1cnc(-c2cc(Oc3ccccn3)ccc2Cl)cn1] | N-(5-(2-chloro-5-(pyridin-2-yloxy)phenyl)pyrazin-2-yl)-5-fluoro-4-methylnicotinamide | 43 |
| 55. | 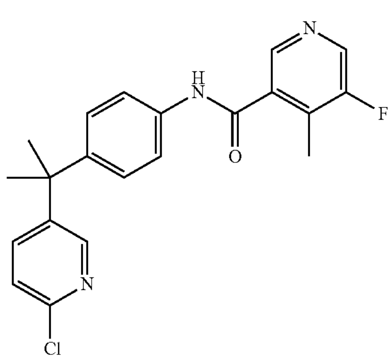 [SMILES: Cc1c(F)cncc1C(=O)Nc1ccc(C(C)(C)c2ccc(Cl)nc2)cc1] | N-(4-(2-(6-chloropyridin-3-yl)propan-2-yl)phenyl)-5-fluoro-4-methylnicotinamide | 1000 |

TABLE 1-continued

| Number | Structure | Compound Name | IL-2 inhibition Jurkat/PHA/ 1% FBS IC50 (nM) |
|---|---|---|---|
| 56. | 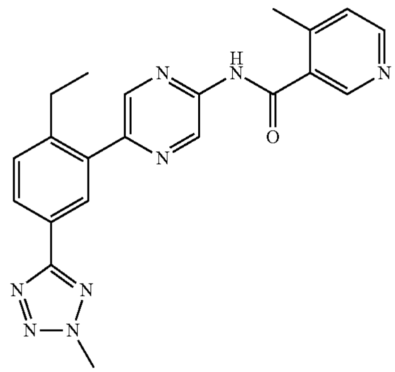 | N-(5-(2-ethyl-5-(2-methyl-2H-tetrazol-5-yl)phenyl)pyrazin-2-yl)-4-methylnicotinamide | 33 |
| 57. | 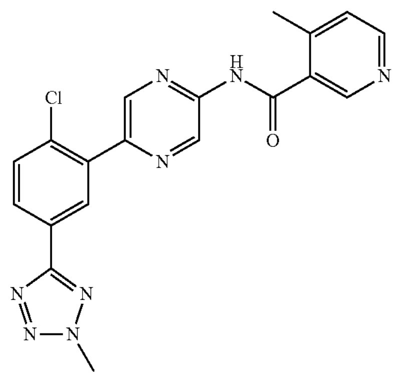 | N-(5-(2-chloro-5-(2-methyl-2H-tetrazol-5-yl)phenyl)pyrazin-2-yl)-4-methylnicotinamide | 28 |
| 58. | 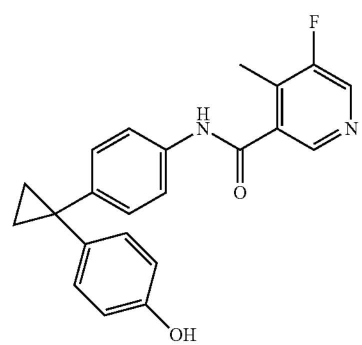 [SMILES: Cc1c(F)cncc1C(=O)Nc1ccc(C2(c3ccc(O)cc3)CC2)cc1] | 5-fluoro-N-(4-(1-(4-hydroxyphenyl)cyclopropyl)phenyl)-4-methylnicotinamide | 1000 |
| 59. | 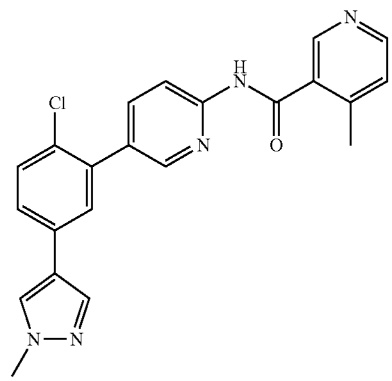 | N-(5-(2-chloro-5-(1-methyl-1H-pyrazol-4-yl)phenyl)pyridin-2-yl)-4-methylnicotinamide | 77 |

TABLE 1-continued

| Number | Structure | Compound Name | IL-2 inhibition Jurkat/PHA/ 1% FBS IC50 (nM) |
|---|---|---|---|
| 60. | 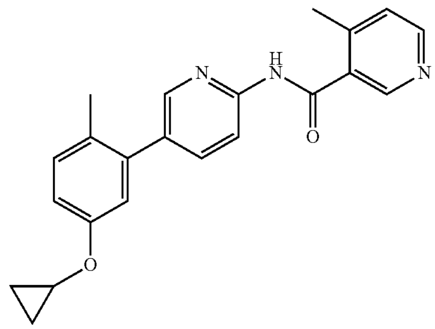 [SMILES: Cc1ccncc1C(=O)Nc1ccc(-c2cc(OC3CC3)ccc2C)cn1] | N-(5-(5-cyclopropoxy-2-methylphenyl)pyridin-2-yl)-4-methylnicotinamide | 132 |
| 61. | 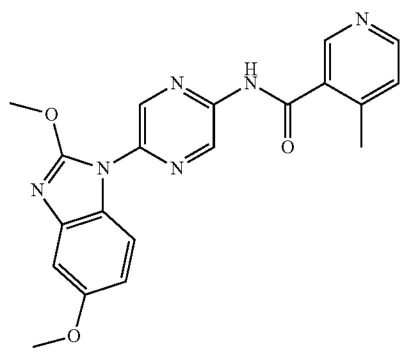 [SMILES: COc1ccc2c(c1)nc(OC)n2-c1cnc(NC(=O)c2cnccc2C)cn1] | N-(5-(2,5-dimethoxy-1H-benzo[d]imidazol-1-yl)pyrazin-2-yl)-4-methylnicotinamide | 113 |
| 62. | 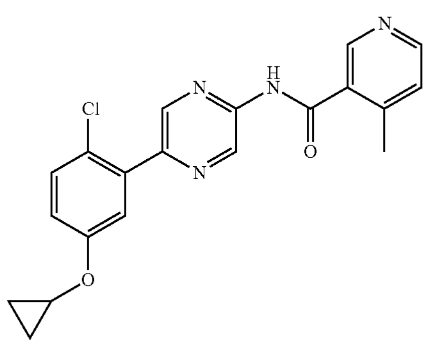 [SMILES: Cc1ccncc1C(=O)Nc1cnc(-c2cc(OC3CC3)ccc2Cl)cn1] | N-(5-(2-chloro-5-cyclopropoxyphenyl)pyrazin-2-yl)-4-methylnicotinamide | 14 |
| 63. | 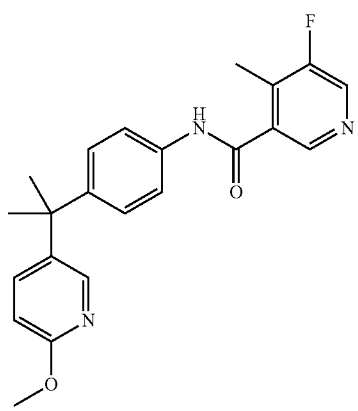 [SMILES: COc1ccc(C(C)(C)c2ccc(NC(=O)c3cncc(F)c3C)cc2)cn1] | 5-fluoro-N-(4-(2-(6-methoxypyridin-3-yl)propan-2-yl)phenyl)-4-methylnicotinamide | 1000 |

TABLE 1-continued

| Number | Structure | Compound Name | IL-2 inhibition Jurkat/PHA/ 1% FBS IC50 (nM) |
|---|---|---|---|
| 64. | 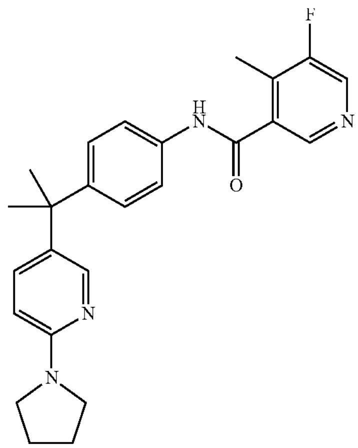 [SMILES: Cc1c(F)cncc1C(=O)Nc1ccc(C(C)(C)c2ccc(N3CCCC3)nc2)cc1] | 5-fluoro-4-methyl-N-(4-(2-(6-(pyrrolidin-1-yl)pyridin-3-yl)propan-2-yl)phenyl)nicotinamide | 1000 |
| 65. | 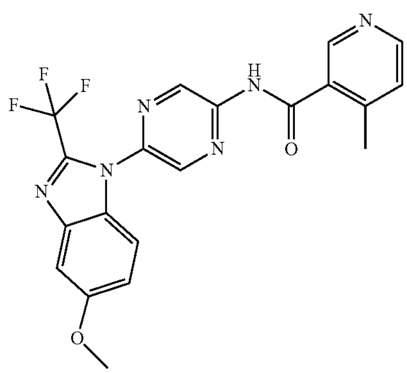 [SMILES: COc1ccc2c(c1)nc(C(F)(F)F)n2-c1cnc(NC(=O)c2cnccc2C)cn1] | N-(5-(5-methoxy-2-(trifluoromethyl)-1H-benzo[d]imidazol-1-yl)pyrazin-2-yl)-4-methylnicotinamide | 93 |
| 66. | 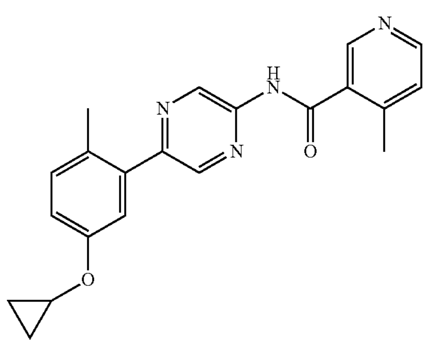 [SMILES: Cc1ccncc1C(=O)Nc1cnc(-c2cc(OC3CC3)ccc2C)cn1] | N-(5-(5-cyclopropoxy-2-methylphenyl)pyrazin-2-yl)-4-methylnicotinamide | 91 |
| 67. | 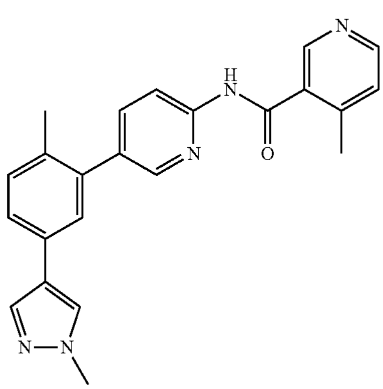 | 4-methyl-N-(5-(2-methyl-5-(1-methyl-1H-pyrazol-4-yl)phenyl)pyridin-2-yl)nicotinamide | 77 |

TABLE 1-continued

| Number | Structure | Compound Name | IL-2 inhibition Jurkat/PHA/ 1% FBS IC50 (nM) |
|---|---|---|---|
| 68. | 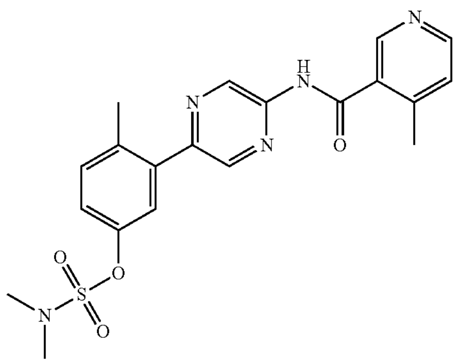 [SMILES: Cc1ccncc1C(=O)Nc1cnc(-c2cc(OS(=O)(=O)N(C)C)ccc2C)cn1] | 4-methyl-3-(5-(4-methylnicotinamido)pyrazin-2-yl)phenyl dimethylsulfamate | 84 |
| 69. | 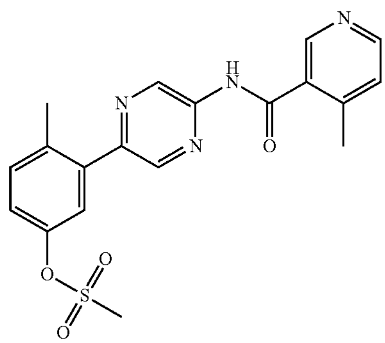 [SMILES: Cc1ccncc1C(=O)Nc1cnc(-c2cc(OS(C)(=O)=O)ccc2C)cn1] | 4-methyl-3-(5-(4-methylnicotinamido)pyrazin-2-yl)phenyl methanesulfonate | 264 |
| 70. | 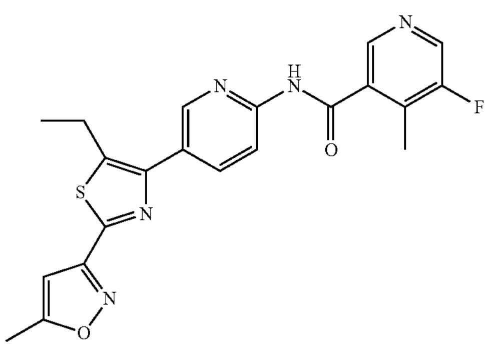 | N-(5-(5-ethyl-2-(5-methylisoxazol-3-yl)thiazol-4-yl)pyridin-2-yl)-5-fluoro-4-methylnicotinamide | 11 |
| 71. | 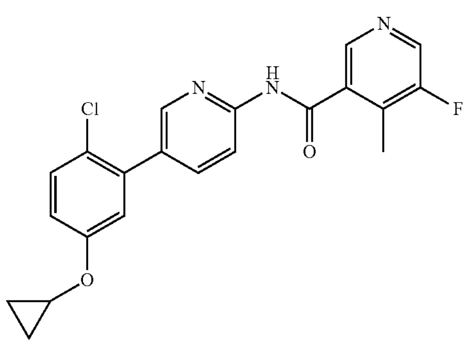 [SMILES: Cc1c(F)cncc1C(=O)Nc1ccc(-c2cc(OC3CC3)ccc2Cl)cn1] | N-(5-(2-chloro-5-cyclopropoxyphenyl)pyridin-2-yl)-5-fluoro-4-methylnicotinamide | 10 |

TABLE 1-continued

| Number | Structure | Compound Name | IL-2 inhibition Jurkat/PHA/ 1% FBS IC50 (nM) |
|---|---|---|---|
| 72. | 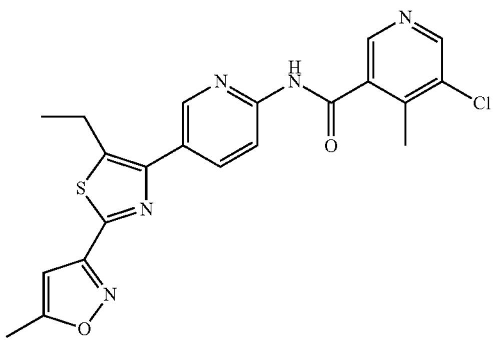 [SMILES: CCc1sc(-c2cc(C)on2)nc1-c1ccc(NC(=O)c2cncc(Cl)c2C)nc1] | 5-chloro-N-(5-(5-ethyl-2-(5-methylisoxazol-3-yl)thiazol-4-yl)pyridin-2-yl)-4-methylnicotinamide | 10 |
| 73. | 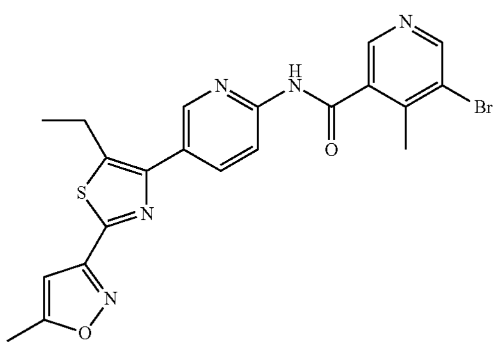 [SMILES: CCc1sc(-c2cc(C)on2)nc1-c1ccc(NC(=O)c2cncc(Br)c2C)nc1] | 5-bromo-N-(5-(5-ethyl-2-(5-methylisoxazol-3-yl)thiazol-4-yl)pyridin-2-yl)-4-methylnicotinamide | 9 |
| 74. | 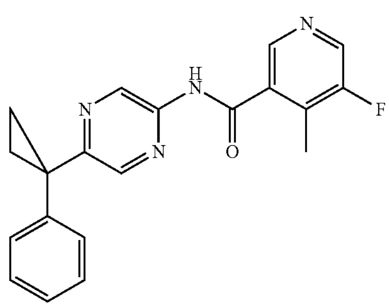 [SMILES: Cc1c(F)cncc1C(=O)Nc1cnc(C2(c3ccccc3)CC2)cn1] | 5-fluoro-4-methyl-N-(5-(1-phenylcyclopropyl)pyrazin-2-yl)nicotinamide | 1000 |
| 75. | 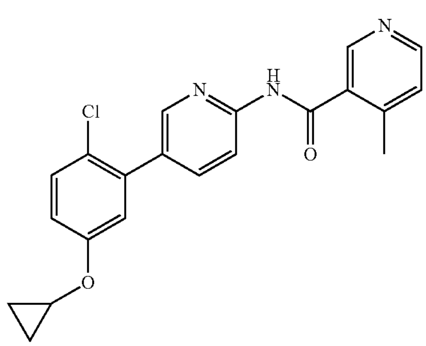 | N-(5-(2-chloro-5-cyclopropoxyphenyl)pyridin-2-yl)-4-methylnicotinamide | 9 |

TABLE 1-continued

| Number | Structure | Compound Name | IL-2 inhibition Jurkat/PHA/ 1% FBS IC50 (nM) |
|---|---|---|---|
| 76. | 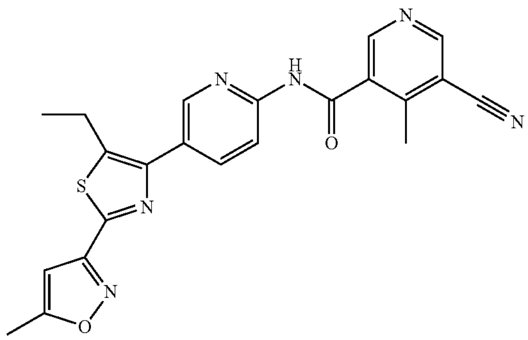 [SMILES: CCc1sc(-c2cc(C)on2)nc1-c1ccc(NC(=O)c2cncc(C#N)c2C)nc1] | 5-cyano-N-(5-(5-ethyl-2-(5-methylisoxazol-3-yl)thiazol-4-yl)pyridin-2-yl)-4-methylnicotinamide | 13 |
| 77. | 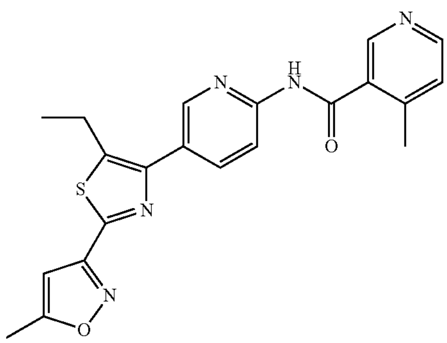 [SMILES: CCc1sc(-c2cc(C)on2)nc1-c1ccc(NC(=O)c2cnccc2C)nc1] | N-(5-(5-ethyl-2-(5-methylisoxazol-3-yl)thiazol-4-yl)pyridin-2-yl)-4-methylnicotinamide | 11 |
| 78. | 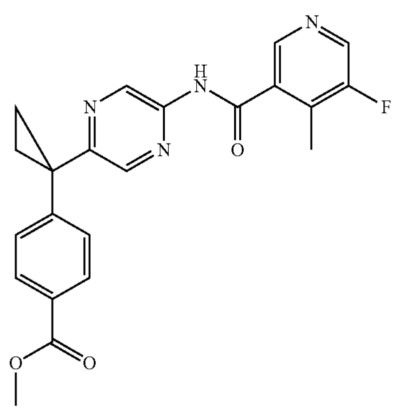 [SMILES: COC(=O)c1ccc(C2(c3cnc(NC(=O)c4cncc(F)c4C)cn3)CC2)cc1] | methyl 4-(1-(5-(5-fluoro-4-methylnicotinamido)pyrazin-2-yl)cyclopropyl)benzoate | 78 |
| 79. | 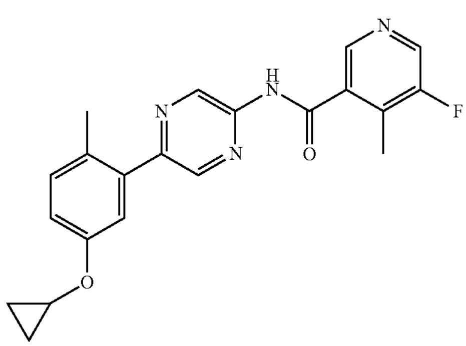 [SMILES: Cc1ccc(OC2CC2)cc1-c1cnc(NC(=O)c2cncc(F)c2C)cn1] | N-(5-(5-cyclopropoxy-2-methylphenyl)pyrazin-2-yl)-5-fluoro-4-methylnicotinamide | 48 |

TABLE 1-continued

| Number | Structure | Compound Name | IL-2 inhibition Jurkat/PHA/ 1% FBS IC50 (nM) |
|---|---|---|---|
| 80. | 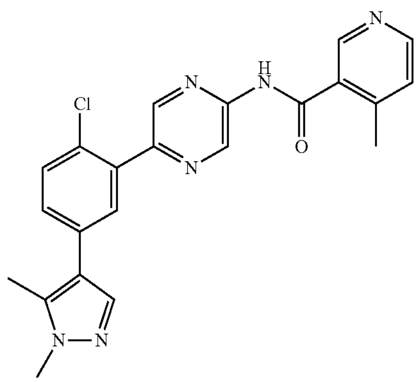 [SMILES: Cc1ccncc1C(=O)Nc1cnc(-c2cc(-c3cnn(C)c3C)ccc2Cl)cn1] | N-(5-(2-chloro-5-(1,5-dimethyl-1H-pyrazol-4-yl)phenyl)pyrazin-2-yl)-4-methylnicotinamide | 26 |
| 81. | 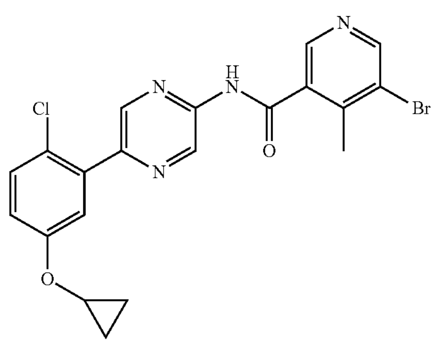 [SMILES: Cc1c(Br)cncc1C(=O)Nc1cnc(-c2cc(OC3CC3)ccc2Cl)cn1] | 5-bromo-N-(5-(2-chloro-5-cyclopropoxyphenyl)pyrazin-2-yl)-4-methylnicotinamide | 11 |
| 82. | 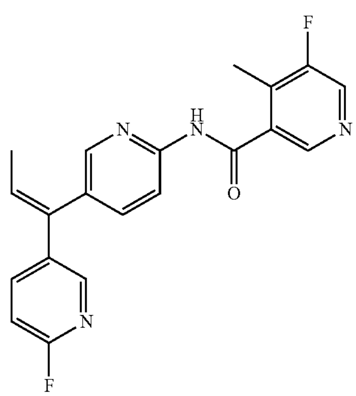 [SMILES: C/C=C(/c1ccc(F)nc1)c1ccc(NC(=O)c2cncc(F)c2C)nc1] | (E)-5-fluoro-N-(5-(1-(6-fluoropyridin-3-yl)prop-1-en-1-yl)pyridin-2-yl)-4-methylnicotinamide | 277 |
| 83. | 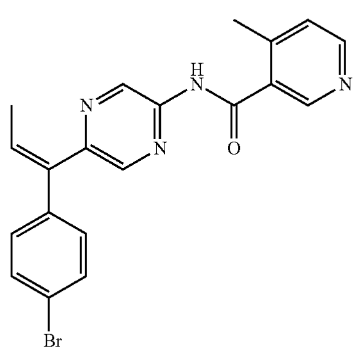 [SMILES: C/C=C(/c1ccc(Br)cc1)c1cnc(NC(=O)c2cnccc2C)cn1] | (Z)-N-(5-(1-(4-bromophenyl)prop-1-en-1-yl)pyrazin-2-yl)-4-methylnicotinamide | 20 |

TABLE 1-continued

| Number | Structure | Compound Name | IL-2 inhibition Jurkat/PHA/ 1% FBS IC50 (nM) |
|---|---|---|---|
| 84. | 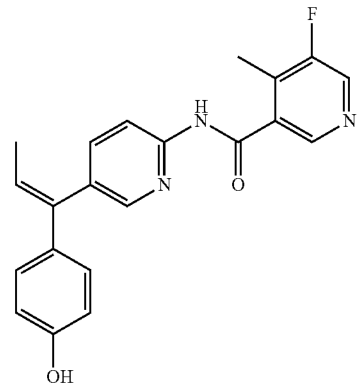 [SMILES: C/C=C(/c1ccc(O)cc1)c1ccc(NC(=O)c2cncc(F)c2C)nc1] | (Z)-5-fluoro-N-(5-(1-(4-hydroxyphenyl)prop-1-en-1-yl)pyridin-2-yl)-4-methylnicotinamide | 173 |
| 85. | 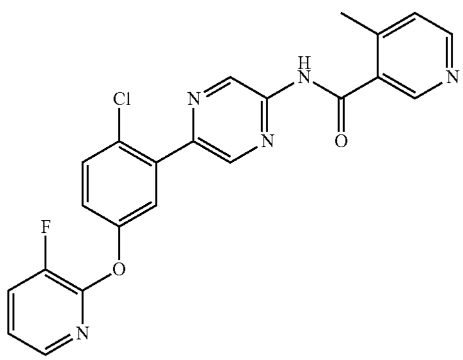 [SMILES: Cc1ccncc1C(=O)Nc1cnc(-c2cc(Oc3ncccc3F)ccc2Cl)cn1] | N-(5-(2-chloro-5-((3-fluoropyridin-2-yl)oxy)phenyl)pyrazin-2-yl)-4-methylnicotinamide | |
| 86. | 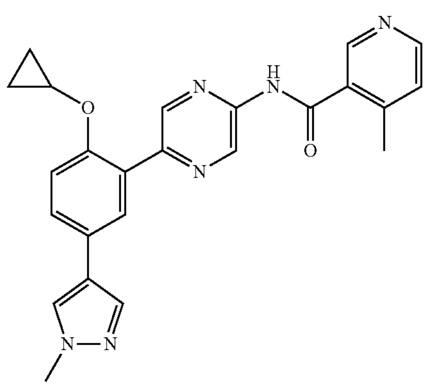 [SMILES: Cc1ccncc1C(=O)Nc1cnc(-c2cc(-c3cnn(C)c3)ccc2OC2CC2)cn1] | N-(5-(2-cyclopropoxy-5-(1-methyl-1H-pyrazol-4-yl)phenyl)pyrazin-2-yl)-4-methylnicotinamide | 61 |
| 87. | 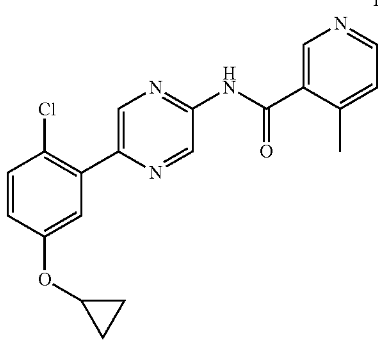 | N-(5-(2-chloro-5-cyclopropoxyphenyl)pyrazin-2-yl)-4-methylnicotinamide hydrochloride | 12 |

TABLE 1-continued

| Number | Structure | Compound Name | IL-2 inhibition Jurkat/PHA/ 1% FBS IC50 (nM) |
|---|---|---|---|
| 88. | 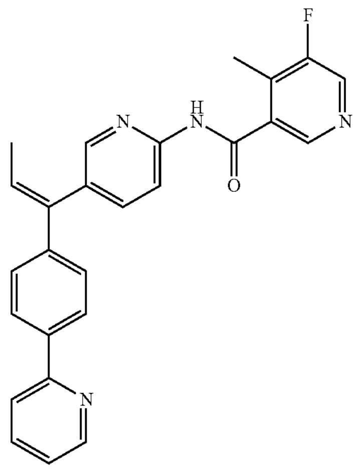 [SMILES: C/C=C(/c1ccc(-c2ccccn2)cc1)c1ccc(NC(=O)c2cncc(F)c2C)nc1] | (Z)-5-fluoro-4-methyl-N-(5-(1-(4-(pyridin-2-yl)phenyl)prop-1-en-1-yl)pyridin-2-yl)nicotinamide | 65 |
| 89. | 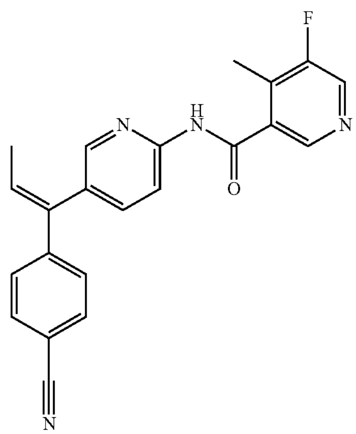 [SMILES: C/C=C(/c1ccc(C#N)cc1)c1ccc(NC(=O)c2cncc(F)c2C)nc1] | (Z)-N-(5-(1-(4-cyanophenyl)prop-1-en-1-yl)pyridin-2-yl)-5-fluoro-4-methylnicotinamide | 113 |
| 90. | 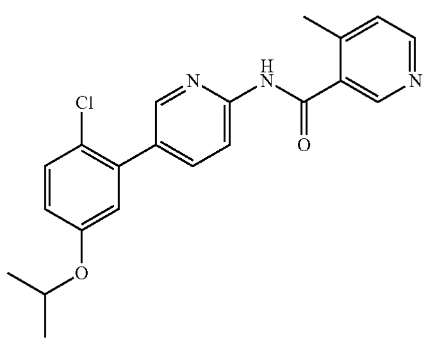 [SMILES: Cc1ccncc1C(=O)Nc1ccc(-c2cc(OC(C)C)ccc2Cl)cn1] | N-(5-(2-chloro-5-isopropoxyphenyl)pyridin-2-yl)-4-methylnicotinamide | 13 |
| 91. | 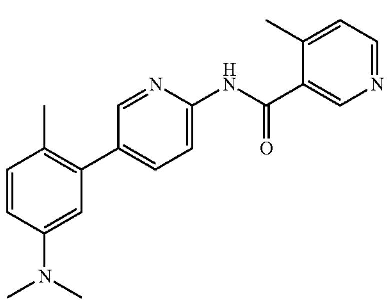 [SMILES: Cc1ccncc1C(=O)Nc1ccc(-c2cc(N(C)C)ccc2C)cn1] | N-(5-(5-(dimethylamino)-2-methylphenyl)pyridin-2-yl)-4-methylnicotinamide | 91 |

TABLE 1-continued

| Number | Structure | Compound Name | IL-2 inhibition Jurkat/PHA/ 1% FBS IC50 (nM) |
|---|---|---|---|
| 92. | 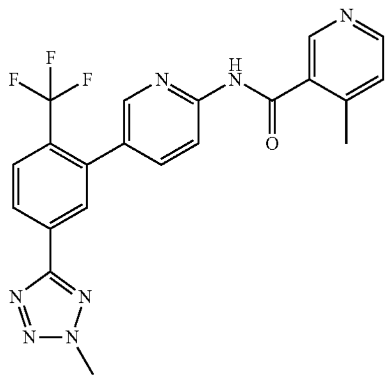 [SMILES: Cc1ccncc1C(=O)Nc1ccc(-c2cc(-c3nnn(C)n3)ccc2C(F)(F)F)cn1] | 4-methyl-N-(5-(5-(2-methyl-2H-tetrazol-5-yl)-2-(trifluoromethyl)phenyl)pyridin-2-yl)nicotinamide | 40 |
| 93. | 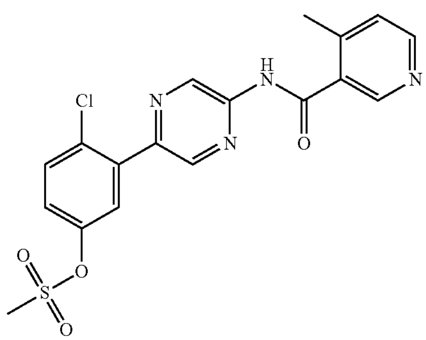 [SMILES: Cc1ccncc1C(=O)Nc1cnc(-c2cc(OS(C)(=O)=O)ccc2Cl)cn1] | 4-chloro-3-(5-(4-methylnicotinamido)pyrazin-2-yl)phenyl methanesulfonate | 57 |
| 94. | 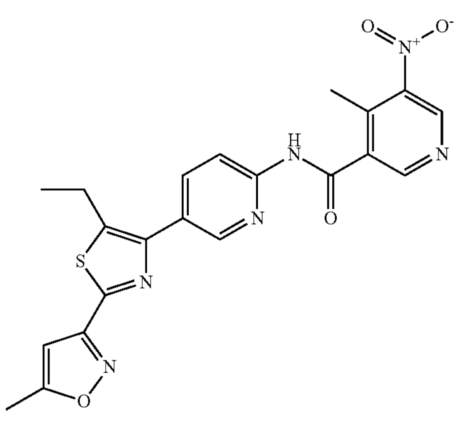 [SMILES: CCc1sc(-c2cc(C)on2)nc1-c1ccc(NC(=O)c2cncc([N+](=O)[O-])c2C)nc1] | N-(5-(5-ethyl-2-(5-methylisoxazol-3-yl)thiazol-4-yl)pyridin-2-yl)-4-methyl-5-nitronicotinamide | 18 |

TABLE 1-continued

| Number | Structure | Compound Name | IL-2 inhibition Jurkat/PHA/ 1% FBS IC50 (nM) |
|---|---|---|---|
| 95. | 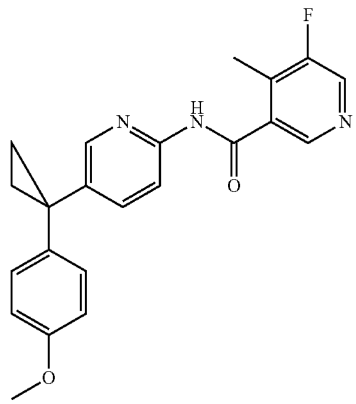 [SMILES: COc1ccc(C2(c3ccc(NC(=O)c4cncc(F)c4C)nc3)CC2)cc1] | 5-fluoro-N-(5-(1-(4-methoxyphenyl)cyclopropyl)pyrazin-2-yl)-4-methylnicotinamide | 274 |
| 96. | 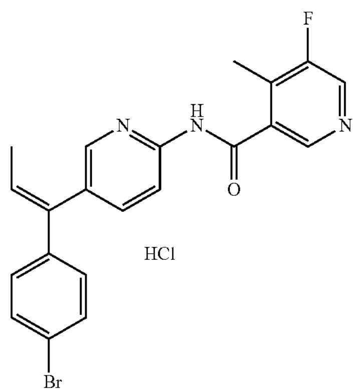 [SMILES: C/C=C(/c1ccc(Br)cc1)c1ccc(NC(=O)c2cncc(F)c2C)nc1 ; Cl] | (Z)-N-(5-(1-(4-bromophenyl)prop-1-en-1-yl)pyridin-2-yl)-5-fluoro-4-methylnicotinamide hydrochloride | 105 |
| 97. | 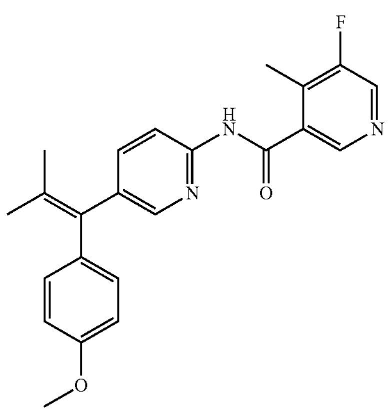 [SMILES: COc1ccc(C(=C(C)C)c2ccc(NC(=O)c3cncc(F)c3C)nc2)cc1] | 5-fluoro-N-(5-(1-(4-methoxyphenyl)-2-methylprop-1-en-1-yl)pyridin-2-yl)-4-methylnicotinamide | 51 |
| 98. | 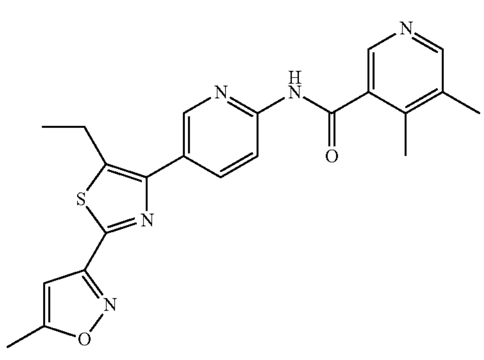 | N-(5-(5-ethyl-2-(5-methylisoxazol-3-yl)thiazol-4-yl)pyridin-2-yl)-4,5-dimethylnicotinamide | 8 |

TABLE 1-continued

| Number | Structure | Compound Name | IL-2 inhibition Jurkat/PHA/ 1% FBS IC50 (nM) |
|---|---|---|---|
| 99. | 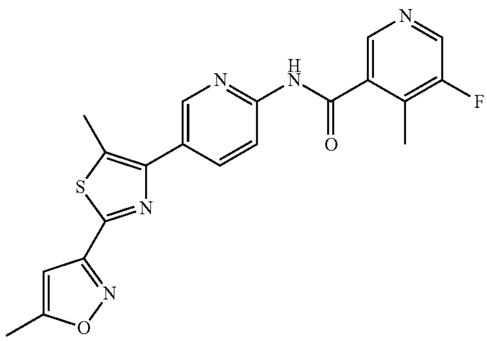 [SMILES: Cc1cc(-c2nc(-c3ccc(NC(=O)c4cncc(F)c4C)nc3)c(C)s2)no1] | 5-fluoro-4-methyl-N-(5-(5-methyl-2-(5-methylisoxazol-3-yl)thiazol-4-yl)pyridin-2-yl)nicotinamide | 11 |
| 100. | 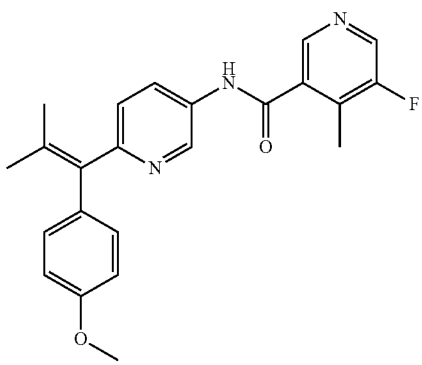 [SMILES: COc1ccc(C(=C(C)C)c2ccc(NC(=O)c3cncc(F)c3C)cn2)cc1] | 5-fluoro-N-(6-(1-(4-methoxyphenyl)-2-methylprop-1-en-1-yl)pyridin-3-yl)-4-methylnicotinamide | 1000 |
| 101. | 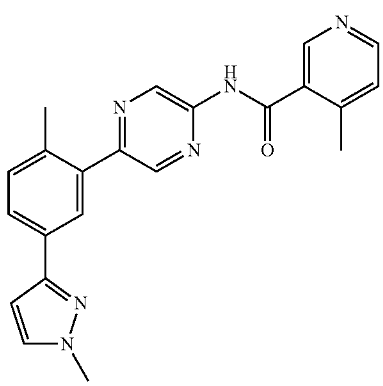 [SMILES: Cc1ccncc1C(=O)Nc1cnc(-c2cc(-c3ccn(C)n3)ccc2C)cn1] | 4-methyl-N-(5-(2-methyl-5-(1-methyl-1H-pyrazol-3-yl)phenyl)pyrazin-2-yl)nicotinamide | 127 |
| 102. | 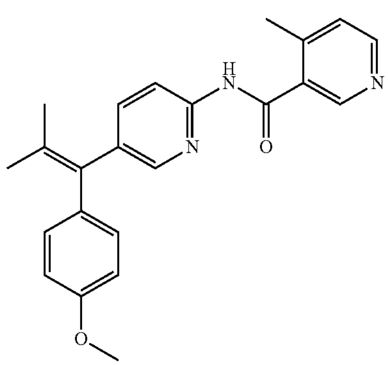 [SMILES: COc1ccc(C(=C(C)C)c2ccc(NC(=O)c3cnccc3C)nc2)cc1] | N-(5-(1-(4-methoxyphenyl)-2-methylprop-1-en-1-yl)pyridin-2-yl)-4-methylnicotinamide | 116 |

TABLE 1-continued

| Number | Structure | Compound Name | IL-2 inhibition Jurkat/PHA/ 1% FBS IC50 (nM) |
|---|---|---|---|
| 103. | 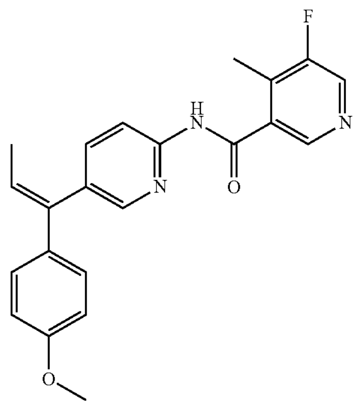 [SMILES: C/C=C(/c1ccc(OC)cc1)c1ccc(NC(=O)c2cncc(F)c2C)nc1] | (Z)-5-fluoro-N-(5-(1-(4-methoxyphenyl)prop-1-en-1-yl)pyridin-2-yl)-4-methylnicotinamide | 16 |
| 104. | 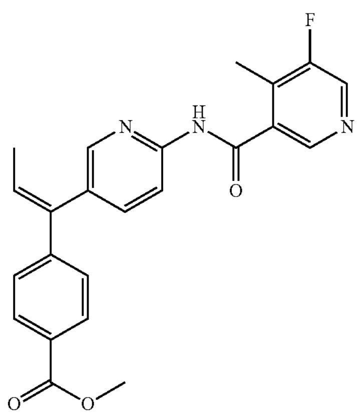 [SMILES: C/C=C(/c1ccc(C(=O)OC)cc1)c1ccc(NC(=O)c2cncc(F)c2C)nc1] | (Z)-methyl 4-(1-(6-(5-fluoro-4-methylnicotinamido)pyridin-3-yl)prop-1-en-1-yl)benzoate | 18 |
| 105. | 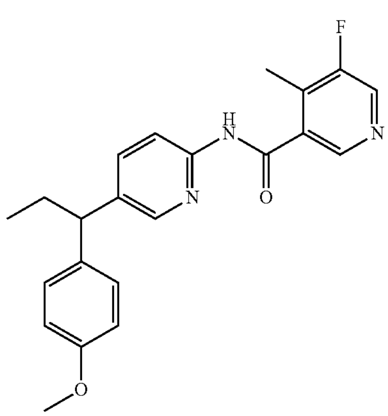 [SMILES: CCC(c1ccc(OC)cc1)c1ccc(NC(=O)c2cncc(F)c2C)nc1] | 5-fluoro-N-(5-(1-(4-methoxyphenyl)propyl)pyridin-2-yl)-4-methylnicotinamide | 1000 |

TABLE 1-continued

| Number | Structure | Compound Name | IL-2 inhibition Jurkat/PHA/ 1% FBS IC50 (nM) |
|---|---|---|---|
| 106. | 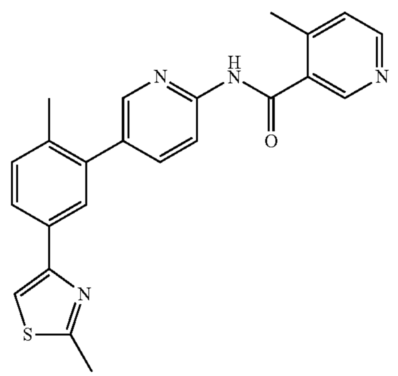 | 4-methyl-N-(5-(2-methyl-5-(2-methylthiazol-4-yl)phenyl)pyridin-2-yl)nicotinamide | |
| 107. | 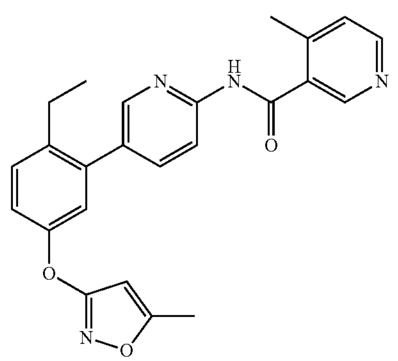 [SMILES: CCc1ccc(Oc2cc(C)on2)cc1-c1ccc(NC(=O)c2cnccc2C)nc1] | N-(5-(2-ethyl-5-((5-methylisoxazol-3-yl)oxy)phenyl)pyridin-2-yl)-4-methylnicotinamide | |
| 108. | 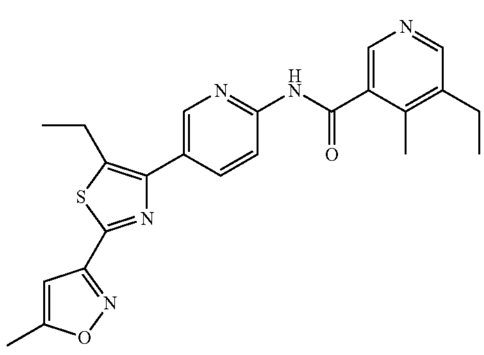 [SMILES: CCc1cncc(C(=O)Nc2ccc(-c3nc(-c4cc(C)on4)sc3CC)cn2)c1C] | 5-ethyl-N-(5-(5-ethyl-2-(5-methylisoxazol-3-yl)thiazol-4-yl)pyridin-2-yl)-4-methylnicotinamide | 8 |
| 109. | 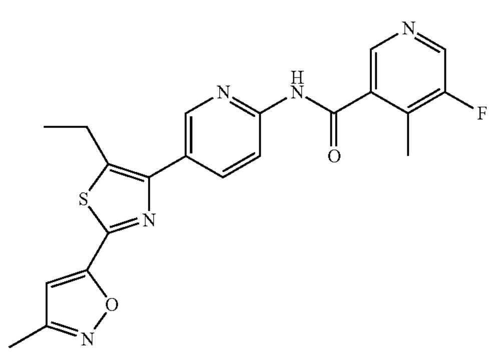 [SMILES: CCc1sc(-c2cc(C)no2)nc1-c1ccc(NC(=O)c2cncc(F)c2C)nc1] | N-(5-(5-ethyl-2-(3-methylisoxazol-5-yl)thiazol-4-yl)pyridin-2-yl)-5-fluoro-4-methylnicotinamide | 10 |

TABLE 1-continued

| Number | Structure | Compound Name | IL-2 inhibition Jurkat/PHA/ 1% FBS IC50 (nM) |
|---|---|---|---|
| 110. | 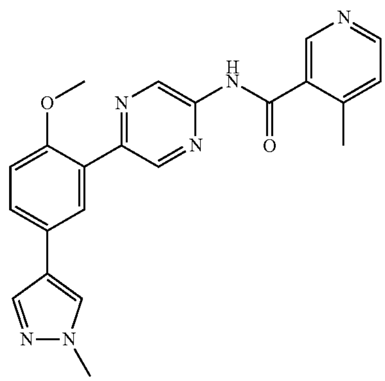 [SMILES: COc1ccc(-c2cnn(C)c2)cc1-c1cnc(NC(=O)c2cnccc2C)cn1] | N-(5-(2-methoxy-5-(1-methyl-1H-pyrazol-4-yl)phenyl)pyrazin-2-yl)-4-methylnicotinamide | 116 |
| 111. | 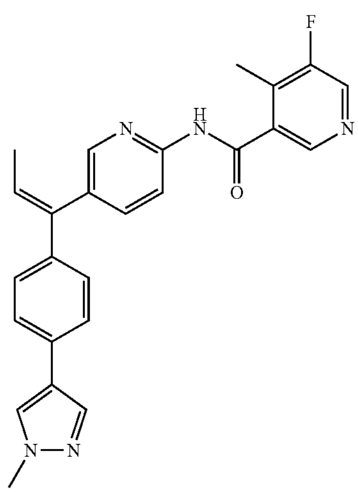 [SMILES: C/C=C(/c1ccc(-c2cnn(C)c2)cc1)c1ccc(NC(=O)c2cncc(F)c2C)nc1] | (Z)-5-fluoro-4-methyl-N-(5-(1-(4-(1-methyl-1H-pyrazol-4-yl)phenyl)prop-1-en-1-yl)pyridin-2-yl)nicotinamide | 876 |
| 112. | 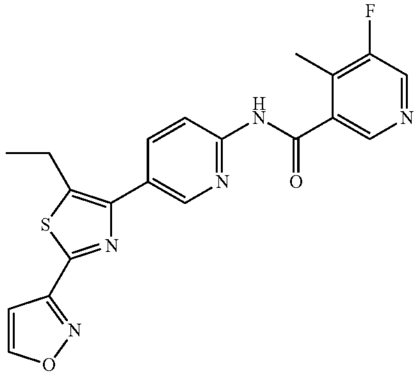 [SMILES: CCc1sc(-c2ccon2)nc1-c1ccc(NC(=O)c2cncc(F)c2C)nc1] | N-(5-(5-ethyl-2-(isoxazol-3-yl)thiazol-4-yl)pyridin-2-yl)-5-fluoro-4-methylnicotinamide | 10 |

TABLE 1-continued

| Number | Structure | Compound Name | IL-2 inhibition Jurkat/PHA/ 1% FBS IC50 (nM) |
|---|---|---|---|
| 113. | 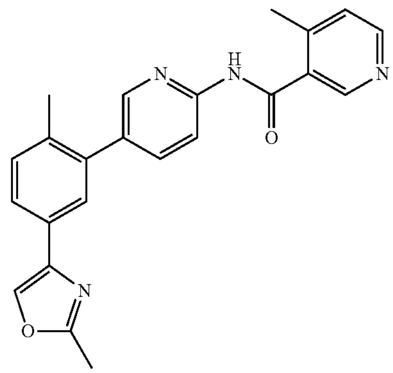 [SMILES: Cc1nc(-c2ccc(C)c(-c3ccc(NC(=O)c4cnccc4C)nc3)c2)co1] | 4-methyl-N-(5-(2-methyl-5-(2-methyloxazol-4-yl)phenyl)pyridin-2-yl)nicotinamide | 45 |
| 114. | 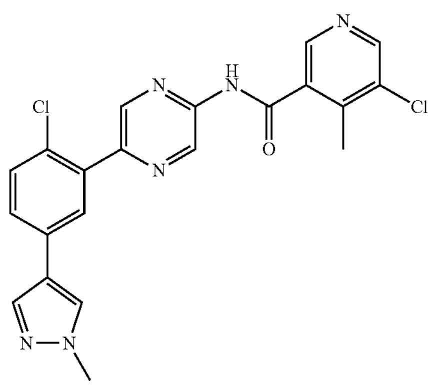 [SMILES: Cc1c(Cl)cncc1C(=O)Nc1cnc(-c2cc(-c3cnn(C)c3)ccc2Cl)cn1] | 5-chloro-N-(5-(2-chloro-5-(1-methyl-1H-pyrazol-4-yl)phenyl)pyrazin-2-yl)-4-methylnicotinamide | 11 |
| 115. | 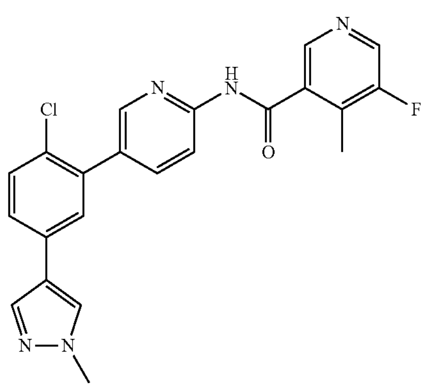 [SMILES: Cc1c(F)cncc1C(=O)Nc1ccc(-c2cc(-c3cnn(C)c3)ccc2Cl)cn1] | N-(5-(2-chloro-5-(1-methyl-1H-pyrazol-4-yl)phenyl)pyridin-2-yl)-5-fluoro-4-methylnicotinamide | 14 |
| 116. | 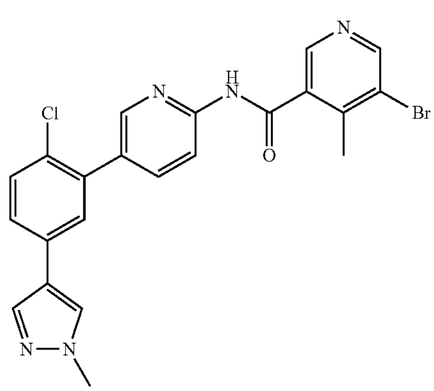 [SMILES: Cc1c(Br)cncc1C(=O)Nc1ccc(-c2cc(-c3cnn(C)c3)ccc2Cl)cn1] | 5-bromo-N-(5-(2-chloro-5-(1-methyl-1H-pyrazol-4-yl)phenyl)pyridin-2-yl)-4-methylnicotinamide | 14 |

TABLE 1-continued

| Number | Structure | Compound Name | IL-2 inhibition Jurkat/PHA/ 1% FBS IC50 (nM) |
|---|---|---|---|
| 117. | 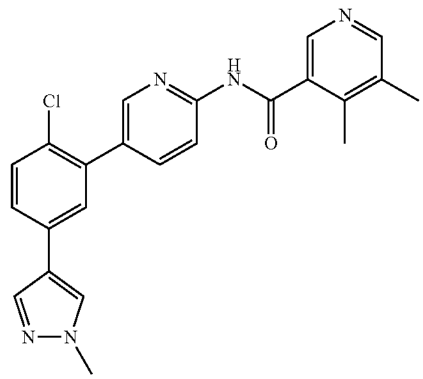 [SMILES: Cc1cncc(C(=O)Nc2ccc(-c3cc(-c4cnn(C)c4)ccc3Cl)cn2)c1C] | N-(5-(2-chloro-5-(1-methyl-1H-pyrazol-4-yl)phenyl)pyridin-2-yl)-4,5-dimethylnicotinamide | 72 |
| 118. | 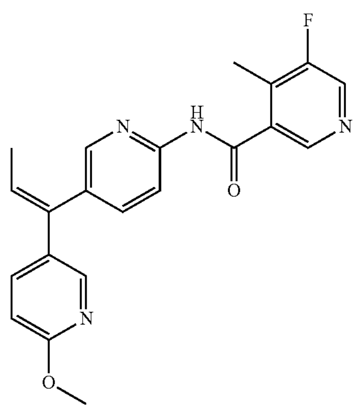 [SMILES: C/C=C(\c1ccc(NC(=O)c2cncc(F)c2C)nc1)c1ccc(OC)nc1] | (E)-5-fluoro-N-(5-(1-(6-methoxypyridin-3-yl)prop-1-en-1-yl)pyridin-2-yl)-4-methylnicotinamide | 43 |
| 119. | 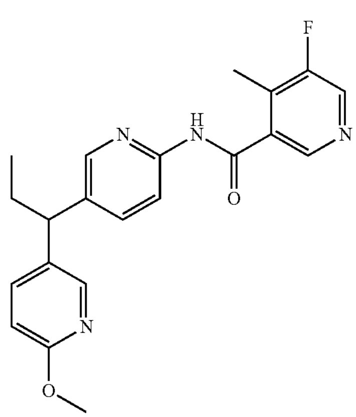 [SMILES: CCC(c1ccc(NC(=O)c2cncc(F)c2C)nc1)c1ccc(OC)nc1] | 5-fluoro-N-(5-(1-(6-methoxypyridin-3-yl)propyl)pyridin-2-yl)-4-methylnicotinamide | 140 |

TABLE 1-continued

| Number | Structure | Compound Name | IL-2 inhibition Jurkat/PHA/ 1% FBS IC50 (nM) |
|---|---|---|---|
| 120. | 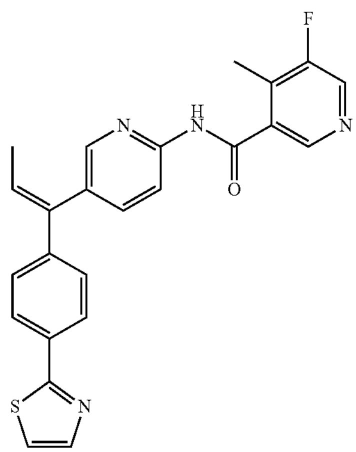 [SMILES: C/C=C(/c1ccc(-c2nccs2)cc1)c1ccc(NC(=O)c2cncc(F)c2C)nc1] | (Z)-5-fluoro-4-methyl-N-(5-(1-(4-(thiazol-2-yl)phenyl)prop-1-en-1-yl)pyridin-2-yl)nicotinamide | 31 |
| 121. | 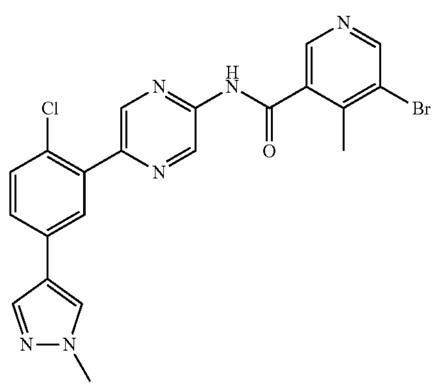 [SMILES: Cc1c(Br)cncc1C(=O)Nc1cnc(-c2cc(-c3cnn(C)c3)ccc2Cl)cn1] | 5-bromo-N-(5-(2-chloro-5-(1-methyl-1H-pyrazol-4-yl)phenyl)pyrazin-2-yl)-4-methylnicotinamide | 11 |
| 122. | 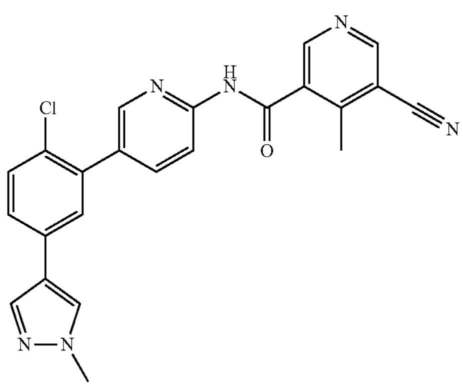 [SMILES: Cc1c(C#N)cncc1C(=O)Nc1ccc(-c2cc(-c3cnn(C)c3)ccc2Cl)cn1] | N-(5-(2-chloro-5-(1-methyl-1H-pyrazol-4-yl)phenyl)pyridin-2-yl)-5-cyano-4-methylnicotinamide | 10 |

TABLE 1-continued

| Number | Structure | Compound Name | IL-2 inhibition Jurkat/PHA/ 1% FBS IC50 (nM) |
|---|---|---|---|
| 123. | 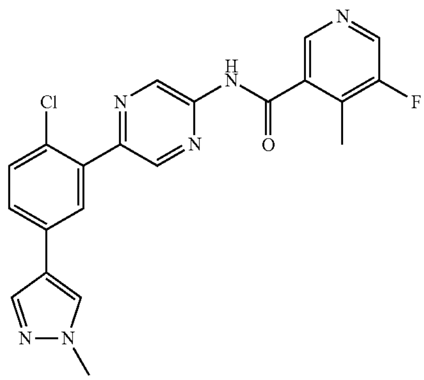 [SMILES: Cc1c(F)cncc1C(=O)Nc1cnc(-c2cc(-c3cnn(C)c3)ccc2Cl)cn1] | N-(5-(2-chloro-5-(1-methyl-1H-pyrazol-4-yl)phenyl)pyrazin-2-yl)-5-fluoro-4-methylnicotinamide | 18 |
| 124. | 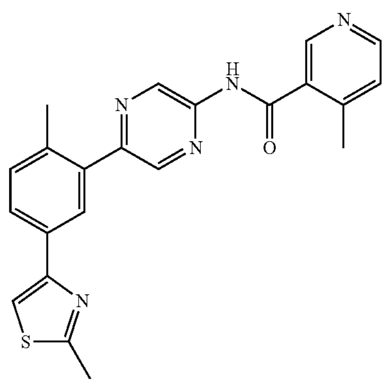 [SMILES: Cc1nc(-c2ccc(C)c(-c3cnc(NC(=O)c4cnccc4C)cn3)c2)cs1] | 4-methyl-N-(5-(2-methyl-5-(2-methylthiazol-4-yl)phenyl)pyrazin-2-yl)nicotinamide | 477 |
| 125. | 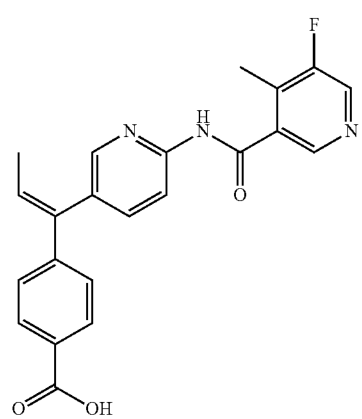 [SMILES: C/C=C(/c1ccc(C(=O)O)cc1)c1ccc(NC(=O)c2cncc(F)c2C)nc1] | (Z)-4-(1-(6-(5-fluoro-4-methylnicotinamido)pyridin-3-yl)prop-1-en-1-yl)benzoic acid | 1000 |
| 126. | 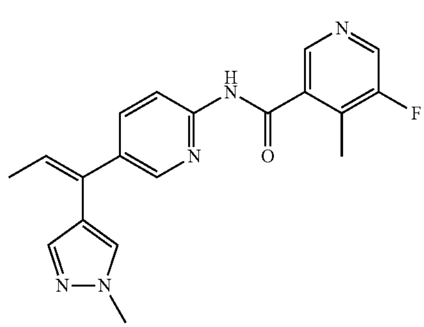 [SMILES: C/C=C(/c1ccc(NC(=O)c2cncc(F)c2C)nc1)c1cnn(C)c1] | (Z)-5-fluoro-4-methyl-N-(5-(1-(1-methyl-1H-pyrazol-4-yl)prop-1-en-1-yl)pyridin-2-yl)nicotinamide | 455 |

TABLE 1-continued

| Number | Structure | Compound Name | IL-2 inhibition Jurkat/PHA/ 1% FBS IC50 (nM) |
|---|---|---|---|
| 127. | 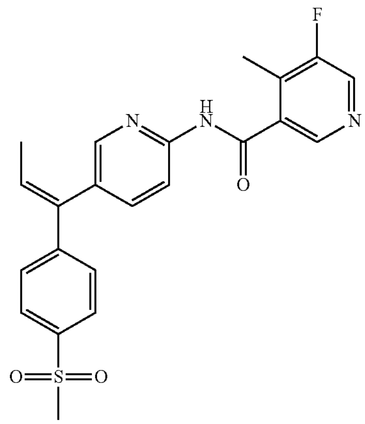 [SMILES: C/C=C(/c1ccc(S(C)(=O)=O)cc1)c1ccc(NC(=O)c2cncc(F)c2C)nc1] | (Z)-5-fluoro-4-methyl-N-(5-(1-(4-(methylsulfonyl)phenyl)prop-1-en-1-yl)pyridin-2-yl)nicotinamide | 1000 |
| 128. | 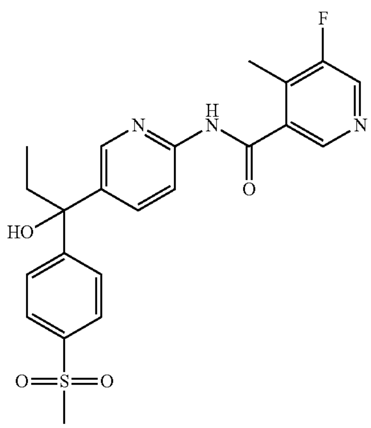 [SMILES: CCC(O)(c1ccc(S(C)(=O)=O)cc1)c1ccc(NC(=O)c2cncc(F)c2C)nc1] | 5-fluoro-N-(5-(1-hydroxy-1-(4-(methylsulfonyl)phenyl)propyl)pyridin-2-yl)-4-methylnicotinamide | 1000 |
| 129. | 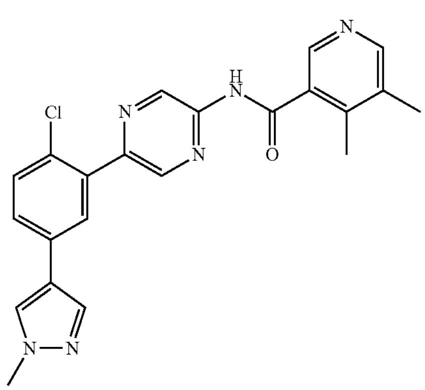 | N-(5-(2-chloro-5-(1-methyl-1H-pyrazol-4-yl)phenyl)pyrazin-2-yl)-4,5-dimethylnicotinamide | 30 |

TABLE 1-continued

| Number | Structure | Compound Name | IL-2 inhibition Jurkat/PHA/ 1% FBS IC50 (nM) |
|---|---|---|---|
| 130. | 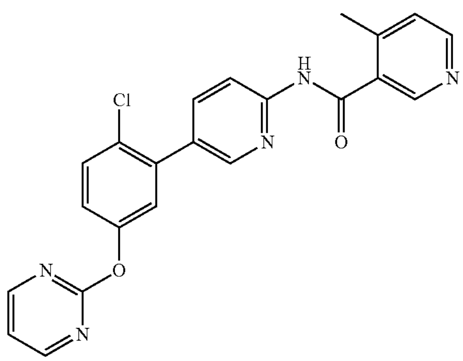 [SMILES: Cc1ccncc1C(=O)Nc1ccc(-c2cc(Oc3ncccn3)ccc2Cl)cn1] | N-(5-(2-chloro-5-(pyrimidin-2-yloxy)phenyl)pyridin-2-yl)-4-methylnicotinamide | 69 |
| 131. | 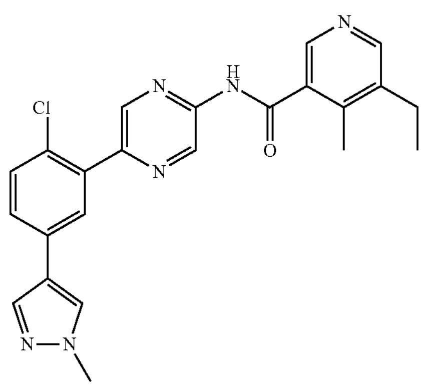 [SMILES: CCc1cncc(C(=O)Nc2cnc(-c3cc(-c4cnn(C)c4)ccc3Cl)cn2)c1C] | N-(5-(2-chloro-5-(1-methyl-1H-pyrazol-4-yl)phenyl)pyrazin-2-yl)-5-ethyl-4-methylnicotinamide | 21 |
| 132. | 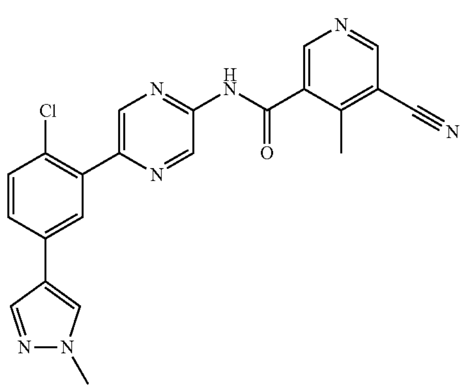 [SMILES: Cc1c(C#N)cncc1C(=O)Nc1cnc(-c2cc(-c3cnn(C)c3)ccc2Cl)cn1] | N-(5-(2-chloro-5-(1-methyl-1H-pyrazol-4-yl)phenyl)pyrazin-2-yl)-5-cyano-4-methylnicotinamide | 77 |

TABLE 1-continued

| Number | Structure | Compound Name | IL-2 inhibition Jurkat/PHA/ 1% FBS IC50 (nM) |
|---|---|---|---|
| 133. | 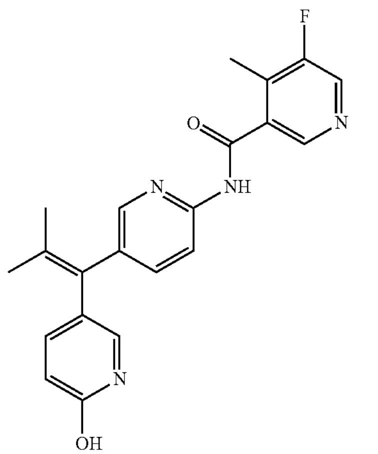 [SMILES: CC(C)=C(c1ccc(O)nc1)c1ccc(NC(=O)c2cncc(F)c2C)nc1] | 5-fluoro-N-(5-(1-(6-hydroxypyridin-3-yl)-2-methylprop-1-en-1-yl)pyridin-2-yl)-4-methylnicotinamide | 1000 |
| 134. | 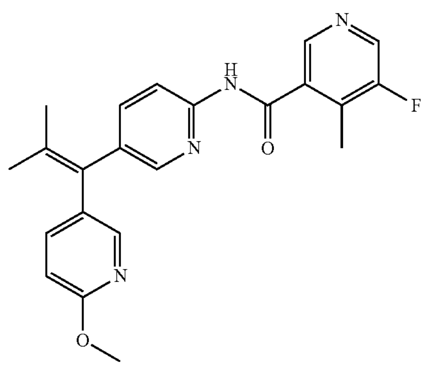 [SMILES: COc1ccc(C(=C(C)C)c2ccc(NC(=O)c3cncc(F)c3C)nc2)cn1] | 5-fluoro-N-(5-(1-(6-methoxypyridin-3-yl)-2-methylprop-1-en-1-yl)pyridin-2-yl)-4-methylnicotinamide | 63 |
| 135. | 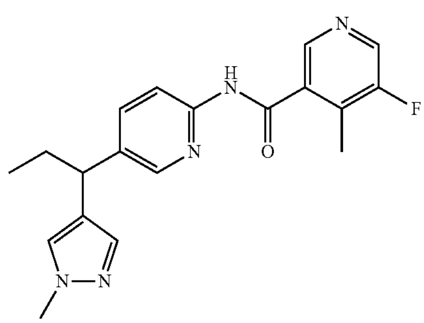 [SMILES: CCC(c1ccc(NC(=O)c2cncc(F)c2C)nc1)c1cnn(C)c1] | 5-fluoro-4-methyl-N-(5-(1-(1-methyl-1H-pyrazol-4-yl)propyl)pyridin-2-yl)nicotinamide | 1000 |
| 136. | 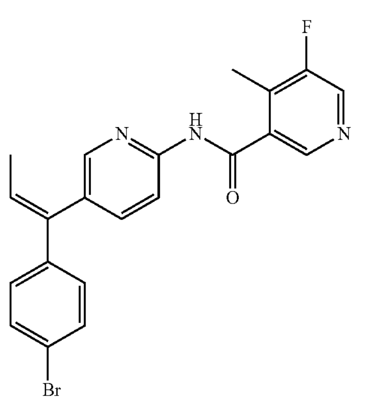 [SMILES: C/C=C(/c1ccc(Br)cc1)c1ccc(NC(=O)c2cncc(F)c2C)nc1] | (Z)-N-(5-(1-(4-bromophenyl)prop-1-en-1-yl)pyridin-2-yl)-5-fluoro-4-methylnicotinamide | 14 |

TABLE 1-continued

| Number | Structure | Compound Name | IL-2 inhibition Jurkat/PHA/ 1% FBS IC50 (nM) |
|---|---|---|---|
| 137. | 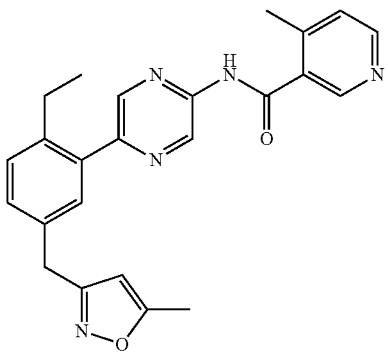 | N-(5-(2-ethyl-5-((5-methylisoxazol-3-yl)oxy)phenyl)pyrazin-2-yl)-4-methylnicotinamide | 17 |
| 138. | 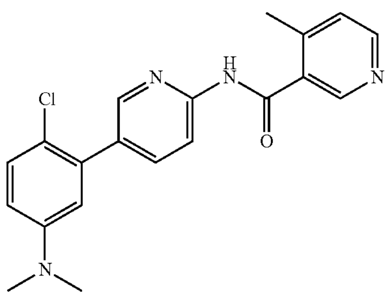 [SMILES: Cc1ccncc1C(=O)Nc1ccc(-c2cc(N(C)C)ccc2Cl)cn1] | N-(5-(2-chloro-5-(dimethylamino)phenyl)pyridin-2-yl)-4-methylnicotinamide | 146 |
| 139. | 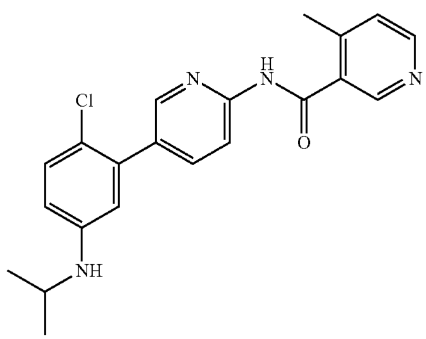 [SMILES: Cc1ccncc1C(=O)Nc1ccc(-c2cc(NC(C)C)ccc2Cl)cn1] | N-(5-(2-chloro-5-(isopropylamino)phenyl)pyridin-2-yl)-4-methylnicotinamide | 58 |
| 140. | 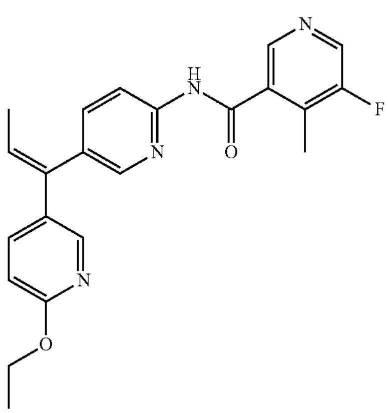 [SMILES: C/C=C(\c1ccc(NC(=O)c2cncc(F)c2C)nc1)c1ccc(OCC)nc1] | (E)-N-(5-(1-(6-ethoxypyridin-3-yl)prop-1-en-1-yl)pyridin-2-yl)-5-fluoro-4-methylnicotinamide | 25 |

TABLE 1-continued

| Number | Structure | Compound Name | IL-2 inhibition Jurkat/PHA/ 1% FBS IC50 (nM) |
|---|---|---|---|
| 141. | 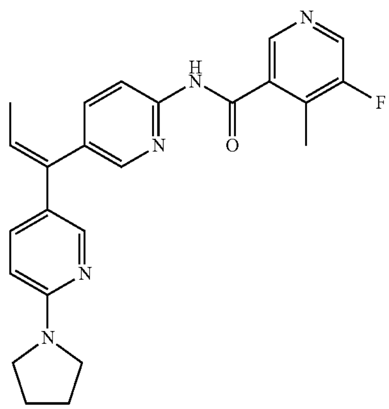 [SMILES: C/C=C(\c1ccc(NC(=O)c2cncc(F)c2C)nc1)c1ccc(N2CCCC2)nc1] | (E)-5-fluoro-4-methyl-N-(5-(1-(6-(pyrrolidin-1-yl)pyridin-3-yl)prop-1-en-1-yl)pyridin-2-yl)nicotinamide | 135 |
| 142. | HCl | N-(5-(2-chloro-5-(1-methyl-1H-pyrazol-4-yl)phenyl)pyrazin-2-yl)-4-methylnicotinamide hydrochloride | 23 |
| 143. | 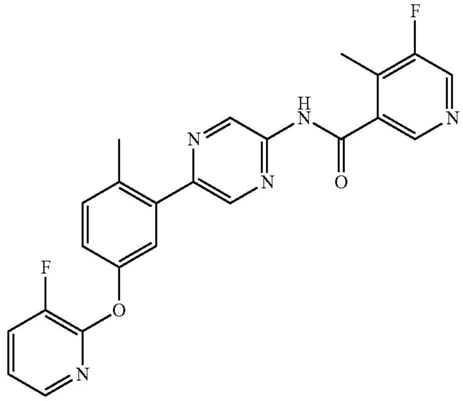 [SMILES: Cc1ccc(Oc2ncccc2F)cc1-c1cnc(NC(=O)c2cncc(F)c2C)cn1] | 5-fluoro-N-(5-(5-((3-fluoropyridin-2-yl)oxy)-2-methylphenyl)pyrazin-2-yl)-4-methylnicotinamide | 35 |

TABLE 1-continued

| Number | Structure | Compound Name | IL-2 inhibition Jurkat/PHA/ 1% FBS IC50 (nM) |
|---|---|---|---|
| 144. | 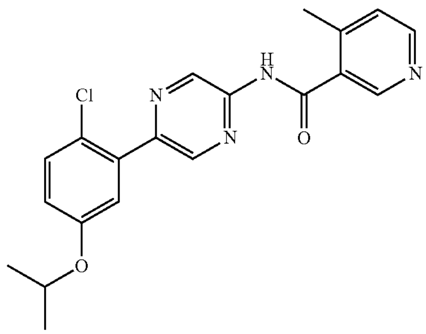 [SMILES: Cc1ccncc1C(=O)Nc1cnc(-c2cc(OC(C)C)ccc2Cl)cn1] | N-(5-(2-chloro-5-isopropoxyphenyl)pyrazin-2-yl)-4-methylnicotinamide | 13 |
| 145. | 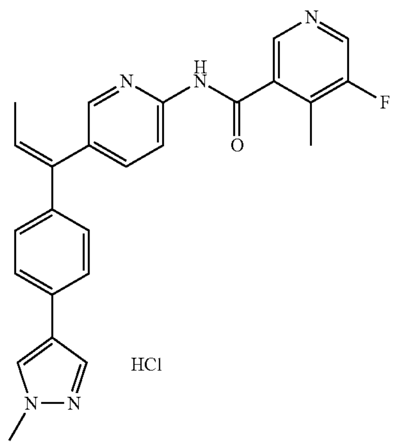 [SMILES: C/C=C(/c1ccc(-c2cnn(C)c2)cc1)c1ccc(NC(=O)c2cncc(F)c2C)nc1 ; Cl] | (Z)-5-fluoro-4-methyl-N-(5-(1-(4-(1-methyl-1H-pyrazol-4-yl)phenyl)prop-1-en-1-yl)pyridin-2-yl)nicotinamide hydrochloride | 118 |
| 146. | 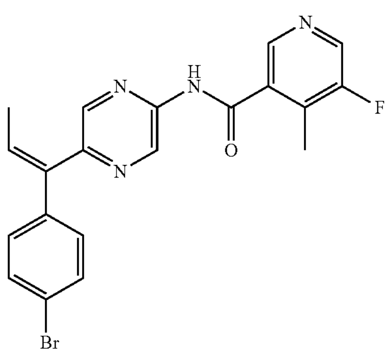 [SMILES: C/C=C(/c1ccc(Br)cc1)c1cnc(NC(=O)c2cncc(F)c2C)cn1] | (Z)-N-(5-(1-(4-bromophenyl)prop-1-en-1-yl)pyrazin-2-yl)-5-fluoro-4-methylnicotinamide | 18 |
| 147. | 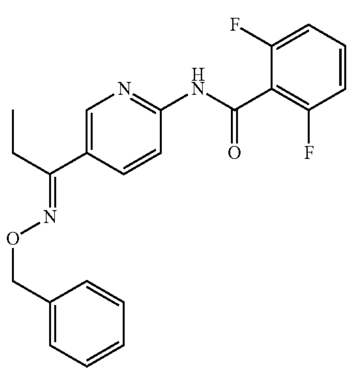 [SMILES: CC/C(=N\OCc1ccccc1)c1ccc(NC(=O)c2c(F)cccc2F)nc1] | (Z)-N-(5-(1-((benzyloxy)imino)propyl)pyridin-2-yl)-2,6-difluorobenzamide | |

TABLE 1-continued

| Number | Structure | Compound Name | IL-2 inhibition Jurkat/PHA/ 1% FBS IC50 (nM) |
|---|---|---|---|
| 148. | 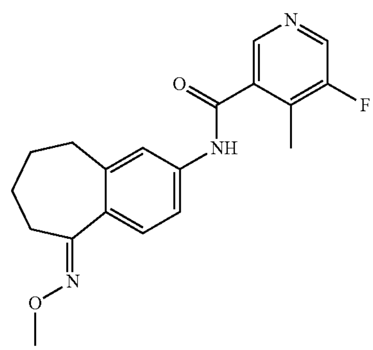 [SMILES: CO/N=C1\CCCCc2cc(NC(=O)c3cncc(F)c3C)ccc21] | (E)-5-fluoro-N-(5-(methoxyimino)-6,7,8,9-tetrahydro-5H-benzo[7]annulen-2-yl)-4-methylnicotinamide | |
| 149. | 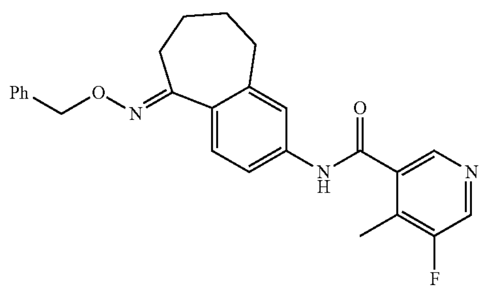 [SMILES: Cc1c(F)cncc1C(=O)Nc1ccc2c(c1)CCCC/C2=N\OCc1ccccc1] | (E)-N-(5-((benzyloxy)imino)-6,7,8,9-tetrahydro-5H-benzo[7]annulen-2-yl)-5-fluoro-4-methylnicotinamide | |
| 150. | 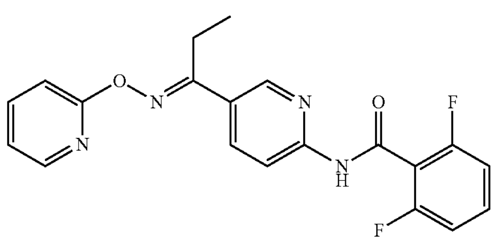 [SMILES: CC/C(=N\Oc1ccccn1)c1ccc(NC(=O)c2c(F)cccc2F)nc1] | (E)-2,6-difluoro-N-(5-(1-((pyridin-2-yloxy)imino)propyl)pyridin-2-yl)benzamide | |
| 151. | 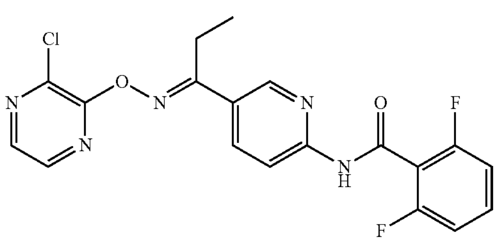 [SMILES: CC/C(=N\Oc1nccnc1Cl)c1ccc(NC(=O)c2c(F)cccc2F)nc1] | (E)-N-(5-(1-(((3-chloropyrazin-2-yl)oxy)imino)propyl)pyridin-2-yl)-2,6-difluorobenzamide | |
| 152. | 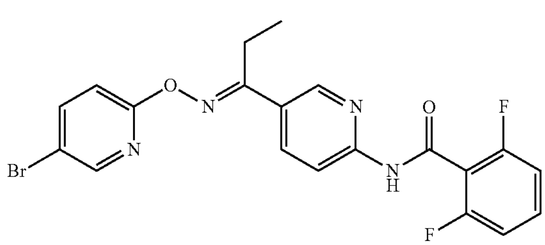 [SMILES: CC/C(=N\Oc1ccc(Br)cn1)c1ccc(NC(=O)c2c(F)cccc2F)nc1] | (E)-N-(5-(1-(((5-bromopyridin-2-yl)oxy)imino)propyl)pyridin-2-yl)-2,6-difluorobenzamide | |

TABLE 1-continued

| Number | Structure | Compound Name | IL-2 inhibition Jurkat/PHA/ 1% FBS IC50 (nM) |
|---|---|---|---|
| 153. | 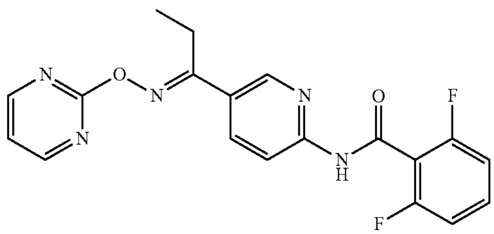 [SMILES: CC/C(=N\Oc1ncccn1)c1ccc(NC(=O)c2c(F)cccc2F)nc1] | (E)-2,6-difluoro-N-(5-(1-((pyrimidin-2-yloxy)imino)propyl)pyridin-2-yl)benzamide | |
| 154. | 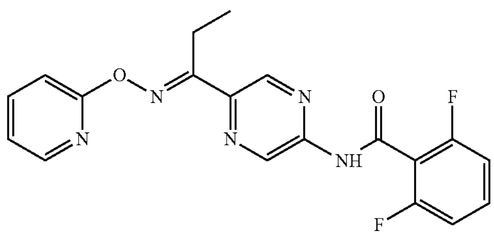 [SMILES: CC/C(=N\Oc1ccccn1)c1cnc(NC(=O)c2c(F)cccc2F)cn1] | (E)-2,6-difluoro-N-(5-(1-((pyridin-2-yloxy)imino)propyl)pyrazin-2-yl)benzamide | |
| 155. | 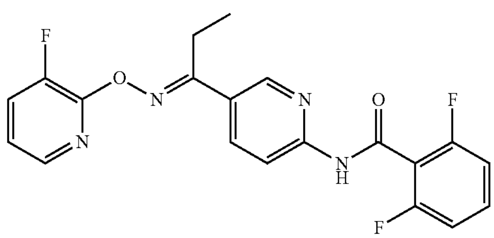 [SMILES: CC/C(=N\Oc1ncccc1F)c1ccc(NC(=O)c2c(F)cccc2F)nc1] | (E)-2,6-difluoro-N-(5-(1-(((3-fluoropyridin-2-yl)oxy)imino)propyl)pyridin-2-yl)benzamide | |
| 156. | 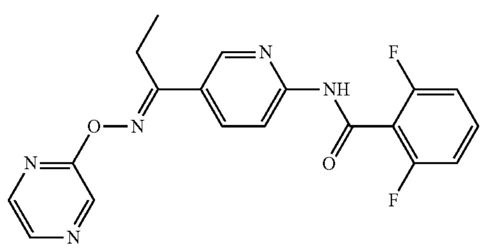 [SMILES: CC/C(=N\Oc1cnccn1)c1ccc(NC(=O)c2c(F)cccc2F)nc1] | (E)-2,6-difluoro-N-(5-(1-((pyrazin-2-yloxy)imino)propyl)pyridin-2-yl)benzamide | |
| 157. | 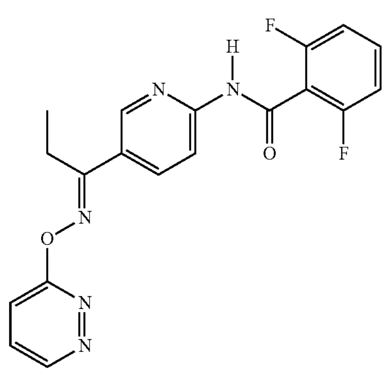 [SMILES: CC/C(=N\Oc1cccnn1)c1ccc(NC(=O)c2c(F)cccc2F)nc1] | (E)-2,6-difluoro-N-(5-(1-((pyridazin-3-yloxy)imino)propyl)pyridin-2-yl)benzamide | |

TABLE 1-continued

| Number | Structure | Compound Name | IL-2 inhibition Jurkat/PHA/ 1% FBS IC50 (nM) |
|---|---|---|---|
| 158. | 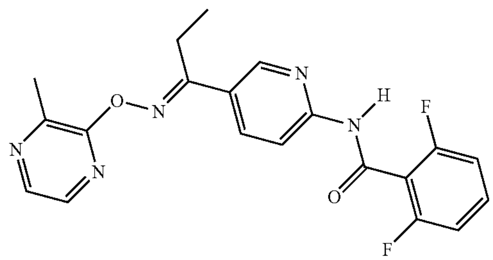 [SMILES: CC/C(=N\Oc1nccnc1C)c1ccc(NC(=O)c2c(F)cccc2F)nc1] | (E)-2,6-difluoro-N-(5-(1-(((3-methylpyrazin-2-yl)oxy)imino)propyl)pyridin-2-yl)benzamide | |
| 159. | 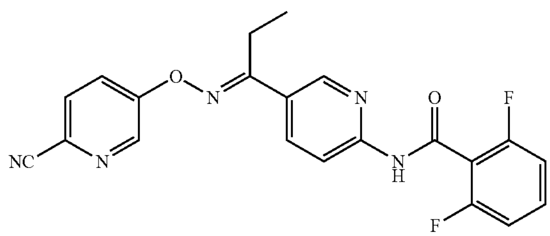 [SMILES: CC/C(=N\Oc1ccc(C#N)nc1)c1ccc(NC(=O)c2c(F)cccc2F)nc1] | (E)-N-(5-(1-(((6-cyanopyridin-3-yl)oxy)imino)propyl)pyridin-2-yl)-2,6-difluorobenzamide | |
| 160. | 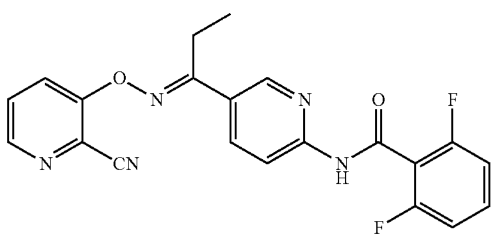 [SMILES: CC/C(=N\Oc1cccnc1C#N)c1ccc(NC(=O)c2c(F)cccc2F)nc1] | (E)-N-(5-(1-(((2-cyanopyridin-3-yl)oxy)imino)propyl)pyridin-2-yl)-2,6-difluorobenzamide | |
| 161. | 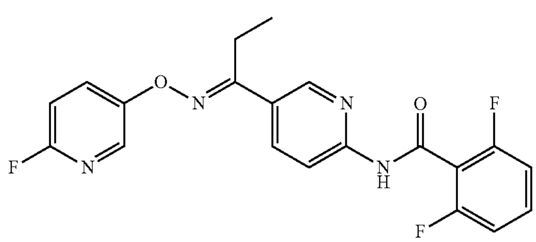 [SMILES: CC/C(=N\Oc1ccc(F)nc1)c1ccc(NC(=O)c2c(F)cccc2F)nc1] | (E)-2,6-difluoro-N-(5-(1-(((6-fluoropyridin-3-yl)oxy)imino)propyl)pyridin-2-yl)benzamide | |
| 162. | 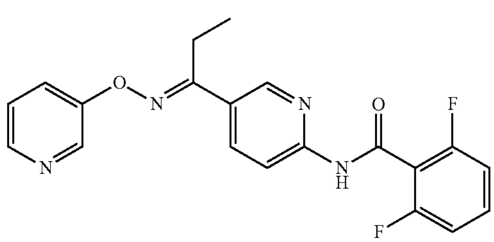 [SMILES: CC/C(=N\Oc1cccnc1)c1ccc(NC(=O)c2c(F)cccc2F)nc1] | ((E)-2,6-difluoro-N-(5-(1-((pyridin-3-yloxy)imino)propyl)pyridin-2-yl)benzamide | |
| 163. | 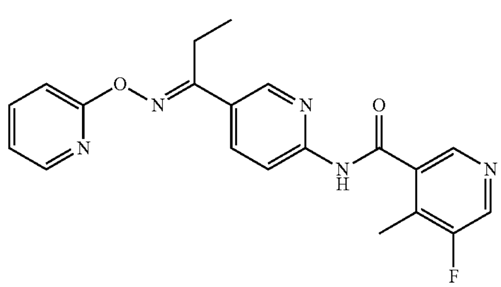 [SMILES: CC/C(=N\Oc1ccccn1)c1ccc(NC(=O)c2cncc(F)c2C)nc1] | (E)-5-fluoro-4-methyl-N-(5-(1-((pyridin-2-yloxy)imino)propyl)pyridin-2-yl)nicotinamide | |

TABLE 1-continued

| Number | Structure | Compound Name | IL-2 inhibition Jurkat/PHA/ 1% FBS IC50 (nM) |
|---|---|---|---|
| 164. | 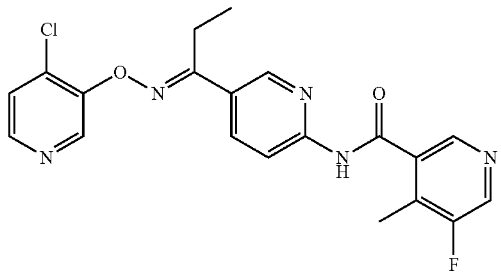 [SMILES: CC/C(=N\Oc1cnccc1Cl)c1ccc(NC(=O)c2cncc(F)c2C)nc1] | (E)-N-(5-(1-(((4-chloropyridin-3-yl)oxy)imino)propyl)pyridin-2-yl)-5-fluoro-4-methylnicotinamide | |
| 165. | 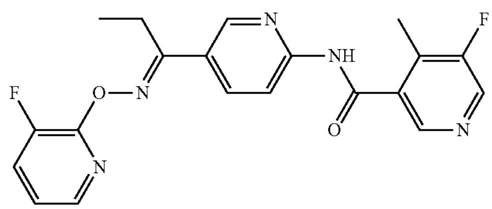 [SMILES: CC/C(=N\Oc1ncccc1F)c1ccc(NC(=O)c2cncc(F)c2C)nc1] | (E)-5-fluoro-N-(5-(1-(((3-fluoropyridin-2-yl)oxy)imino)propyl)pyridin-2-yl)-4-methylnicotinamide | |
| 166. | 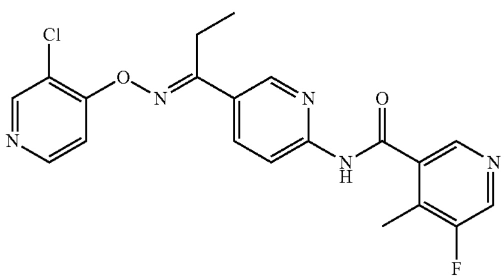 [SMILES: CC/C(=N\Oc1ccncc1Cl)c1ccc(NC(=O)c2cncc(F)c2C)nc1] | (E)-N-(5-(1-(((3-chloropyridin-4-yl)oxy)imino)propyl)pyridin-2-yl)-5-fluoro-4-methylnicotinamide | |
| 167. | 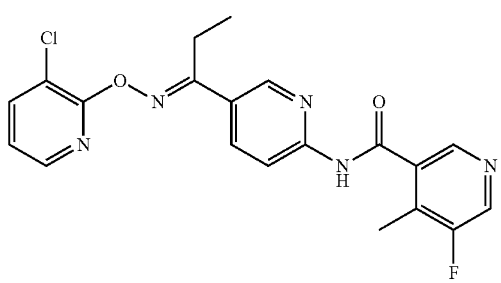 [SMILES: CC/C(=N\Oc1ncccc1Cl)c1ccc(NC(=O)c2cncc(F)c2C)nc1] | (E)-N-(5-(1-(((3-chloropyridin-2-yl)oxy)imino)propyl)pyridin-2-yl)-5-fluoro-4-methylnicotinamide | |
| 168. | 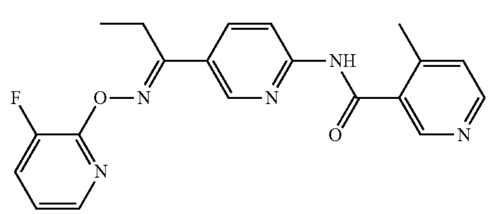 [SMILES: CC/C(=N\Oc1ncccc1F)c1ccc(NC(=O)c2cnccc2C)nc1] | (E)-N-(5-(1-(((3-fluoropyridin-2-yl)oxy)imino)propyl)pyridin-2-yl)-4-methylnicotinamide | |

TABLE 1-continued

| Number | Structure | Compound Name | IL-2 inhibition Jurkat/PHA/ 1% FBS IC50 (nM) |
|---|---|---|---|
| 169. | 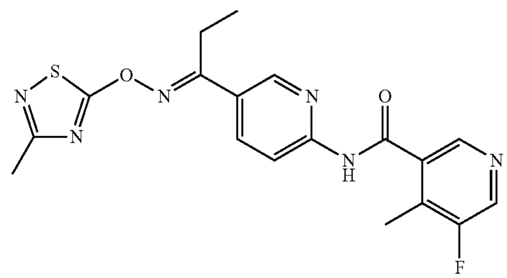 [SMILES: CC/C(=N\Oc1nc(C)ns1)c1ccc(NC(=O)c2cncc(F)c2C)nc1] | (E)-5-fluoro-4-methyl-N-(5-(1-(((3-methyl-1,2,4-thiadiazol-5-yl)oxy)imino)propyl)pyridin-2-yl)nicotinamide | |
| 170. | 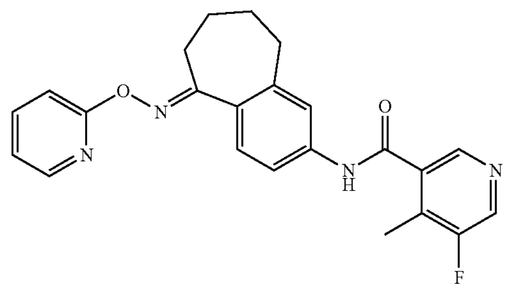 [SMILES: Cc1c(F)cncc1C(=O)Nc1ccc2c(c1)CCCC/C2=N\Oc1ccccn1] | (E)-5-fluoro-4-methyl-N-(5-((pyridin-2-yloxy)imino)-6,7,8,9-tetrahydro-5H-benzo[7]annulen-2-yl)nicotinamide | |
| 171. | 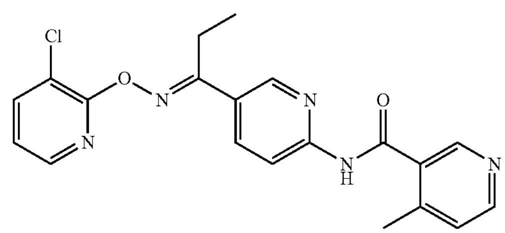 [SMILES: CC/C(=N\Oc1ncccc1Cl)c1ccc(NC(=O)c2cnccc2C)nc1] | (E)-N-(5-(1-(((3-chloropyridin-2-yl)oxy)imino)propyl)pyridin-2-yl)-4-methylnicotinamide | |
| 172. | 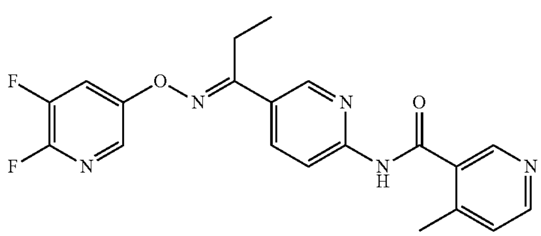 [SMILES: CC/C(=N\Oc1cnc(F)c(F)c1)c1ccc(NC(=O)c2cnccc2C)nc1] | (E)-N-(5-(1-(((5,6-difluoropyridin-3-yl)oxy)imino)propyl)pyridin-2-yl)-4-methylnicotinamide | |
| 173. | 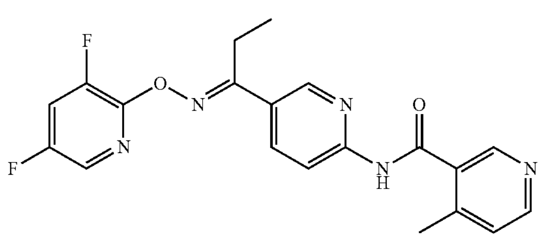 [SMILES: CC/C(=N\Oc1ncc(F)cc1F)c1ccc(NC(=O)c2cnccc2C)nc1] | (E)-N-(5-(1-(((3,5-difluoropyridin-2-yl)oxy)imino)propyl)pyridin-2-yl)-4-methylnicotinamide | |
| 174. | 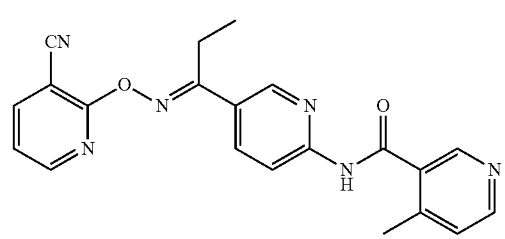 | (E)-N-(5-(1-(((3-cyanopyridin-2-yl)oxy)imino)propyl)pyridin-2-yl)-4-methylnicotinamide | |

TABLE 1-continued

| Number | Structure | Compound Name | IL-2 inhibition Jurkat/PHA/ 1% FBS IC50 (nM) |
|---|---|---|---|
| 175. | 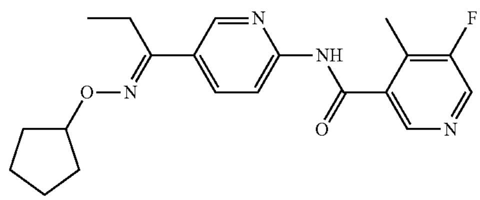 [SMILES: CC/C(=N\OC1CCCC1)c1ccc(NC(=O)c2cncc(F)c2C)nc1] | (E)-N-(5-(1-((cyclopentyloxy)imino)propyl)pyridin-2-yl)-5-fluoro-4-methylnicotinamide | |
| 176. | 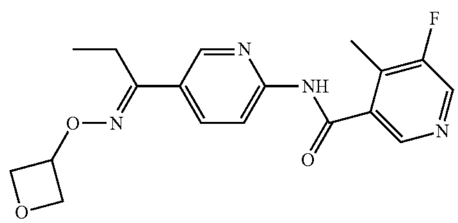 [SMILES: CC/C(=N\OC1COC1)c1ccc(NC(=O)c2cncc(F)c2C)nc1] | (E)-5-fluoro-4-methyl-N-(5-(1-((oxetan-3-yloxy)imino)propyl)pyridin-2-yl)nicotinamide | |
| 177. | 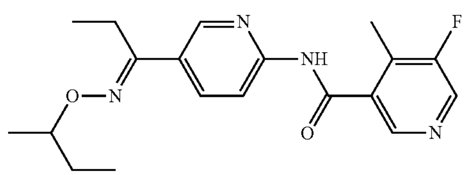 [SMILES: CC/C(=N\OC(C)CC)c1ccc(NC(=O)c2cncc(F)c2C)nc1] | (E)-N-(5-(1-(sec-butoxyimino)propyl)pyridin-2-yl)-5-fluoro-4-methylnicotinamide | |
| 178. | 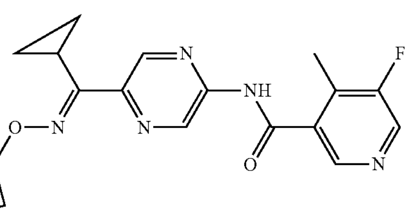 | (E)-N-(5-(cyclopropyl((oxetan-3-yloxy)imino)methyl)pyrazin-2-yl)-5-fluoro-4-methylnicotinamide | |
| 179. | 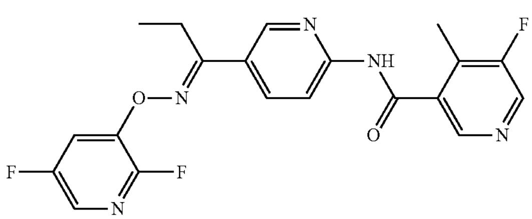 [SMILES: CC/C(=N\Oc1cc(F)cnc1F)c1ccc(NC(=O)c2cncc(F)c2C)nc1] | (E)-N-(5-(1-(((2,5-difluoropyridin-3-yl)oxy)imino)propyl)pyridin-2-yl)-5-fluoro-4-methylnicotinamide | |
| 180. | 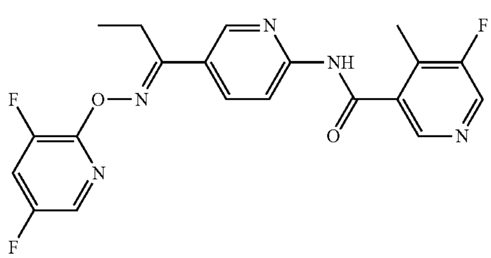 [SMILES: CC/C(=N\Oc1ncc(F)cc1F)c1ccc(NC(=O)c2cncc(F)c2C)nc1] | (E)-N-(5-(1-(((3,5-difluoropyridin-2-yl)oxy)imino)propyl)pyridin-2-yl)-5-fluoro-4-methylnicotinamide | |
| 181. | 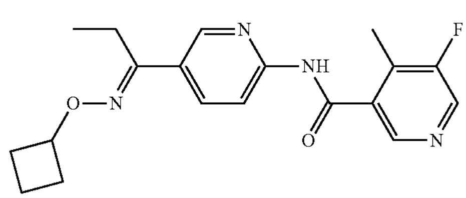 [SMILES: CC/C(=N\OC1CCC1)c1ccc(NC(=O)c2cncc(F)c2C)nc1] | (E)-N-(5-(1-(cyclobutoxyimino)propyl)pyridin-2-yl)-5-fluoro-4-methylnicotinamide | |

TABLE 1-continued

| Number | Structure | Compound Name | IL-2 inhibition Jurkat/PHA/ 1% FBS IC50 (nM) |
|---|---|---|---|
| 182. | 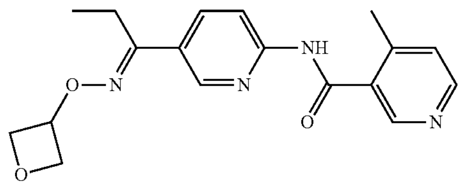 [SMILES: CC/C(=N\OC1COC1)c1ccc(NC(=O)c2cnccc2C)nc1] | (E)-4-methyl-N-(5-(1-((oxetan-3-yloxy)imino)propyl)pyridin-2-yl)nicotinamide | |
| 183. | 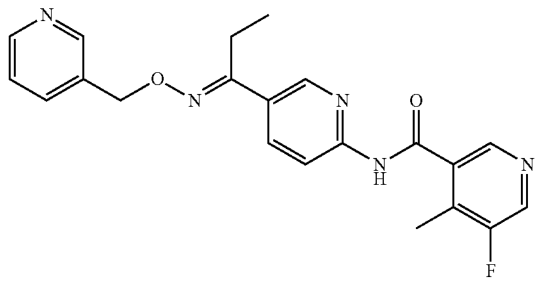 [SMILES: CC/C(=N\OCc1cccnc1)c1ccc(NC(=O)c2cncc(F)c2C)nc1] | (E)-5-fluoro-4-methyl-N-(5-(1-((pyridin-3-ylmethoxy)imino)propyl)pyridin-2-yl)nicotinamide | |
| 184. | 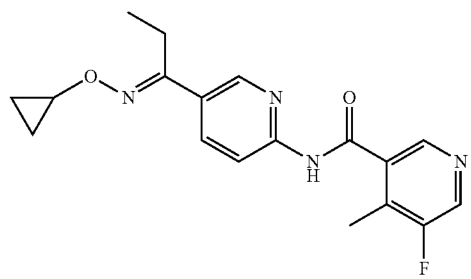 [SMILES: CC/C(=N\OC1CC1)c1ccc(NC(=O)c2cncc(F)c2C)nc1] | (E)-N-(5-(1-(cyclopropoxyimino)propyl)pyridin-2-yl)-5-fluoro-4-methylnicotinamide | |
| 185. | 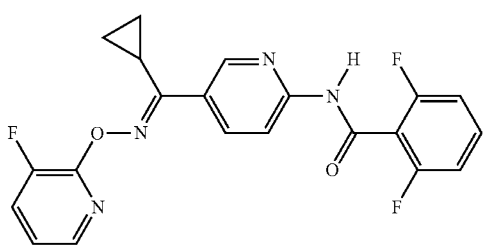 [SMILES: O=C(Nc1ccc(/C(=N/Oc2ncccc2F)C2CC2)cn1)c1c(F)cccc1F] | (E)-N-(5-(cyclopropyl(((3-fluoropyridin-2-yl)oxy)imino)methyl)pyridin-2-yl)-2,6-difluorobenzamide | |
| 186. | 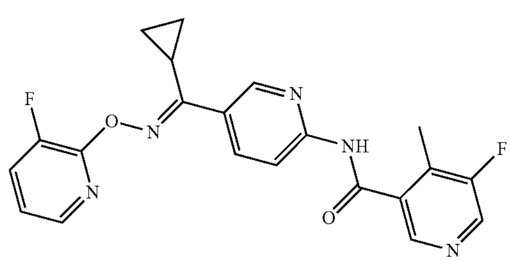 [SMILES: Cc1c(F)cncc1C(=O)Nc1ccc(/C(=N/Oc2ncccc2F)C2CC2)cn1] | (E)-N-(5-(cyclopropyl(((3-fluoropyridin-2-yl)oxy)imino)methyl)pyridin-2-yl)-5-fluoro-4-methylnicotinamide | |
| 187. | 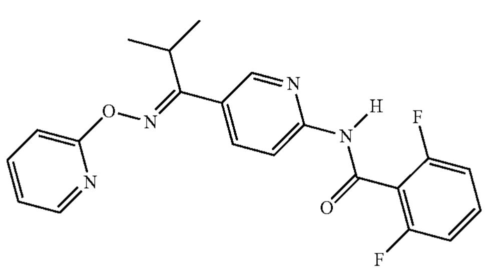 [SMILES: CC(C)/C(=N\Oc1ccccn1)c1ccc(NC(=O)c2c(F)cccc2F)nc1] | (E)-2,6-difluoro-N-(5-(2-methyl-1-((pyridin-2-yloxy)imino)propyl)pyridin-2-yl)benzamide | |

TABLE 1-continued

| Number | Structure | Compound Name | IL-2 inhibition Jurkat/PHA/ 1% FBS IC50 (nM) |
|---|---|---|---|
| 188. | 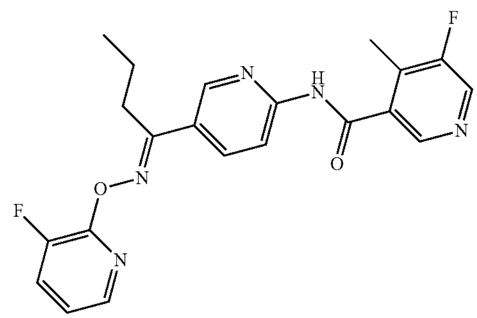 [SMILES: CCC/C(=N\Oc1ncccc1F)c1ccc(NC(=O)c2cncc(F)c2C)nc1] | (E)-5-fluoro-N-(5-(1-(((3-fluoropyridin-2-yl)oxy)imino)butyl)pyridin-2-yl)-4-methylnicotinamide | |
| 189. | 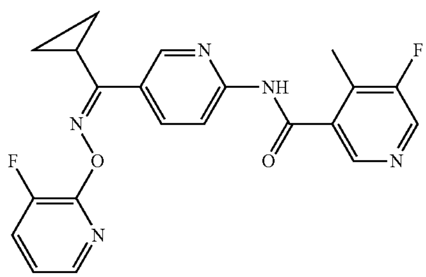 [SMILES: Cc1c(F)cncc1C(=O)Nc1ccc(/C(=N\Oc2ncccc2F)C2CC2)cn1] | (Z)-N-(5-(cyclopropyl(((3-fluoropyridin-2-yl)oxy)imino)methyl)pyridin-2-yl)-5-fluoro-4-methylnicotinamide | |
| 190. | 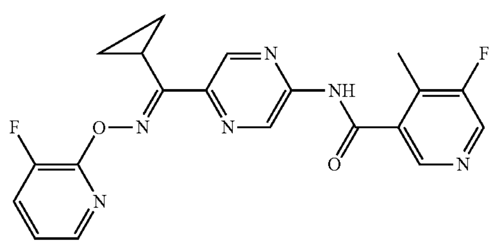 [SMILES: Cc1c(F)cncc1C(=O)Nc1cnc(/C(=N/Oc2ncccc2F)C2CC2)cn1] | (E)-N-(5-(cyclopropyl(((3-fluoropyridin-2-yl)oxy)imino)methyl)pyrazin-2-yl)-5-fluoro-4-methylnicotinamide | |
| 191. | 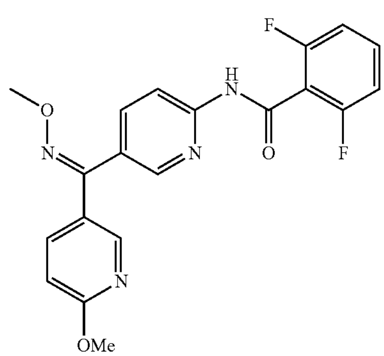 [SMILES: CO/N=C(\c1ccc(NC(=O)c2c(F)cccc2F)nc1)c1ccc(OC)nc1] | (E)-2,6-difluoro-N-(5-((methoxyimino)(6-methoxypyridin-3-yl)methyl)pyridin-2-yl)benzamide | |

TABLE 1-continued

| Number | Structure | Compound Name | IL-2 inhibition Jurkat/PHA/ 1% FBS IC50 (nM) |
|---|---|---|---|
| 192. | 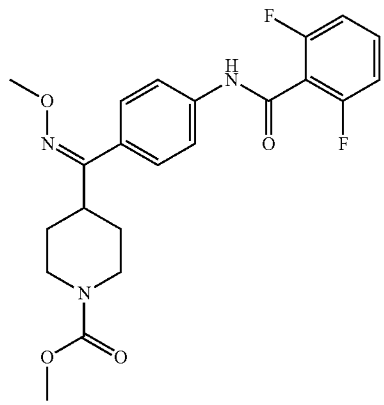 [SMILES: CO/N=C(\c1ccc(NC(=O)c2c(F)cccc2F)cc1)C1CCN(C(=O)OC)CC1] | (Z)-methyl 4-((4-(2,6-difluorobenzamido)phenyl)(methoxyimino)methyl)piperidine-1-carboxylate | |
| 193. | 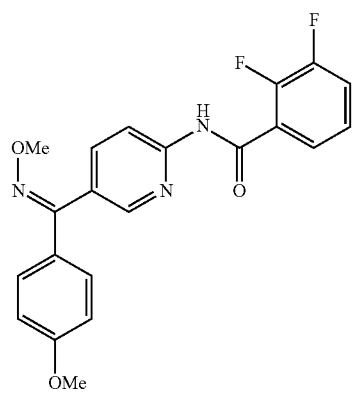 [SMILES: CO/N=C(/c1ccc(OC)cc1)c1ccc(NC(=O)c2cccc(F)c2F)nc1] | 2,3-difluoro-N-(5-((methoxyimino)(4-methoxyphenyl)methyl)pyridin-2-yl)benzamide | |
| 194. | 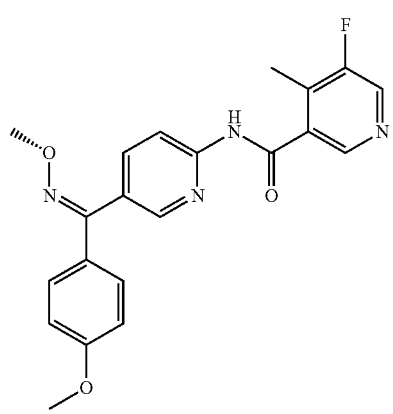 | 5-fluoro-N-(5-((methoxyimino)(4-methoxyphenyl)methyl)pyridin-2-yl)-4-methylnicotinamide | |

TABLE 1-continued

| Number | Structure | Compound Name | IL-2 inhibition Jurkat/PHA/ 1% FBS IC50 (nM) |
|---|---|---|---|
| 195. | 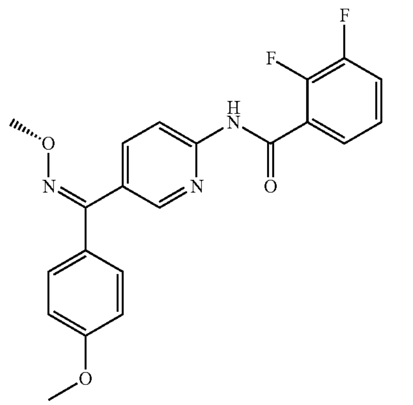 | 2,3-difluoro-N-(5-((methoxyimino)(4-methoxyphenyl)methyl)pyridin-2-yl)benzamide | |
| 196. | 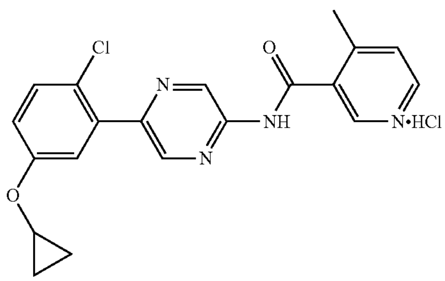 | N-(5-(2-chloro-5-cyclopropoxyphenyl)pyrazin-2-yl)-4-methylnicotinamide hydrochloride | |
| 197. | 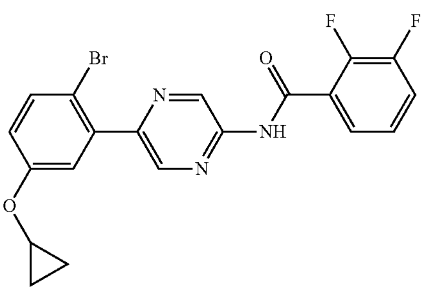 [SMILES: O=C(Nc1cnc(-c2cc(OC3CC3)ccc2Br)cn1)c1cccc(F)c1F] | N-(5-(2-bromo-5-cyclopropoxyphenyl)pyrazin-2-yl)-2,3-difluorobenzamide | |
| 198. | 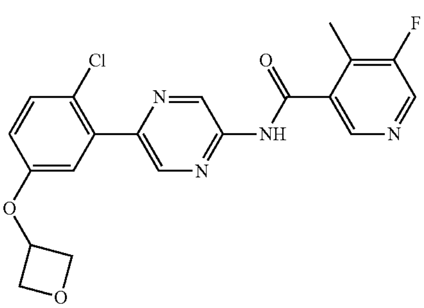 [SMILES: Cc1c(F)cncc1C(=O)Nc1cnc(-c2cc(OC3COC3)ccc2Cl)cn1] | N-(5-(2-chloro-5-(oxetan-3-yloxy)phenyl)pyrazin-2-yl)-5-fluoro-4-methylnicotinamide | |

TABLE 1-continued

| Number | Structure | Compound Name | IL-2 inhibition Jurkat/PHA/ 1% FBS IC50 (nM) |
|---|---|---|---|
| 199. | 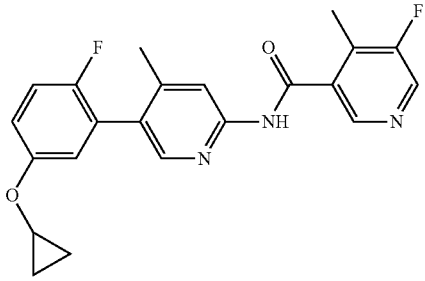 [SMILES: Cc1cc(NC(=O)c2cncc(F)c2C)ncc1-c1cc(OC2CC2)ccc1F] | N-(5-(5-cyclopropoxy-2-fluorophenyl)-4-methylpyridin-2-yl)-5-fluoro-4-methylnicotinamide | |
| 200. | 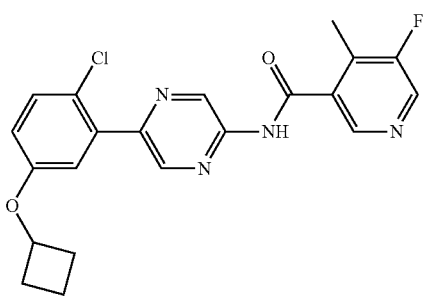 [SMILES: Cc1c(F)cncc1C(=O)Nc1cnc(-c2cc(OC3CCC3)ccc2Cl)cn1] | N-(5-(2-chloro-5-cyclobutoxyphenyl)pyrazin-2-yl)-5-fluoro-4-methylnicotinamide | |
| 201. | 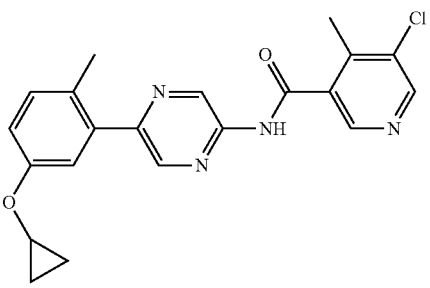 [SMILES: Cc1ccc(OC2CC2)cc1-c1cnc(NC(=O)c2cncc(Cl)c2C)cn1] | 5-chloro-N-(5-(5-cyclopropoxy-2-methylphenyl)pyrazin-2-yl)-4-methylnicotinamide | |
| 202. | 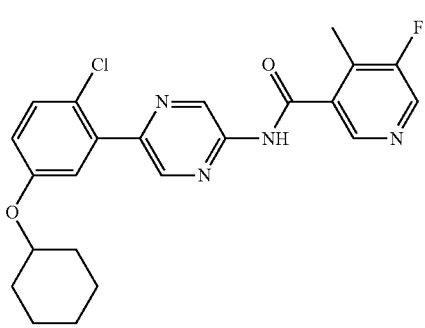 [SMILES: Cc1c(F)cncc1C(=O)Nc1cnc(-c2cc(OC3CCCCC3)ccc2Cl)cn1] | N-(5-(2-chloro-5-(cyclohexyloxy)phenyl)pyrazin-2-yl)-5-fluoro-4-methylnicotinamide | |
| 203. | 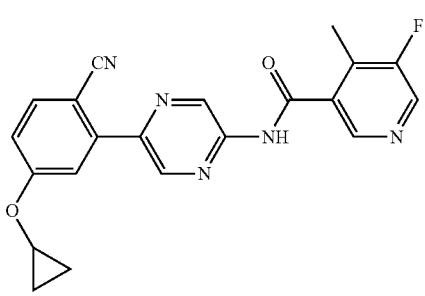 [SMILES: Cc1c(F)cncc1C(=O)Nc1cnc(-c2cc(OC3CC3)ccc2C#N)cn1] | N-(5-(2-cyano-5-cyclopropoxyphenyl)pyrazin-2-yl)-5-fluoro-4-methylnicotinamide | |

TABLE 1-continued

| Number | Structure | Compound Name | IL-2 inhibition Jurkat/PHA/ 1% FBS IC50 (nM) |
|---|---|---|---|
| 204. | 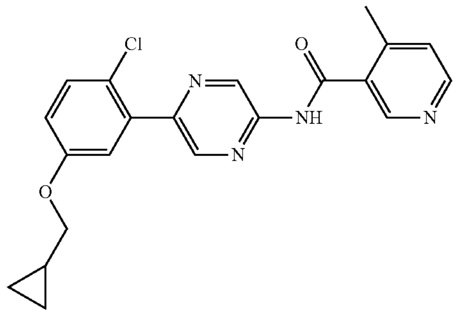 [SMILES: Cc1ccncc1C(=O)Nc1cnc(-c2cc(OCC3CC3)ccc2Cl)cn1] | N-(5-(2-chloro-5-(cyclopropylmethoxy)phenyl)pyrazin-2-yl)-4-methylnicotinamide | |
| 205. | 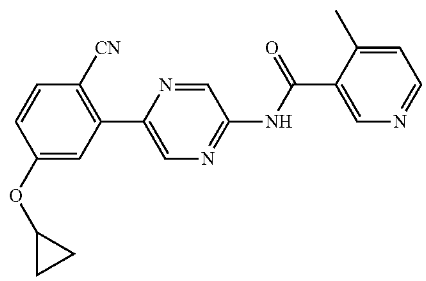 [SMILES: Cc1ccncc1C(=O)Nc1cnc(-c2cc(OC3CC3)ccc2C#N)cn1] | N-(5-(2-cyano-5-cyclopropoxyphenyl)pyrazin-2-yl)-4-methylnicotinamide | |
| 206. | 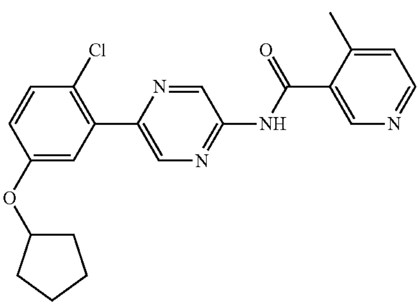 [SMILES: Cc1ccncc1C(=O)Nc1cnc(-c2cc(OC3CCCC3)ccc2Cl)cn1] | N-(5-(2-chloro-5-(cyclopentyloxy)phenyl)pyrazin-2-yl)-4-methylnicotinamide | |
| 207. | 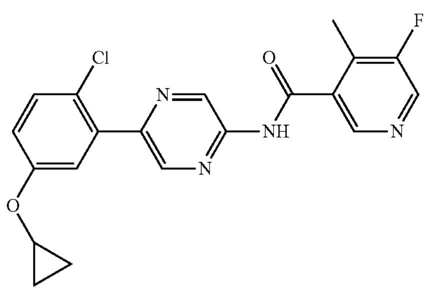 [SMILES: Cc1c(F)cncc1C(=O)Nc1cnc(-c2cc(OC3CC3)ccc2Cl)cn1] | N-(5-(2-chloro-5-cyclopropoxyphenyl)pyrazin-2-yl)-5-fluoro-4-methylnicotinamide | |
| 208. | 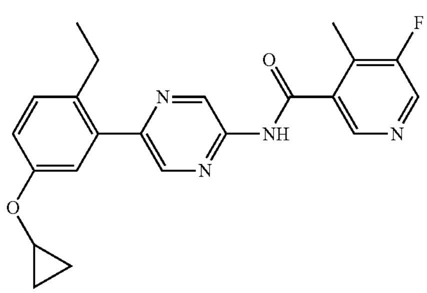 [SMILES: CCc1ccc(OC2CC2)cc1-c1cnc(NC(=O)c2cncc(F)c2C)cn1] | N-(5-(5-cyclopropoxy-2-ethylphenyl)pyrazin-2-yl)-5-fluoro-4-methylnicotinamide | |

TABLE 1-continued

| Number | Structure | Compound Name | IL-2 inhibition Jurkat/PHA/ 1% FBS IC50 (nM) |
|---|---|---|---|
| 209. | 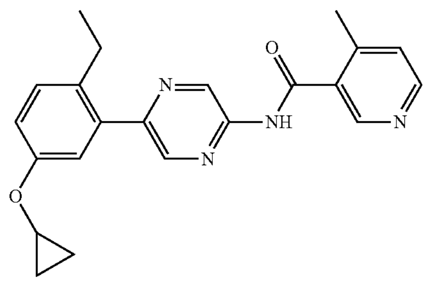 [SMILES: CCc1ccc(OC2CC2)cc1-c1cnc(NC(=O)c2cnccc2C)cn1] | N-(5-(5-cyclopropoxy-2-ethylphenyl)pyrazin-2-yl)-4-methylnicotinamide | |
| 210. | 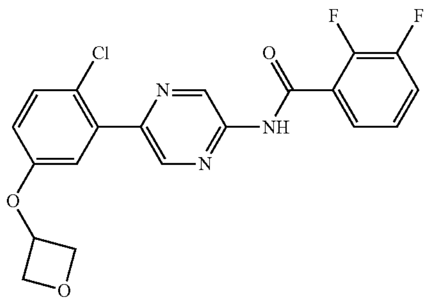 [SMILES: O=C(Nc1cnc(-c2cc(OC3COC3)ccc2Cl)cn1)c1cccc(F)c1F] | N-(5-(2-chloro-5-(oxetan-3-yloxy)phenyl)pyrazin-2-yl)-2,3-difluorobenzamide | |
| 211. | 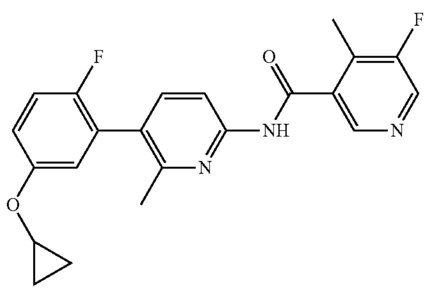 [SMILES: Cc1nc(NC(=O)c2cncc(F)c2C)ccc1-c1cc(OC2CC2)ccc1F] | N-(5-(5-cyclopropoxy-2-fluorophenyl)-6-methylpyridin-2-yl)-5-fluoro-4-methylnicotinamide | |
| 212. | 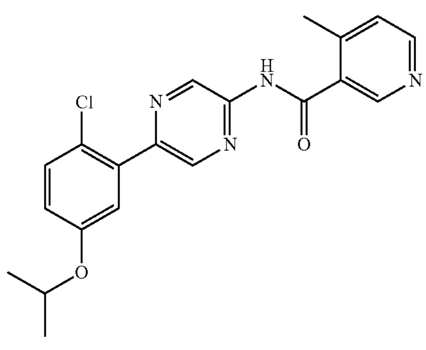 [SMILES: Cc1ccncc1C(=O)Nc1cnc(-c2cc(OC(C)C)ccc2Cl)cn1] | N-(5-(2-chloro-5-isopropoxyphenyl)pyrazin-2-yl)-4-methylnicotinamide | |
| 213. | 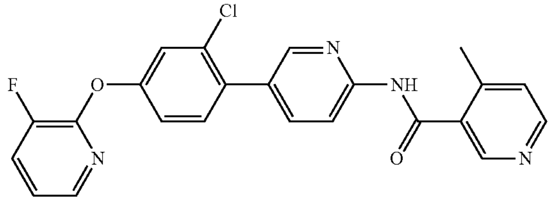 [SMILES: Cc1ccncc1C(=O)Nc1ccc(-c2ccc(Oc3ncccc3F)cc2Cl)cn1] | N-(5-(2-chloro-4-((3-fluoropyridin-2-yl)oxy)phenyl)pyridin-2-yl)-4-methylnicotinamide | |

| Number | Structure | Compound Name | IL-2 inhibition Jurkat/PHA/ 1% FBS IC50 (nM) |
| --- | --- | --- | --- |
| 214. | 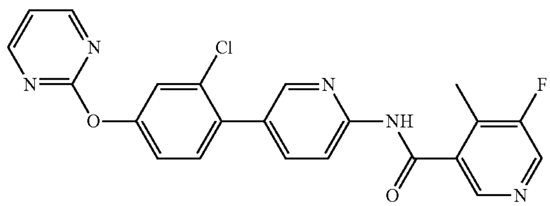 [SMILES: Cc1c(F)cncc1C(=O)Nc1ccc(-c2ccc(Oc3ncccn3)cc2Cl)cn1] | N-(5-(2-chloro-4-(pyrimidin-2-yloxy)phenyl)pyridin-2-yl)-5-fluoro-4-methylnicotinamide | |
| 215. | 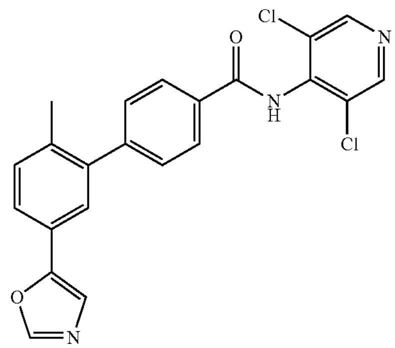 [SMILES: Cc1ccc(-c2cnco2)cc1-c1ccc(C(=O)Nc2c(Cl)cncc2Cl)cc1] | N-(3,5-dichloropyridin-4-yl)-2'-methyl-5'-(oxazol-5-yl)-[1,1'-biphenyl]-4-carboxamide | |
| 216. | 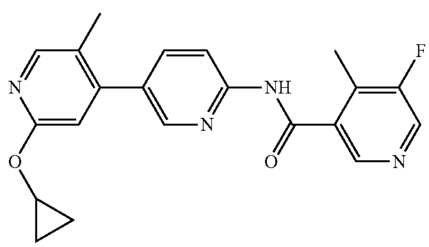 [SMILES: Cc1cnc(OC2CC2)cc1-c1ccc(NC(=O)c2cncc(F)c2C)nc1] | N-(2'-cyclopropoxy-5'-methyl-[3,4'-bipyridin]-6-yl)-5-fluoro-4-methylnicotinamide | |
| 217. | 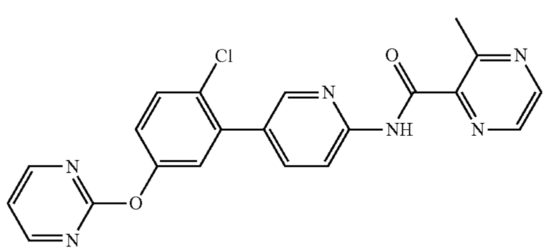 | N-(5-(2-chloro-5-(pyrimidin-2-yloxy)phenyl)pyridin-2-yl)-3-methylpyrazine-2-carboxamide | |
| 218. | 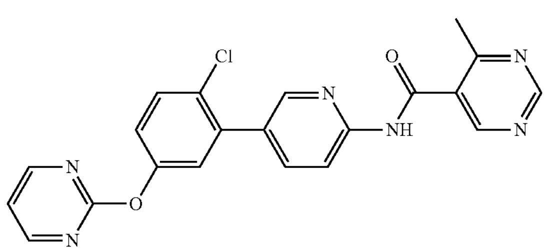 | N-(5-(2-chloro-5-(pyrimidin-2-yloxy)phenyl)pyridin-2-yl)-4-methylpyrimidine-5-carboxamide | |

TABLE 1-continued

| Number | Structure | Compound Name | IL-2 inhibition Jurkat/PHA/ 1% FBS IC50 (nM) |
|---|---|---|---|
| 219. | 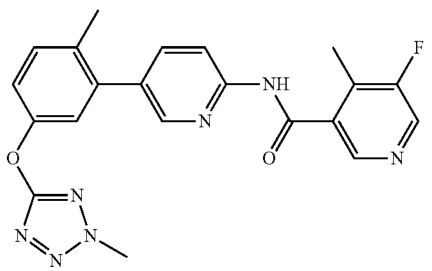 [SMILES: Cc1ccc(Oc2nnn(C)n2)cc1-c1ccc(NC(=O)c2cncc(F)c2C)nc1] | 5-fluoro-4-methyl-N-(5-(2-methyl-5-((2-methyl-2H-tetrazol-5-yl)oxy)phenyl)pyridin-2-yl)nicotinamide | |
| 220. | 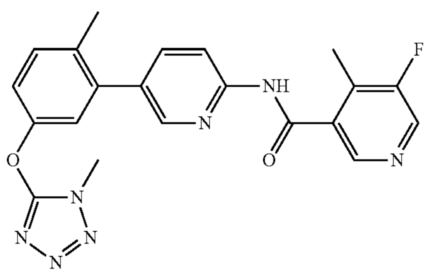 [SMILES: Cc1ccc(Oc2nnnn2C)cc1-c1ccc(NC(=O)c2cncc(F)c2C)nc1] | 5-fluoro-4-methyl-N-(5-(2-methyl-5-((1-methyl-1H-tetrazol-5-yl)oxy)phenyl)pyridin-2-yl)nicotinamide | |
| 221. | 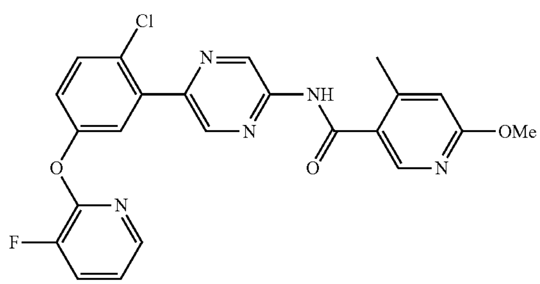 [SMILES: COc1cc(C)c(C(=O)Nc2cnc(-c3cc(Oc4ncccc4F)ccc3Cl)cn2)cn1] | N-(5-(2-chloro-5-((3-fluoropyridin-2-yl)oxy)phenyl)pyrazin-2-yl)-6-methoxy-4-methylnicotinamide | |
| 222. | 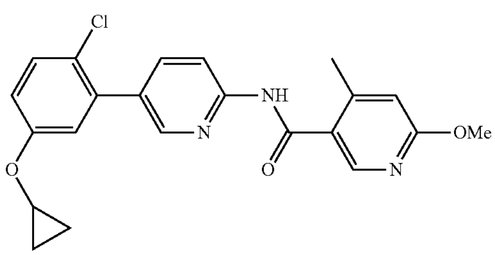 [SMILES: COc1cc(C)c(C(=O)Nc2ccc(-c3cc(OC4CC4)ccc3Cl)cn2)cn1] | N-(5-(2-chloro-5-cyclopropoxyphenyl)pyridin-2-yl)-6-methoxy-4-methylnicotinamide | |
| 223. | 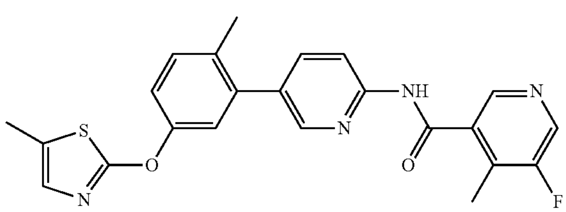 [SMILES: Cc1cnc(Oc2ccc(C)c(-c3ccc(NC(=O)c4cncc(F)c4C)nc3)c2)s1] | 5-fluoro-4-methyl-N-(5-(2-methyl-5-((5-methylthiazol-2-yl)oxy)phenyl)pyridin-2-yl)nicotinamide | |
| 224. | 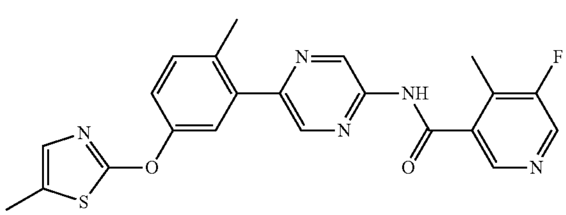 [SMILES: Cc1cnc(Oc2ccc(C)c(-c3cnc(NC(=O)c4cncc(F)c4C)cn3)c2)s1] | 5-fluoro-4-methyl-N-(5-(2-methyl-5-((5-methylthiazol-2-yl)oxy)phenyl)pyrazin-2-yl)nicotinamide | |

TABLE 1-continued

| Number | Structure | Compound Name | IL-2 inhibition Jurkat/PHA/ 1% FBS IC50 (nM) |
|---|---|---|---|
| 225. | 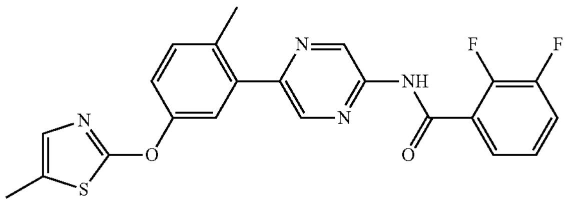 [SMILES: Cc1cnc(Oc2ccc(C)c(-c3cnc(NC(=O)c4cccc(F)c4F)cn3)c2)s1] | 2,3-difluoro-N-(5-(2-methyl-5-((5-methylthiazol-2-yl)oxy)phenyl)pyrazin-2-yl)benzamide | |
| 226. | 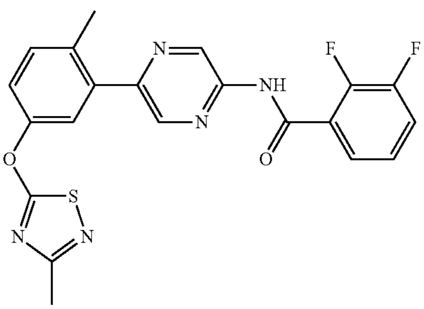 | 2,3-difluoro-N-(5-(2-methyl-5-((3-methyl-1,2,4-thiadiazol-5-yl)oxy)phenyl)pyrazin-2-yl)benzamide | |
| 227. | 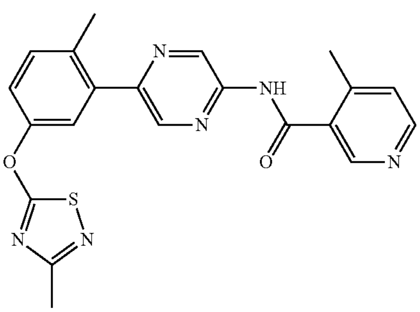 [SMILES: Cc1nsc(Oc2ccc(C)c(-c3cnc(NC(=O)c4cnccc4C)cn3)c2)n1] | 4-methyl-N-(5-(2-methyl-5-((3-methyl-1,2,4-thiadiazol-5-yl)oxy)phenyl)pyrazin-2-yl)nicotinamide | |
| 228. | 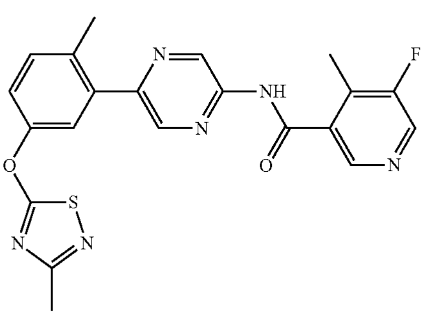 | 5-fluoro-4-methyl-N-(5-(2-methyl-5-((3-methyl-1,2,4-thiadiazol-5-yl)oxy)phenyl)pyrazin-2-yl)nicotinamide | |
| 229. | 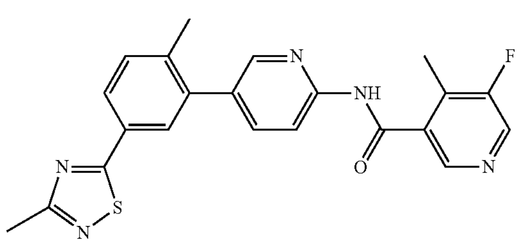 [SMILES: Cc1nsc(-c2ccc(C)c(-c3ccc(NC(=O)c4cncc(F)c4C)nc3)c2)n1] | 5-fluoro-4-methyl-N-(5-(2-methyl-5-(3-methyl-1,2,4-thiadiazol-5-yl)phenyl)pyridin-2-yl)nicotinamide | |

TABLE 1-continued

| Number | Structure | Compound Name | IL-2 inhibition Jurkat/PHA/ 1% FBS IC50 (nM) |
|---|---|---|---|
| 230. | 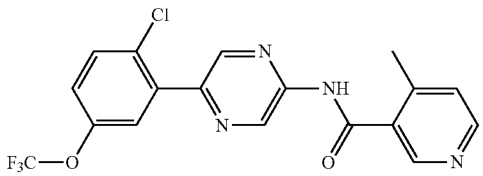 [SMILES: Cc1ccncc1C(=O)Nc1cnc(-c2cc(OC(F)(F)F)ccc2Cl)cn1] | N-(5-(2-chloro-5-(trifluoromethoxy)phenyl)pyrazin-2-yl)-4-methylnicotinamide | |
| 231. | 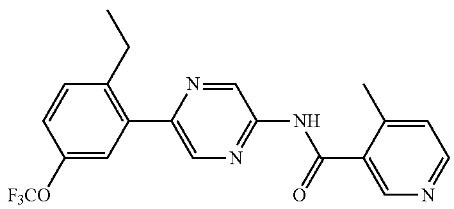 [SMILES: CCc1ccc(OC(F)(F)F)cc1-c1cnc(NC(=O)c2cnccc2C)cn1] | N-(5-(2-ethyl-5-(trifluoromethoxy)phenyl)pyrazin-2-yl)-4-methylnicotinamide | |
| 232. | 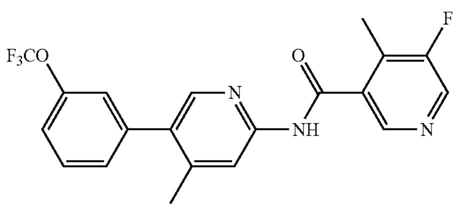 [SMILES: Cc1cc(NC(=O)c2cncc(F)c2C)ncc1-c1cccc(OC(F)(F)F)c1] | 5-fluoro-4-methyl-N-(4-methyl-5-(3-(trifluoromethoxy)phenyl)pyridin-2-yl)nicotinamide | |
| 233. | 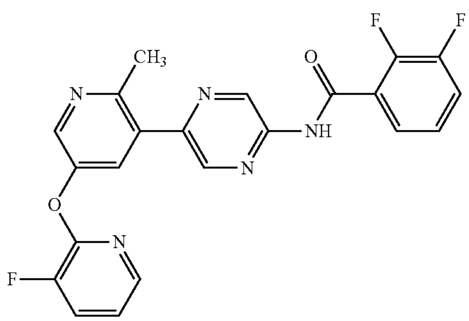 [SMILES: Cc1ncc(Oc2ncccc2F)cc1-c1cnc(NC(=O)c2cccc(F)c2F)cn1] | 2,3-difluoro-N-(5-(5-((3-fluoropyridin-2-yl)oxy)-2-methylpyridin-3-yl)pyrazin-2-yl)benzamide | |
| 234. | 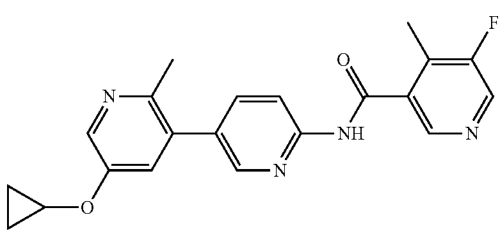 [SMILES: Cc1ncc(OC2CC2)cc1-c1ccc(NC(=O)c2cncc(F)c2C)nc1] | N-(5'-cyclopropoxy-2'-methyl-[3,3'-bipyridin]-6-yl)-5-fluoro-4-methylnicotinamide | |
| 235. | 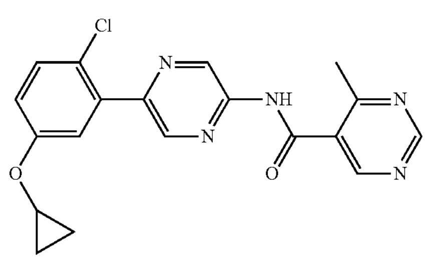 [SMILES: Cc1ncncc1C(=O)Nc1cnc(-c2cc(OC3CC3)ccc2Cl)cn1] | N-(5-(2-chloro-5-cyclopropoxyphenyl)pyrazin-2-yl)-4-methylpyrimidine-5-carboxamide | |

TABLE 1-continued

| Number | Structure | Compound Name | IL-2 inhibition Jurkat/PHA/ 1% FBS IC50 (nM) |
|---|---|---|---|
| 236. | 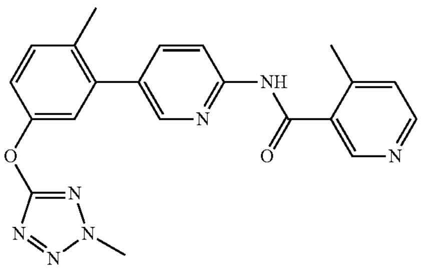 [SMILES: Cc1ccncc1C(=O)Nc1ccc(-c2cc(Oc3nnn(C)n3)ccc2C)cn1] | 4-methyl-N-(5-(2-methyl-5-((2-methyl-2H-tetrazol-5-yl)oxy)phenyl)pyridin-2-yl)nicotinamide | |
| 237. | 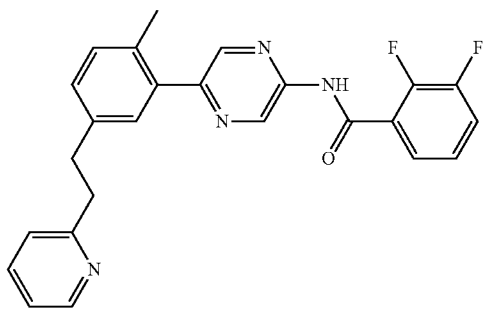 [SMILES: Cc1ccc(CCc2ccccn2)cc1-c1cnc(NC(=O)c2cccc(F)c2F)cn1] | 2,3-difluoro-N-(5-(2-methyl-5-(2-(pyridin-2-yl)ethyl)phenyl)pyrazin-2-yl)benzamide | |
| 238. | 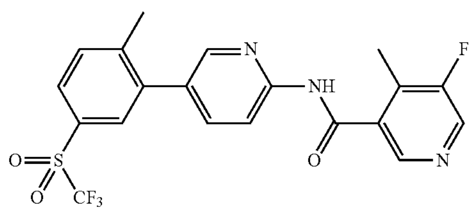 | 5-fluoro-4-methyl-N-(5-(2-methyl-5-((trifluoromethyl)sulfonyl)phenyl)pyridin-2-yl)nicotinamide | |
| 239. | 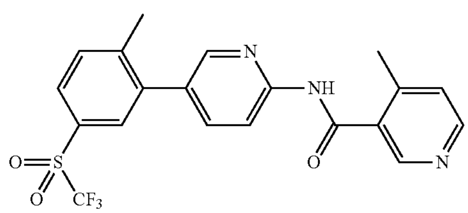 [SMILES: Cc1ccncc1C(=O)Nc1ccc(-c2cc(S(=O)(=O)C(F)(F)F)ccc2C)cn1] | 4-methyl-N-(5-(2-methyl-5-((trifluoromethyl)sulfonyl)phenyl)pyridin-2-yl)nicotinamide | |
| 240. | 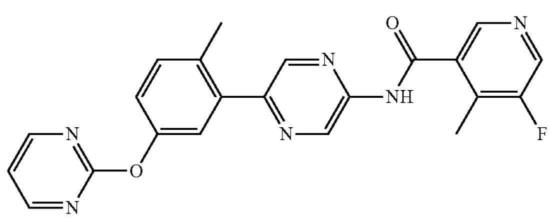 [SMILES: Cc1ccc(Oc2ncccn2)cc1-c1cnc(NC(=O)c2cncc(F)c2C)cn1] | 5-fluoro-4-methyl-N-(5-(2-methyl-5-(pyrimidin-2-yloxy)phenyl)pyrazin-2-yl)nicotinamide | |
| 241. | 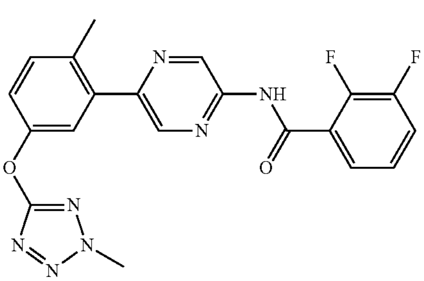 [SMILES: Cc1ccc(Oc2nnn(C)n2)cc1-c1cnc(NC(=O)c2cccc(F)c2F)cn1] | 2,3-difluoro-N-(5-(2-methyl-5-((2-methyl-2H-tetrazol-5-yl)oxy)phenyl)pyrazin-2-yl)benzamide | |

TABLE 1-continued

| Number | Structure | Compound Name | IL-2 inhibition Jurkat/PHA/ 1% FBS IC50 (nM) |
|---|---|---|---|
| 242. | 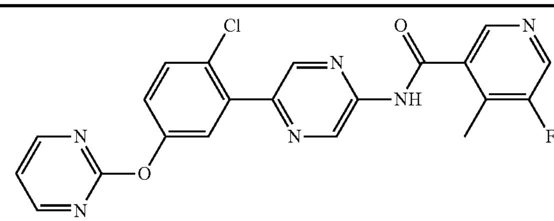 | N-(5-(2-chloro-5-(pyrimidin-2-yloxy)phenyl)pyrazin-2-yl)-5-fluoro-4-methylnicotinamide | |

Mechanism of Action

Activation of T-lymphocytes in response to an antigen is dependent on calcium ion oscillations. Calcium ion oscillations in T-lymphocytes are triggered through stimulation of the T-cell antigen receptor, and involve calcium ion influx through the stored-operated $Ca^{2+}$-release-activated $Ca^{2+}$ (CRAC) channel. Although a detailed electrophysiological profile of the channel exists, the molecular structure of the CRAC ion channel had not been identified till the recent identification of the pore-forming unit, named Orai1/CRACM1 (Vig, Science (2006), 312:1220-3, Feske, Nature (2006), 441:179-85. Thus, inhibition of CRAC ion channels can be measured by measuring inhibition of the $I_{CRAC}$ current. Calcium ion oscillations in T-cells have been implicated in the activation of several transcription factors (e.g., NFAT, Oct/Oap and NFκB) which are critical for T-cell activation (Lewis, Biochemical Society Transactions (2003), 31:925-929, the entire teachings of which are incorporated herein by reference). Without wishing to be bound by any theory, it is believed that because the compounds of the invention inhibit the activity of CRAG ion channels, they inhibit immune cell activation.

Methods of Treatment and Prevention

A effective amount of a compound of the invention or a pharmaceutically acceptable salt, solvate, clathrate, and prodrug thereof, or a pharmaceutical composition comprising a compound of the invention, or a pharmaceutically acceptable salt, solvate, clathrate, and prodrug thereof, is administered to a patient in need of immunosuppression or in need of treatment or prevention of an inflammatory condition, an immune disorder, or an allergic disorder. Such patients may be treatment naïve or may experience partial or no response to conventional therapies.

Responsiveness of a particular inflammatory condition, immune disorder, or allergic disorder in a subject can be measured directly (e.g., measuring blood levels of inflammatory cytokines (such as IL-2, IL-4, IL-5, IL-13, GM-CSF, TNFα, IFN-γ and the like) after administration of a compound of this invention), or can be inferred based on an understanding of disease etiology and progression. The compounds of the invention, or pharmaceutically acceptable salts, solvates, clathrates, and prodrugs thereof can be assayed in vitro or in vivo, for the desired therapeutic or prophylactic activity, prior to use in humans. For example, known animal models of inflammatory conditions, immune disorders, or allergic disorders can be used to demonstrate the safety and efficacy of compounds of this invention.

Pharmaceutical Compositions and Dosage Forms

Pharmaceutical compositions and dosage forms of the invention comprise one or more active ingredients in relative amounts and formulated in such a way that a given pharmaceutical composition or dosage form can be used for immunosuppression or to treat or prevent inflammatory conditions, immune disorders, and allergic disorders. Preferred pharmaceutical compositions and dosage forms comprise a compound of the invention, or a pharmaceutically acceptable prodrug, salt, solvate, or clathrate thereof, optionally in combination with one or more additional active agents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmacopeia (USP)SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) *Drug Stability: Principles & Practice,* 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient including a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention include a compound of the invention, or a pharmaceutically acceptable salt, solvate, clathrate, or prodrug thereof in an amount of from about 1 mg to about 1000 mg, preferably in an amount of from about 50 mg to about 500 mg, and most preferably in an amount of from about 75 mg to about 350 mg. The typical total daily dosage of a compound of the invention, or a pharmaceutically acceptable salt, solvate, clathrate, or prodrug thereof can range from about 1 mg to about 5000 mg per day, preferably in an amount from about 50 mg to about 1500 mg per day, more preferably from about 75 mg to about 1000 mg per day. It is within the skill of the art to determine the appropriate dose and dosage form for a given patient.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences* (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences* (1980 & 1990) 16th and 18th eds., Mack Publishing, Easton Pa. and *Introduction to Pharmaceutical Dosage Forms* (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences* (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Combination Therapy

The methods for immunosuppression or for treating or preventing inflammatory conditions and immune disorders in a patient in need thereof can further comprise administering to the patient being administered a compound of this invention, an effective amount of one or more other active agents. Such active agents may include those used conventionally for immunosuppression or for inflammatory conditions or immune disorders. These other active agents may also be those that provide other benefits when administered in combination with the compounds of this invention. For example, other therapeutic agents may include, without limitation, steroids, non-steroidal anti-inflammatory agents, antihistamines, analgesics, immunosuppressive agents and suitable mixtures thereof. In such combination therapy treatment, both the compounds of this invention and the other drug agent(s) are administered to a subject (e.g., humans, male or female) by conventional methods. The agents may be administered in a single dosage form or in separate dosage forms. Effective amounts of the other therapeutic agents and dosage forms are well known to those skilled in the art. It is well within the skilled artisan's purview to determine the other therapeutic agent's optimal effective-amount range.

In one embodiment of the invention where another therapeutic agent is administered to a subject, the effective amount of the compound of this invention is less than its effective amount when the other therapeutic agent is not administered. In another embodiment, the effective amount of the conventional agent is less than its effective amount when the compound of this invention is not administered. In this way, undesired side effects associated with high doses of either agent may be minimized. Other potential advantages (including without limitation improved dosing regimens and/or reduced drug cost) will be apparent to those of skill in the art.

In one embodiment relating to autoimmune and inflammatory conditions, the other therapeutic agent may be a steroid or a non-steroidal anti-inflammatory agent. Particularly useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, "Analgesic-Antipyretic and Antiinflammatory Agents and Drugs Employed in the Treatment of Gout" in *Goodman & Gilman's The Pharmacological Basis of Therapeutics* 617-57 (Perry B. Molinhoff and Raymond W. Ruddon eds., 9$^{th}$ ed 1996) and Glen R. Hanson, "Analgesic, Antipyretic and Anti-Inflammatory Drugs" in *Remington: The Science and Practice of Pharmacy Vol II* 1196-1221 (A. R. Gennaro ed. 19th ed. 1995) which are hereby incorporated by reference in their entireties.

Of particular relevance to allergic disorders, the other therapeutic agent may be an antihistamine. Useful antihistamines include, but are not limited to, loratadine, cetirizine, fexofenadine, desloratadine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine, and mixtures thereof. For a more detailed description of antihistamines, see Goodman & Gilman's *The Pharmacological Basis of Therapeutics* (2001) 651-57, 10th ed).

Immunosuppressive agents include glucocorticoids, corticosteroids (such as Prednisone or Solumedrol), T-cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, busulfan, and cyclophosphamide), folic acid antagonists (such as aminopterin and methotrexate), antibiotics (such as rapamycin, actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins).

The foregoing and other useful combination therapies will be understood and appreciated by those of skill in the art. Potential advantages of such combination therapies include a different efficacy profile, the ability to use less of each of the individual active ingredients to minimize toxic side effects, synergistic improvements in efficacy, improved ease of administration or use and/or reduced overall expense of compound preparation or formulation.

Other Embodiments

The compounds of this invention may be used as research tools (for example, as a positive control for evaluating other potential CRAG inhibitors, or IL-2, IL-4, IL-5, IL-13, GM-CSF, TNFα, and/or IFN-γ inhibitors). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Experimental Rationale

Without wishing to be bound by theory, it is believed that the compounds of this invention inhibit CRAG ion channels, thereby inhibiting production of IL-2 and other key cytokines involved with inflammatory and immune responses. The examples that follow demonstrate these properties.

Synthesis of Exemplary Compounds of the Invention

Representative Synthetic Procedures

Example 1

Synthesis of N-(5-(2-chloro-5-(1-methyl-1H-pyrazol-4-yl)phenyl)pyrazin-2-yl)-4-methylnicotinamide (compound 53)

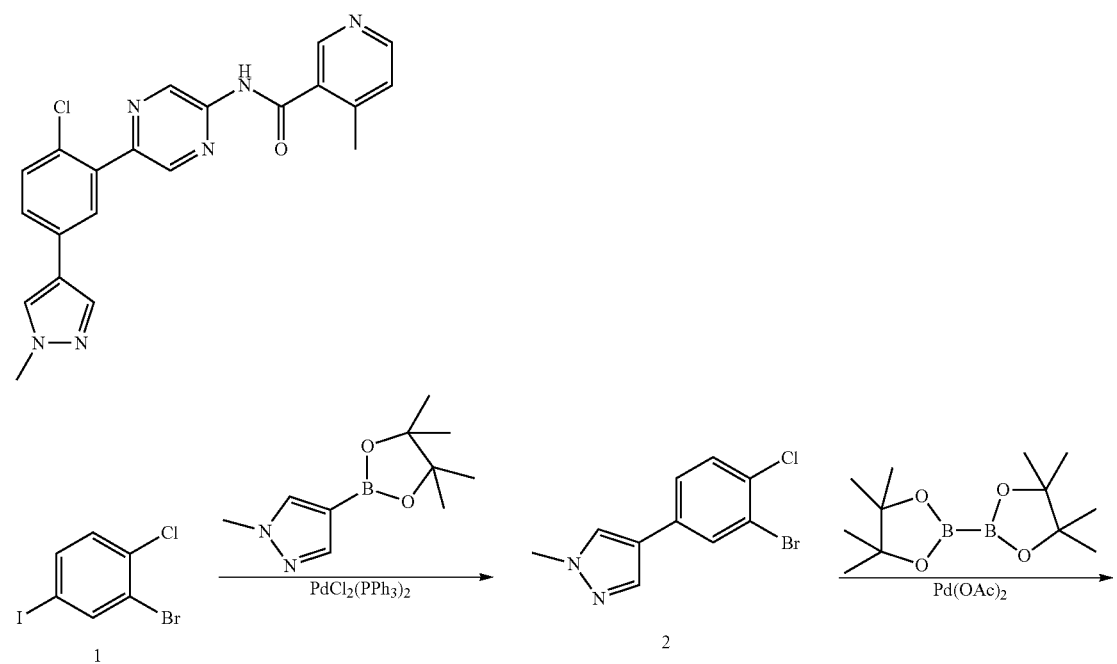

-continued

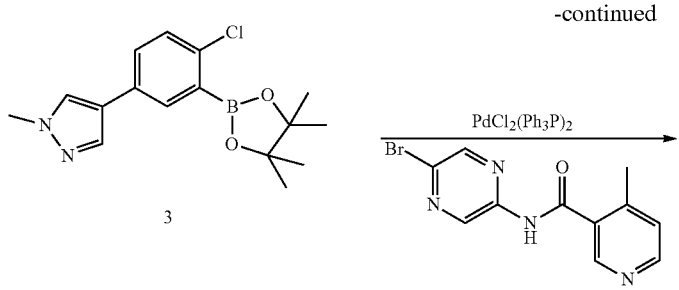

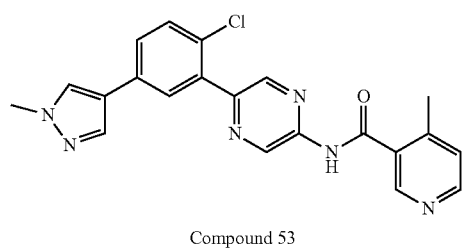

Compound 53

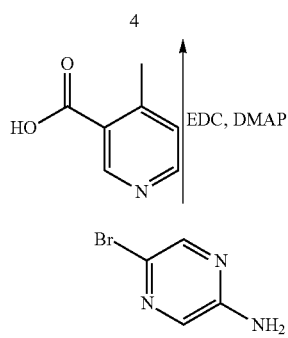

4

4-(3-bromo-4-chlorophenyl)-1-methyl-1H-pyrazole (2)

To a stirred solution of 1 (1 mmol, 1 equivalent (eq.)) and 1-methyl-4-tetramethyldioxaborolanyl-pyrazole (1 eq.) in dioxane/water (10:1) (3 mL) was added $PdCl_2(Ph_3P)_2$ (0.1 eq.), $K_2CO_3$ (2 eq.). The mixture was heated in microwave at 90° C. for 4 hr. The crude product was then extracted with DCM, and purified with column chromatography on silica gel to provide pure 4-(3-bromo-4-chlorophenyl)-1-methyl-1H-pyrazole (2) in 80% yield.

4-(4-chloro-3-(4,4,5,5-tetramethyl-1,3,2-dioxaborolan-2-yl)phenyl)-1-methyl-1H-pyrazole (3)

A suspension of 2 (1 eq.), bis(pinacolato)diboron (1.25 eq.), KOAc (1 eq.), and $Pd(OAc)_2$ (0.2 eq.) in DMF (2 mL) was heated to 86° C. for 3-4 hr. The reaction mixture was then allowed to cool to room temperature (rt) before being quenched with water, extracted with DCM, and filtered with a small silica gel funnel. The crude product, 4-(4-chloro-3-(4,4,5,5-tetramethyl-1,3,2-dioxaborolan-2-yl)phenyl)-1-methyl-1H-pyrazole (3), was generated in 60-80% yield and was used directly for the next step without further purification.

N-(5-bromopyrazin-2-yl)-4-methylnicotinamide (4)

To a mixture of 2-amino-5-bromopyrazine (1 eq.), 4-methylnicotinic acid (1.2 eq.), and DMAP (1 eq.) in DCM was added EDC (1.25 eq.). The resultant suspension was stirred at rt for 4 days. The precipitations were collected and washed with DCM to afford N-(5-bromopyrazin-2-yl)-4-methylnicotinamide (4) in 30% yield.

N-(5-(2-chloro-5-(1-methyl-1H-pyrazol-4-yl)phenyl)pyrazin-2-yl)-4-methylnicotinamide (compound 53)

To a stirred solution of 3 (2 eq.) and 4 (1.5 eq.) in dioxane/water (10:1) (5 mL) in a microwave tube was added $PdCl_2(Ph_3P)_2$ (0.2 eq.) and $K_2CO_3$ (2 eq.). The mixture was heated in a microwave reactor at 110° C. for 2 hr. Upon finishing and allowing the reaction mixture to cool to rt, the crude product was extracted with DCM (3×5 mL). The desired product, N-(5-(2-chloro-5-(1-methyl-1H-pyrazol-4-yl)phenyl)pyrazin-2-yl)-4-methylnicotinamide was obtained in 60% yield after column chromatography in silica gel. H-NMR (CDCl$_3$) δ 9.78 (s, $^1$H), 8.82 (s, $^1$H), 8.78 (s, $^1$H), 8.72-7.25 (m, 8H), 3.99 (s, $^3$H), 2.61 (s, $^3$H); ESMS calc'd for $C_{217}ClN_6O$: 404.12. Found: 405.1 (M+H)$^+$.

Example 2

Compounds Synthesized According to the Synthetic Procedure of Example 1

The following compounds were synthesized in a similar manner according to the procedure described above in Example 1.

N-(5-(2-chloro-5-(1-methyl-1H-pyrazol-4-yl)phenyl)pyridin-2-yl)-5-cyano-4-methylnicotinamide (compound 122)

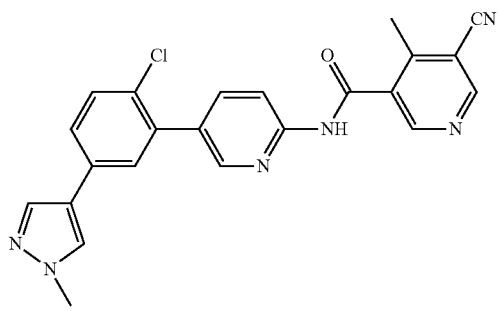 [SMILES: Cc1c(C#N)cncc1C(=O)Nc1ccc(-c2cc(-c3cnn(C)c3)ccc2Cl)cn1]

$^1$H-NMR (DMSO-d$_6$) δ 10.5 (br, $^1$H), 9.05 (s, $^1$H), 8.94 (s, $^1$H), 8.5 (d, $^1$H, J=2), 8.3 (d, $^1$H, J=8.4), 8.24 (s, $^1$H), 8.0 (dd, $^1$H, J$_1$=2.4, J$_2$=8.4), 7.96 (s, $^1$H), 7.7 (d, $^1$H, J=2), 7.5-7.6 (m,

2H), 3.88 (s, ³H), 2.62 (s, ³H) ppm; ESMS calc'd for C₂₁₇ClN₆O: 428.1. found: 429.1 (M+H⁺).

N-(5-(2-chloro-5-(1-methyl-¹H-pyrazol-4-yl)phenyl)pyridin-2-yl)-5-fluoro-4-methylnicotinamide (compound 115)

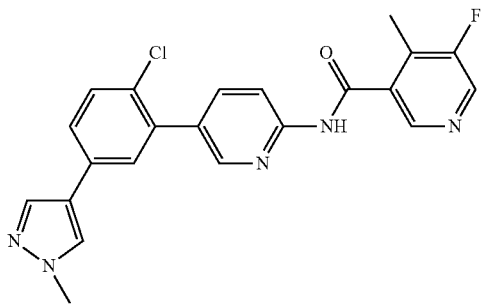 [SMILES: Cc1c(F)cncc1C(=O)Nc1ccc(-c2cc(-c3cnn(C)c3)ccc2Cl)cn1]

¹H-NMR (CDCl₃) δ 8.69 (s, ¹H), 8.63 (s, ¹H), 8.48 (s, ¹H), 8.4 (d, ¹H, J=8.4), 8.3 (d, ¹H, J=2.4), 7.9 (dd, ¹H, J₁=2.4, J₂=8.4), 7.77 (s, ¹H), 7.65 (s, ¹H), 7.4 (m, ³H), 3.96 (s, ³H), 2.51 (s, ³H) ppm; ESMS calc'd for C₂₂H₁₇ClFN₅O: 421.1. found: 422.1 (M+H⁺).

5-bromo-N-(5-(2-chloro-5-(1-methyl-¹H-pyrazol-4-yl)phenyl)pyridin-2-yl)-4-methylnicotinamide (compound 116)

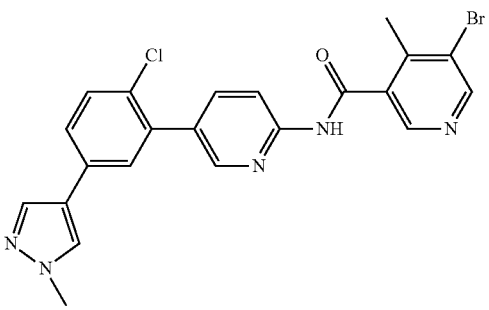 [SMILES: Cc1c(Br)cncc1C(=O)Nc1ccc(-c2cc(-c3cnn(C)c3)ccc2Cl)cn1]

ESMS calc'd for C₂₂H₁₇BrClN₅O: 481.0. found: 482.0 (M+H⁺).

N-(5-(2-chloro-5-(1-methyl-¹H-pyrazol-4-yl)phenyl)pyridin-2-yl)-4,5-dimethylnicotinamide (compound 117)

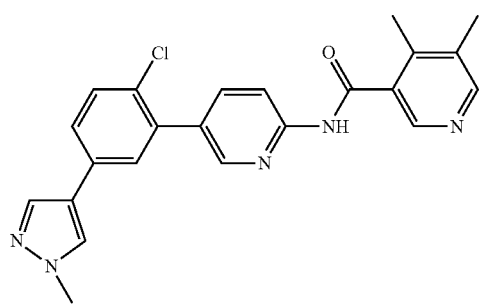 [SMILES: Cc1cncc(C(=O)Nc2ccc(-c3cc(-c4cnn(C)c4)ccc3Cl)cn2)c1C]

¹H-NMR (CDCl₃) δ 9.38 (s, ¹H), 8.60 (s, ¹H), 8.4 (d, ¹H, J=8.8), 8.34 (s, ¹H), 7.9 (d, ¹H, J=1.6), 7.9 (dd, ¹H, J₁=2.4, J₂=8.8), 7.78 (s, ¹H), 7.6-7.7 (m, ¹H), 7.4-7.5 (m, 2H), 7.4 (d, ¹H, J=2), 3.96 (s, ³H), 2.42 (s, ³H), 2.24 (s, ³H) ppm; ESMS calc'd for C₂₃H₂₀ClN₅O: 417.1. found: 418.1 (M+H⁺).

5-chloro-N-(5-(2-chloro-5-(1-methyl-¹H-pyrazol-4-yl)phenyl)pyrazin-2-yl)-4-methylnicotinamide (compound 114)

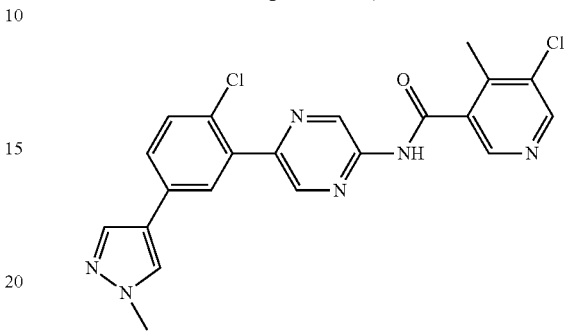

¹H-NMR (CDCl₃) δ 9.77 (s, ¹H), 8.76 (s, ¹H), 8.6-8.7 (m, ³H), 7.78 (s, ¹H), 7.74 (s, ¹H), 7.67 (s, ¹H), 7.48 (s, 2H), 3.95 (s, ³H), 2.60 (s, ³H) ppm; ESMS calc'd for C₂₁H₁₆Cl₂N₆O: 438.1. found: 439.0 (M+H⁺).

5-bromo-N-(5-(2-chloro-5-(1-methyl-¹H-pyrazol-4-yl)phenyl)pyrazin-2-yl)-4-methylnicotinamide (compound 121)

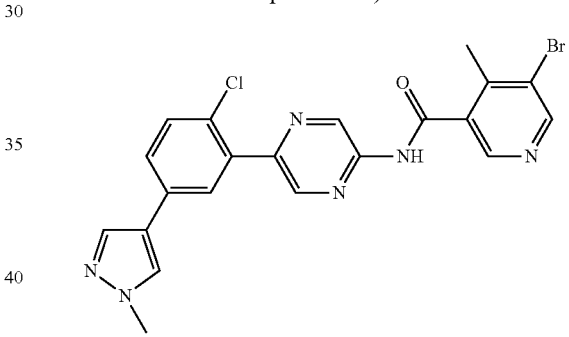

¹H-NMR (CDCl₃) δ 9.77 (s, ¹H), 8.79 (s, ¹H), 8.6-8.7 (m, ³H), 7.78 (s, ¹H), 7.74 (s, ¹H), 7.66 (s, ¹H), 7.48 (s, 2H), 3.95 (s, ³H), 2.62 (s, ³H) ppm; ESMS calc'd for C₂₁H₁₆BrClN₆O: 482.0. found: 483.0 (M+H⁺).

N-(5-(2-chloro-5-(1-methyl-¹H-pyrazol-4-yl)phenyl)pyrazin-2-yl)-5-ethyl-4-methylnicotinamide (compound 131)

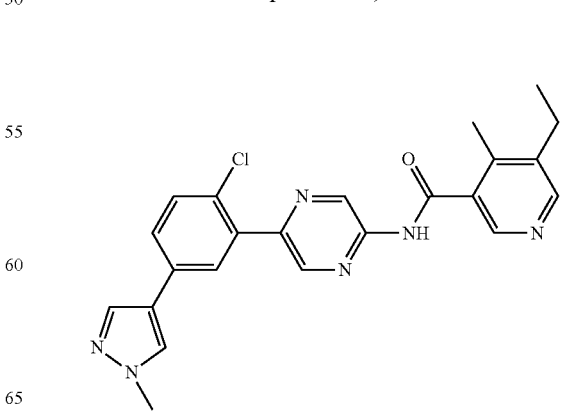

¹H-NMR (CDCl₃) δ 9.80 (s, ¹H), 8.68 (s, ¹H), 8.64 (s, ¹H), 8.5 (m, 2H), 7.79 (s, ¹H), 7.75 (s, ¹H), 7.67 (s, ¹H), 7.48 (s, 2H), 3.96 (s, ³H), 2.7 (q, 2H, J=7.6), 2.51 (s, ³H), 1.3 (t, ³H, J=7.6) ppm; ESMS calc'd for C₂₃H₂₁ClN₆O: 432.2. found: 433.1 (M+H⁺).

N-(5-(2-chloro-5-(1-methyl-¹H-pyrazol-4-yl)phenyl)pyrazin-2-yl)-4-methylnicotinamide hydrochloride (compound 142)

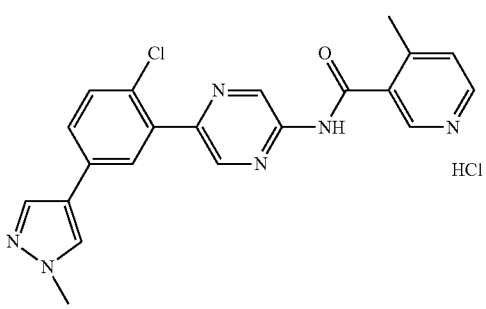 [SMILES: Cc1ccncc1C(=O)Nc1cnc(-c2cc(-c3cnn(C)c3)ccc2Cl)cn1 ; Cl]

¹H-NMR (DMSO-d₆) δ 11.8 (br, ¹H), 9.56 (s, ¹H), 9.13 (s, ¹H), 8.90 (s, ¹H), 8.80 (s, ¹H), 8.0 (d, ¹H, J=6), 7.76 (s, ¹H), 7.8 (d, ¹H, J=2.4), 7.7 (dd, ¹H, J₁=2.4, J₂=8.4), 7.61 (s, ¹H), 7.59 (s, ¹H), 3.87 (s, ³H), 2.69 (s, ³H) ppm; ESMS calc'd for C₂₁H₁₇ClN₆O: 440.1. found: 405.1 (M-Cl⁻).

N-(5-(2-chloro-5-(1-methyl-¹H-pyrazol-4-yl)phenyl)pyrazin-2-yl)-4,5-dimethylnicotinamide (compound 129)

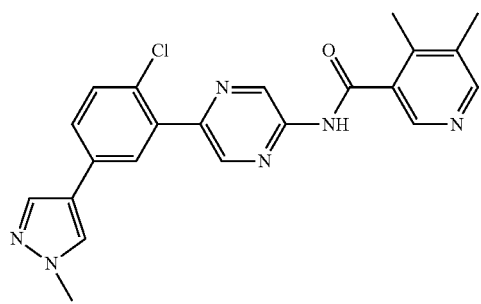 [SMILES: Cc1cncc(C(=O)Nc2cnc(-c3cc(-c4cnn(C)c4)ccc3Cl)cn2)c1C]

¹H-NMR (CDCl₃) δ 9.79 (s, ¹H), 8.6-8.7 (m, ³H), 8.47 (s, ¹H), 7.78 (s, ¹H), 7.74 (s, ¹H), 7.67 (s, ¹H), 7.48 (s, 2H), 3.96 (s, ³H), 2.46 (s, ³H), 2.33 (s, ³H) ppm; ESMS calc'd for C₂₂H₁₉ClN₆O: 418.1. found: 419.1 (M+H⁺).

N-(5-(2-chloro-5-(1-methyl-¹H-pyrazol-4-yl)phenyl)pyrazin-2-yl)-5-cyano-4-methylnicotinamide (compound 132)

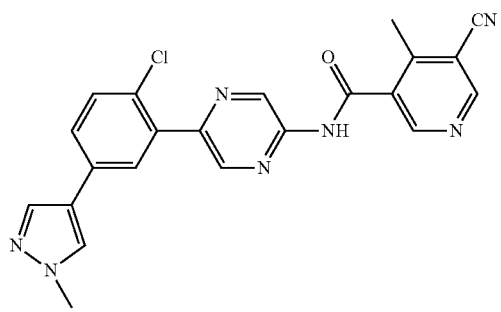

¹H-NMR (CDCl₃) δ 9.76 (s, ¹H), 8.97 (s, ¹H), 8.93 (s, ¹H), 8.75 (s, ¹H), 8.40 (br, ¹H), 7.78 (s, ¹H), 7.7 (d, ¹H, J=1.6), 7.67 (s, ¹H), 7.49 (s, 2H), 3.96 (s, ³H), 2.80 (s, ³H) ppm; ESMS calc'd for C₂₂H₁₆ClN₇O: 429.1. found: 430.1 (M+H⁺).

N-(5-(2-ethyl-5-(1-methyl-¹H-pyrazol-4-yl)phenyl)pyridin-2-yl)-4-methylnicotinamide (compound 7)

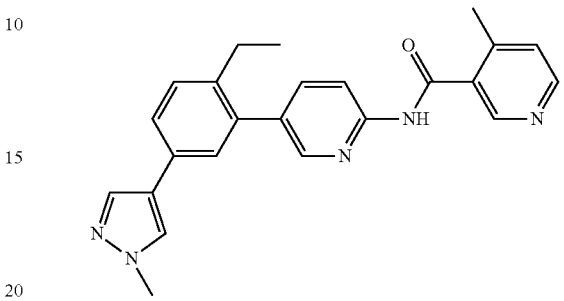

¹H-NMR (CDCl₃) δ 9.26 (s, ¹H), 8.78 (s, ¹H), 8.5 (d, ¹H, J=4.8), 8.4 (d, ¹H, J=8.8), 8.0 (d, ¹H, J=2.4), 7.7 (m, 2H), 7.63 (s, ¹H), 7.4 (dd, ¹H, J₁=2, J₂=8), 7.3 (d, ¹H, J=8), 7.2 (d, ¹H, J=2), 7.2 (d, ¹H, J=3.8), 3.95 (s, ³H), 2.6 (q, 2H, J=7.6), 2.56 (s, ³H), 1.1 (t, ³H, J=7.6) ppm; ESMS calc'd for C₂₄H₂₃N₅O: 397.2. found: 398.2 (M+H⁺).

N-(5-(2-ethyl-5-(1-methyl-¹H-pyrazol-4-yl)phenyl)pyrazin-2-yl)-4-methylnicotinamide (compound 8)

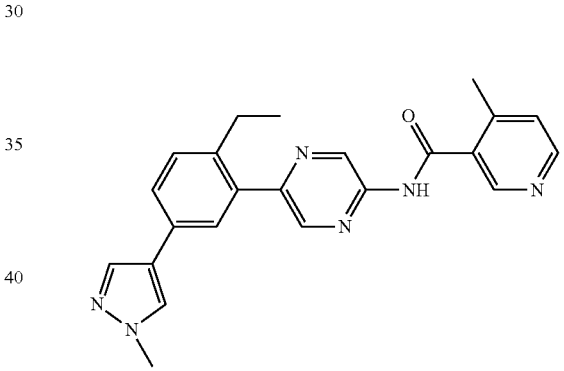

¹H-NMR (CDCl₃) δ 9.75 (s, ¹H), 8.82 (s, ¹H), 8.6 (d, ¹H, J=5.2), 8.57 (br, ¹H), 8.4 (d, ¹H, J=1.6), 7.77 (s, ¹H), 7.63 (s, ¹H), 7.5 (m, 2H), 7.3 (d, ¹H, J=8), 7.2 (m, ¹H), 3.94 (s, ³H), 2.7 (q, 2H, J=7.6), 2.60 (s, ³H), 1.2 (t, ³H, J=7.6) ppm; ESMS calc'd for C₂₃H₂₂N₆O: 398.2. found: 399.2 (M+H⁺).

5-fluoro-4-methyl-N-(5-(5-(1-methyl-¹H-pyrazol-4-yl)-2-(trifluoromethoxy)phenyl)pyrazin-2-yl)nicotinamide (compound 22)

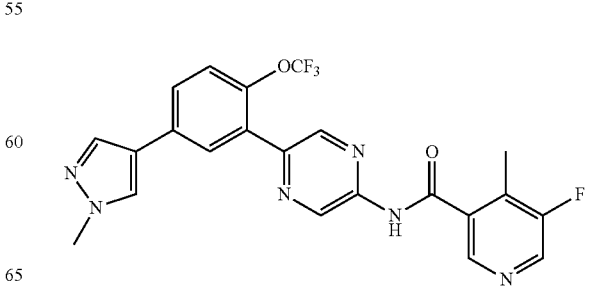

¹H-NMR (CDCl₃) δ 9.77 (s, ¹H), 8.73 (s, ¹H), 8.67 (s, ¹H), 8.52 (s, ¹H), 8.28 (s, ¹H), 8.01 (s, ¹H), 7.81 (s, ¹H), 7.66 (s, ¹H), 7.62-7.34 (m, 2H), 3.98 (s, ³H), 2.52 (s, ³H); ESMS calc'd for C₂₂H₁₆F₄N₆O₂: 472.13. Found: 473.2 (M+H)⁺.

N-(5-(2-chloro-5-(1-methyl-¹H-pyrazol-4-yl)phenyl)pyrazin-2-yl)-5-fluoro-4-methylnicotinamide (compound 123)

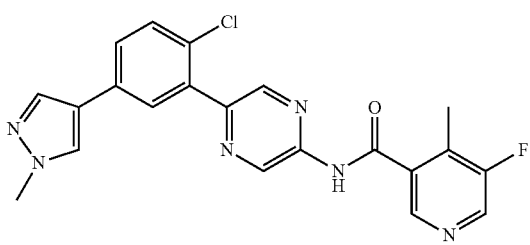 [SMILES: Cc1c(F)cncc1C(=O)Nc1cnc(-c2cc(-c3cnn(C)c3)ccc2Cl)cn1]

¹H-NMR (CDCl₃.₁) δ 9.76 (s, ¹H), 8.76 (s, ¹H), 8.66 (s, ¹H), 8.52 (s, ¹H), 8.42 (s, ¹H), 7.81-7.22 (m, 5H), 3.97 (s, ³H), 2.53 (s, ³H); ESMS calc'd for C₂₁H₁₆ClFN₆O: 422.11. Found: 423.1 (M+H)⁺.

N-(5-(2-chloro-5-(3-fluoropyridin-4-yl)phenyl)pyrazin-2-yl)-4-methylnicotinamide (compound 24)

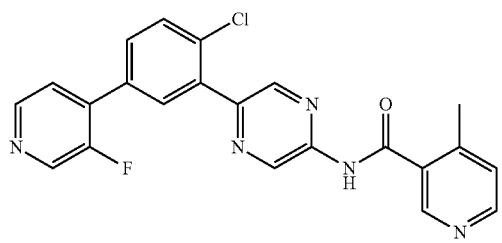 [SMILES: Cc1ccncc1C(=O)Nc1cnc(-c2cc(-c3ccncc3F)ccc2Cl)cn1]

¹H-NMR (CDCl₃) δ 9.81 (s, ¹H), 8.81 (s, ¹H), 8.76 (s, ¹H), 8.70-7.40 (m, 9H), 2.63 (s, ³H); ESMS calc'd for C₂₂H₁₅ClFN₅O: 419.09. Found: 420.1 (M+H)⁺.

5-fluoro-N-(5-(2-methoxy-5-(1-methyl-¹H-pyrazol-4-yl)phenyl)pyrazin-2-yl)-4-methylnicotinamide (compound 6)

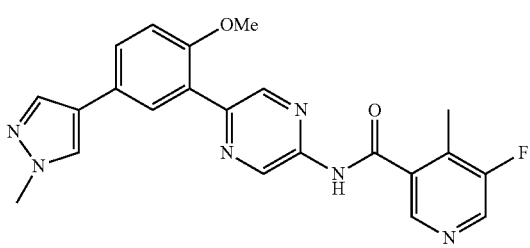 [SMILES: COc1ccc(-c2cnn(C)c2)cc1-c1cnc(NC(=O)c2cncc(F)c2C)cn1]

¹H-NMR (CDCl₃) δ 9.72 (s, ¹H), 8.87 (s, ¹H), 8.68 (s, ¹H), 8.59-7.01 (m, 7H), 3.98 (s, ³H), 3.91 (s, ³H), 2.52 (s, ³H); ESMS calc'd for C₂₀H₁₉FN₆O₂: 418.16. Found: 419.2 (M+H)⁺.

N-(5-(2-chloro-5-(1,5-dimethyl-¹H-pyrazol-4-yl)phenyl)pyrazin-2-yl)-4-methylnicotinamide (compound 80)

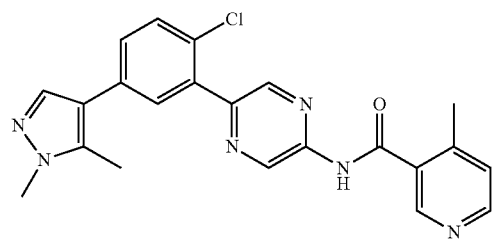 [SMILES: Cc1ccncc1C(=O)Nc1cnc(-c2cc(-c3cnn(C)c3C)ccc2Cl)cn1]

¹H-NMR (CDCl₃) δ 9.80 (s, ¹H), 8.79 (s, ¹H), 8.72-7.07 (m, 8H), 3.82 (s, ³H), 2.62 (s, ³H), 2.41 (s, ³H); ESMS calc'd for C₂₂H₁₉ClN₆O: 418.13. Found: 419.1 (M+H)⁺.

N-(5-(2-chloro-5-(¹H-pyrazol-4-yl)phenyl)pyrazin-2-yl)-4-methylnicotinamide (compound 1)

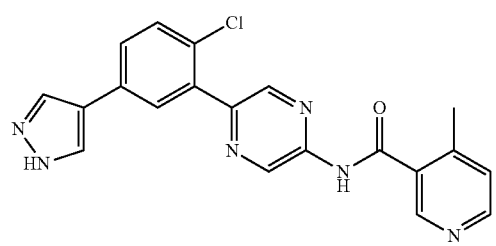 [SMILES: Cc1ccncc1C(=O)Nc1cnc(-c2cc(-c3cn[nH]c3)ccc2Cl)cn1]

¹H-NMR (CDCl₃) δ 10.36 (s, ¹H), 9.68 (s, ¹H), 8.73 (s, ¹H), 8.19-7.42 (m, 9H), 2.81 (s, ³H); ESMS calc'd for C₂₀H₁₅ClN₆O: 390.10. Found: 391.1 (M+H)⁺.

4-methyl-N-(5-(2-methyl-5-(1-methyl-¹H-pyrazol-4-yl)phenyl)pyrazin-2-yl)nicotinamide (compound 52)

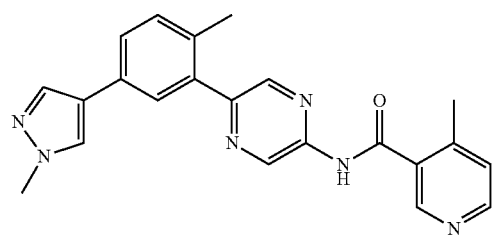 [SMILES: Cc1ccncc1C(=O)Nc1cnc(-c2cc(-c3cnn(C)c3)ccc2C)cn1]

¹H-NMR (CDCl₃) δ 9.76 (s, ¹H), 8.82 (s, ¹H), 8.68-7.23 (m, 9H), 3.99 (s, ³H), 2.62 (s, ³H), 2.42 (3, ³H); ESMS calc'd for C₂₂H₂₀IN₆O: 384.17. Found: 385.2 (M+H)⁺.

153

N-(5-(2-ethoxy-5-(1-methyl-¹H-pyrazol-4-yl)phenyl)pyrazin-2-yl)-4-methylnicotinamide (compound 2)

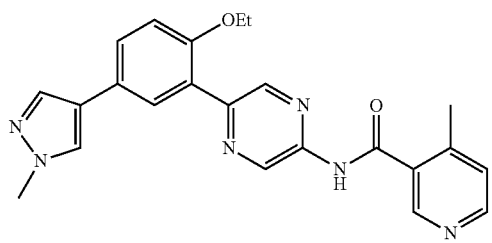

¹H-NMR (CDCl₃) δ 9.75 (s, ¹H), 9.02 (s, ¹H), 8.82 (s, ¹H), 8.63-6.97 (m, 8H), 4.09 (m, 2H), 3.98 (s, ³H), 2.61 (s, ³H), 1.20 (m, ³H); ESMS calc'd for C₂₃H₂₂N₆O₂: 414.18. Found: 415.2 (M+H)⁺.

N-(5-(2-cyclopropoxy-5-(1-methyl-¹H-pyrazol-4-yl)phenyl)pyrazin-2-yl)-4-methylnicotinamide (compound 86)

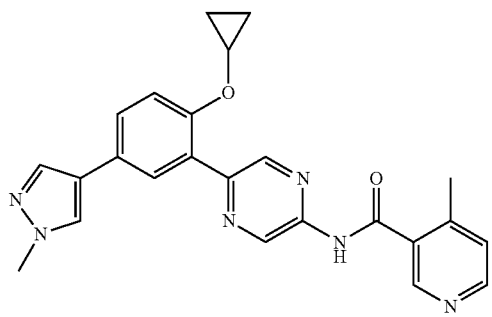 [SMILES: Cc1ccncc1C(=O)Nc1cnc(-c2cc(-c3cnn(C)c3)ccc2OC2CC2)cn1]

¹H-NMR (CDCl₃) δ 9.76 (s, ¹H), 9.01 (s, ¹H), 8.83-6.97 (m, 9H), 3.98 (s, ³H), 3.81 (m, ¹H), 2.61 (s, ³H), 1.27-0.78 (m, 4H); ESMS calc'd for C₂₄H₂₂N₆O₂: 426.18. Found: 427.2 (M+H)⁺.

N-(5-(2-chloro-5-(1-methyl-¹H-pyrazol-4-yl)phenyl)pyridin-2-yl)-4-methylnicotinamide (compound 59)

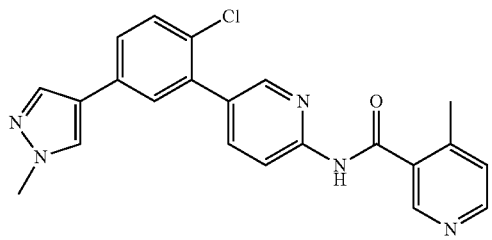

¹H-NMR (CDCl₃) δ 8.80 (s, ¹H), 8.62-7.22 (m, 10H), 3.98 (s, ³H), 2.59 (s, ³H); ESMS calc'd for C₂₂H₁₈ClN₅O: 403.12. Found: 404.1 (M+H)⁺.

154

4-methyl-N-(5-(2-methyl-5-(1-methyl-¹H-pyrazol-4-yl)phenyl)pyridin-2-yl)nicotinamide (compound 67)

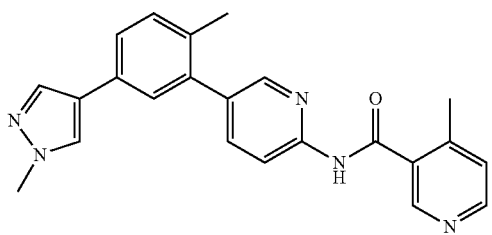 [SMILES: Cc1ccncc1C(=O)Nc1ccc(-c2cc(-c3cnn(C)c3)ccc2C)cn1]

¹H-NMR (CDCl₃) δ 8.81 (s, ¹H), 8.63-7.22 (m, 10H), 3.98 (s, ³H), 2.60 (s, ³H), 2.28 (s, ³H); ESMS calc'd for C₂₃H₂₁N₅O: 383.17. Found: 384.2 (M+H)⁺.

N-(5-(2-isopropoxy-5-(1-methyl-¹H-pyrazol-4-yl)phenyl)pyrazin-2-yl)-4-methylnicotinamide (compound 19)

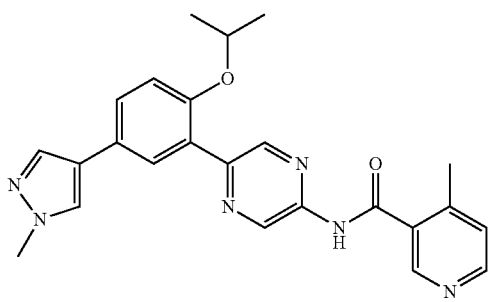 [SMILES: Cc1ccncc1C(=O)Nc1cnc(-c2cc(-c3cnn(C)c3)ccc2OC(C)C)cn1]

¹H-NMR (CDCl₃) δ 9.74 (s, ¹H), 9.07 (s, ¹H), 8.82 (s, ¹H), 8.63-6.95 (m, 8H), 4.62 (m, 2H), 3.97 (s, ³H), 2.61 (s, ³H), 1.40 (d, 6H); ESMS calc'd for C₂₄H₂₄N₆O₂: 428.20. Found: 429.2 (M+H)⁺.

N-(5-(2-methoxy-5-(1-methyl-¹H-pyrazol-4-yl)phenyl)pyrazin-2-yl)-4-methylnicotinamide (compound 110)

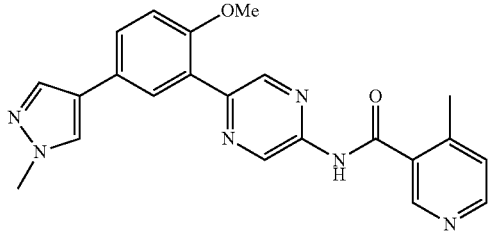 [SMILES: COc1ccc(-c2cnn(C)c2)cc1-c1cnc(NC(=O)c2cnccc2C)cn1]

¹H-NMR (CDCl₃) δ 9.74 (s, ¹H), 8.91 (s, ¹H), 8.80-7.01 (m, 8H), 3.99 (s, ³H), 3.97 (s, ³H), 2.61 (s, ³H); ESMS calc'd for C₂₂H₂₀N₆O₂: 400.16. Found: 401.2 (M+H)⁺.

4-methyl-N-(5-(2-methyl-5-(1-methyl-1H-pyrazol-3-yl)phenyl)pyrazin-2-yl)nicotinamide (compound 101)

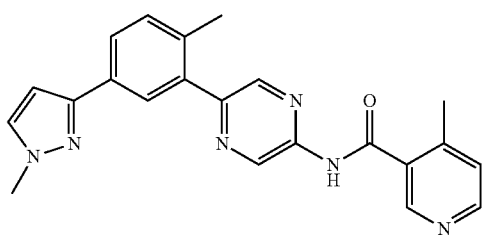 [SMILES: Cc1ccncc1C(=O)Nc1cnc(-c2cc(-c3ccn(C)n3)ccc2C)cn1]

$^1$H-NMR (CDCl$_3$) δ 9.76 (s, $^1$H), 8.82 (s, $^1$H), 8.62-7.25 (m, 8H), 6.58 (s, $^1$H), 3.99 (s, $^3$H), 2.62 (s, $^3$H), 2.41 (s, $^3$H); ESMS calc'd for C$_{22}$H$_{20}$N$_6$O: 384.17. Found: 385.2 (M+H)$^+$.

Example 3

Synthesis of N-(5-(5-ethyl-2-(5-methylisoxazol-3-yl)thiazol-4-yl)pyridin-2-yl)-4-methylnicotinamide (compound 77)

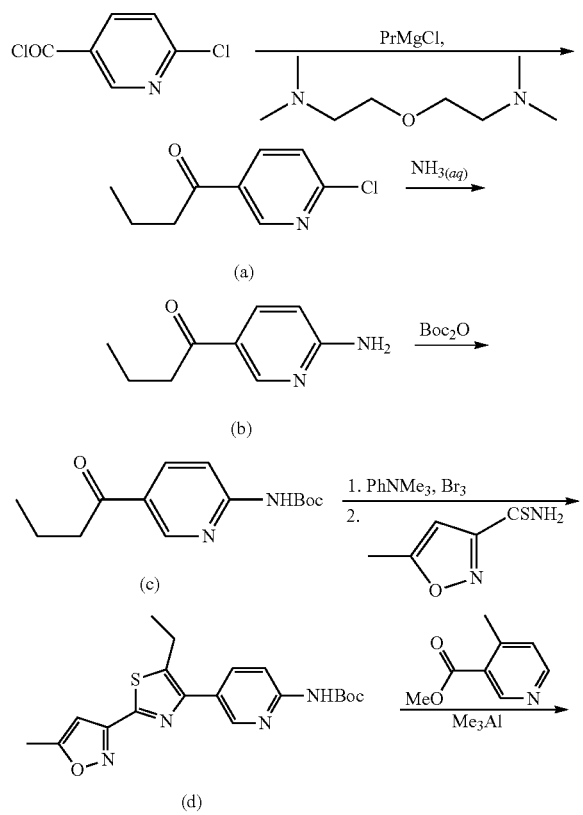

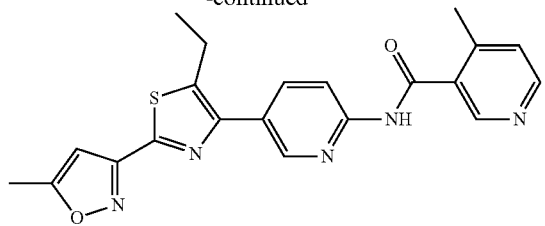

Compound 77

1-(6-chloropyridin-3-yl)butan-1-one (a)

A mixture of propyl-magnesium chloride (42 mmol, 21 mL×2.0 M in THF) and 2,2'-oxybis(N,N-dimethylethanamine) (42 mmol) in THF (40 mL) was cooled to 0° C. 6-chloronicotinoyl chloride (28 mmol) was added in one portion and the mixture was kept at 0° C. for 40 min. The mixture was poured over water (200 mL) and extracted with DCM (200 mL). The organic layer was dried and concentrated to give 1-(6-chloropyridin-3-yl)butan-1-one (a, 5.1 g) as a white crude product.

1-(6-aminopyridin-3-yl)butan-1-one (b)

3.5 g of the above ketone (a) was placed in a microwave reactor, and 20 mL of NH$_3$ (aq. conc.) was added and the reactor was sealed and heated at 140° C. for 2 h. The reaction mixture was poured over water (50 mL), filtered, and rinsed with EtOH/water (1:1) to give 1-(6-aminopyridin-3-yl)butan-1-one (b, 3.5 g) as a white crude product.

Tert-butyl (5-butyrylpyridin-2-yl)carbamate (c)

The above amine (b) (2.0 g) was dissolved in THF (50 mL) and Boc$_2$O (1.5 eq.), and DMAP (0.1 eq.) was added, and the mixture was stirred at rt for 2 h. The mixture was concentrated and distributed in DCM/water (50 mL each), and DCM layer passed through a plug of silica gel to give a crude product (2.4 g), which was triturated in EA/Hexanes (10 mL/40 mL) to give tert-butyl (5-butyrylpyridin-2-yl)carbamate (c, 1.5 g) as a pure white powder.

5-(5-ethyl-2-(5-methylisoxazol-3-yl)thiazol-4-yl)pyridin-2-amine (d)

5.0 g of (c) was treated with trimethylphenylamine tribromide (20.0 mmol) in boiling THF (80 mL) at 80° C. for 4 h. The mixture was cooled down, passed through a plug of silica gel, and eluted with EA/hexanes (1:1) to give crude bromide intermediate as orange solids (6.0 g), which was heated with 5-methylisoxazole-3-carbothioamide (16 mmol) in EtOH (100 mL)/AcOH (1 mL) for 6 h. The reaction mixture was concentrated, neutralized with NaHCO$_3$ and extracted with DCM. The organic layer was passed through silica gel plug and eluted from MeOH/DCM (1:9), followed by recrystallization of the resulted crude product gave 5-(5-ethyl-2-(5-methylisoxazol-3-yl)thiazol-4-yl)pyridin-2-amine (d, 2.3 g) as white solids.

N-(5-(5-ethyl-2-(5-methylisoxazol-3-yl)thiazol-4-yl)pyridin-2-yl)-4-methylnicotinamide (compound 77)

To a mixture of 80 mg of the above amine (d) and methyl 4-methylnicotinate (40 mg) in toluene (5 mL) was added a solution of Me₃Al (0.8 mmol, 0.4 mL×2.0 M), and the resulting solution was heated at 110° C. for 4 h. The mixture was diluted with DCM (5 mL)/1N NaOH (5 mL), and organic layer was purified by column to give compound 77 as white solids (10 mg). ¹H-NMR (CDCl₃) δ 8.81 (s, ¹H), 8.5 (m, 2H), 8.4 (d, ¹H, J=9), 8.3 (br, ¹H), 8.1 (dd, ¹H, J₁=9, J₂=2), 7.3 (m, ¹H), 6.61 (s, ¹H), 3.0 (q, 2H, J=8), 2.59 (s, ³H), 2.52 (s, ³H), 1.4 (t, ³H, J=8) ppm; ESMS calc'd for C₂₁H₁₉N₅O₂S: 405.1. found: 406.2 (M+H⁺).

Example 4

Compounds Synthesized According to the Synthetic Procedure of Example 3

The following compounds were synthesized in a similar manner according to the procedure described above in Example 3.

N-(5-(5-ethyl-2-(5-methylisoxazol-3-yl)thiazol-4-yl)pyridin-2-yl)-5-fluoro-4-methylnicotinamide (compound 70)

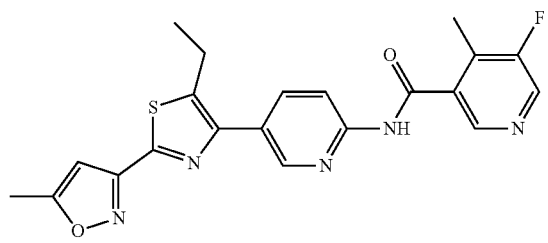 [SMILES: CCc1sc(-c2cc(C)on2)nc1-c1ccc(NC(=O)c2cncc(F)c2C)nc1]

¹H-NMR (CDCl₃) δ 9.12 (s, ¹H), 8.61 (s, ¹H), 8.4-8.5 (m, ³H), 8.1 (dd, ¹H, J₁=8.4, J₂=2.4), 6.61 (s, ¹H), 3.0 (q, 2H, J=7.6), 2.52 (s, ³H), 2.5 (d, ³H, J=2), 1.4 (t, ³H, J=7.6) ppm; ESMS calc'd for C₂₁H₁₈FN₅O₂S: 423.1. found: 424.3 (M+H⁺).

5-bromo-N-(5-(5-ethyl-2-(5-methylisoxazol-3-yl)thiazol-4-yl)pyridin-2-yl)-4-methylnicotinamide (compound 73)

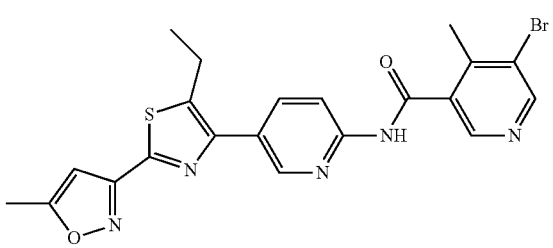 [SMILES: CCc1sc(-c2cc(C)on2)nc1-c1ccc(NC(=O)c2cncc(Br)c2C)nc1]

¹H-NMR (CDCl₃) δ 8.77 (s, ¹H), 8.67 (s, ¹H), 8.56 (s, ¹H), 8.49 (br, ¹H), 8.4 (d, ¹H, J=9), 8.1 (dd, ¹H, J₁=8.4, J₂=1.6), 6.60 (s, ¹H), 3.0 (q, 2H, J=7.6), 2.60 (s, ³H), 2.52 (s, ³H), 1.4 (t, ³H, J=7.6) ppm; ESMS calc'd for C₂₁H₁₈BrN₅O₂S: 483.0. found: 484.0 (M+H⁺).

5-chloro-N-(5-(5-ethyl-2-(5-methylisoxazol-3-yl)thiazol-4-yl)pyridin-2-yl)-4-methylnicotinamide (compound 72)

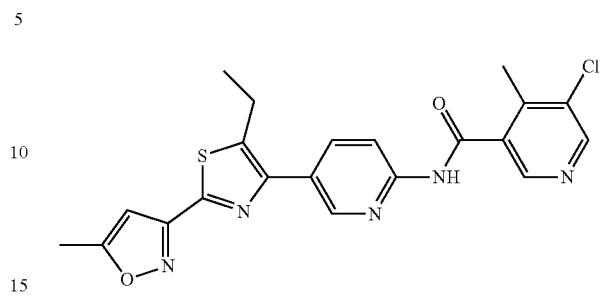

¹H-NMR (CDCl₃) δ 8.66 (s, ¹H), 8.61 (s, ¹H), 8.4 (d, ¹H, J=8.4), 8.37 (br, ¹H), 8.1 (dd, ¹H, J₁=8.4, J₂=2.4), 6.60 (s, ¹H), 3.0 (q, 2H, J=7.6), 2.59 (s, ³H), 2.52 (s, ³H), 1.4 (t, ³H, J=7.6) ppm; ESMS calc'd for C₂₁H₁₈ClN₅O₂S: 439.1. found: 440.1 (M+H⁺).

N-(5-(5-ethyl-2-(5-methylisoxazol-3-yl)thiazol-4-yl)pyridin-2-yl)-4,5-dimethylnicotinamide (compound 98)

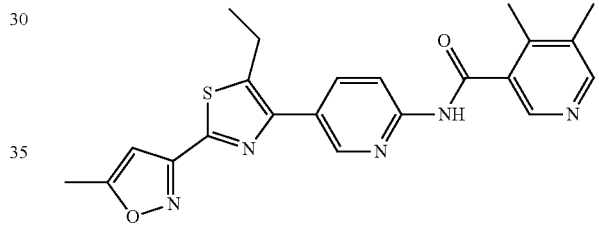

¹H-NMR (CDCl₃) δ 9.14 (s, ¹H), 8.59 (s, ¹H), 8.5 (d, ¹H, J=8.8), 8.38 (s, ¹H), 8.3 (d, ¹H, J=2), 8.1 (dd, ¹H, J₁=8.8, J₂=2.4), 6.60 (s, ¹H), 3.0 (q, 2H, J=7.6), 2.52 (s, ³H), 2.41 (s, ³H), 2.26 (s, ³H), 1.4 (t, ³H, J=7.6) ppm; ESMS calc'd for C₂₂H₂₁N₅O₂S: 419.1. found: 420.1 (M+H⁺).

N-(5-(5-ethyl-2-(5-methylisoxazol-3-yl)thiazol-4-yl)pyridin-2-yl)-4-methyl-5-nitronicotinamide (compound 94)

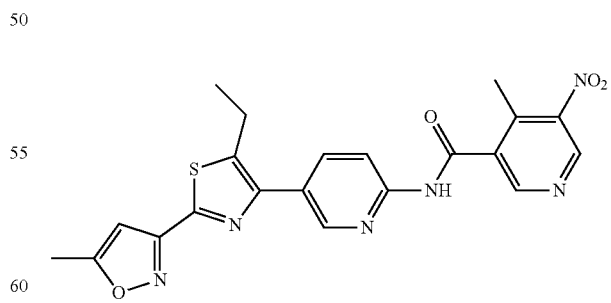

¹H-NMR (CDCl₃) δ 9.14 (s, ¹H), 8.93 (s, ¹H), 8.63 (s, ¹H), 8.6 (d, ¹H, J=2), 8.4 (d, ¹H, J=8.4), 8.1 (dd, ¹H, J₁=8.4, J₂=2.0), 6.60 (s, ¹H), 3.0 (q, 2H, J=7.6), 2.72 (s, ³H), 2.52 (s, ³H), 1.4 (t, ³H, J=7.6) ppm; ESMS calc'd for C₂₁H₁₈N₆O₄S: 450.1. found: 451.2 (M+H⁺).

5-ethyl-N-(5-(5-ethyl-2-(5-methylisoxazol-3-yl)thiazol-4-yl)pyridin-2-yl)-4-methylnicotinamide (compound 108)

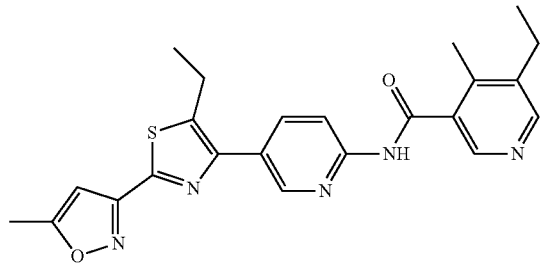 [SMILES: CCc1cncc(C(=O)Nc2ccc(-c3nc(-c4cc(C)on4)sc3CC)cn2)c1C]

$^1$H-NMR (CDCl$_3$) δ 8.61 (s, 2H), 8.5 (d, $^1$H, J=2.0), 8.4 (m, 2H), 8.1 (dd, $^1$H, J$_1$=8.4, J$_2$=2.0), 6.61 (s, $^1$H), 3.0 (q, 2H, J=7.6), 2.7 (q, 2H, J=7.6), 2.52 (s, $^3$H), 2.48 (s, $^3$H), 1.4 (t, $^3$H, J=7.6), 1.2 (t, $^3$H, J=7.6) ppm; ESMS calc'd for C$_{23}$H$_{23}$N$_5$O$_2$S: 433.2. found: 434.1 (M+H$^+$).

N-(5-(5-ethyl-2-(3-methylisoxazol-5-yl)thiazol-4-yl)pyridin-2-yl)-5-fluoro-4-methylnicotinamide (compound 109)

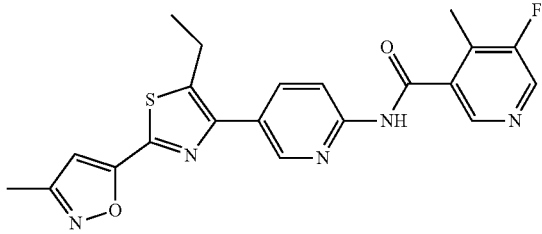 [SMILES: CCc1sc(-c2cc(C)no2)nc1-c1ccc(NC(=O)c2cncc(F)c2C)nc1]

ESMS calc'd for C$_{21}$H$_{18}$FN$_5$O$_2$S: 423.1. found: 424.1 (M+H').

N-(5-(5-ethyl-2-(isoxazol-3-yl)thiazol-4-yl)pyridin-2-yl)-5-fluoro-4-methylnicotinamide (compound 112)

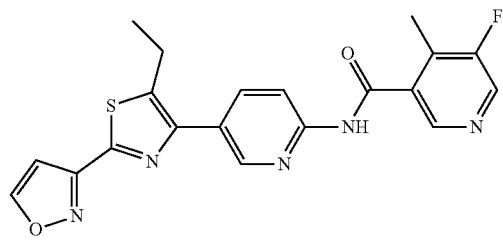 [SMILES: CCc1sc(-c2ccon2)nc1-c1ccc(NC(=O)c2cncc(F)c2C)nc1]

$^1$H-NMR (CDCl$_3$) δ 8.65 (s, 2H), 8.5 (d, 2H, J=6.0), 8.4 (d, $^1$H, J=8.8), 8.3 (m, $^1$H), 8.1 (dd, $^1$H, J$_1$=8.4, J$_2$=2.4), 6.98 (s, $^1$H), 3.0 (q, 2H, J=7.6), 2.51 (s, $^3$H), 1.4 (t, $^3$H, J=7.6) ppm; ESMS calc'd for C$_{20}$H$_{16}$FN$_3$O$_2$S: 409.1. found: 410.1 (M+H$^+$).

5-fluoro-4-methyl-N-(5-(5-methyl-2-(5-methylisoxazol-3-yl)thiazol-4-yl)pyridin-2-yl)nicotinamide (compound 99)

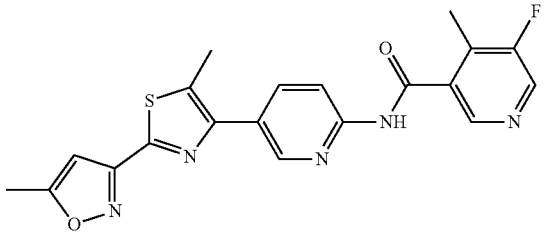 [SMILES: Cc1cc(-c2nc(-c3ccc(NC(=O)c4cncc(F)c4C)nc3)c(C)s2)no1]

$^1$H-NMR (CDCl$_3$) δ 8.6 (m, $^3$H), 8.51 (s, $^1$H), 8.4 (d, $^1$H, J=8.8), 8.1 (dd, $^1$H, J$_1$=8.8, J$_2$=2.4), 6.61 (s, $^1$H), 2.65 (s, $^3$H), 2.52 (s, $^3$H), 2.51 (s, $^3$H) ppm; ESMS calc'd for C$_{20}$H$_{16}$FN$_5$O$_2$S: 409.1. found: 410.2 (M+H$^+$).

5-cyano-N-(5-(5-ethyl-2-(5-methylisoxazol-3-yl)thiazol-4-yl)pyridin-2-yl)-4-methylnicotinamide (compound 76)

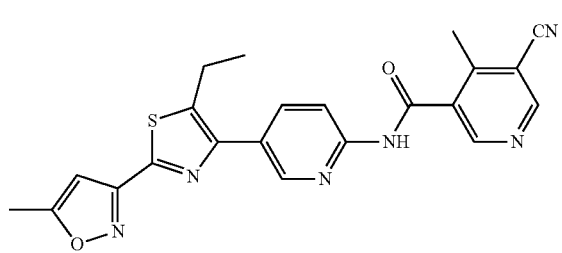 [SMILES: CCc1sc(-c2cc(C)on2)nc1-c1ccc(NC(=O)c2cncc(C#N)c2C)nc1]

$^1$H-NMR (CDCl$_3$) δ 8.92 (s, $^1$H), 8.86 (s, $^1$H), 8.69 (s, $^1$H), 8.5 (m, 2H), 8.1 (dd, $^1$H, J$_1$=8.8, J$_2$=2.4), 6.62 (s, $^1$H), 3.0 (q, 2H, J=7.6), 2.75 (s, $^3$H), 2.52 (s, $^3$H), 1.4 (t, $^3$H, J=7.6) ppm; ESMS calc'd for C$_{22}$H$_{18}$N$_6$O$_2$S: 430.1. found: 431.4 (M+H$^+$).

Example 5

Synthesis of N-(5-(2-chloro-5-cyclopropoxyphenyl)pyrazin-2-yl)-4-methylnicotinamide (compound 62)

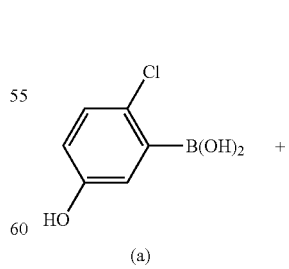

(a)

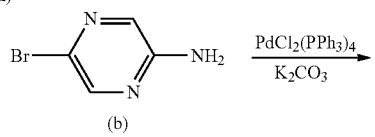

(b)

-continued

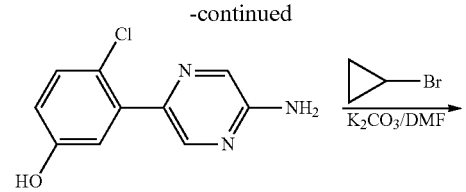

(c)

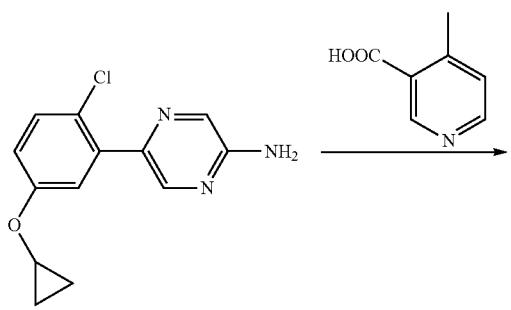

(d)

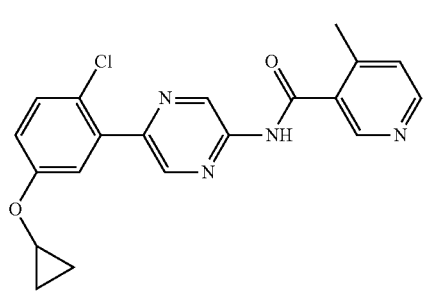

Compound 62

A mixture of 20 mmol each of (2-chloro-5-hydroxyphenyl)boronic acid (a) and 5-bromopyrazin-2-amine (b) and 1 mmol PdCl$_2$(PPh$_3$)$_2$ in dioxane (100 mL)/water (10 mL) was heated at 100° C. for 6 h. The organic layer was dried, concentrated, and crystallized from 50% EA/Hexanes to give product (c) as a grayish solid (17 mmol, 85% yield).

5 mmol of the above solid (c) and 7.5 mmol of cyclopropyl bromide was dissolved in DMF (20 mL), K$_2$CO$_3$ (6.5 mmol) was added, and mixture was heated in microwave reactor at 180° C. for 10 h. The reaction mixture was quenched with water (100 mL) and extracted with EA (2×100 mL). The combined EA layer was concentrated and purified by column to give product (d) as a brownish solid (2.5 mmol, 50% yield).

The free amine (d) (2 mmol) was treated with 3 mmol each of 4-methylnicotinic acid, TEA, and T3P in EA (50 mL), and the mixture was refluxed for 16 h. The reaction mixture was washed with water (2×50 mL) and purified by column to give compound 62 as a white solid (0.65 mmol, 33% yield). $^1$H-NMR (DMSO-d$_6$) δ 11.54 (br, $^1$H), 9.56 (d, $^1$H, J=1.6), 8.78 (d, $^1$H, J=1.6), 8.75 (s, $^1$H), 8.6 (d, $^1$H, J=4.8), 7.6 (d, $^1$H, J=8.8), 7.4 (d, $^1$H, J=4.8), 7.3 (d, $^1$H, J=2.4), 7.2 (dd, $^1$H, J$_1$=8.8, J$_2$=2.4), 4.0 (m, $^1$H), 2.50 (s, $^3$H), 0.9 (m, 4H) ppm; ESMS calc'd for C$_{20}$H$_{17}$ClN$_4$O$_2$: 380.1. found: 381.1 (M+H$^+$).

Example 6

Compounds Synthesized According to the Synthetic Procedure of Example 5

The following compounds were synthesized in a similar manner according to the procedure described above in Example 5.

N-(5-(2-chloro-5-cyclopropoxyphenyl)pyrazin-2-yl)-4-methylnicotinamide hydrochloride (compound 87)

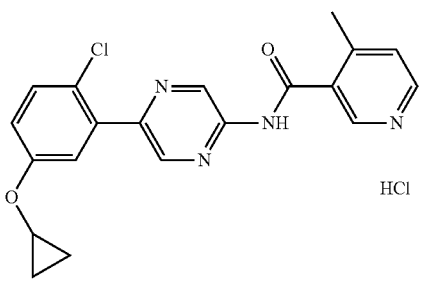 [SMILES: Cc1ccncc1C(=O)Nc1cnc(-c2cc(OC3CC3)ccc2Cl)cn1 ; Cl]

To a solution of N-(5-(2-chloro-5-cyclopropoxyphenyl)pyrazin-2-yl)-4-methylnicotinamide (compound 62) (0.20 g) in EtOAc (20 mL) was added HCl in ether (0.5 mL×2M). The solution was stirred at rt for 30 min. The mixture was then concentrated and triturated with 30% EtOAc/Hexanes to give 0.11 g of the product, N-(5-(2-chloro-5-cyclopropoxyphenyl)pyrazin-2-yl)-4-methylnicotinamide (compound 87). $^1$H-NMR (DMSO-d$_6$) δ 11.62 (br, $^1$H), 9.56 (d, $^1$H, J=5.6 Hz), 8.90 (s, $^1$H), 8.76 (d, $^1$H, J=1.6), 8.7 (m, $^1$H), 8.6 (d, $^1$H, J=4.8), 7.6 (d, $^1$H, J=5.2), 7.5 (d, $^1$H, J=8.8), 7.3 (d, $^1$H, J=3.2), 7.2 (dd, $^1$H, J$_1$=8.8, J$_2$=3.2), 4.0 (m, $^1$H), 2.56 (s, $^3$H), 0.9 (m, 4H) ppm; ESMS calc'd for C$_{20}$H$_{17}$ClN$_4$O$_2$: 416.1. found: 381.1 (M-Cl$^-$).

N-(5-(2-chloro-5-cyclopropoxyphenyl)pyridin-2-yl)-4-methylnicotinamide (compound 75)

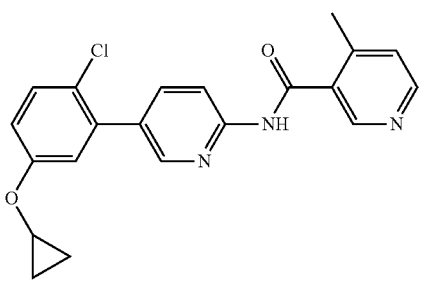 [SMILES: Cc1ccncc1C(=O)Nc1ccc(-c2cc(OC3CC3)ccc2Cl)cn1]

$^1$H-NMR (CDCl$_3$) δ 9.24 (s, $^1$H), 8.76 (s, $^1$H), 8.5 (d, $^1$H, J=4.8), 8.4 (d, $^1$H, J=8.8), 8.1 (d, $^1$H, J=2), 7.9 (dd, $^1$H, J$_1$=2, J$_2$=8.4), 7.4 (d, $^1$H, J=8.8), 7.2 (d, $^1$H, J=5.6), 7.0 (dd, $^1$H, J$_1$=8.8, J$_2$=3.2), 6.9 (d, $^1$H, J=3.2), 3.8 (m, $^1$H), 2.55 (s, $^3$H), 0.8 (m, 4H) ppm; ESMS calc'd for C$_{21}$H$_{18}$ClN$_3$O$_2$: 379.1. found: 380.4 (M+H$^+$).

163

N-(5-(2-chloro-5-cyclopropoxyphenyl)pyridin-2-yl)-5-fluoro-4-methylnicotinamide (compound 71)

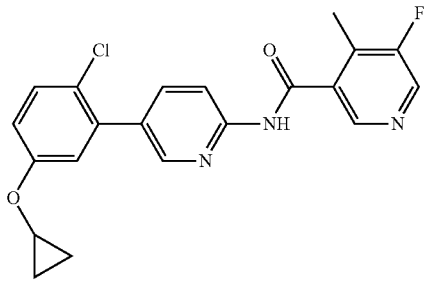

$^1$H-NMR (CDCl$_3$) δ 9.25 (s, $^1$H), 8.60 (s, $^1$H), 8.4-8.5 (m, 2H), 8.1 (d, $^1$H, J=2.4), 7.9 (dd, $^1$H, J$_1$=2.4, J$_2$=8.4), 7.4 (d, $^1$H, J=8.8), 7.0 (dd, $^1$H, J$_1$=8.8, J$_2$=2.8), 6.9 (d, $^1$H, J=2.8), 3.8 (m, $^1$H), 2.48 (s, $^3$H), 0.8 (m, 4H) ppm; ESMS calc'd for C$_{21}$H$_{17}$ClFN$_3$O$_2$: 397.1. found: 398.4 (M+H$^+$).

5-bromo-N-(5-(2-chloro-5-cyclopropoxyphenyl)pyrazin-2-yl)-4-methylnicotinamide (compound 81)

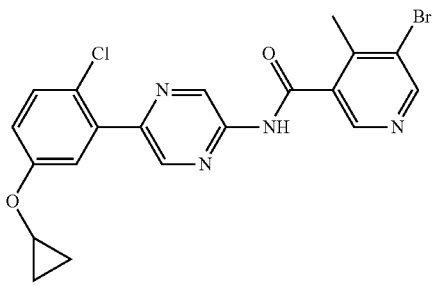 [SMILES: Cc1c(Br)cncc1C(=O)Nc1cnc(-c2cc(OC3CC3)ccc2Cl)cn1]

$^1$H-NMR (CDCl$_3$) δ 9.75 (s, $^1$H), 8.80 (s, $^1$H), 8.67 (s, 2H), 8.4 (br, $^1$H), 7.4 (d, $^1$H, J=8.8), 7.3 (d, $^1$H, J=2.8), 7.1 (dd, $^1$H, J$_1$=8.8, J$_2$=3.2), 3.8 (m, $^1$H), 2.62 (s, $^3$H), 0.8 (m, 4H) ppm; ESMS calc'd for C$_{20}$H$_{16}$BrClN$_4$O$_2$: 458.0. found: 459.0 (M+H$^+$).

N-(5-(2-chloro-5-(pyridin-2-yloxy)phenyl)pyrazin-2-yl)-5-fluoro-4-methylnicotinamide (compound 54)

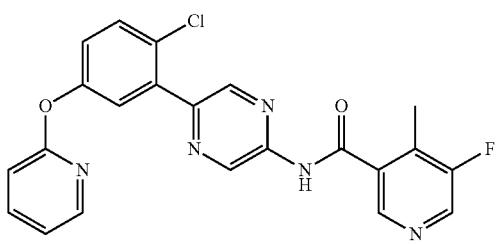 [SMILES: Cc1c(F)cncc1C(=O)Nc1cnc(-c2cc(Oc3ccccn3)ccc2Cl)cn1]

$^1$H-NMR (CDCl$_3$) δ 9.75 (s, $^1$H), 8.80 (s, $^1$H), 8.71 (s, $^1$H), 8.53 (s, $^1$H), 8.48-6.90 (m, 8H), 2.52 (s, $^3$H); ESMS calc'd for C$_{22}$H$_{15}$ClFN$_5$O$_2$: 435.09. Found: 436.1 (M+H$^+$).

164

N-(5-(5-cyclopropoxy-2-methylphenyl)pyrazin-2-yl)-5-fluoro-4-methylnicotinamide (compound 79)

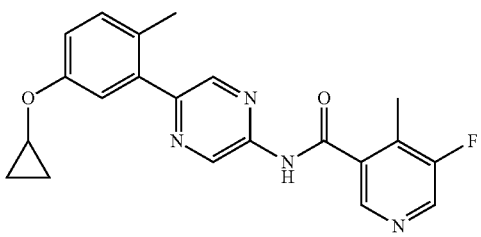 [SMILES: Cc1ccc(OC2CC2)cc1-c1cnc(NC(=O)c2cncc(F)c2C)cn1]

$^1$H-NMR (CDCl$_3$) δ 9.76 (s, $^1$H), 8.69 (s, $^1$H), 8.56 (s, $^1$H), 8.42 (s, $^1$H), 8.31 (s, $^1$H), 7.30-6.95 (m, $^3$H), 3.79 (m, $^1$H), 2.58 (s, $^3$H), 2.35 (s, $^3$H), 1.02-0.78 (m, 4H); ESMS calc'd for C$_{21}$H$_{19}$FN$_4$O$_2$: 378.15. Found: 379.1 (M+H)$^+$.

4-methyl-N-(5-(5-(pyridin-2-yloxy)-2-(trifluoromethoxy)phenyl)pyrazin-2-yl)nicotinamide (compound 51)

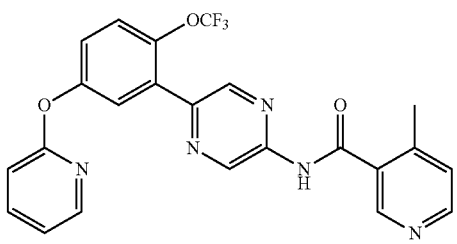 [SMILES: Cc1ccncc1C(=O)Nc1cnc(-c2cc(Oc3ccccn3)ccc2OC(F)(F)F)cn1]

$^1$H-NMR (CDCl$_3$) δ 9.75 (s, $^1$H), 8.82 (s, $^1$H), 8.76 (s, $^1$H), 8.63-6.98 (m, 10H), 2.62 (s, $^3$H); ESMS calc'd for C$_{23}$H$_{16}$F$_3$N$_5$O$_3$: 467.12. Found: 468.1 (M+H)$^+$.

4-chloro-3-(5-(4-methylnicotinamido)pyrazin-2-yl)phenyl methanesulfonate (compound 93)

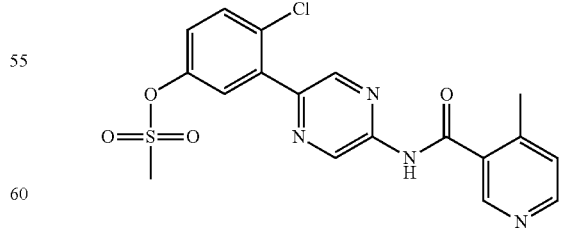

$^1$H-NMR (CDCl$_3$) δ 9.78 (s, $^1$H), 8.81 (s, $^1$H), 8.75 (s, $^1$H), 8.71 (s, $^1$H), 8.62-7.25 (m, 5H), 3.25 (s, $^3$H), 2.59 (s, $^3$H); ESMS calc'd for C$_{18}$H$_{15}$ClN$_4$O$_4$S: 418.05. Found: 419.1 (M+H)$^+$.

N-(5-(5-((3-fluoropyridin-2-yl)oxy)-2-(trifluoromethoxy)phenyl)pyrazin-2-yl)-4-methylnicotinamide (compound 38)

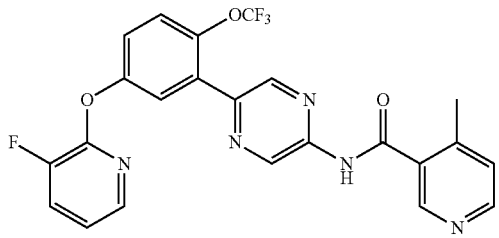 [SMILES: Cc1ccncc1C(=O)Nc1cnc(-c2cc(Oc3ncccc3F)ccc2OC(F)(F)F)cn1]

¹H-NMR (CDCl₃) δ 9.75 (s, ¹H), 9.28 (s, ¹H), 8.79-7.01 (m, 10H), 2.59 (s, ³H); ESMS calc'd for C₂₃H₁₅F₄N₅O₃: 485.11. Found: 486.1 (M+H)⁺.

4-methyl-3-(5-(4-methylnicotinamido)pyrazin-2-yl)phenyl dimethylsulfamate (compound 68):

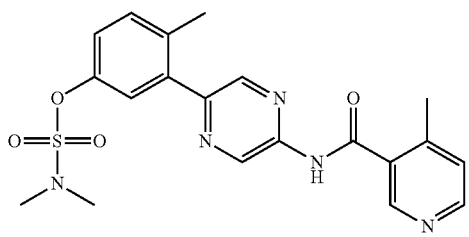 [SMILES: Cc1ccncc1C(=O)Nc1cnc(-c2cc(OS(=O)(=O)N(C)C)ccc2C)cn1]

¹H-NMR (CDCl₃) δ 9.74 (s, ¹H), 8.83 (s, ¹H), 8.69-7.24 (m, 7H), 3.01 (s, 6H), 2.61 (s, ³H), 2.43 (s, ³H); ESMS calc'd for C₂₀H₂₁N₅O₄S: 427.13. Found: 428.1 (M+H)⁺.

N-(5-(5-cyclopropoxy-2-methylphenyl)pyrazin-2-yl)-4-methylnicotinamide (compound 66)

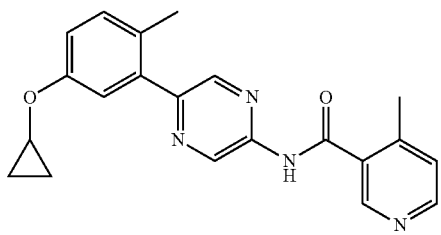 [SMILES: Cc1ccncc1C(=O)Nc1cnc(-c2cc(OC3CC3)ccc2C)cn1]

¹H-NMR (CDCl₃) δ 9.76 (s, ¹H), 8.81 (s, ¹H), 8.63-7.01 (m, 7H), 3.79 (m, ¹H), 2.61 (s, ³H), 2.38 (s, ³H), 1.42-0.75 (m, 4H); ESMS calc'd for C₂₁H₂₀N₄O₂: 360.16. Found: 361.2 (M+H)⁺.

N-(5-(5-cyclopropoxy-2-methylphenyl)pyridin-2-yl)-4-methylnicotinamide (compound 60)

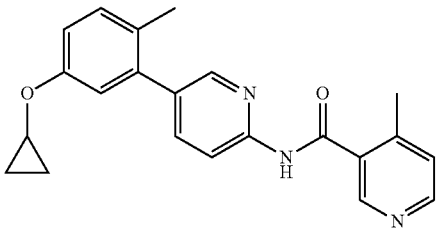 [SMILES: Cc1ccncc1C(=O)Nc1ccc(-c2cc(OC3CC3)ccc2C)cn1]

¹H-NMR (CDCl₃) δ 9.73 (s, ¹H), 8.81 (s, ¹H), 8.62-7.23 (m, 8H), 3.79 (m, ¹H), 2.61 (s, ³H), 2.20 (s, ³H), 1.42-0.77 (m, 4H); ESMS calc'd for C₂₂H₂₁N₃O₂: 359.16. Found: 360.2 (M+H)⁺.

N-(5-(5-((3-fluoropyridin-2-yl)oxy)-2-methylphenyl)pyrazin-2-yl)-4-methylnicotinamide (compound 36)

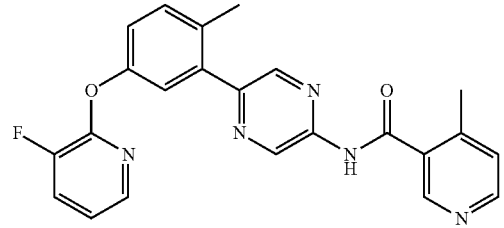 [SMILES: Cc1ccncc1C(=O)Nc1cnc(-c2cc(Oc3ncccc3F)ccc2C)cn1]

¹H-NMR (CDCl₃) δ 9.76 (s, ¹H), 8.81 (s, ¹H), 8.58-6.97 (m, 10H), 2.60 (s, ³H), 2.48 (s, ³H); ESMS calc'd for C₂₃H₁₈FN₅O₂: 415.14. Found: 416.1 (M+H)⁺.

4-methyl-3-(5-(4-methylnicotinamido)pyrazin-2-yl)phenyl methanesulfonate (compound 69)

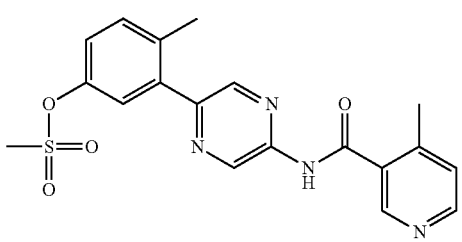 [SMILES: Cc1ccncc1C(=O)Nc1cnc(-c2cc(OS(C)(=O)=O)ccc2C)cn1]

¹H-NMR (CDCl₃) δ 9.76 (s, ¹H), 8.81 (s, ¹H), 8.63-7.25 (m, 7H), 3.21 (s, ³H), 2.61 (s, ³H), 2.44 (s, ³H); ESMS calc'd for C₁₉H₁₈N₄O₄S: 398.10. Found: 399.1 (M+H)⁺.

N-(5-(2-cyano-5-(oxetan-3-yloxy)phenyl)pyrazin-2-yl)-4-methylnicotinamide (compound 39)

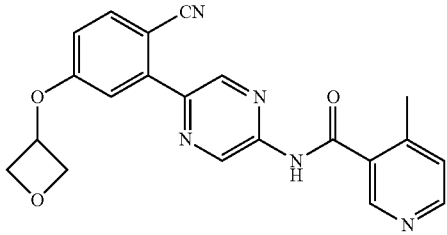 [SMILES: Cc1ccncc1C(=O)Nc1cnc(-c2cc(OC3COC3)ccc2C#N)cn1]

$^1$H-NMR (CDCl$_3$) δ 9.79 (s, $^1$H), 8.84-6.71 (m, 8H), 5.37 (m, $^1$H), 5.20-4.64 (m, 4H), 2.61 (s, $^3$H); ESMS calc'd for C$_{21}$H$_{17}$N$_5$O$_3$: 387.13. Found: 388.1 (M+H)$^+$.

Example 7

Synthesis of N-(4-(2,5-dimethoxy-$^1$H-benzo[d]imidazol-1-yl)phenyl)-4-methylnicotinamide (compound 43)

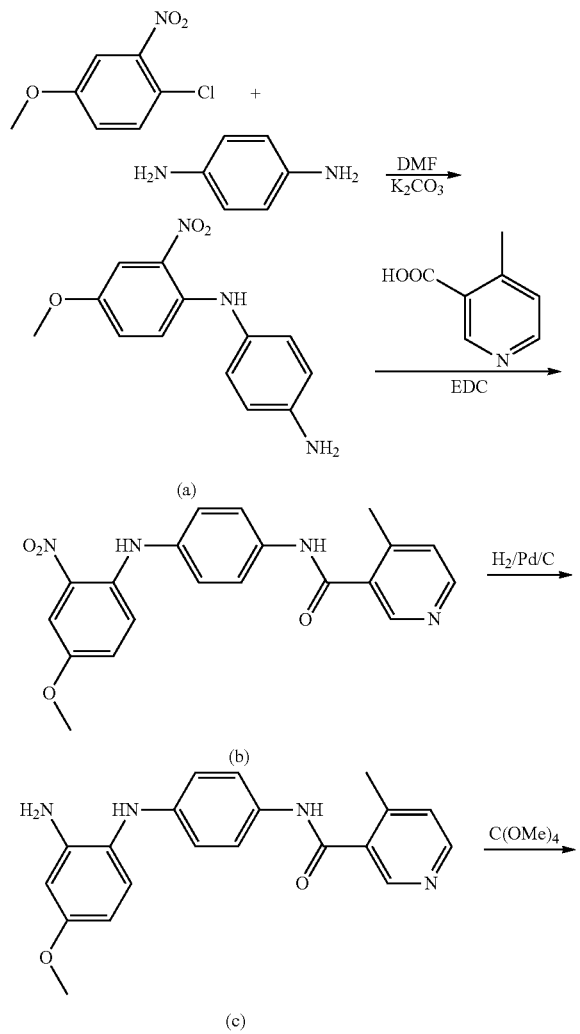

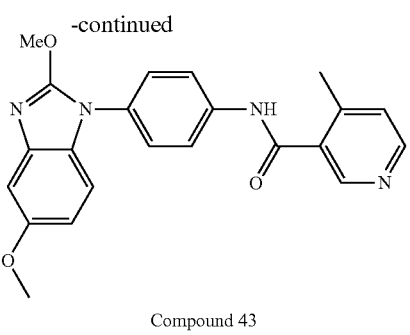

Compound 43

N1-(4-methoxy-2-nitrophenyl)benzene-1,4-diamine (a)

A mixture of 1-chloro-4-methoxy-2-nitrobenzene (100 mmol), benzene-1,4-diamine (200 mmol), and K$_2$CO$_3$ (220 mmol) in DMF (120 mL) was heated at 150° C. for 16 h. The whole mixture was loaded on silica gel and dried in vacuum. The silica gel was eluted with 20% EA/hexanes to remove a dark brown band and collected from 30-70% EA/hexanes elution. The eluant was concentrated and triturated with 30% EA/hexanes to give N1-(4-methoxy-2-nitrophenyl)benzene-1,4-diamine (a) as black solids (6.8 g, 26%).

N-(4-((4-methoxy-2-nitrophenyl)amino)phenyl)-4-methylnicotinamide (b)

The dried mother liquor obtained above (4.0 g) was treated with 4-methylnicotinic acid (20 mmol) and EDC (20 mmol) in DCM (100 mL), and the mixture was stirred at rt for 16 h. The solution was concentrated and purified by column to give N-(4-((4-methoxy-2-nitrophenyl)amino)phenyl)-4-methylnicotinamide (b) as brown solids (3.2 g).

N-(4-((2-amino-4-methoxyphenyl)amino)phenyl)-4-methylnicotinamide (c)

The above solid (b, 3.2 g) was hydrogenated under H$_2$ balloon in the presence of 5% Pd/C in EA (100 mL). The catalysts was filtered off, and the filtrate was concentrated to give N-(4-((2-amino-4-methoxyphenyl)amino)phenyl)-4-methylnicotinamide (c, 3.0 g) as a yellowish oil.

N-(4-(2,5-dimethoxy-$^1$H-benzo[d]imidazol-1-yl)phenyl)-4-methylnicotinamide (compound 43)

1.0 g of the above oil was dissolved in THF (20 mL), and C(OMe)$_4$ (1.0 mL) was added followed by the addition of 0.1 mL AcOH. The mixture was refluxed for 16 h. The volatiles were removed, and the residue was purified by column to give compound 43 as white solids (0.85 g). $^1$H-NMR (CDCl$_3$) δ 8.76 (s, $^1$H), 8.6 (d, $^1$H, J=5.2), 8.0 (br, $^1$H), 7.8 (d, 2H, J=8.4), 7.5 (d, 2H, J=8.4), 7.3 (m, $^1$H), 7.2 (d, $^1$H, J=2.4), 7.1 (d, $^1$H, J=8.8), 6.8 (d, $^1$H, J=8.8), 4.19 (s, $^3$H), 3.86 (s, $^3$H), 2.57 (s, $^3$H) ppm; ESMS calc'd for C$_{22}$H$_{20}$N$_4$O$_3$: 388.2. found: 389.2 (M+H$^+$).

Example 8

Compounds Synthesized According to the Synthetic Procedure of Example 7

The following compounds were synthesized in a similar manner according to the procedure described above in Example 7.

N-(6-(5-methoxy-2-(trifluoromethyl)-¹H-benzo[d]imidazol-1-yl)pyridin-3-yl)-4-methylnicotinamide (compound 46)

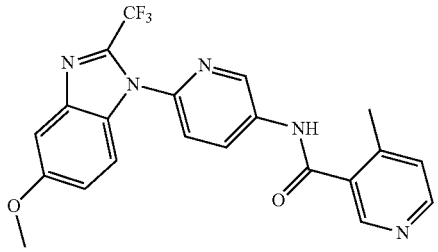 [SMILES: COc1ccc2c(c1)nc(C(F)(F)F)n2-c1ccc(NC(=O)c2cnccc2C)cn1]

¹H-NMR (CDCl₃) δ 9.49 (s, ¹H), 8.9 (d, ¹H, J=2.4), 8.73 (s, ¹H), 8.7 (dd, ¹H, J₁=2.8, J₂=8.8), 8.5 (d, ¹H, J=5.2), 7.5 (d, ¹H, J=8.8), 7.3 (d, ¹H, J=2.4), 7.24 (s, ¹H), 7.2 (d, ¹H, J=5.2), 7.0 (dd, ¹H, J₁=2.4, J₂=8.8), 3.88 (s, ³H), 2.56 (s, ³H) ppm; ESMS calc'd for C₂₁H₁₆F₃N₅O₂: 427.1. found: 428.2 (M+H⁺).

5-fluoro-N-(6-(5-methoxy-2-(trifluoromethyl)-¹H-benzo[d]imidazol-1-yl)pyridin-3-yl)-4-methylnicotinamide (compound 47)

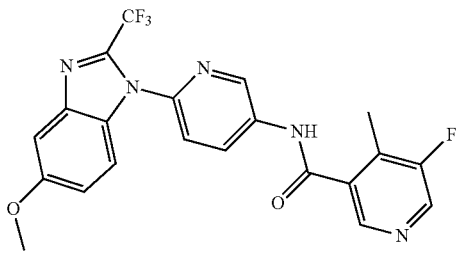 [SMILES: COc1ccc2c(c1)nc(C(F)(F)F)n2-c1ccc(NC(=O)c2cncc(F)c2C)cn1]

¹H-NMR (CDCl₃) δ 8.8 (d, ¹H, J=2.4), 8.64 (s, ¹H), 8.54 (s, ¹H), 8.0 (br, ¹H), 7.6 (d, ¹H, J=8.4), 7.4 (d, ¹H, J=2.4), 7.31 (s, ¹H), 7.21 (s, ¹H), 7.0 (dd, ¹H, J₁=2.4, J₂=8.4), 3.89 (s, ³H), 2.52 (s, ³H) ppm; ESMS calc'd for C₂₁H₁₅F₄N₅O₂: 445.1. found: 446.2 (M+H').

N-(5-(2,5-dimethoxy-¹H-benzo[d]imidazol-1-yl)pyrazin-2-yl)-4-methylnicotinamide (compound 61)

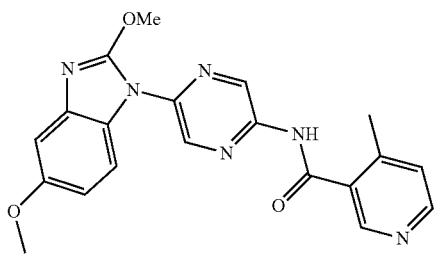 [SMILES: COc1ccc2c(c1)nc(OC)n2-c1cnc(NC(=O)c2cnccc2C)cn1]

¹H-NMR (DMSO-d₃) δ 11.57 (br, ¹H), 9.4 (d, ¹H, J=1.6), 8.9 (d, ¹H, J=1.6), 8.71 (s, ¹H), 8.6 (d, ¹H, J=5.2), 7.6 (d, ¹H, J=8.8), 7.4 (d, ¹H, J=5.2), 7.1 (d, ¹H, J=2.8), 6.8 (dd, ¹H, J₁=2.8, J₂=8.8), 4.19 (s, ³H), 3.79 (s, ³H), 2.46 (s, ³H) ppm; ESMS calc'd for C₂₀H₁₅N₆O₃: 390.1. found: 391.2 (M+H⁺).

N-(4-(2,5-dimethoxy-¹H-benzo[d]imidazol-1-yl)phenyl)-5-fluoro-4-methylnicotinamide (compound 42)

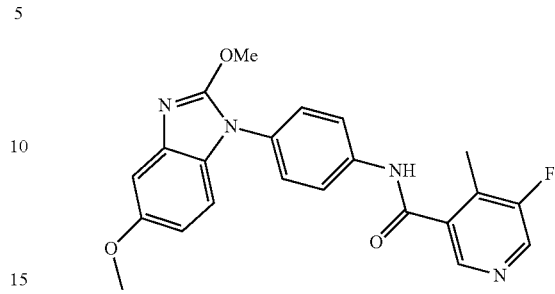

¹H-NMR (CDCl₃) δ 8.55 (s, ¹H), 8.46 (s, ¹H), 8.3 (br, ¹H), 7.8 (d, 2H, J=8.4), 7.5 (d, 2H, J=8.4), 7.2 (d, ¹H, J=2.4), 7.1 (d, ¹H, J=8.8), 6.8 (dd, ¹H, J₁=8.8, J₂=2.4), 4.18 (s, ³H), 3.85 (s, ³H), 2.47 (s, ³H) ppm; ESMS calc'd for C₂₂H₁₉FN₄O₃: 406.1. found: 407.3 (M+H⁺).

Example 9

Synthesis of 4-methyl-N-(5-(2-methyl-5-(pyridin-3-ylethynyl)phenyl)pyrazin-2-yl)nicotinamide (compound 44)

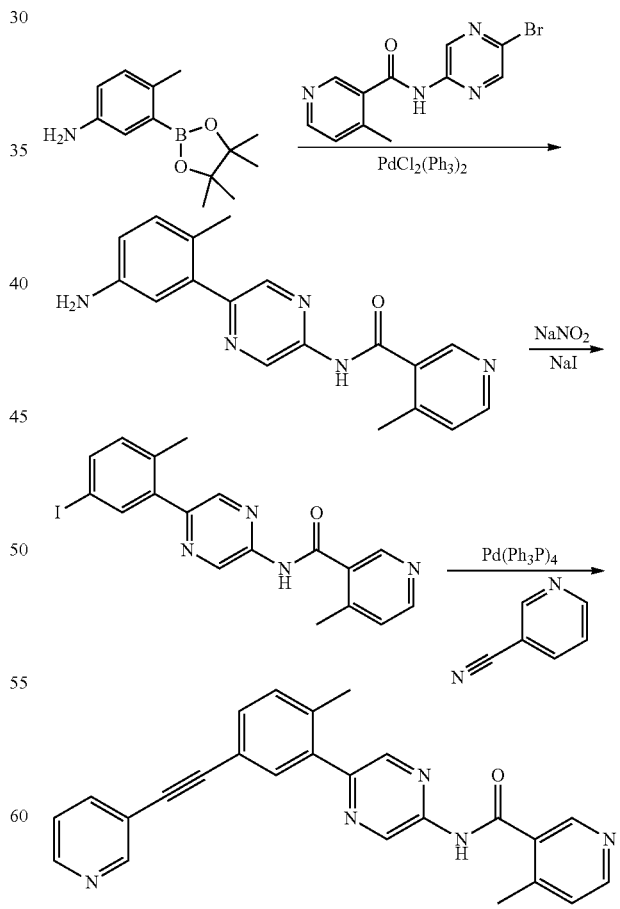

Compound 44

To 4-methyl-3-(4,4,5,5-tetramethyl-1,3,2-dioxaborolan-2-yl)aniline (1 eq.) in a dioxane/water (10:1) solution was added N-(5-bromopyrazin-2-yl)-4-methylnicotinamide (1 eq.), PdCl$_2$(Ph$_3$P)$_2$ (0.2 eq.), and K$_2$CO$_3$ (2 eq.), and the mixture was heated in microwave at 110.0 for 2-4 hr. The product (N-(5-(5-amino-2-methylphenyl)pyrazin-2-yl)-4-methylnicotinamide) was purified with silica gel column chromatography producing a yield of 50-60%.

To N-(5-(5-amino-2-methylphenyl)pyrazin-2-yl)-4-methylnicotinamide (1 eq.) in a water/HOAc/acetone (1/1/0.7) solution was added NaNO$_2$ (1.5 eq.) at 0° C., stirred for 30 min., keeping the reaction solution at 0° C., and urea (0.5 eq.) was added and stirred for 5 min. Finally, NaI (2 eq.) was added and stirred for 1 hr. The reaction was quenched with concentrated NaOH solution till pH ~7, the product (N-(5-(5-iodo-2-methylphenyl)pyrazin-2-yl)-4-methylnicotinamide) was extracted with DCM and purified with silica gel column chromatography with a yield of ~60%.

A suspension solution of 3-ethynylpyridine (2 eq.), N-(5-(5-iodo-2-methylphenyl)pyrazin-2-yl)-4-methylnicotinamide (1 eq.), TEA (3 eq.), Pd(Ph$_3$P)$_4$ (0.2 eq.) and catalytic amount of CuI in toluene was heated at 100° C. for 2 hr. The reaction mixture was purified with silica gel column chromatography to give pure compound 44 in a yield of ~50%. $^1$H-NMR (CDCl$_3$) δ 9.79 (s, $^1$H), 8.84 (s, $^1$H), 8.74 (s, $^1$H) 8.62-7.25 (m, 10H), 2.60 (s, $^3$H), 2.48 (s, $^3$H); ESMS calc'd for C$_{25}$H$_{19}$N$_5$O: 405.16. Found: 406.2 (M+H)$^+$.

Example 10

Synthesis of 4-methyl-N-(5-(6-methylbenzo[d][1,3]dioxol-5-yl)pyrazin-2-yl)nicotinamide (compound 50)

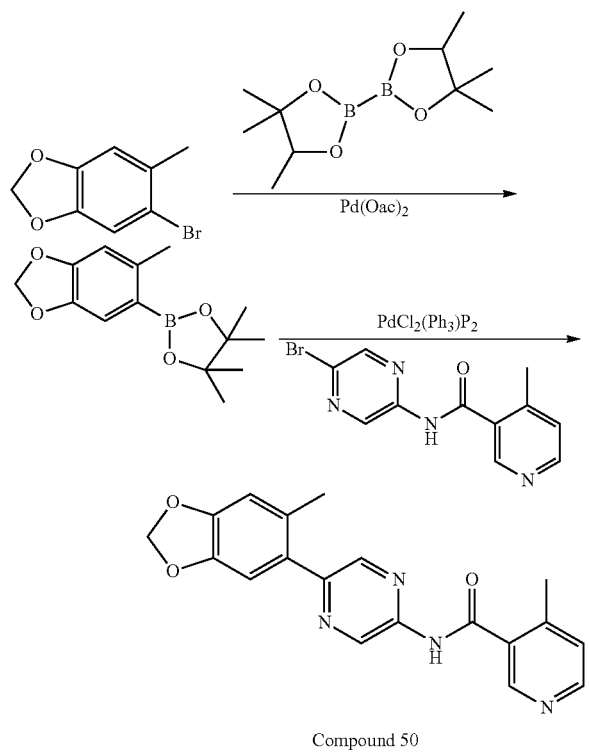

Compound 50

A suspension solution of 5-bromo-6-methylbenzo[d][1,3]dioxole (1 eq.), bis(pinacolato)diboron (1.25 eq.), KOAc (2.6 eq.), and Pd(OAc)$_2$ (0.2 eq.) in DMF was heated at 85° C. for 3 h. The reaction was quenched with water, extracted with DCM, and filtered with a small silica gel column. The crude product was directly used for the next step.

To 4,4,5,5-tetramethyl-2-(6-methylbenzo[d][1,3]dioxol-5-yl)-1,3,2-dioxaborolane (2 eq.) in a dioxane/water (10:1) solution was added N-(5-bromopyrazin-2-yl)-4-methylnicotinamide (1 eq.), PdCl$_2$(Ph$_3$P)$_2$ (0.2 eq.), and K$_2$CO$_3$ (2 eq.), and the mixture was heated in microwave at 100° C. for 2-4 hr. The product 4-methyl-N-(5-(6-methylbenzo[d][1,3]dioxol-5-yl)pyrazin-2-yl)nicotinamide was purified with silica gel column chromatography producing a yield of 30-40%. $^1$H-NMR (CDCl$_3$) δ 9.73 (s, $^1$H), 8.85-6.79 (m, 7H), 5.99 (s, 2H), 2.61 (s, $^3$H), 2.42 (s, $^3$H); ESMS calc'd for C$_{19}$H$_{16}$N$_4$O$_3$: 348.12. Found: 349.1 (M+H)$^+$.

Example 11

Synthesis of N-(5-(2-chloro-5-isopropoxyphenyl)pyrazin-2-yl)-4-methylnicotinamide (compound 144)

The following is a general procedure for Suzuki coupling, alkylation, and acylation, which was used to synthesize compound 144.

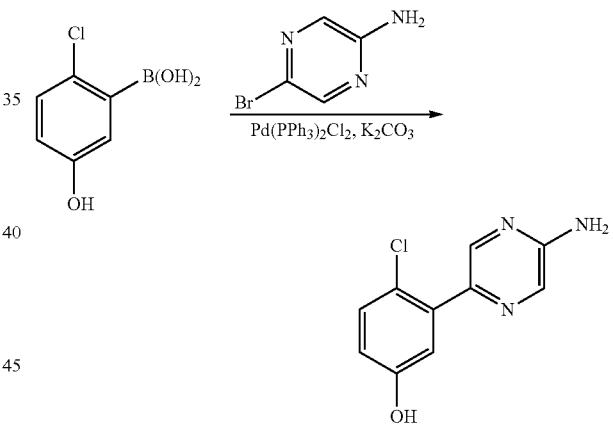

To the solution of (2-chloro-5-hydroxyphenyl)boronic acid (2.1 g, 12.2 mmol) in dioxane/H$_2$O (30 mL/10 mL) was added 5-bromopyrazin-2-amine (2.2 g, 12.6 mmol), K$_2$CO$_3$ (3.1 g, 22.4 mmol), and Pd(PPh$_3$)$_2$Cl$_2$ (0.3 g, 0.42 mmol). The reaction was heated at 90° C. for 12 hr before it was diluted with EtOAc/H$_2$O (100 mL/100 mL). The organic phase was dried over Na$_2$SO$_4$ and concentrated. Column chromatography gave 3-(5-aminopyrazin-2-yl)-4-chlorophenol (2.2 g, 83%) as an off-white solid.

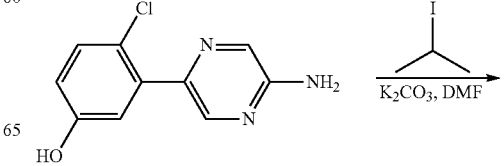

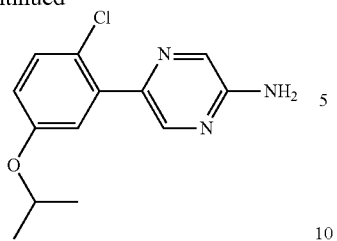

To the solution of 3-(5-aminopyrazin-2-yl)-4-chlorophenol (0.12 g, 0.54 mmol) in DMF (4 mL) was added 2-iodopropane (0.22 mL, 2.17 mmol) and K$_2$CO$_3$ (0.3 g, 2.17 mmol). The solution was heated in microwave at 80° C. for 2 hr. The solution was diluted with H$_2$O (15 mL) and extracted with EtOAc (15 mL). The organic phase was dried over Na$_2$SO$_4$ and concentrated. Column chromatography gave 5-(2-chloro-5-isopropoxyphenyl)pyrazin-2-amine (0.09 g, 63%) as a colorless oil.

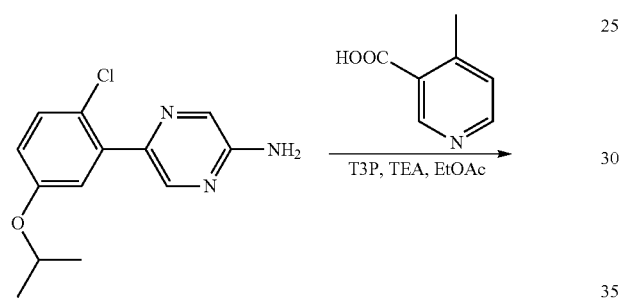

Compound 144

To the solution of 5-(2-chloro-5-isopropoxyphenyl)pyrazin-2-amine (0.05 g, 0.19 mmol) in EtOAc (3 mL) was added 4-methylnicotinic acid (0.05 g, 0.46 mmol), propylphosphonic anhydride (T3P) (50% wt in EtOAc, 0.34 mL, 0.57 mmol), and TEA (0.1 mL, 0.76 mmol). The solution was heated in microwave at 90° C. for 30 min. The solution was diluted with EtOAc (15 mL) and washed with H$_2$O (20 mL). The organic phase was dried over Na$_2$SO$_4$ and concentrated. Column chromatography gave compound 144 (0.054 g, 75%). $^1$H-NMR (400 MHz, CDCl$_3$) δ 9.76 (d, J=1.5, $^1$H), 9.08 (s, $^1$H), 8.76 (s, $^1$H), 8.60 (d, J=1.5, $^1$H), 8.57 (d, J=5.1, $^1$H), 7.37 (d, J=8.8, $^1$H), 7.25 (d, J=5.1, $^1$H), 7.17 (d, J=3.0, $^1$H), 6.91 (dd, J=3.0, 8.8, $^1$H), 4.59 (dt, J=6.1, 12.1, $^1$H), 2.58 (s, $^3$H), 1.35 (d, J=6.1, 7H); ESMS calc'd (C$_{20}$H$_{19}$ClN$_4$O$_2$): 382.1. found: 383.1 (M+H).

Example 12

Synthesis of N-(5-(2-chloro-5-isopropoxyphenyl)pyridin-2-yl)-4-methylnicotinamide (compound 90)

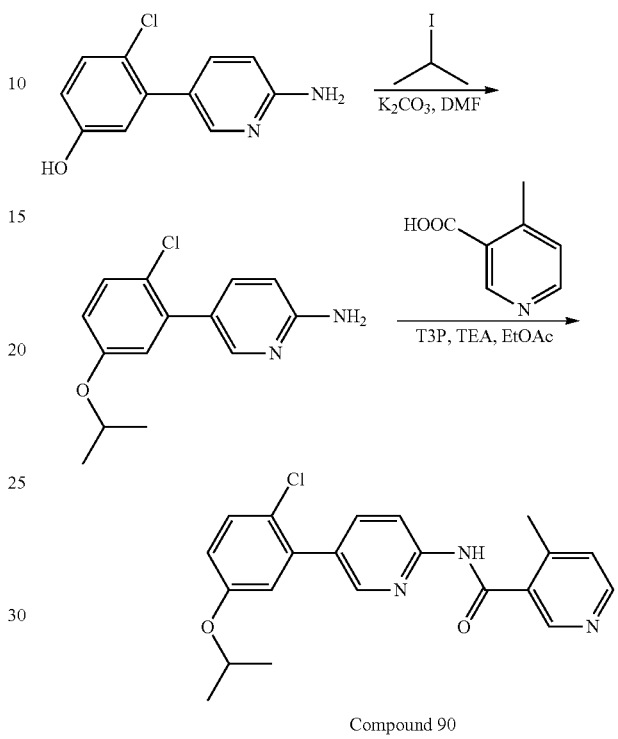

Compound 90

Compound 90 was prepared following the general procedures provided in the schematic above. $^1$H-NMR (400 MHz, CDCl$_3$) δ 9.09 (s, $^1$H), 8.77 (s, $^1$H), 8.53 (d, J=5.1, $^1$H), 8.43 (d, J=8.6, $^1$H), 8.14-8.10 (m, $^1$H), 7.89 (dd, J=2.4, 8.6, $^1$H), 7.37 (d, J=8.7, $^1$H), 7.21 (d, J=5.1, $^1$H), 6.88-6.80 (m, 2H), 4.56 (dt, J=6.0, 12.1, $^1$H), 2.56 (s, $^3$H), 1.36 (t, J=4.3, 6H); ESMS calc'd (C$_{21}$H$_{20}$ClN$_3$O$_2$): 381.1. found: 382.1 (M+H).

Example 13

Synthesis of N-(5-(2-chloro-4-cyclopropoxyphenyl)pyridin-2-yl)-4-methylnicotinamide (compound 9)

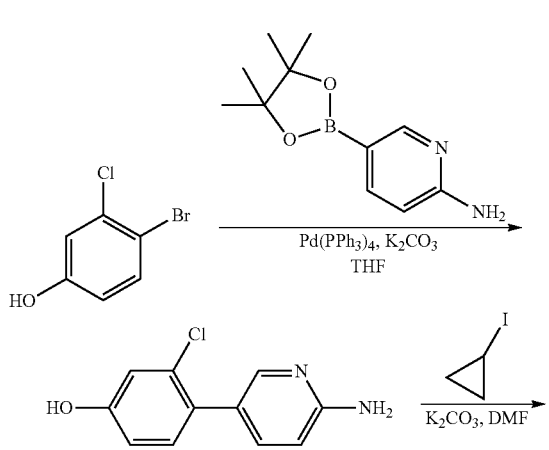

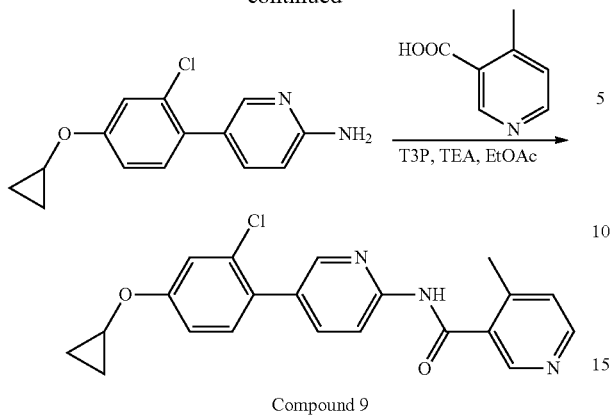

Compound 9

Compound 9 was prepared following the general procedures provided in the schematic above. ¹H-NMR (400 MHz, CDCl₃) δ 9.01 (s, ¹H), 8.77 (s, ¹H), 8.53 (d, J=5.1, ¹H), 8.41 (d, J=8.6, ¹H), 8.11 (d, J=2.3, ¹H), 7.86 (dd, J=2.4, 8.6, ¹H), 7.22 (dd, J=2.9, 5.5, ³H), 7.03 (dd, J=2.5, 8.5, ¹H), 3.83-3.74 (m, ¹H), 2.56 (s, ³H), 0.89-0.76 (m, 4H); ESMS calc'd (C₂₁H₁₈ClN₃O₂): 379.1. found: 380.1 (M+H).

Example 14

Synthesis of 5-fluoro-N-(5-(5-((3-fluoropyridin-2-yl)oxy)-2-methylphenyl)pyrazin-2-yl)-4-methylnicotinamide (compound 143)

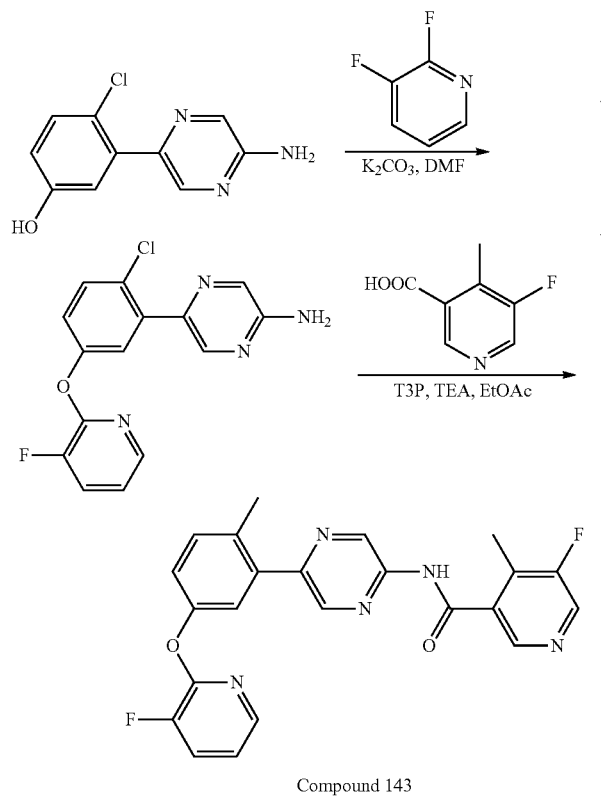

Compound 143

Compound 143 was prepared following the general procedures provided in the schematic above. ¹H-NMR (400 MHz, CDCl₃) δ 9.72 (d, J=1.4, ¹H), 8.74 (d, J=8.7, ¹H), 8.60 (s, ¹H), 8.51 (d, J=1.0, ¹H), 8.39 (d, J=1.5, ¹H), 7.92 (dd, J=1.5, 4.9, ¹H), 7.47 (ddd, J=1.5, 7.9, 9.7, ¹H), 7.36 (d, J=8.4, ¹H), 7.30 (d, J=2.5, ¹H), 7.18 (dd, J=2.6, 8.3, ¹H), 6.99 (ddd, J=3.2, 4.9, 8.0, ¹H), 2.51 (d, J=2.0, ³H), 2.44 (d, J=5.1, ³H); ESMS calc'd (C₂₃H₁₇F₂N₅O₂): 433.1. found: 434.1 (M+H).

Example 15

Synthesis of N-(5-(2-chloro-5-(pyrimidin-2-yloxy)phenyl)pyrazin-2-yl)-4-methylnicotinamide (compound 16)

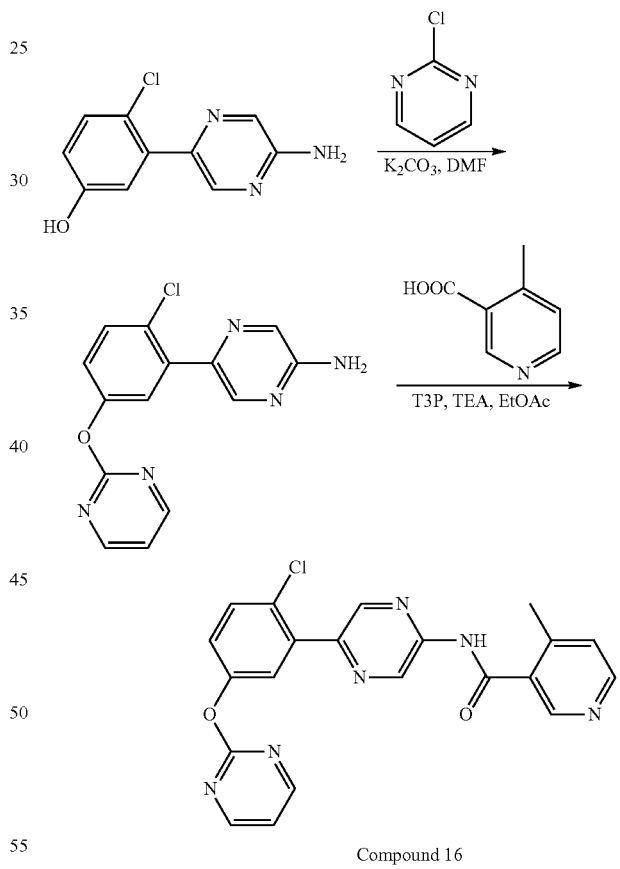

Compound 16

Compound 16 was prepared following the general procedures provided in the schematic above. ¹H-NMR (400 MHz, CDCl₃) δ 9.75 (d, J=1.5, ¹H), 8.81 (s, ¹H), 8.76 (d, J=1.5, ¹H), 8.59 (dd, J=4.9, 8.9, ³H), 8.47 (s, ¹H), 7.58 (dd, J=5.8, 7.6, 2H), 7.27 (d, J=3.1, 2H), 7.08 (t, J=4.8, ¹H), 2.59 (s, ³H); ESMS calc'd (C₂₁H₁₅F₂N₆O₂): 418.1. found: 419.0 (M+H).

Example 16

Synthesis of N-(5-(2-chloro-5-(pyrimidin-2-yloxy)phenyl)pyridin-2-yl)-5-fluoro-4-methylnicotinamide (compound 23)

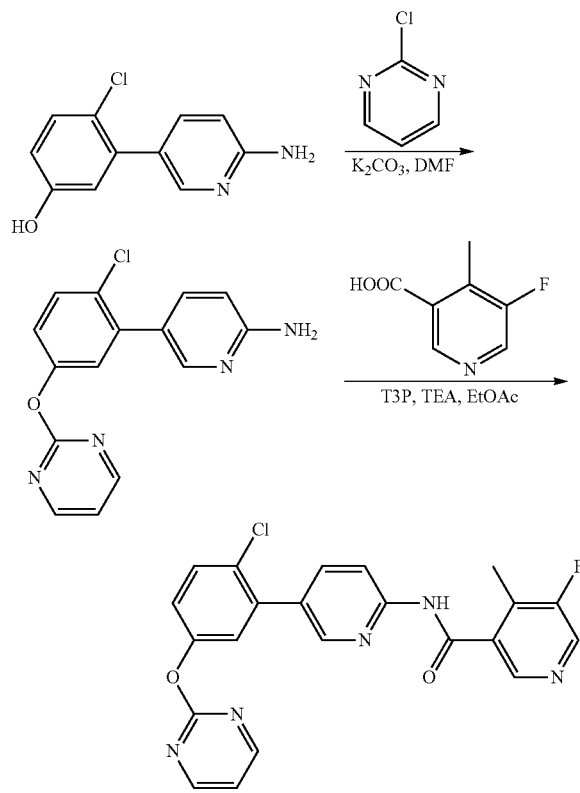

Compound 23

Compound 23 was prepared following the general procedures provided in the schematic above. $^1$H-NMR (400 MHz, CDCl$_3$) δ 8.65-8.56 (m, 4H), 8.49 (s, $^1$H), 8.42 (d, J=8.6, $^1$H), 8.35 (d, J=1.7, $^1$H), 7.95 (dd, J=2.4, 8.6, $^1$H), 7.60-7.54 (m, $^1$H), 7.21 (dd, J=2.3, 7.9, 2H), 7.09 (q, J=4.8, $^1$H), 2.48 (t, J=9.0, $^3$H); ESMS calc'd (C$_{22}$H$_{15}$ClFN$_5$O$_2$): 435.1. found: 436.1 (M+H).

Example 17

Synthesis of N-(5-(2-chloro-5-(isopropylamino)phenyl)pyridin-2-yl)-4-methylnicotinamide (compound 139)

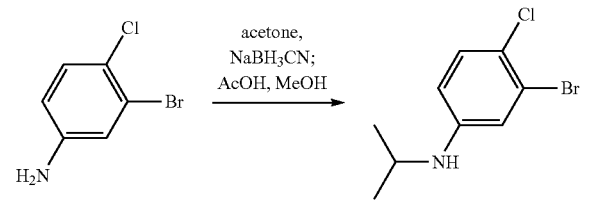

To the solution of 3-bromo-4-chloroaniline (0.5 g, 3.92 mmol) in MeOH/Acetone (20 mL/5 mL) was added NaBH$_3$CN (1 g, 15.9 mmol) followed by AcOH (1 mL). The reaction was stirred at room temperature for 2 hr. The reaction solution was concentrated and diluted with EtOAc (20 mL). The organic phase was washed with NaHCO$_3$ (20 mL), dried over NaSO$_4$, and concentrated. Column chromatography gave 3-bromo-4-chloro-N-isopropylaniline (0.79 g, 81%).

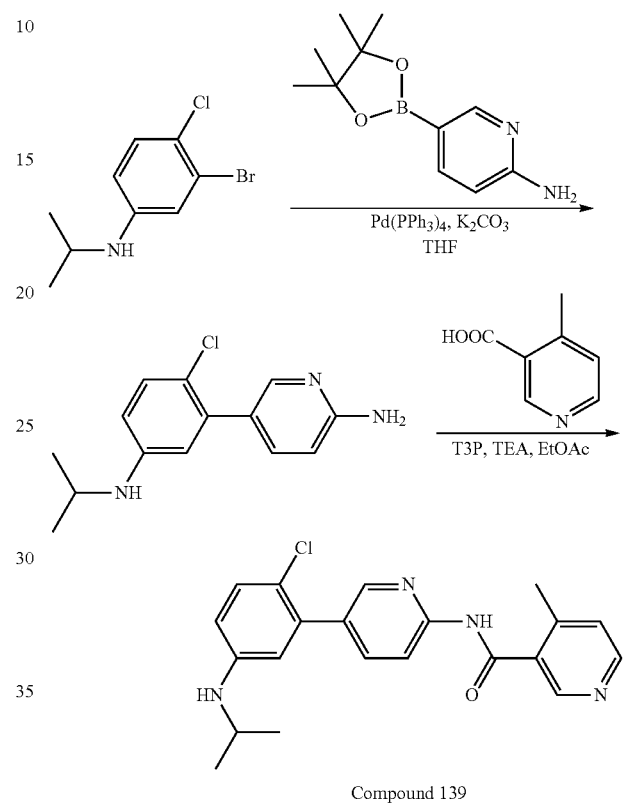

Compound 139

Compound 139 was prepared following the general procedures provided in the schematic above. $^1$H-NMR (400 MHz, CDCl$_3$) δ 9.64 (s, $^1$H), 8.74 (s, $^1$H), 8.47 (d, J=5.1, $^1$H), 8.42 (d, J=8.5, $^1$H), 7.90 (d, J=1.7, $^1$H), 7.86 (dd, J=2.3, 8.5, $^1$H), 7.24 (d, J=8.7, $^1$H), 7.16 (d, J=5.1, $^1$H), 6.54 (dd, J=2.8, 8.7, $^1$H), 6.45 (d, J=2.8, $^1$H), 3.62 (dt, J=6.3, 12.6, 2H), 2.53 (s, $^3$H), 1.23 (d, J=6.2, 6H); ESMS calc'd (C$_{21}$H$_{21}$ClN$_4$O): 380.1. found: 381.2 (M+H).

Example 18

Synthesis of N-(5-(2-chloro-5-(pyrimidin-2-yloxy)phenyl)pyridin-2-yl)-4-methylnicotinamide (compound 130)

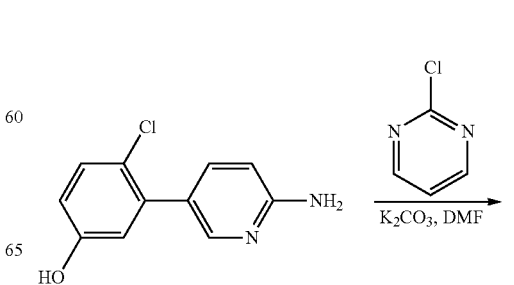

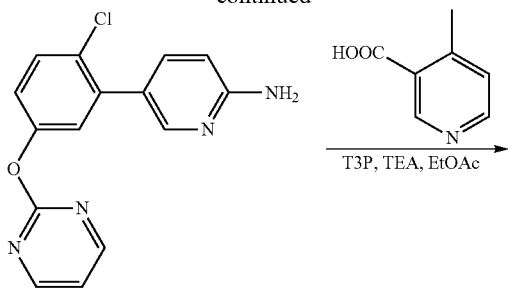

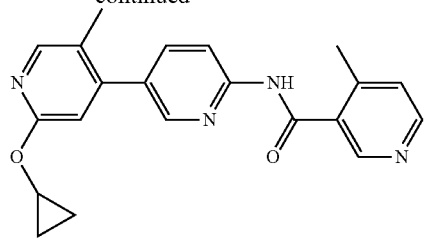

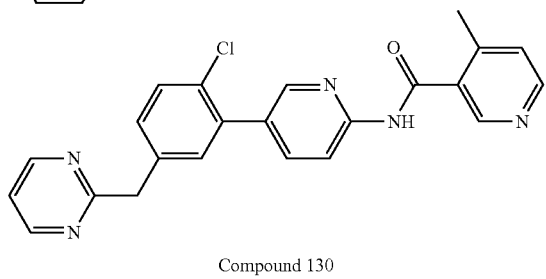

Compound 130

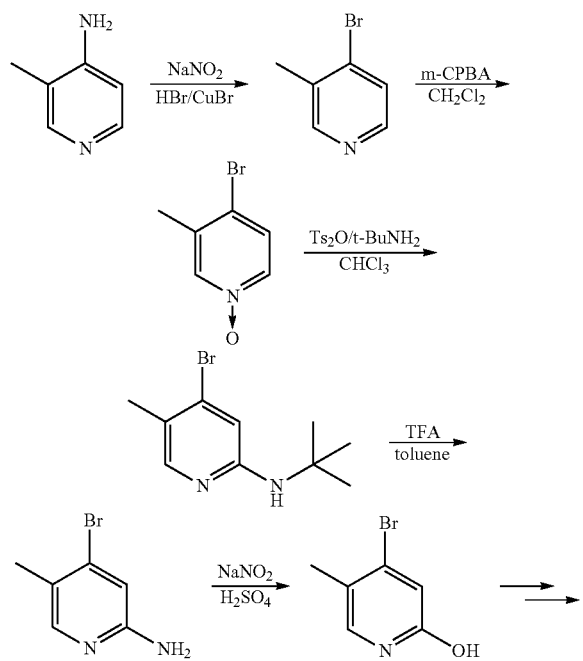

Compound 20

Compound 130 was prepared following the general procedures provided in the schematic above. $^1$H-NMR (400 MHz, CDCl$_3$) δ 8.78 (s, $^1$H), 8.68 (s, $^1$H), 8.59 (d, J=4.8, 2H), 8.56 (d, J=5.1, $^1$H), 8.44 (d, J=8.6, $^1$H), 8.30 (d, J=1.8, $^1$H), 7.94 (dd, J=2.4, 8.6, $^1$H), 7.59-7.51 (m, $^1$H), 7.21 (dt, J=3.7, 7.1, $^3$H), 7.09 (t, J=4.8, $^1$H), 2.56 (s, $^3$H); ESMS calc'd (C$_{22}$H$_{16}$ClN$_3$O$_2$): 417.1. found: 418.1 (M+H).

Example 19

Synthesis of N-(2'-cyclopropoxy-5'-methyl-[3,4'-bipyridin]-6-yl)-4-methylnicotinamide (compound 20)

Into a 3000-mL four-necked round-bottom flask was placed a solution of 3-methylpyridin-4-amine (120 g, 1.11 mol, 1.00 eq.) in hydrogen bromide (720 mL). This was followed by the addition of a solution of sodium nitrite (153 g, 2.22 mol, 2.00 eq.) in water (500 mL) dropwise with stirring at −15° C. for 2 hours. The resulting solution was stirred for 15 min at −10° C. To this was added copper(I) bromide (80 g, 559.44 mmol, 0.50 eq.) in several batches at −15° C. The resulting solution was allowed to react, with stirring, for an additional 5 h at room temperature. The reaction mixture was cooled to 0° C. with a water/ice bath. The pH value of the solution was adjusted to 10 with sodium hydroxide (40%). The solids were filtered out. The resulting solution was extracted with 3×800 mL of dichloromethane, and the organic layers combined. The resulting mixture was washed with 1×500 mL of ammonium chloride. The mixture was dried over anhydrous sodium sulfate and concentrated under vacuum. The residue was applied onto a silica gel column with dichloromethane/petroleum ether (1:1). This resulted in 100 g (52%) of 4-bromo-3-methylpyridine as a yellow liquid.

Into a 2000-mL three-necked round-bottom flask was placed a solution of 4-bromo-3-methylpyridine (100 g, 581.40 mmol, 1.00 eq.) in dichloromethane (1500 mL) and meta-chloroperbenzoic acid (110 g, 635.84 mmol, 1.09 eq.). The resulting solution was stirred for 15 h at room temperature. The resulting solution was diluted with 500 mL of water. The resulting solution was extracted with 5×300 mL of dichloromethane, and the organic layers were combined. The resulting mixture was washed with 1×500 mL of saturated sodium bicarbonate. The mixture was dried over sodium sulfate and concentrated under vacuum. The resulting mixture was washed with 200 mL of ethyl acetate/petroleum ether (1:5). This resulted in 95 g (87%) of product as a yellow solid.

Into a 1000-mL three-necked round-bottom flask was placed a solution of 4-bromo-3-methylpyridine N-oxide (30 g, 159.57 mmol, 1.00 eq.) in chloroform (600 mL) and 2-methylpropan-2-amine (58.2 g, 797.26 mmol, 5.00 eq.). This was followed by the addition of 4-methylbenzenesulfonic anhydride (105 g, 322.09 mmol, 2.02 eq.) in several batches at 0-5° C. The resulting solution was stirred for 30 min at 0-5° C. in a water/ice bath. The resulting mixture was washed with 1×600 mL of water. The mixture was dried over anhydrous sodium sulfate and concentrated under vacuum. The residue was applied onto a silica gel column with ethyl acetate/petroleum ether (1:20). This resulted in 6 g (15%) of 4-bromo-N-tert-butyl-5-methylpyridin-2-amine as a yellow liquid.

Into a 250-mL three-necked round-bottom flask was placed a solution of 4-bromo-N-tert-butyl-5-methylpyridin-2-amine (6 g, 24.69 mmol, 1.00 eq.) in toluene (60 mL) and trifluoroacetic acid (20 mL). The resulting solution was stirred for 15 h at 70° C. in an oil bath. The resulting mixture was concentrated under vacuum. The pH value of the solution was adjusted to 7 with saturated sodium bicarbonate. The resulting solution was extracted with 2×100 mL of ethyl acetate and the organic layers combined and dried over anhydrous sodium sulfate and concentrated under vacuum. The resulting mixture was washed with 2×20 mL of ethyl acetate/petroleum ether (1:5). This resulted in 4.3 g (93%) of 4-bromo-5-methylpyridin-2-amine as a light yellow solid.

Into a 250-mL three-necked round-bottom flask was placed 4-bromo-5-methylpyridin-2-amine (4.5 g, 24.06 mmol, 1.00 eq.), 10% sulfuric acid (60 mL). This was followed by the addition of a solution of $NaNO_2$ (2 g, 28.99 mmol, 1.20 eq.) in water (10 mL) dropwise with stirring at 0-5° C. The resulting solution was stirred for 3 h at room temperature. The pH value of the solution was adjusted to 7 with saturated sodium bicarbonate. The solids were collected by filtration, washed with 2×20 mL of water, 1×10 mL of ethanol, and 2×20 mL of hexane. The solid was dried in an oven. This resulted in 3.57 g (77%) of 4-bromo-5-methylpyridin-2-ol as an off-white solid.

Compound 20 was prepared from 4-bromo-5-methylpyridin-2-ol following the general procedures above in Example 13. $^1$H-NMR (400 MHz, $CDCl_3$) δ 8.76 (d, J=21.1, 2H), 8.57 (d, J=4.9, $^1$H), 8.45 (d, J=8.5, $^1$H), 8.17 (d, J=1.8, $^1$H), 8.14 (s, $^1$H), 7.77 (dd, J=2.3, 8.5, $^1$H), 7.24 (d, J=5.0, $^1$H), 6.65 (s, $^1$H), 4.26-4.16 (m, $^1$H), 2.57 (s, $^3$H), 2.21 (s, $^3$H), 0.84-0.78 (m, 4H); ESMS calc'd ($C_{21}H_{20}N_4O_2$): 360.2. found: 361.2 (M+H).

Example 20

Synthesis of N-(2'-cyclopropoxy-5'-methyl-[3,4'-bipyridin]-6-yl)-5-fluoro-4-methylnicotinamide (compound 28)

Compound 28

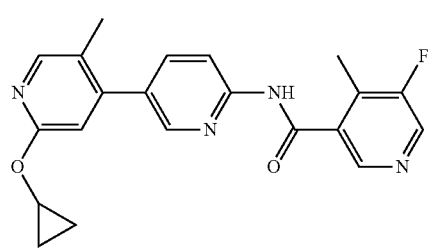

Compound 28 was prepared following the general procedures provided above in Example 19. $^1$H-NMR (400 MHz, $CDCl_3$) δ $^1$H-NMR (400 MHz, $CDCl_3$) δ 8.63-8.60 (m, 2H), 8.51 (d, J=0.9, $^1$H), 8.43 (d, J=8.6, $^1$H), 8.22 (d, J=1.6, $^1$H), 8.15 (s, $^1$H), 7.78 (dd, J=2.3, 8.5, $^1$H), 6.66 (s, $^1$H), 4.26-4.14 (m, $^1$H), 2.50 (d, J=2.0, $^3$H), 2.21 (s, $^3$H), 0.84-0.77 (m, 4H); ESMS calc'd ($C_{21}H_{19}FN_4O_2$): 378.1. found: 379.2 (M+H).

Example 21

Synthesis of N-(5-(5-(dimethylamino)-2-methylphenyl)pyridin-2-yl)-4-methylnicotinamide (compound 91)

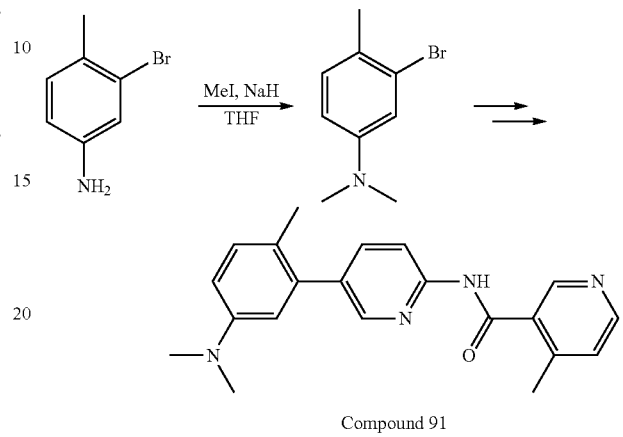

Compound 91

To the solution of 3-bromo-4-methylaniline (0.45 g, 2.42 mmol) in THF (20 mL) was added NaH (60%, 0.5 g, 12.5 mmol) and MeI (1.5 mL, 24.0 mmol). The reaction was heated at 80.0 for 12 hr before it was diluted with EtOAc (20 mL). The solution was washed with $H_2O$ (30 mL), dried over $Na_2SO_4$, and concentrated. Column chromatography gave 3-bromo-N,N,4-trimethylaniline (0.44 g, 85%). From 3-bromo-N,N,4-trimethylaniline, compound 91 is prepared following general procedures of Suzuki and amide couplings provided above in Example 13. $^1$H-NMR (400 MHz, $CDCl_3$) δ 8.79 (s, $^1$H), 8.60-8.55 (m, 2H), 8.39 (d, J=8.5, $^1$H), 8.22 (d, J=1.7, $^1$H), 7.78 (dd, J=2.3, 8.5, $^1$H), 7.23 (d, J=5.1, $^1$H), 7.16 (d, J=8.5, $^1$H), 6.73 (dd, J=2.8, 8.4, $^1$H), 6.58 (d, J=2.8, $^1$H), 2.95 (s, 6H), 2.57 (s, $^3$H), 2.18 (s, $^3$H); ESMS calc'd ($C_{21}H_{22}N_4O$): 346.2. found: 347.2 (M+H).

Example 22

Synthesis of N-(5-(2-chloro-5-(dimethylamino)phenyl)pyridin-2-yl)-4-methylnicotinamide (compound 138)

Compound 138

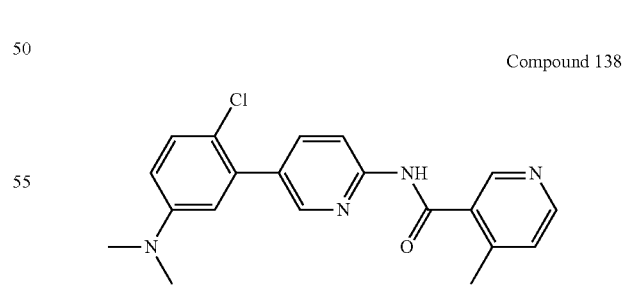

Compound 138 was prepared following the general procedures provided above in Example 21. $^1$H-NMR (400 MHz, $CDCl_3$) δ 8.78 (s, $^1$H), 8.64 (s, $^1$H), 8.56 (d, J=5.1, $^1$H), 8.41 (d, J=8.5, $^1$H), 8.31-8.25 (m, $^1$H), 7.91 (dd, J=2.3, 8.5, $^1$H), 7.32 (d, J=8.9, $^1$H), 7.23 (d, J=5.1, $^1$H), 6.68 (dd, J=3.1, 8.9, $^1$H), 6.61 (d, J=3.1, $^1$H), 2.98 (s, 6H), 2.57 (s, $^3$H); ESMS calc'd ($C_{20}H_{19}ClN_4O$): 366.2. found: 367.2 (M+H).

Example 23

Synthesis of N-(5-(2-chloro-5-((3-fluoropyridin-2-yl)amino)phenyl)pyridin-2-yl)-4-methylnicotinamide (compound 15)

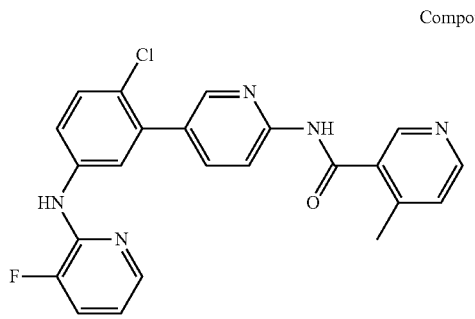

Compound 15

Compound 15 was prepared following the general procedures above in Example 21. $^1$H-NMR (400 MHz, CDCl$_3$) δ 8.80 (s, $^1$H), 8.58 (d, J=5.1, $^1$H), 8.42 (dd, J=5.4, 8.5, $^3$H), 8.01 (d, J=4.4, $^1$H), 7.95 (dd, J=2.4, 8.5, $^1$H), 7.77 (d, J=2.7, $^1$H), 7.64 (dd, J=2.7, 8.7, $^1$H), 7.44 (d, J=8.7, $^1$H), 7.34-7.23 (m, 2H), 6.78 (dd, J=4.0, 7.5, $^1$H), 6.68 (s, $^1$H), 2.58 (s, $^3$H); ESMS calc'd (C$_{23}$H$_{17}$ClN$_5$O): 433.1. found: 434.1 (M+H).

Example 24

Synthesis of 4-methyl-N-(6-methyl-5-(3-(trifluoromethoxy)phenyl)pyrazin-2-yl)nicotinamide (compound 21)

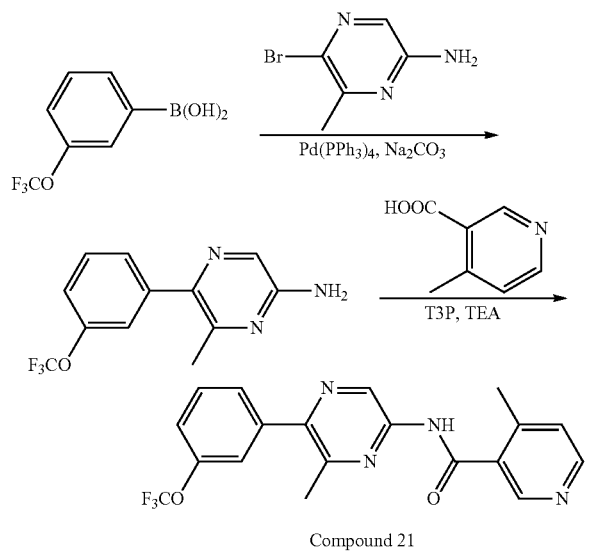

Compound 21

Compound 21 was prepared following the general procedures of Suzuki and amide couplings provided above in Example 11. $^1$H-NMR (400 MHz, CDCl$_3$) δ 9.56 (s, $^1$H), 8.84 (s, $^1$H), 8.75 (s, $^1$H), 8.58 (d, J=5.1, $^1$H), 7.53 (dd, J=4.6, 7.1, 2H), 7.47 (s, $^1$H), 7.30 (d, J=7.6, $^1$H), 7.25 (d, J=5.1, $^1$H), 2.58 (s, 6H); ESMS calc'd (C$_{19}$H$_{15}$F$_3$N$_4$O$_2$): 388.1. found: 389.1 (M+H).

Example 25

Synthesis of N-(5-(2-chloro-5-(2-methyl-2H-tetrazol-5-yl)phenyl)pyrazin-2-yl)-5-fluoro-4-methylnicotinamide (compound 26)

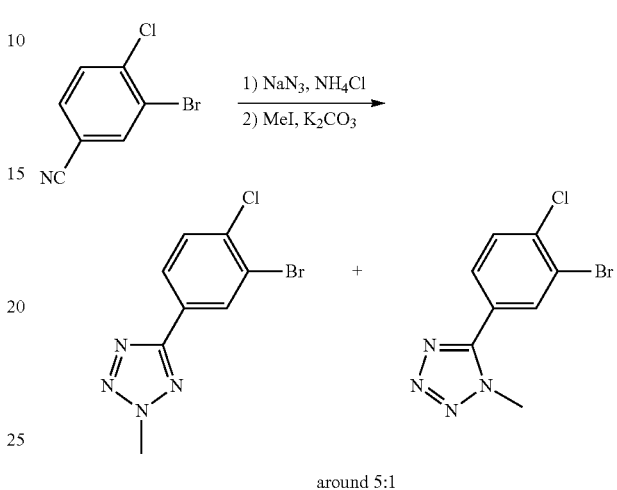

around 5:1

A solution of 3-chloro-4-bromobenzonitrile (21.65 g, 0.1 mol, 1.0 eq.) in 100 mL DMF placed at 90° C. oil bath was treated with sodium azide (13.0 g, 0.2 mol, 2.0 eq.) and ammonium chloride (21.4 g, 0.4 mol) in two portions (for both reagents) over 15 minutes. The reaction mixture was stirred at 90° C. for 2 hours. The reaction mixture was cooled to room temperature, diluted with 200 mL EtOAc, and passed through a filtration funnel to remove solid substances. The solution was concentrated on a rotary evaporator to remove EtOAc. To the resulting DMF solution was added K$_2$CO$_3$ (41.4 g, 0.3 mol), and the mixture was placed on a rotary evaporator at 50° C. for 1 hour to remove residual ammonium chloride and ammonia. The slurry was placed in an ice-water bath. Methyl iodide (6.4 g, 0.15 mol) was added in 4 portions over 1 hour. The reaction mixture was stirred for 48 hours while the ice-water bath was warmed up naturally to room temperature. Routine aqueous workup was performed, and the residue was purified by recrystallization to remove the region-isomer, yielding 5-(3-bromo-4-chlorophenyl)-2-methyl-2H-tetrazole (16.7 g, 61%) as an off-white solid.

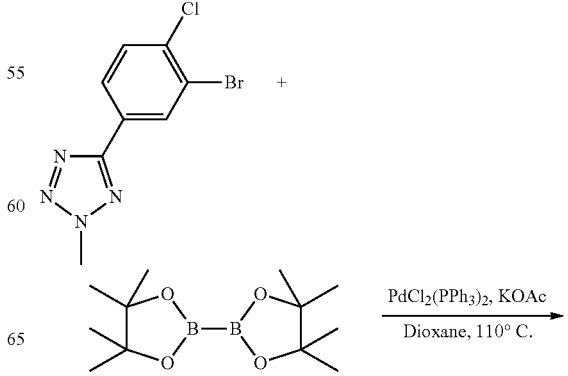

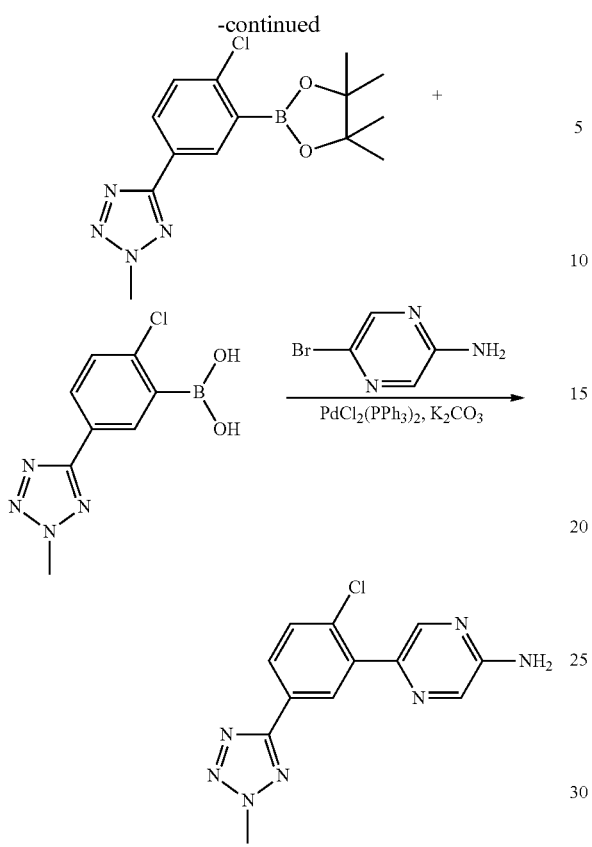

5-(3-bromo-4-chlorophenyl)-2-methyl-2H-tetrazole (0.55 g, 2.0 mmol), bis(pinacolato)diboron (0.76 g, 3.0 mmol), KOAc (0.6 g, 6.0 mmol), and palladium catalyst (0.042 g, 0.06 mmol) in 10 mL dioxane in a sealed-tube was subjected to 3 cycles of vacuum nitrogen purge. The sealed-tube was placed in 110° C. oil bath for 18 hours. The crude product (an off-white solid) from routine workup contained both the desired product and hydrolyzed boronic acid that was used in the next step without purification. The resulting crude product, 5-bromopyrazin-2-amine (0.35 g, 2.0 mmol), K₂CO₃ (0.8 g, 6.0 mmol), and Pd(PPh₃)₂Cl₂ (0.028 g, 0.04 mmol) in 10 mL dioxane in a sealed-tube was subjected to 3 cycles of vacuum nitrogen purge. The sealed-tube was placed in 90° C. oil bath for 15 hours. Routine workup and column separation yielded 5-(2-chloro-5-(2-methyl-2H-tetrazol-5-yl)phenyl)pyrazin-2-amine (0.38 g, 66% for both steps) as an off-white solid.

Compound 26

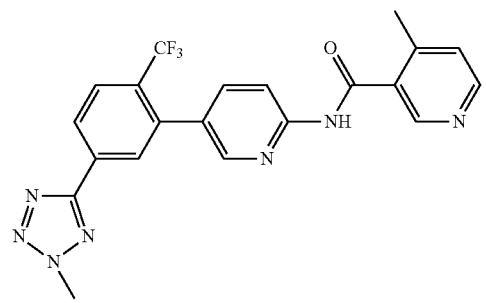 [SMILES: Cc1ccncc1C(=O)Nc1ccc(-c2cc(-c3nnn(C)n3)ccc2C(F)(F)F)cn1]

Compound 26 was prepared following a general amide coupling procedure with 5-fluoro-4-methylnicotinic acid and 5-(2-chloro-5-(2-methyl-2H-tetrazol-5-yl)phenyl)pyrazin-2-amine, prepared as above. ¹H-NMR (400 MHz, CDCl₃) δ 9.79 (d, J=1.5, ¹H), 8.75 (d, J=1.5, ¹H), 8.68 (s, ¹H), 8.56 (s, ¹H), 8.46 (d, J=2.1, ¹H), 8.33 (s, ¹H), 8.17 (dd, J=2.1, 8.4, ¹H), 7.65 (d, J=8.4, ¹H), 4.42 (s, ³H), 2.54 (d, J=2.0, ³H); ESMS calc'd ($C_{19}H_{14}ClFN_8O$): 424.1. found: 425.1 (M+H).

4-methyl-N-(5-(5-(2-methyl-2H-tetrazol-5-yl)-2-(trifluoromethyl)phenyl)pyridin-2-yl)nicotinamide (compound 92)

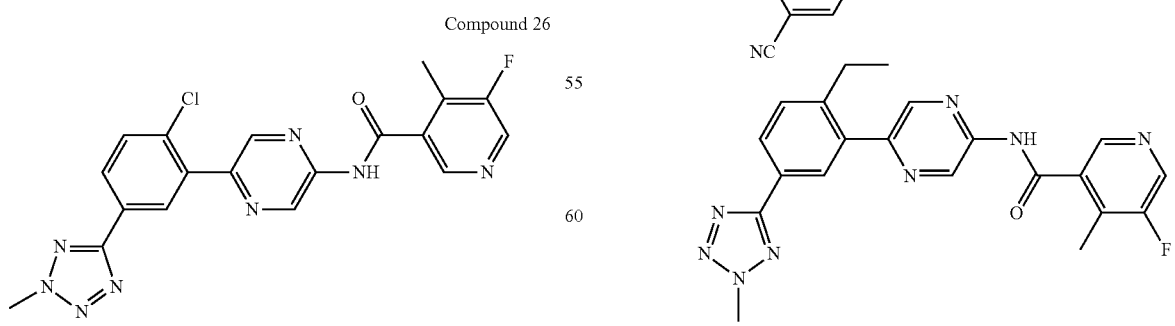

Compound 92 prepared via experimental procedure for compound 26. ¹H-NMR (CDCl₃) δ 8.81 (s, ¹H), 8.7 (br, ¹H), 8.6 (d, ¹H, J=4.8), 8.4 (d, ¹H, J=8.4), 8.3 (¹H, J=8.0), 8.2 (d, ¹H, J=2.4), 8.14 (s, ¹H), 7.9 (d, ¹H, J=8.0), 7.8 (dd, ¹H, J₁=8.4, J₂=2.0), 7.2 (d, ¹H, J=4.8), 4.44 (s, ³H), 2.60 (s, ³H) ppm; ESMS calc'd for $C_{21}H_{16}F_3N_7O$: 439.1. found: 440.2 (M+H⁺).

Example 26

Synthesis of N-(5-(2-ethyl-5-(2-methyl-2H-tetrazol-5-yl)phenyl)pyrazin-2-yl)-5-fluoro-4-methylnicotinamide (compound 27)

Compound 27

4-ethylbenzonitrile (1.31 g, 10 mmol) was added to 6 mL of 9N $H_2SO_4$ at 0° C. NBS (10 mmol) was added, followed by 6 mL of $CH_3CN$. The flask was wrapped with aluminum foil, and the mixture was stirred vigorously at room temperature for 2 days. Ether/aqueous extraction followed by column separation gave 3-bromo-4-ethylbenzonitrile as colorless oil (1.30 g, 61.6%).

Compound 27 was prepared following general procedures from 3-bromo-4-ethylbenzonitrile above (Example 25). $^1$H-NMR (400 MHz, $CDCl_3$) δ 9.75 (d, J=1.3, $^1$H), 8.75 (s, $^1$H), 8.64 (s, $^1$H), 8.54 (s, $^1$H), 8.44 (d, J=1.4, $^1$H), 8.20-8.13 (m, 2H), 7.50 (d, J=8.7, $^1$H), 4.40 (s, $^3$H), 2.82 (q, J=7.5, 2H), 2.53 (d, J=1.9, $^3$H), 1.19 (t, J=7.5, $^3$H); ESMS calc'd ($C_{21}H_{19}FN_8O$): 418.2. found: 419.2 (M+H).

4-methyl-N-(5-(2-methyl-5-(2-methylthiazol-4-yl) phenyl)pyrazin-2-yl)nicotinamide (compound 124)

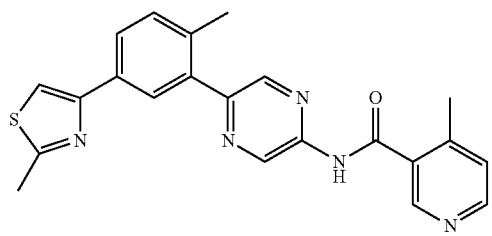 [SMILES: Cc1nc(-c2ccc(C)c(-c3cnc(NC(=O)c4cnccc4C)cn3)c2)cs1]

Compound 124 was prepared following general procedures from Example 25. $^1$H-NMR ($CDCl_3$) δ 9.75 (s, $^1$H), 8.81 (s, $^1$H), 8.64-7.26 (m, 8H), 2.78 (s, $^3$H), 2.60 (s, $^3$H), 2.43 (s, $^3$H); ESMS calc'd for $C_{22}H_{19}N_5OS$: 401.13. Found: 402.1 (M+H)$^+$.

Example 27

Synthesis of (Z)-5-fluoro-N-(5-(1-(4-methoxyphenyl)prop-1-en-1-yl)pyridin-2-yl)-4-methylnicotinamide (compound 103)

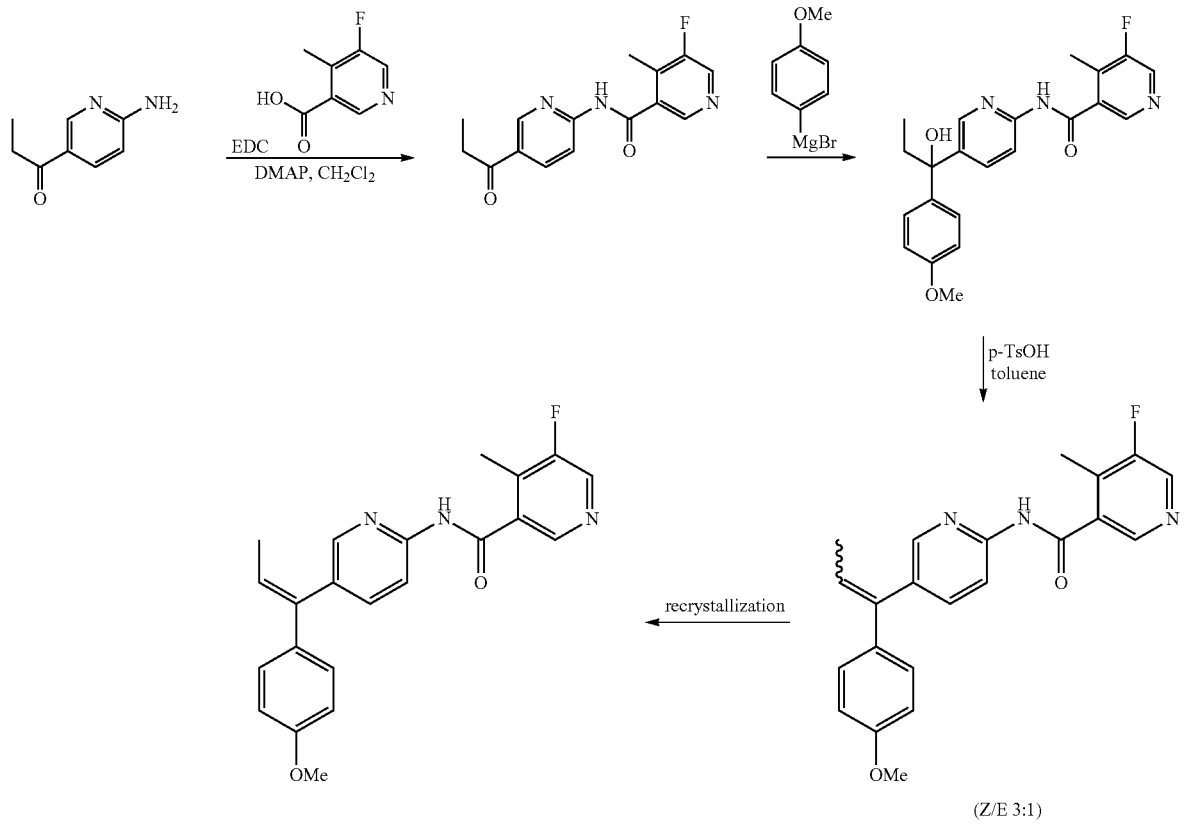

To a solution of 1-(6-aminopyridin-3-yl)propan-1-one (0.7 g, 4.70 mmol) in 20 mL of $CH_2Cl_2$ at room temperature was added 5-fluoro-4-methylnicotinic acid (0.8 g, 5.16 mmol), EDC (0.99 g, 5.16 mmol), and DMAP (1.14 g, 9.40 mmol). The solution was stirred at room temperature for overnight. The solvent was removed, and the residue was treated with $K_2CO_3$ (2.0 g) and heated in 30 mL of methanol at 50° C. for 10 minutes. The solvent was removed under reduced pressure. The residue was taken into ethyl acetate, and the resulting solution was washed with brine, dried over anhydrous sodium sulfate, and concentrated. The residue was recrystallized from ethyl acetate to give 5-fluoro-4-methyl-N-(5-propionylpyridin-2-yl)nicotinamide (950 mg) as a white solid. ESMS calculated ($C_{15}H_{14}FN_3O_2$) 287.1. found: 288.1 (M+H).

To a solution of 5-fluoro-4-methyl-N-(5-propionylpyridin-2-yl)nicotinamide (500 mg, 1.74 mmol) in 20 mL of anhydrous THF at 0° C. was added dropwise a solution of (4-methoxyphenyl)magnesium bromide in THF (0.5 M, 8.0 mL, 4.0 mmol) over 5 minutes. The solution was warmed to room temperature and stirred sealed under $N_2$ for overnight.

The reaction solution was quenched with saturated NaHCO$_3$ and extracted with EtOAc. The organic phases were combined, washed with brine, dried over anhydrous sodium sulfate, and concentrated. The residue was purified by flash column chromatography on silica gel (0-100% EtOAc/hexanes) to give 5-fluoro-N-(5-(1-hydroxy-1-(4-methoxyphenyl)propyl)pyridin-2-yl)-4-methylnicotinamide (820 mg) as a white solid. ESMS calculated (C$_{22}$H$_{22}$FN$_3$O$_3$) 395.1. found: 396.1 (M+H).

To a solution of 5-fluoro-N-(5-(1-hydroxy-1-(4-methoxyphenyl)propyl)pyridin-2-yl)-4-methylnicotinamide (400 mg, 1.01 mmol) in 10 mL of toluene was added 0.2 g of p-TsOH. The solution was heated under N$_2$ at 100° C. for 1 hour. After cooling to room temperature, the reaction mixture was washed with saturated NaHCO$_3$ and concentrated. The residue was recrystallized from 6 mL of anhydrous MeOH to give a 3:1 (Z/E) mixture of 5-fluoro-N-(5-(1-(4-methoxyphenyl)prop-1-en-1-yl)pyridin-2-yl)-4-methylnicotinamide (250 mg) as a white solid.

The 3:1 (Z/E) mixture (250 mg) prepared above was further recrystallized from hot anhydrous MeOH to give desired (Z)-5-fluoro-N-(5-(1-(4-methoxyphenyl)prop-1-en-1-yl)pyridin-2-yl)-4-methylnicotinamide (123 mg) as a white solid. $^1$H-NMR (400 MHz, CDCl$_3$) δ 8.69 (br s, $^1$H), 8.61 (s, $^1$H), 8.47 (s, $^1$H), 8.35 (d, J=8.4 Hz, 1H), 8.00 (s, $^1$H), 7.61 (dd, J=8.4, 2.0 Hz, $^1$H), 7.12 (d, J=8.1 Hz, 2H), 6.83 (d, J=8.1 Hz, 2H), 6.17 (q, J=7.2 Hz, $^1$H), 3.82 (s, $^3$H), 2.50 (d, J=1.3 Hz, $^3$H), 1.77 (d, J=7.2 Hz); ESMS calculated (C$_{22}$H$_{20}$FN$_3$O$_2$) 377.1. found: 378.1 (M+H).

Example 28

Synthesis of (Z)—N-(5-(1-(4-bromophenyl)prop-1-en-1-yl)pyridin-2-yl)-5-fluoro-4-methylnicotinamide (compound 136)

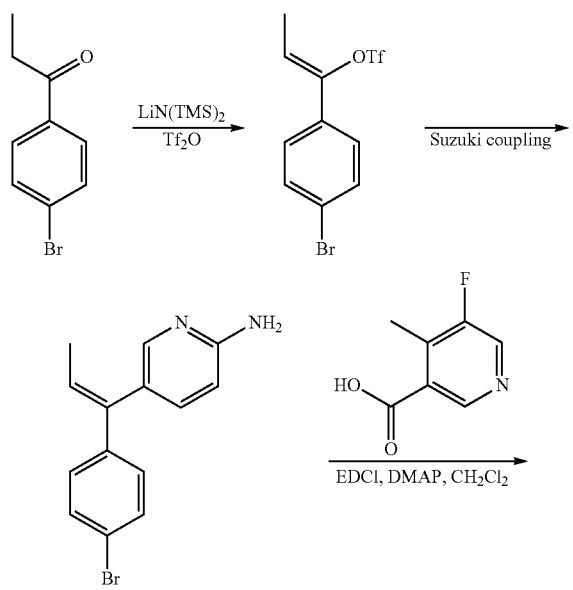

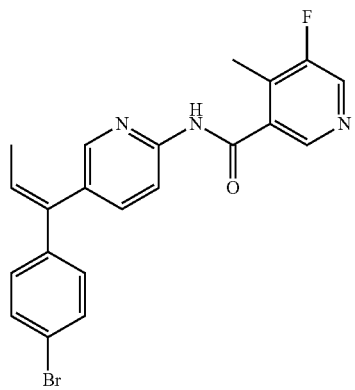

To a solution of 1-(4-bromophenyl)propan-1-one (1.02 g, 4.79 mmol) in 10 mL of anhydrous THF at −78° C. under N$_2$ was added dropwise a 1.0 M solution of LiN(TMS)$_2$ in THF (5 mL, 5.0 mmol). The solution was stirred at −78° C. for 30 minutes. Then, to the solution was added triflic anhydride (1.38 g, 4.88 mmol) at −78° C. The solution was stirred at −78° C. for 1 hour then quenched with ice water. The mixture was warmed up to room temperature and taken into ethyl acetate. The solution was washed with saturated NaHCO$_3$ and brine, dried over anhydrous sodium sulfate, and concentrated. The residue was purified by flash column chromatography on silica gel (eluted with 0-100% EtOAc/hexanes) to give a 7:1 (Z/E) mixture of 1-(4-bromophenyl)prop-1-en-1-yl trifluoromethanesulfonate (1.20 g) as a yellow oil. The mixture was used directly for next operation without further separation of the two isomers. ESMS calculated (C$_{10}$H$_8$BrF$_3$O$_3$S) 346. found: 347 (M+H).

To a solution of the enol triflate prepared above (1.0 g, 2.91 mmol) in 20 mL of anhydrous THF was added 5-(4,4,5,5-tetramethyl-1,3,2-dioxazolidin-2-yl)pyridin-2-amine (880 mg, 3.94 mmol), potassium carbonate (828 mg, 6.0 mmol), and Pd(PPh$_3$)$_4$ (100 mg). The mixture was sealed under N$_2$, and the solution was heated at 90° C. for overnight. The solvent was removed under reduced pressure, and the residue was purified by flash column chromatography on silica gel (eluted with 0-100% EtOAc/hexanes) to give 5-(1-(4-bromophenyl)prop-1-en-1-yl)pyridin-2-amine as a white solid. ESMS calculated (C$_{14}$H$_{13}$BrN$_2$) 288. found: 289 (M+H).

To a solution of 5-(1-(4-bromophenyl)prop-1-en-1-yl)pyridin-2-amine (75 mg, 0.26 mmol) in 1 mL of CH$_2$Cl$_2$ at room temperature was added 5-fluoro-4-methylnicotinic acid (80 mg, 0.52 mmol), EDC (100 mg, 0.52 mmol), and DMAP (12.7 mg, 0.1 mmol). The solution was stirred at room temperature for overnight. The solvent was removed, and the residue was treated with Na$_2$CO$_3$ (200 mg) and heated in 3 mL of methanol to reflux, then cooled. The solvent was removed under reduced pressure. The residue was taken into ethyl acetate, and the resulting solution was washed with brine, dried over anhydrous sodium sulfate, and concentrated. The residue was purified by flash chromatography to produce 55 mg of (Z)—N-(5-(1-(4-bromophenyl)prop-1-en-1-yl)pyridin-2-yl)-5-fluoro-4-methylnicotinamide (compound 136). ESMS calculated (C$_2$$^1$H$_{17}$BrFN$_3$O) 425.1. found: 426.1 (M+H).

Example 29

Synthesis of (Z)—N-(5-(1-(4-bromophenyl)prop-1-en-1-yl)pyridin-2-yl)-4-methylnicotinamide (compound 10)

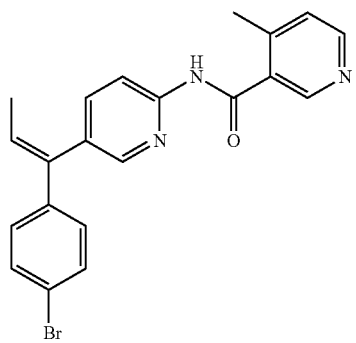 [SMILES: C/C=C(/c1ccc(Br)cc1)c1ccc(NC(=O)c2cnccc2C)nc1]

(Z)—N-(5-(1-(4-bromophenyl)prop-1-en-1-yl)pyridin-2-yl)-4-methylnicotinamide was prepared from 5-(1-(4-bromophenyl)prop-1-en-1-yl)pyridin-2-amine and 4-methylnicotinic acid analogously, as described for Example 28. $^1$H-NMR (400 MHz, CDCl$_3$) δ 9.47 (s, $^1$H), 8.75 (s, $^1$H), 8.48 (d, J=8.8 Hz, $^1$H), 8.39 (d, J=8.4 Hz), 7.70 (d, J=2.0 Hz, $^1$H), 7.56 (dd, J=8.4, 2.2 Hz, $^1$H), 7.41 (d, J=8.4 Hz, 2H), 7.16 (d, J=5.2 Hz, $^1$H), 7.04 (d, J=8.4 Hz, 2H), 6.23 (q, J=7.0 Hz, $^1$H), 2.54 (s, $^3$H), 1.76 (d, J=7.0 Hz, $^3$H); ESMS calculated (C$_{21}$H$_{18}$BrN$_3$O) 407.1. found: 408.1 (M+H).

Example 30

Synthesis of (Z)-5-fluoro-4-methyl-N-(5-(1-(4-(4-methyl-$^1$H-imidazol-1-yl)phenyl)prop-1-en-1-yl)pyridin-2-yl)nicotinamide (compound 11)

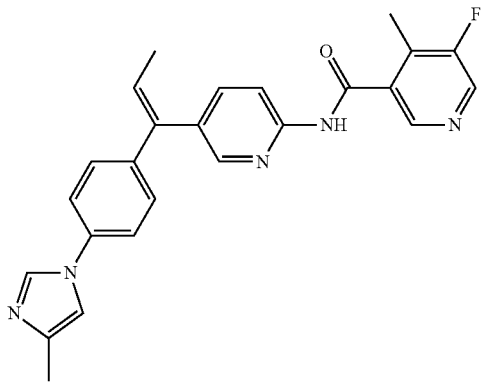 [SMILES: C/C=C(/c1ccc(-n2cnc(C)c2)cc1)c1ccc(NC(=O)c2cncc(F)c2C)nc1]

To a solution of (Z)—N-(5-(1-(4-bromophenyl)prop-1-en-1-yl)pyridin-2-yl)-5-fluoro-4-methylnicotinamide (10 mg) in 1 mL of DMSO was added 4-methyl-1-H-imidazole (10 mg), CuI (5 mg), L-proline (7 mg), and K$_2$CO$_3$ (25 mg). Under N$_2$, the mixture was sealed and heated to 115° C. for 3 hours. After cooling to room temperature, the mixture was partitioned between EtOAc and H$_2$O. The aqueous phase was extracted with EtOAc twice, and the combined organic phases were washed with brine, dried over Na$_2$SO$_4$, and concentrated. Flash chromatography of the residue on silica gel (eluted with 0-100% EtOAc/hexanes) gave 7 mg of (Z)-5-fluoro-4-methyl-N-(5-(1-(4-(4-methyl-$^1$H-imidazol-1-yl)phenyl)prop-1-en-1-yl)pyridin-2-yl)nicotinamide as a white solid. $^1$H-NMR (400 MHz, CDCl$_3$) δ 9.05 (s, $^1$H), 8.61 (s, $^1$H), 8.45 (s, $^1$H), 8.39 (d, J=8.6 Hz, $^1$H), 7.95 (d, J=2.0 Hz, $^1$H), 7.75 (d, J=1.3 Hz, $^1$H), 7.62 (dd, J=8.6, 2.0 Hz, $^1$H), 7.31-7.25 (m, 4H), 7.00 (s, $^1$H), 6.30 (q, J=7.2 Hz, $^1$H), 2.49 (d, J=2.0 Hz, $^1$H), 2.29 (s, $^3$H), 1.82 (d, J=7.2 Hz, $^3$H); ESMS calculated (C$_{23}$H$_{22}$FN$_5$O) 427.1. found: 428.1 (M+H).

Example 31

Synthesis of (Z)-5-fluoro-4-methyl-N-(5-(1-(4-(1-methyl-$^1$H-imidazol-5-yl)phenyl)prop-1-en-1-yl)pyridin-2-yl)nicotinamide (compound 13)

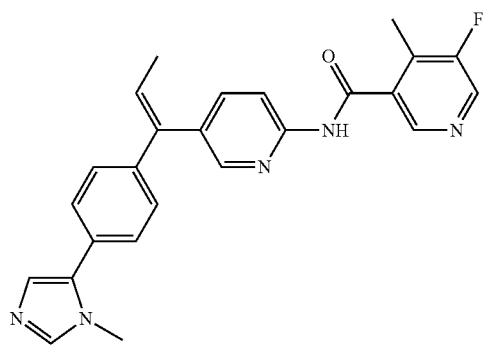 [SMILES: C/C=C(/c1ccc(-c2cncn2C)cc1)c1ccc(NC(=O)c2cncc(F)c2C)nc1]

To a solution of (Z)—N-(5-(1-(4-bromophenyl)prop-1-en-1-yl)pyridin-2-yl)-5-fluoro-4-methylnicotinamide (10 mg) in 1 mL of anhydrous DMF was added 1-methyl-5-(tributylstannyl)-$^1$H-imidazole (15 mg), potassium carbonate (20 mg), and Pd(PPh$_3$)$_4$ (5 mg). The mixture was sealed under N$_2$, and the solution was heated at 90° C. for overnight. The solvent was removed under reduced pressure, and the residue was purified by flash chromatography on silica gel (eluted with 0-100% EtOAc/hexanes) to give (Z)-5-fluoro-4-methyl-N-(5-(1-(4-(1-methyl-$^1$H-imidazol-5-yl)phenyl)prop-1-en-1-yl)pyridin-2-yl)nicotinamide (7.5 mg) as a white solid. $^1$H-NMR (400 MHz, CDCl$_3$) δ 9.27 (s, $^1$H), 8.62 (s, $^1$H), 8.46 (s, $^1$H), 8.39 (d, J=8.6 Hz, $^1$H), 8.02 (d, J=2.0 Hz, $^1$H), 7.63 (dd, J=8.6, 2.0 Hz, $^1$H), 7.51 (s, $^1$H), 7.33 (d, J=8.6 Hz, 2H), 7.26 (d, J=8.6 Hz, 2H), 7.10 (s, $^1$H), 6.33 (q, J=7.2 Hz, $^1$H), 3.69 (s, $^3$H), 2.49 (d, J=2.0 Hz, $^3$H), 1.82 (d, J=7.2 Hz, $^3$H); ESMS calculated (C$_{23}$H$_{22}$FN$_5$O) 427.1. found: 428.1 (M+H).

Example 32

Synthesis of (Z)-5-fluoro-4-methyl-N-(5-(1-(4-(pyridin-2-yl)phenyl)prop-1-en-1-yl)pyridin-2-yl)nicotinamide (compound 88)

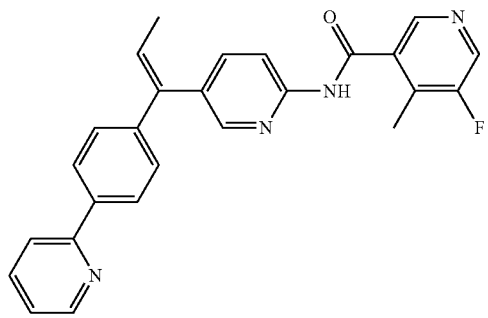 [SMILES: C/C=C(/c1ccc(-c2ccccn2)cc1)c1ccc(NC(=O)c2cncc(F)c2C)nc1]

To a solution of (Z)—N-(5-(1-(4-bromophenyl)prop-1-en-1-yl)pyridin-2-yl)-5-fluoro-4-methylnicotinamide (20 mg) in 1 mL of anhydrous THF was added 2-pyridyl zinc bromide (0.5 M in THF, 0.2 mL) and Pd(PPh$_3$)$_4$ (10 mg). The mixture was sealed under N$_2$, and the solution was heated at 110° C. for 1 hour. The solvent was removed under reduced pressure, and the residue was purified by flash column chromatography on silica gel (eluted with 0-100% EtOAc/hexanes) to give (Z)-5-fluoro-4-methyl-N-(5-(1-(4-(pyridin-2-yl)phenyl)prop-1-en-1-yl)pyridin-2-yl)nicotinamide (10.5 mg) as a white solid. $^1$H-NMR (400 MHz, CDCl$_3$) δ 9.17 (s, $^1$H), 8.69 (d, J=4.8 Hz, $^1$H), 8.61 (s, $^1$H), 8.44 (s, $^1$H), 8.39 (d, J=8.5 hz, $^1$H), 7.94-7.23 (m, 9H), 6.36 (q, J=7.2 hz, $^1$H), 2.49 (d, J=2.0 Hz, $^3$H), 1.82 (d, J=7.2 Hz, $^3$H); ESMS calculated (C$_{26}$H$_{21}$FN$_4$O) 424.1. found: 425.1 (M+H).

Example 33

Synthesis of (Z)—N-(5-(1-(4-cyanophenyl)prop-1-en-1-yl)pyridin-2-yl)-5-fluoro-4-methylnicotinamide (compound 89)

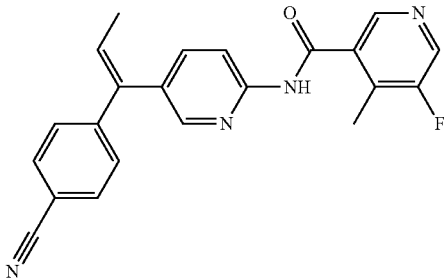 [SMILES: C/C=C(/c1ccc(C#N)cc1)c1ccc(NC(=O)c2cncc(F)c2C)nc1]

To a solution of (Z)—N-(5-(1-(4-bromophenyl)prop-1-en-1-yl)pyridin-2-yl)-5-fluoro-4-methylnicotinamide (20 mg) in 1 mL of anhydrous DMF was added zinc cyanide (30 mg) and Pd(PPh$_3$)$_4$ (10 mg). The mixture was sealed under N$_2$ and heated at 130° C. for 30 minutes. The solvent was removed under reduced pressure, and the residue was purified by flash chromatography on silica gel (eluted with 0-100% EtOAc/hexanes) to give (Z)—N-(5-(1-(4-cyanophenyl)prop-1-en-1-yl)pyridin-2-yl)-5-fluoro-4-methylnicotinamide (11 mg) as a white solid. $^1$H-NMR (400 MHz, CDCl$_3$) δ 8.71 (s, $^1$H), 8.61 (s, $^1$H), 8.48 (s, $^1$H), 8.39 (d, J=8.6 Hz, $^1$H), 8.0 (d, J=2.0 Hz, $^1$H), 7.59-7.56 (m, $^3$H), 7.29 (d, J=8.6 Hz, 2H), 6.40 (q, J=7.2 Hz, $^1$H), 2.50 (d, J=2.0 Hz, $^3$H), 1.84 (d, J=7.2 Hz, $^3$H); ESMS calculated (C$_{22}$H$_{17}$FN$_4$O) 372.1. found: 373.1 (M+H).

Example 34

Synthesis of (Z)-5-fluoro-4-methyl-N-(5-(1-(4-(1-methyl-$^1$H-pyrazol-4-yl)phenyl)prop-1-en-1-yl)pyridin-2-yl)nicotinamide hydrochloride (compound 145)

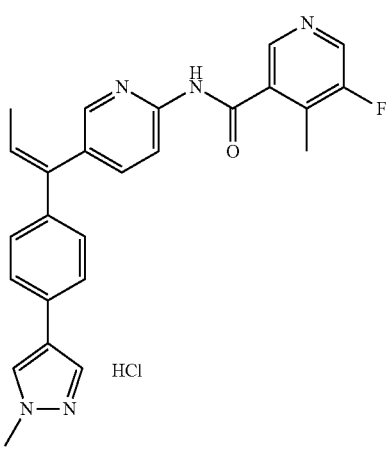 [SMILES: C/C=C(/c1ccc(-c2cnn(C)c2)cc1)c1ccc(NC(=O)c2cncc(F)c2C)nc1 ; Cl]

(Z)-5-fluoro-4-methyl-N-(5-(1-(4-(1-methyl-$^1$H-pyrazol-4-yl)phenyl)prop-1-en-1-yl)pyridin-2-yl)nicotinamide hydrochloride was prepared by Suzuki coupling of (Z)—N-(5-(1-(4-bromophenyl)prop-1-en-1-yl)pyridin-2-yl)-5-fluoro-4-methylnicotinamide and 1-methylpyrazole-4-boronic acid pinacol ester, followed by HCl salt formation. $^1$H-NMR (400 MHz, CD$_3$OD): δ 8.75-7.25 (m, 1$^1$H), 6.50 (q, J=7.2 Hz, $^1$H), 3.95 (s, $^3$H), 2.56 (d, J=2.0 Hz, $^3$H), 1.88 (d, $^3$H, J=7.2 Hz); ESMS calculated (C$_{23}$H$_{23}$ClFN$_5$O) 463.9. found: 428.1 (M-Cl).

Example 35

Synthesis of (Z)—N-(5-(1-(4-bromophenyl)prop-1-en-1-yl)pyrazin-2-yl)-5-fluoro-4-methylnicotinamide (compound 146)

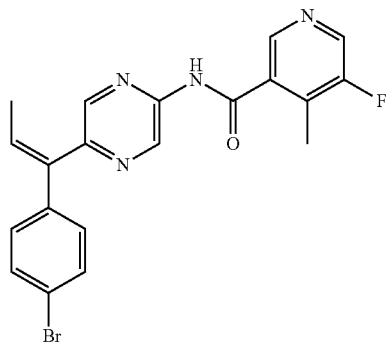 [SMILES: C/C=C(/c1ccc(Br)cc1)c1cnc(NC(=O)c2cncc(F)c2C)cn1]

(Z)—N-(5-(1-(4-bromophenyl)prop-1-en-1-yl)pyrazin-2-yl)-5-fluoro-4-methylnicotinamide was prepared by Suzuki coupling of 1-(4-bromophenyl)prop-1-en-1-yl trifluoromethanesulfonate and 5-(4,4,5,5-tetramethyl-1,3,2-dioxaborolan-2-yl)pyrazin-2-amine followed by amide formation, similarly as described for the preparation of (Z)—N-(5-(1-(4-bromophenyl)prop-1-en-1-yl)pyridin-2-yl)-5-fluoro-4-methylnicotinamide (compound 136, Example 28). $^1$H-NMR (400 MHz, CDCl$_3$) δ 9.72 (d, J=1.7 Hz, $^1$H), 8.62 (s, $^1$H), 8.52 (br s, 2H), 8.14 (d, J=1.7 Hz, $^1$H), 7.44 (d, J=8.8 Hz, 2H), 7.09 (d, J=8.8 Hz, 2H), 6.37 (q, J=7.2 Hz, $^1$H), 0.251 (d, J=2.0 Hz, $^3$H), 1.90 (d, J=7.2 Hz, $^3$H); ESMS calculated (C$_2$$^1$H$_{17}$BrFN$_3$O) 426.05. found: 427.1 (M+H).

Example 36

Synthesis of (Z)—N-(5-(1-(4-bromophenyl)prop-1-en-1-yl)pyrazin-2-yl)-4-methylnicotinamide (compound 83)

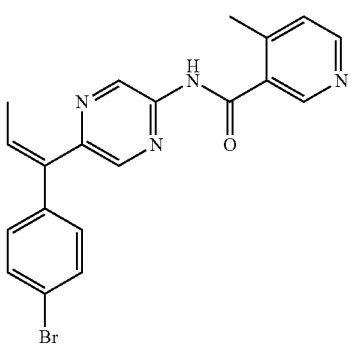 [SMILES: C/C=C(/c1ccc(Br)cc1)c1cnc(NC(=O)c2cnccc2C)cn1]

(Z)—N-(5-(1-(4-bromophenyl)prop-1-en-1-yl)pyrazin-2-yl)-4-methylnicotinamide was prepared analogously as described for the preparation of (Z)—N-(5-(1-(4-bromophenyl)prop-1-en-1-yl)pyrazin-2-yl)-5-fluoro-4-methylnicotinamide (compound 136, Example 28). ¹H-NMR (400 MHz, CDCl₃) δ 9.72 (d, J=1.4 Hz, ¹H), 8.79 (s, ¹H), 8.60 (s, ¹H), 8.58 (d, J=5.1 Hz, ¹H), 8.12 (d, J=1.5 Hz, ¹H), 7.24 (d, J=5.1 Hz, ¹H), 7.43 (d, J=8.6 Hz, 2H), 7.09 (d, J=8.6 Hz, 2H), 6.36 (q, J=7.2 Hz, ¹H), 2.58 (s, ³H), 1.89 (d, J=7.2 Hz, ³H); ESMS calculated (C₂₀H₁₇BrN₄O) 408.1. found: 409.1 (M+H).

Example 37

Synthesis of (Z)—N-(4-(1-(4-bromophenyl)prop-1-en-1-yl)-3-methylphenyl)-5-fluoro-4-methylnicotinamide (compound 4)

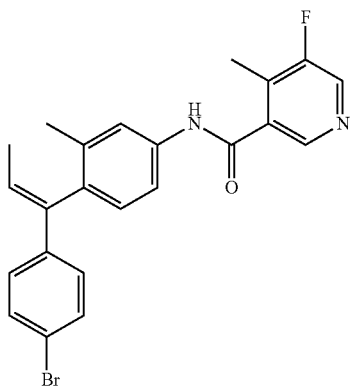 [SMILES: C/C=C(/c1ccc(Br)cc1)c1ccc(NC(=O)c2cncc(F)c2C)cc1C]

(Z)—N-(4-(1-(4-bromophenyl)prop-1-en-1-yl)-3-methylphenyl)-5-fluoro-4-methylnicotinamide was prepared by Suzuki coupling of 1-(4-bromophenyl)prop-1-en-1-yl trifluoromethanesulfonate and 3-methyl-4-(4,4,5,5-tetramethyl-1,3,2-dioxaborolan-2-yl)aniline followed by amide formation, similarly as described for the preparation of (Z)—N-(5-(1-(4-bromophenyl)prop-1-en-1-yl)pyridin-2-yl)-5-fluoro-4-methylnicotinamide (compound 136, Example 28). ¹H-NMR (400 MHz, CDCl₃) δ 8.53 (s, ¹H), 8.44 (s, ¹H), 7.92 (s, ¹H), 7.58 (s, ¹H), 7.48 (m, 2H), 7.36 (d, J=8.0 Hz, 2H), 7.08 (d, J=8.0 Hz, ¹H), 7.06 (d, J=8.0 Hz, 2H), 6.32 (q, J=7.2 Hz, ¹H), 2.47 (d, J=1.3 Hz, 3H), 2.07 (s, ³H), 1.61 (d, J=7.2 Hz, ³H); ESMS calculated (C₂₃H₂₀BrFN₂O) 438.1. found: 439.1 (M+H).

Example 38

Synthesis of 5-fluoro-N-(5-(1-(4-methoxyphenyl)-2-methylprop-1-en-1-yl)pyridin-2-yl)-4-methylnicotinamide (compound 97)

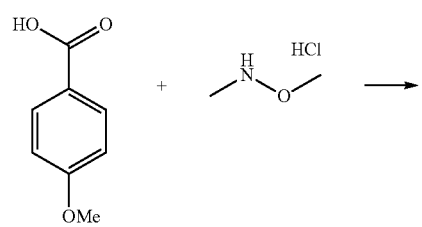

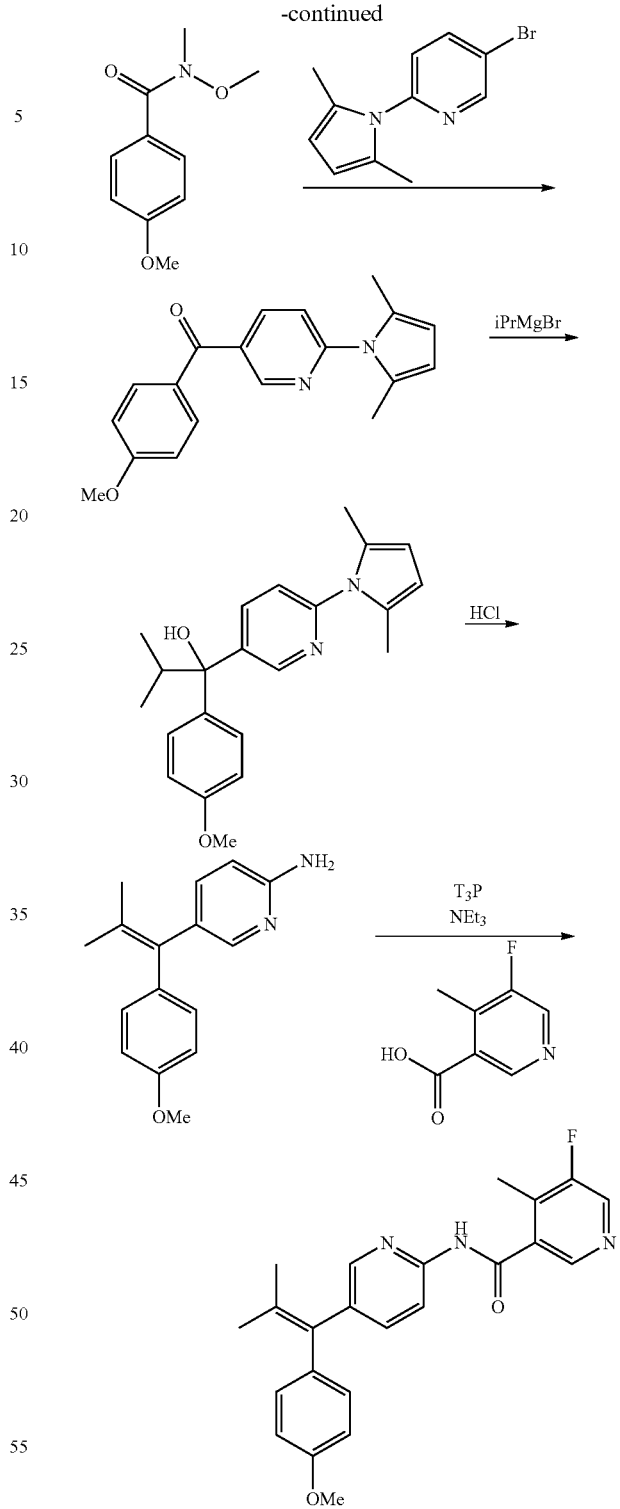

To 4-methoxybenzoic acid (100 g, 657.89 mmol) was added SOCl₂ (200 g, 1.68 mol). To the solution was added a solution of N-methoxymethanamine hydrochloride (71.5 g, 729.59 mmol) in 500 mL of DCM. The mixture was stirred 2 hours with refluxing. To the mixture was added Et₃N (300 g, 2.97 mol). The solution was allowed to react, with stirring, for 30 minutes while the temperature was maintained at room temperature. When the reaction was completed, it was quenched by 500 mL water and extracted by DCM. Removal of solvent followed by purification by flash column chromatography on silica gel gave 110 g (86%) of N,4-dimethoxy-N-methylbenzamide as a yellow liquid.

To a solution of 5-bromo-2-(2,5-dimethyl-$^1$H-pyrrol-1-yl)pyridine (20 g, 79.68 mmol) in 500 mL of ether under $N_2$ was added n-BuLi (48 g, 18.75 mmol, 1.50 eq., 2.5M) dropwise with stirring at −78° C. over a period of 10 minutes. To the solution was added N,4-dimethoxy-N-methylbenzamide (15.6 g, 80.00 mmol) dropwise with stirring at −78° C. over a period of 5 minutes. The resulting solution was allowed to react, with stirring, for 10 minutes at −78° C. and then quenched by the adding of $H_2O$. The mixture was extracted with DCM, and the organic phase was dried and concentrated. The residue was purified by flash column chromatography on silica gel to give 10 g (41%) of (6-(2,5-dimethyl-$^1$H-pyrrol-1-yl)pyridin-3-yl)(4-methoxyphenyl)methanone as a white solid.

To a solution of (6-(2,5-dimethyl-$^1$H-pyrrol-1-yl)pyridin-3-yl)(4-methoxyphenyl)methanone (2 g, 6.54 mmol) in THF (30 mL) under $N_2$ was added isopropylmagnesium chloride (3.6 mL, 2M) dropwise with stirring at 0-5° C. The resulting solution was stirred at −5° C. for 1 hour and then with water. The mixture was extracted with DCM, and the organic phase was dried and concentrated. The residue was purified by flash column chromatography on silica gel to give 1.5 g of 1-(6-(2,5-dimethyl-$^1$H-pyrrol-1-yl)pyridin-3-yl)-1-(4-methoxyphenyl)-2-methylpropan-1-ol as a yellow oil.

To a solution of 1-(6-(2,5-dimethyl-$^1$H-pyrrol-1-yl)pyridin-3-yl)-1-(4-methoxyphenyl)-2-methylpropan-1-ol (2.3 g, 6.57 mmol) in 20 mL of EtOH was added HCl (5.3 g, 53.73 mmol, 8.18 eq., 37%). The solution was heated to reflux for 1 hour. After cooling down to room temperature, the solution was neutralized with NaOH to pH 8. The mixture was extracted with ethyl acetate. The organic phase was washed with brine, dried, and concentrated. The residue was purified by flash column chromatography on silica gel to give 1.5 g (90%) of 5-(1-(4-methoxyphenyl)-2-methylprop-1-enyl)pyridin-2-amine as a white solid.

compound 97

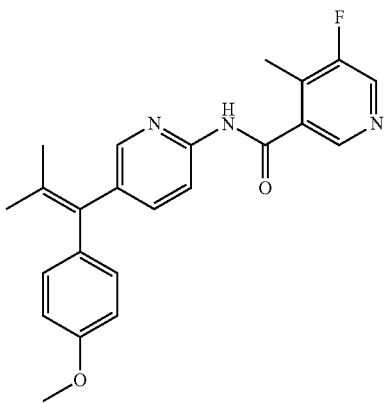

To a solution of 5-(1-(4-methoxyphenyl)-2-methylprop-1-enyl)pyridin-2-amine (50 mg, 0.197 mmol) in 5 mL of EtOAc at room temperature was added 5-fluoro-4-methylnicotinic acid (50 mg), triethylamine (130 mg), and T3P (318 mg, 50% solution in DMF). The solution was heated in microwave reactor at 100° C. for 1 hour. The reaction was quenched with water and neutralized with $K_2CO_3$ to pH 7. The organic phase was concentrated under reduced pressure. The residue was purified by flash column chromatography on silica gel to give 38 mg of 5-fluoro-N-(5-(1-(4-methoxyphenyl)-2-methylprop-1-en-1-yl)pyridin-2-yl)-4-methylnicotinamide. $^1$H-NMR (400 MHz, $CDCl_3$) δ 8.75 (br s, $^1$H), 8.57 (s, $^1$H), 8.46 (s, $^1$H), 8.24 (d, J=8.6 Hz, $^1$H), 7.90 (br s, $^1$H), 7.51 (dd, J=8.6, 2.0 Hz, $^1$H), 7.02 (d, J=8.6 Hz, 2H), 6.84 (d, J=8.6 Hz, 2H), 3.81 (s, $^3$H), 2.47 (d, J=1.8 Hz, $^3$H), 1.84 (s, $^3$H), 1.82 (s, $^3$H); ESMS calculated ($C_{23}H_{22}FN_3O_2$) 391.1. found: 392.1 (M+H).

Example 39

Synthesis of N-(5-(1-(4-methoxyphenyl)-2-methylprop-1-en-1-yl)pyridin-2-yl)-4-methylnicotinamide (compound 102)

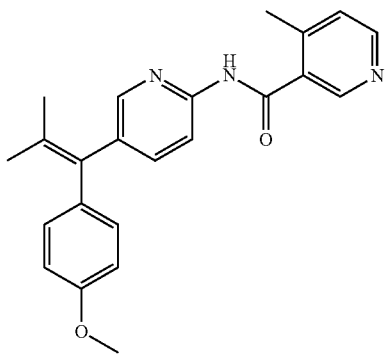 [SMILES: COc1ccc(C(=C(C)C)c2ccc(NC(=O)c3cnccc3C)nc2)cc1]

N-(5-(1-(4-methoxyphenyl)-2-methylprop-1-en-1-yl)pyridin-2-yl)-4-methylnicotinamide was prepared from 5-(1-(4-methoxyphenyl)-2-methylprop-1-enyl)pyridin-2-amine and 4-methylnicotinic acid analogously as described for the preparation of 5-fluoro-N-(5-(1-(4-methoxyphenyl)-2-methylprop-1-en-1-yl)pyridin-2-yl)-4-methylnicotinamide (compound 97, Example 38). $^1$H-NMR (400 MHz, $CDCl_3$) δ 9.26 (s, $^1$H), 8.73 (s, $^1$H), 8.51 (d, J=5.1 Hz, $^1$H), 8.27 (d, J=8.6 Hz, $^1$H), 7.72 (dd, J=8.6, 2.0 Hz, $^1$H), 7.17 (d, J=5.1 Hz), 7.01 (d, J=8.6 Hz, 2H), 6.84 (d, J=8.6 Hz, 2H), 3.81 (s, $^3$H), 2.52 (s, $^3$H), 1.84 (s, $^3$H), 1.79 (s, $^3$H); ESMS calculated ($C_{23}H_{23}N_3O_2$) 373.1. found: 374.1 (M+H).

Example 40

Synthesis of 5-fluoro-N-(5-((methoxyimino)(4-methoxyphenyl)methyl)pyridin-2-yl)-4-methylnicotinamide (compound 18)

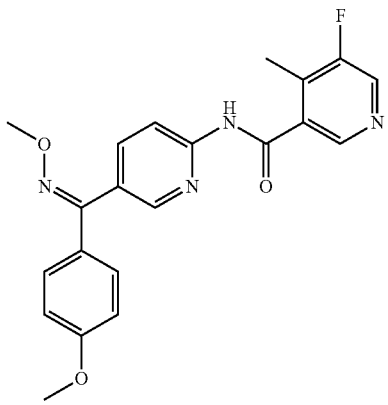 [SMILES: CO/N=C(/c1ccc(OC)cc1)c1ccc(NC(=O)c2cncc(F)c2C)nc1]

To a solution of tert-butyl (5-(methoxy(methyl)carbamoyl)pyridin-2-yl)carbamate (281 mg, 1.0 mmol) in 10 mL of anhydrous THF at 0° C. was added dropwise a solution of (4-methoxyphenyl)magnesium bromide in THF (0.5 M, 5 mL, 2.5 mmol) over 5 minutes. The solution was warmed room temperature and stirred sealed under $N_2$ for overnight. The reaction solution was quenched with saturated $NaHCO_3$ and extracted with EtOAc. The organic phases were combined, washed with brine, dried over anhydrous sodium sulfate, and concentrated. The residue was purified by flash column chromatography on silica gel (eluted with 0-100% EtOAc/hexanes) to give 250 mg of tert-butyl (5-(4-methoxybenzoyl)pyridin-2-yl)carbamate as a white solid. ESMS calculated ($C_{18}H_{20}N_2O_4$) 328.1. found: 329.1 (M+H).

To a solution of tert-butyl (5-(4-methoxybenzoyl)pyridin-2-yl)carbamate (130 mg, 0.4 mmol) in 2 mL of MeOH and 2 mL of THF was added O-methylhydroxylamine hydrochloride (620 mg, 8 mmol), and $NaOAc.H_2O$ (1.09 g, 8 mmol). The mixture was stirred at room temperature overnight. The reaction was basified with 10% NaOH solution and extracted with DCM. The organic phase was dried over anhydrous sodium sulfate and concentrated under reduced pressure. The residue was purified by flash column chromatography on silica gel to give tert-butyl (5-((methoxyimino)(4-methoxyphenyl)methyl)pyridin-2-yl)carbamate as a mixture of Z/E isomers. ESMS calculated ($C_{19}H_{23}N_3O_4$) 357.1. found: 358.2 (M+H).

To a solution of (6-aminopyridin-3-yl)(4-methoxyphenyl)methanone O-methyl oxime (120 mg, 0.336 mmol) in 2 mL of DCM was added 2 mL of trifluoroacetic acid. The solution was stirred at room temperature for 2 hours. The solvent was removed. The residue was taken into 10 mL of EtOAc. The solution was washed with 10% NaOH and brine, dried, and concentrated to give 90 mg of (Z)-(6-aminopyridin-3-yl)(4-methoxyphenyl)methanone O-methyl oxime as a mixture of Z/E isomers. ESMS calculated ($C_{14}H_{15}N_3O_2$) 257.1. found: 258.1 (M+H).

5-fluoro-N-(5-((methoxyimino)(4-methoxyphenyl)methyl)pyridin-2-yl)-4-methylnicotinamide was prepared from (Z)-(6-aminopyridin-3-yl)(4-methoxyphenyl)methanone O-methyl oxime and 5-fluoro-4-methylnicotinic acid analogously as described for the preparation Example 28. $^1$H-NMR (400 MHz, $CDCl_3$) major isomer: δ 9.04 (s, $^1$H), 8.59 (s, $^1$H), 8.47 (br s, $^1$H), 8.41 (d, J=8.6 Hz, $^1$H), 8.12 (dd, J=2.0, 0.7 Hz, $^1$H), 7.80 (dd, J=8.6, 2.0 Hz, $^1$H), 7.41 (d, J=8.6 Hz, 2H), 6.89 (d, J=8.6 Hz, 2H), 3.97 (s, $^3$H), 3.84 (s, $^3$H), 2.48 (d, J=2.0 Hz, $^3$H); ESMS calculated ($C_{21}H_{19}FN_4O_3$) 394.1. found: 395.1 (M+H).

Example 41

Synthesis of 5-fluoro-N-(4-(1-(4-methoxyphenyl)cyclopropyl)phenyl)-4-methylnicotinamide (compound 31)

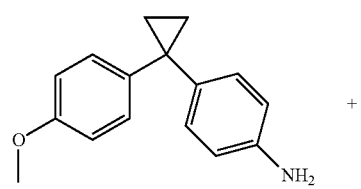

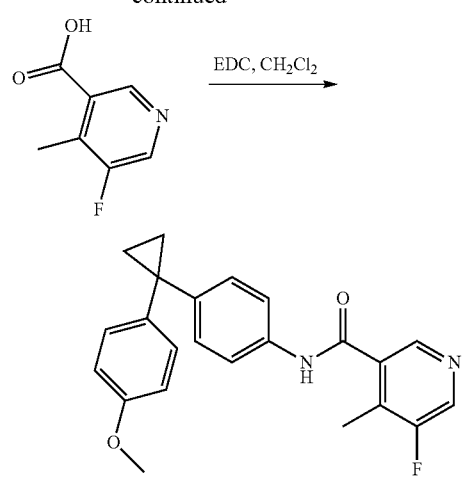

The same EDC coupling was used as Example 28 to produce compound 31 $^1$H-NMR (400 MHz, $CDCl_3$) δ 8.52 (s, $^1$H), 8.46 (s, $^1$H), 7.57 (s, $^1$H), 7.50 (d, J=8.5 Hz, 2H), 7.22 (d, J=8.4 Hz, 2H), 7.20-7.14 (m, 2H), 6.88-6.76 (m, 2H), 3.79 (s, $^3$H), 2.44 (d, J=2.0 Hz, $^3$H), 1.26 (d, J=4.4 Hz, 4H); ESMS calculated ($C_{23}H_{21}FN_2O_2$) 376.2. found: 377.2 (M+H).

Example 42

Synthesis of methyl 4-(1-(5-(5-fluoro-4-methylnicotinamido)pyrazin-2-yl)cyclopropyl)benzoate (compound 78)

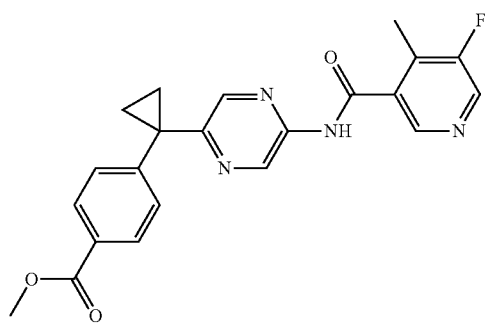 [SMILES: COC(=O)c1ccc(C2(c3cnc(NC(=O)c4cncc(F)c4C)cn3)CC2)cc1]

The same EDC coupling used as in Example 28 to produce compound 78. $^1$H-NMR (400 MHz, $CDCl_3$) δ 9.51 (d, J=1.5 Hz, $^1$H), 8.57 (s, $^1$H), 8.50 (d, J=1.2 Hz, $^1$H), 8.26 (s, $^1$H), 8.06 (d, J=8.3 Hz, 2H), 7.75 (d, J=1.6 Hz, $^1$H), 7.48 (d, J=8.4 Hz, 2H), 3.94 (s, $^3$H), 2.47 (d, J=2.0 Hz, $^3$H), 1.82-1.65 (m, 2H), 1.43-1.33 (m, 2H); ESMS calculated ($C_{22}H_{19}FN_4O_3$): 406.1. found: 407.1 (M+H).

Example 43

Synthesis of (Z)-methyl 4-(1-(6-(5-fluoro-4-methyl-nicotinamido)pyridin-3-yl)prop-1-en-1-yl)benzoate (compound 104)

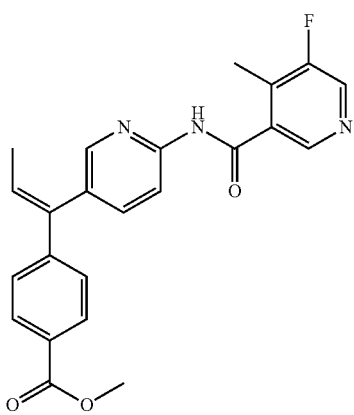 [SMILES: C/C=C(/c1ccc(C(=O)OC)cc1)c1ccc(NC(=O)c2cncc(F)c2C)nc1]

The same EDC coupling used as in Example 28 was used to produce compound 104. $^1$H-NMR (400 MHz, CDCl$_3$) δ 8.71-8.54 (m, 2H), 8.49 (d, J=1.2 Hz, $^1$H), 8.38 (d, J=8.4 Hz, $^1$H), 8.15-8.04 (m, $^1$H), 7.96 (d, J=8.5 Hz, 2H), 7.60 (dd, J=8.5, 2.3 Hz, $^1$H), 7.30-7.21 (m, 2H), 6.39 (q, J=7.1 Hz, $^1$H), 3.91 (s, $^3$H), 2.50 (d, J=2.0 Hz, $^3$H), 1.84 (d, J=7.1 Hz, $^3$H); ESMS calculated (C$_{23}$H$_{20}$FN$_3$O$_3$): 405.15. found: 406.15 (M+H).

Example 44

Synthesis of (Z)-5-fluoro-4-methyl-N-(5-(1-(4-(thiazol-2-yl)phenyl)prop-1-en-1-yl)pyridin-2-yl)nicotinamide (compound 120)

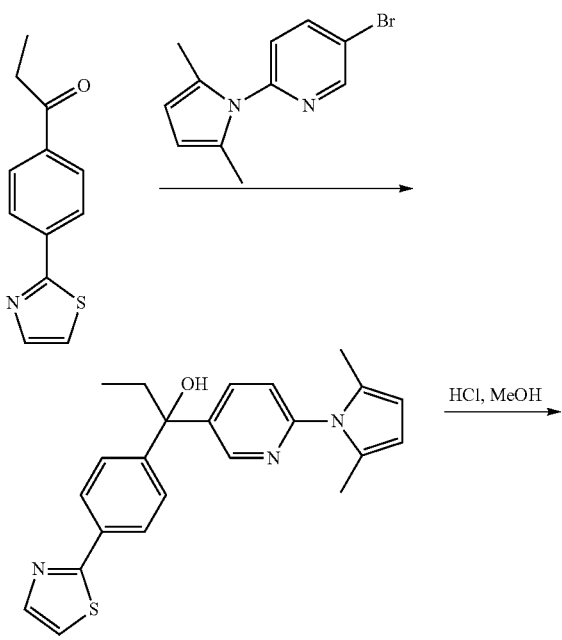

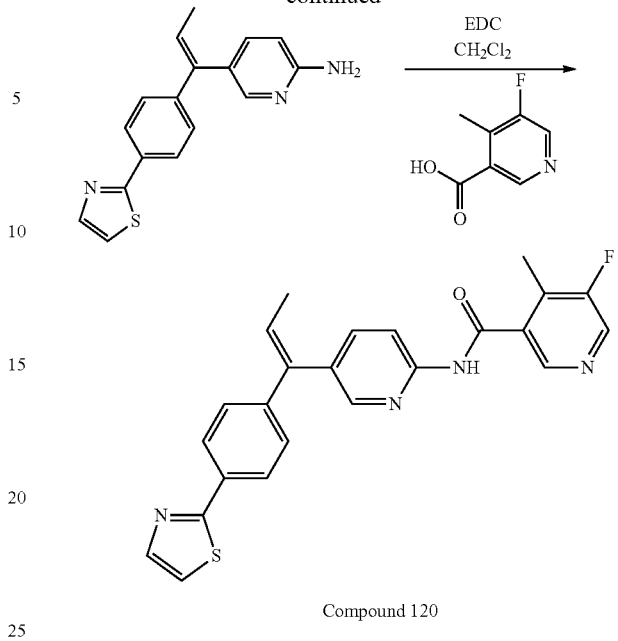

Compound 120

To a solution of 5-bromo-2-(2,5-dimethyl-$^1$H-pyrrol-1-yl)pyridine (300 mg, 1.19 mmol) in 5 mL of ether under N$_2$ was added 2.5M n-BuLi in hexanes (2.1 mL, 1.19 mmol, 1.5 eq.) dropwise with stirring at −78° C. over a period of 10 minutes. To the solution was added 1-(4-(thiazol-2-yl)phenyl)propan-1-one (217.3 mg, 1.0 mmol) dropwise in Et$_2$O while stirring at −78° C. over a period of 5 minutes. The resulting solution was allowed to react, with stirring, for 10 minutes at −78° C. and then quenched by the adding of H$_2$O. The mixture was extracted with DCM, and the organic phase was dried and concentrated producing 214 mg (55%) of 1-(6-(2,5-dimethyl-$^1$H-pyrrol-1-yl)pyridin-3-yl)-1-(4-(thiazol-2-yl)phenyl)propan-1-ol.

To a solution 1-(6-(2,5-dimethyl-$^1$H-pyrrol-1-yl)pyridin-3-yl)-1-(4-(thiazol-2-yl)phenyl)propan-1-ol (217 mg, 0.557 mmol) in 3 mL of MeOH was added conc. HCl (1 mL). The solution was heated to reflux for 1 hour. After cooling down to room temperature, the solution was neutralized with NaOH, then NaHCO$_3$(sol). The mixture was extracted with ethyl acetate. The organic phase was washed with brine, dried, and concentrated. The residue was purified by flash column chromatography on silica gel to give 73 mg (45%) of (Z)-5-(1-(4-(thiazol-2-yl)phenyl)prop-1-en-1-yl)pyridin-2-amine as a 3:1 mixture of Z/E isomers. This amine was then coupled using EDC and 5-fluoro-4-methylnicotinic acid as in Example 28 followed by column chromatography purification to produce Compound 120. $^1$H-NMR (400 MHz, CDCl$_3$) δ 8.64 (s, $^1$H), 8.53 (s, $^1$H), 8.52 (d, J=1.2 Hz, $^1$H), 8.43 (d, J=8.5 Hz, $^1$H), 8.22 (d, J=2.3 Hz, $^1$H), 7.94-7.85 (m, 2H), 7.74 (dd, J=8.5, 2.4 Hz, $^1$H), 7.45-7.35 (m, $^3$H), 6.35 (q, J=7.1 Hz, $^1$H), 2.52 (d, J=2.0 Hz, $^3$H), 1.79 (d, J=7.1 Hz, $^3$H); ESMS calculated (C$_{24}$H$_{19}$FN$_4$OS): 430.1. found: 431.1 (M+H).

Example 45

Synthesis of (Z)—N-(5-((ethoxyimino)(4-methoxyphenyl)methyl)pyridin-2-yl)-5-fluoro-4-methylnicotinamide (compound 29)

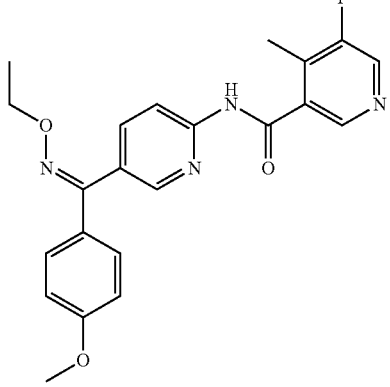

(Z)—N-(5-((ethoxyimino) (4-methoxyphenyl)methyl)pyridin-2-yl)-5-fluoro-4-methylnicotinamide was synthesized according to experimental procedure for Example 40.

$^1$H-NMR (400 MHz, CDCl$_3$) major isomer: δ 8.65 (s, $^1$H), 8.60 (s, $^1$H), 8.49 (br s, $^1$H), 8.40 (d, J=80 Hz, $^1$H), 8.30 (m, $^1$H), 8.26 (m, $^1$H), 7.83 (dd, J=0.8, 8.0 Hz, $^1$H), 7.42 (m, 2H), 6.89 (m, 2H), 4.25 (m, 2H), 3.84 (s, $^3$H), 2.49 (d, J=2.0 Hz, $^3$H), 1.30 (t, J=6 Hz, $^3$H); ESMS calculated (C$_{22}$H$_{21}$FN$_4$O$_3$) 408.2. found: 409.2 (M+H).

Example 46

Synthesis of (E)-N-(5-(1-(6-ethoxypyridin-3-yl)prop-1-en-1-yl)pyridin-2-yl)-5-fluoro-4-methylnicotinamide (compound 140)

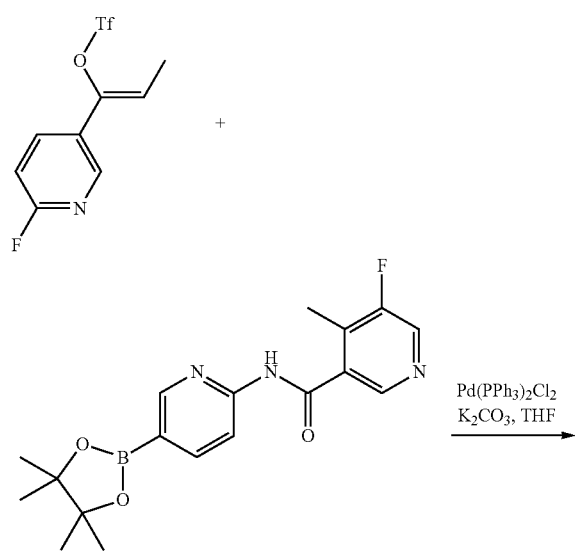

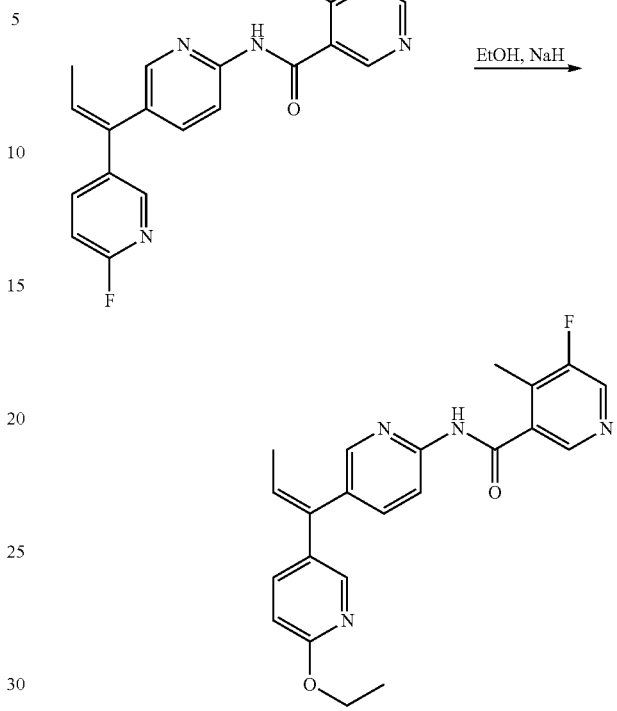

(Z)-1-(6-fluoropyridin-3-yl)prop-1-en-1-yl trifluoromethanesulfonate (255 mg, 0.894 mmol) was dissolved in 5 mL of THF along with bistriphenylphosphine palladium dichloride (62 mg, 0.089 mmol), 5-fluoro-4-methyl-N-(5-(4,4,5,5-tetramethyl-1,3,2-dioxaborolan-2-yl)pyridin-2-yl)nicotinamide (319 mg, 0.0894 mmol), and potassium carbonate (190 mg, 2.68 mmol). The reaction was heated to 80° C. for 2 hours and then cooled. After normal work up and purification by column, 144 mg of (E)-5-fluoro-N-(5-(1-(6-fluoropyridin-3-yl)prop-1-en-1-yl)pyridin-2-yl)-4-methylnicotinamide was isolated in 43% yield.

(E)-5-fluoro-N-(5-(1-(6-fluoropyridin-3-yl)prop-1-en-1-yl)pyridin-2-yl)-4-methylnicotinamide (144 mg, 0.393 mmol) was dissolved in ethanol and stirred at room temperature. Excess sodium hydride was added and allowed to stir at room temperature for 3 hours until complete conversion of the fluoro to the ethoxy group. Water and ethyl acetate were added to the reaction, and the product was extracted using ethyl acetate. After drying and evaporation of the solvent, the product was purified by column chromatography using hexane/ethyl acetate to isolate 135 mg of (E)-N-(5-(1-(6-ethoxypyridin-3-yl)prop-1-en-1-yl)pyridin-2-yl)-5-fluoro-4-methylnicotinamide. $^1$H-NMR (400 MHz, CDCl$_3$) δ 9.05 (s, $^1$H), 8.60 (s, $^1$H), 8.45 (d, J=1.2 Hz, $^1$H), 8.37 (d, J=8.5 Hz, $^1$H), 7.95 (ddd, J=20.9, 2.5, 0.9 Hz, $^1$H), 7.60 (dd, J=8.5, 2.3 Hz, $^1$H), 7.37 (dd, J=8.6, 2.6 Hz, $^1$H), 6.65 (dd, J=8.6, 0.8 Hz, $^1$H), 6.16 (q, J=7.0 Hz, $^1$H), 4.35 (q, J=7.1 Hz, 2H), 2.48 (d, J=2.0 Hz, $^3$H), 1.79 (d, J=7.1 Hz, $^3$H), 1.39 (t, J=7.1 Hz, $^3$H); ESMS calculated (C$_{22}$H$_{21}$FN$_4$O$_2$): 392.2. found: 393.3 (M+H).

Example 47

Synthesis of (E)-5-fluoro-4-methyl-N-(5-(1-(6-(pyrrolidin-1-yl)pyridin-3-yl)prop-1-en-1-yl)pyridin-2-yl)nicotinamide (compound 141)

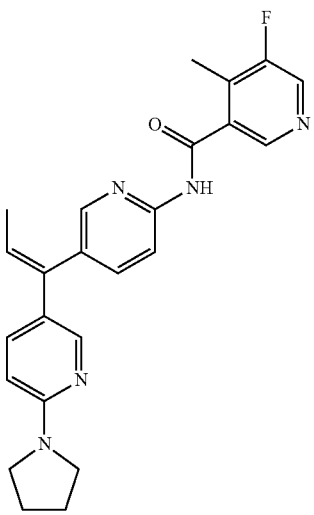 [SMILES: C/C=C(\c1ccc(NC(=O)c2cncc(F)c2C)nc1)c1ccc(N2CCCC2)nc1]

Using the experimental procedure in Example 46, the final step was modified by reacting (E)-5-fluoro-N-(5-(1-(6-fluoropyridin-3-yl)prop-1-en-1-yl)pyridin-2-yl)-4-methylnicotinamide with pyrrolidine and sodium hydride in DMF to produce (E)-N-(5-(1-(6-ethoxypyridin-3-yl)prop-1-en-1-yl)pyridin-2-yl)-5-fluoro-4-methylnicotinamide (compound 141). $^1$H-NMR (400 MHz, CDCl$_3$) δ 8.61 (s, $^1$H), 8.48 (s, $^1$H), 8.33 (d, J=8.5 Hz, $^1$H), 8.05 (s, $^1$H), 8.02 (d, J=2.4 Hz, $^1$H), 7.61 (dd, J=8.5, 2.3 Hz, $^1$H), 7.24 (dd, J=8.8, 2.6 Hz, $^1$H), 6.28 (dd, J=8.8, 0.8 Hz, $^1$H), 6.08 (q, J=7.0 Hz, $^1$H), 3.50-3.37 (m, 4H), 2.50 (d, J=1.9 Hz, $^3$H), 2.06-1.94 (m, 4H), 1.78 (d, J=7.1 Hz, $^3$H); ESMS calculated (C$_{24}$H$_{24}$FN$_5$O): 417.2. found: 418.2 (M+H).

Example 48

Synthesis of (E)-5-fluoro-N-(5-(1-(6-methoxypyridin-3-yl)prop-1-en-1-yl)pyridin-2-yl)-4-methylnicotinamide (compound 118)

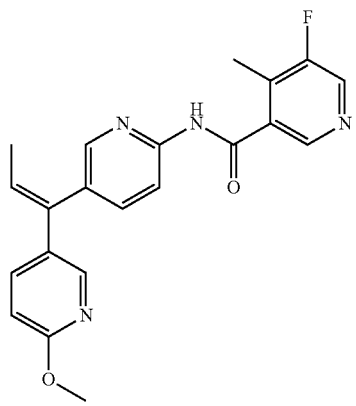 [SMILES: C/C=C(\c1ccc(NC(=O)c2cncc(F)c2C)nc1)c1ccc(OC)nc1]

Using the experimental procedure in Example 46, the final step was conducted in methanol to produce (E)-5-fluoro-N-(5-(1-(6-methoxypyridin-3-yl)prop-1-en-1-yl)pyridin-2-yl)-4-methylnicotinamide (compound 118). $^1$H-NMR (400 MHz, CDCl$_3$) δ 8.68 (s, $^1$H), 8.61 (s, $^1$H), 8.49 (d, J=1.2 Hz, $^1$H), 8.36 (d, J=8.5 Hz, $^1$H), 8.05-7.99 (m, 2H), 7.60 (dd, J=8.4, 2.4 Hz, $^1$H), 7.38 (dd, J=8.6, 2.6 Hz, $^1$H), 6.67 (dd, J=8.6, 0.7 Hz, $^1$H), 6.17 (q, J=7.1 Hz, $^1$H), 3.94 (s, $^3$H), 2.49 (d, J=2.0 Hz, $^3$H), 1.81 (d, J=7.1 Hz, $^3$H); ESMS calculated (C$_{21}$H$_{19}$FN$_4$O$_2$): 378.4. found: 379.4 (M+H).

Example 49

Synthesis of 5-fluoro-N-(5-(1-(6-methoxypyridin-3-yl)propyl)pyridin-2-yl)-4-methylnicotinamide (compound 119)

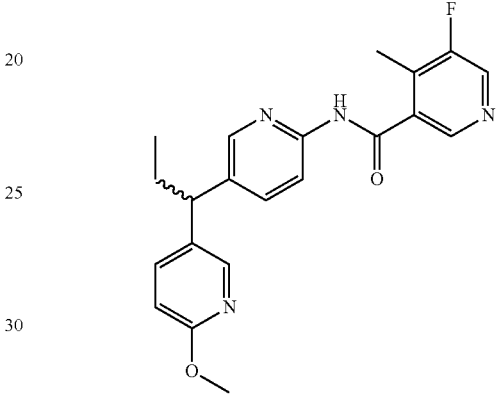

(E)-5-fluoro-N-(5-(1-(6-methoxypyridin-3-yl)prop-1-en-1-yl)pyridin-2-yl)-4-methylnicotinamide (compound 118, Example 48) was dissolved in methanol in a microwave tube. Excess formic acid was added and the tube sealed and heated to 100° C. for 1.5 hours. The double bond was completely removed, and methanol was then evaporated. Saturated sodium bicarbonate solution was added and extracted with ethyl acetate. The product was purified by column chromatography. $^1$H-NMR (400 MHz, CDCl$_3$) δ 9.30 (s, $^1$H), 8.56 (s, $^1$H), 8.45 (d, J=1.3 Hz, $^1$H), 8.27 (d, J=8.6 Hz, $^1$H), 8.03 (d, J=2.5 Hz, $^1$H), 7.86 (d, J=2.3 Hz, $^1$H), 7.60 (dd, J=8.6, 2.4 Hz, $^1$H), 7.34 (dd, J=8.6, 2.5 Hz, $^1$H), 6.69 (dd, J=8.5, 0.8 Hz, $^1$H), 3.92 (s, $^3$H), 3.70 (t, J=7.8 Hz, $^1$H), 2.45 (d, J=2.0 Hz, $^3$H), 2.07-1.95 (m, 2H), 0.91 (t, J=7.3 Hz, $^3$H); ESMS calculated (C$_{21}$H$_{21}$FN$_4$O$_2$): 380.2. found: 381.2 (M+H).

Example 50

Synthesis of 5-fluoro-N-(5-(1-(6-methoxypyridin-3-yl)-2-methylprop-1-en-1-yl)pyridin-2-yl)-4-methylnicotinamide (compound 134)

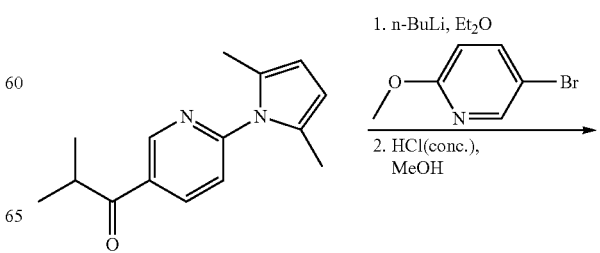

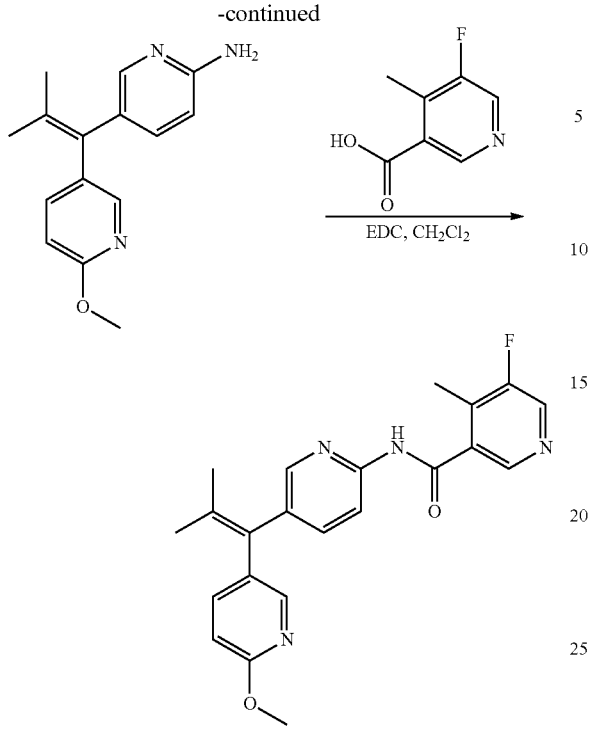

5-bromo-2-methoxypyridine (135 mg, 0.557 mmol) was dissolved in diethylether and cooled to −78° C. in a dry ice/IPA bath. 1.39 mL of 2.5M n-BuLi in hexanes was added slowly to the solution and allowed to stir for 35 min. The ketone (135 mg, 0.557 mol) was added to the solution and gradually warmed to room temperature. The reaction mixture was quenched with 1N HCl and stirred for 1 hour until the compound undergoes complete dehydration. Saturated sodium bicarbonate aqueous solution was then added to quench the HCl, and the reaction was extracted with ethyl acetate and dried over sodium sulfate. The volatiles were removed, the residue was redissolved in methanol, and 1 mL of concentrated HCl was added and sealed in a microwave vial. The mixture was heated to 80° C. for 35 min and then cooled to room temperature. After evaporation of the methanol, saturated aqueous solution of sodium bicarbonate was added followed by methylene chloride. After normal workup and drying over sodium sulfate, the solvent was removed and the product was purified using flash chromatography. 62 mg of 5-(1-(6-methoxypyridin-3-yl)-2-methylprop-1-en-1-yl)pyridin-2-amine was isolated as a 44% yield for two steps. EDC coupling as in Example 28 produced 58 mg (61% yield) of 5-fluoro-N-(5-(1-(6-methoxypyridin-3-yl)-2-methylprop-1-en-1-yl)pyridin-2-yl)-4-methylnicotinamide. $^1$H-NMR (400 MHz, CDCl$_3$) δ 8.58 (s, $^1$H), 8.56 (s, $^1$H), 8.48 (d, J=1.3 Hz, $^1$H), 8.25 (d, J=8.9 Hz, $^1$H), 7.98 (t, J=3.0 Hz, 2H), 7.51 (dd, J=8.5, 2.3 Hz, $^1$H), 7.32-7.20 (m, $^1$H), 6.69 (dd, J=8.5, 0.8 Hz, $^1$H), 3.94 (s, $^3$H), 2.47 (d, J=2.0 Hz, $^3$H), 1.86 (d, J=6.5 Hz, 6H); ESMS calculated (C$_{22}$H$_{21}$FN$_4$O$_2$): 392.2 found: 393.2 (M+H).

Other compounds shown in Table 1 were synthesized in a similar manner according to the procedure provided above in Examples 1-50.

Example 51

(Z)—N-(5-(1-((benzyloxy)imino)propyl)pyridin-2-yl)-2,6-difluorobenzamide

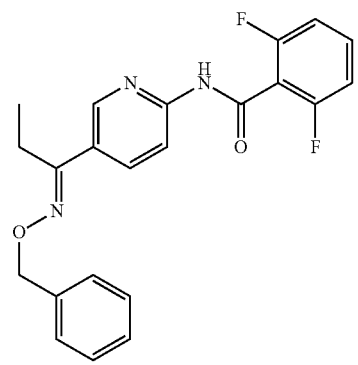 [SMILES: CC/C(=N\OCc1ccccc1)c1ccc(NC(=O)c2c(F)cccc2F)nc1]

$^1$H NMR (400 MHz, CDCl$_3$) δ 9.35 (s, $^1$H), 8.36 (d, J=8.9 Hz, $^1$H), 8.29 (d, J=2.4 Hz, $^1$H), 8.01 (dd, J=8.8, 2.4 Hz, $^1$H), 7.51-7.28 (m, 6H), 6.94 (t, J=8.2 Hz, 2H), 5.23 (s, 2H), 2.73 (q, J=7.6 Hz, 2H), 2.17 (s, $^1$H), 1.11 (t, J=7.6 Hz, $^3$H). ESMS calc'd. (C$_{22}$H$_{19}$F$_2$N$_3$O$_2$) 395.1. found: 396.1 (M+H).

Procedure:

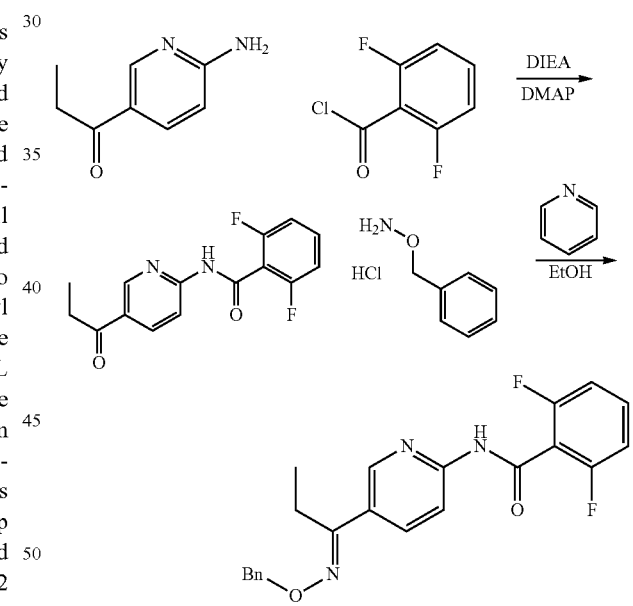

1-(6-aminopyridin-3-yl)propan-1-one (2.0 g, 13.3 mmol) was dissolved in methylene chloride (50 ml) along with dimethylamine pyridine (813.5 mg, 6.7 mmol) and diisopropylethylamine (5.16 g, 40.0 mmol). The reaction was cooled to 0° C. and 2,6-difluorobenzoyl chloride (4.7 g, 26.6 mmol) was added. The reaction was stirred for 3 hours then quenched with a saturated aqueous solution of sodium bicarbonate. The aqueous layer was extracted twice more with methylene chloride and the organic layer was dried over magnesium sulfate. After column chromatography with ethyl acetate/hexane, pure amide was isolated in a 90.5% yield with 3.5 g of product.

The ketone (350 mg) was then dissolved in ethanol (3.5 ml) and pyridine (1 ml). The o-benzylhydroxylamine (380 mg, 0.24 mmol) was added to the reaction and allowed heated to 60 C for 30 min in microwave. The reaction was completed and water was added and product was extracted with ethyl acetate. Purification with ethyl acetate column was performed and 41.6 mg was isolated in a (93%) yield of (E)-N-(5-(1-((benzyloxy)imino)propyl)pyridin-2-yl)-2,6-difluorobenzamide.

Examples 52 and 53 below were synthesized according to the synthetic procedure of Example 51:

Example 52

(E)-5-fluoro-N-(5-(methoxyimino)-6,7,8,9-tetrahydro-5H-benzo[7]annulen-2-yl)-4-methylnicotinamide

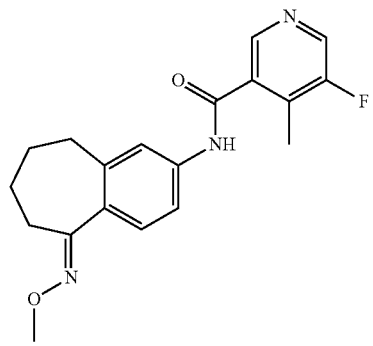 [SMILES: CO/N=C1\CCCCc2cc(NC(=O)c3cncc(F)c3C)ccc21]

$^1$H NMR (400 MHz, CDCl$_3$) δ 8.53 (s, $^1$H), 8.47 (s, $^1$H), 7.72 (s, $^1$H), 7.56 (s, $^1$H), 7.45 (d, J=8.2 Hz, $^1$H), 7.41-7.34 (m, $^1$H), 3.99 (s, $^3$H), 2.77 (t, J=6.7 Hz, 2H), 2.71-2.60 (m, 2H), 2.46 (d, J=1.9 Hz, $^3$H), 1.76-1.81 (m, 2H), 1.61-1.64 (m, 2H). ESMS calc'd. (C$_9$H$_{20}$FN$_3$O$_2$) 341.1. found: 342.1 (M+H).

Example 53

(E)-N-(5-((benzyloxy)imino)-6,7,8,9-tetrahydro-5H-benzo[7]annulen-2-yl)-5-fluoro-4-methylnicotinamide

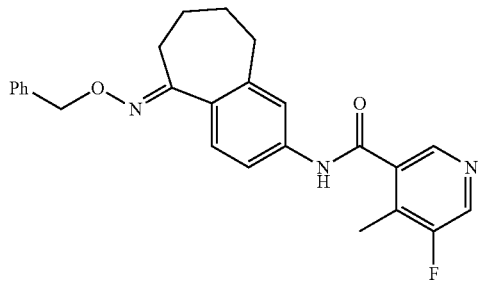 [SMILES: Cc1c(F)cncc1C(=O)Nc1ccc2c(c1)CCCC/C2=N\OCc1ccccc1]

ESMS calc'd. (C$_{25}$H$_{24}$FN$_3$O$_2$) 417.2. found: 418.2 (M+H).

Example 54

(E)-2,6-difluoro-N-(5-(1-((pyridin-2-yloxy)imino)propyl)pyridin-2-yl)benzamide

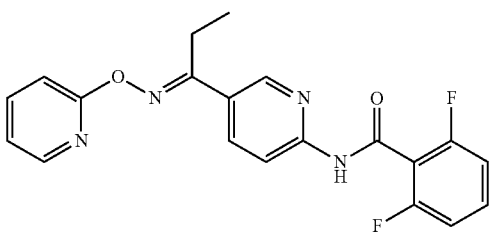 [SMILES: CC/C(=N\Oc1ccccn1)c1ccc(NC(=O)c2c(F)cccc2F)nc1]

$^1$H NMR (400 MHz, CDCl$_3$) δ 8.93 (s, $^1$H), 8.58 (dt, J=2.2, 1.1 Hz, $^1$H), 8.45 (d, J=8.6 Hz, $^1$H), 8.33-8.25 (m, $^1$H), 8.16 (dd, J=8.8, 2.2 Hz, $^1$H), 7.81-7.70 (m, $^1$H), 7.50-7.39 (m, $^1$H), 7.10-6.94 (m, $^3$H), 3.01 (dd, J=7.7, 1.6 Hz, 2H), 1.36-1.19 (m, $^3$H). ESMS calc'd. (C$_{20}$H$_{16}$F$_2$N$_4$O$_2$) 382.1. found: 383.1 (M+H).

Procedure:

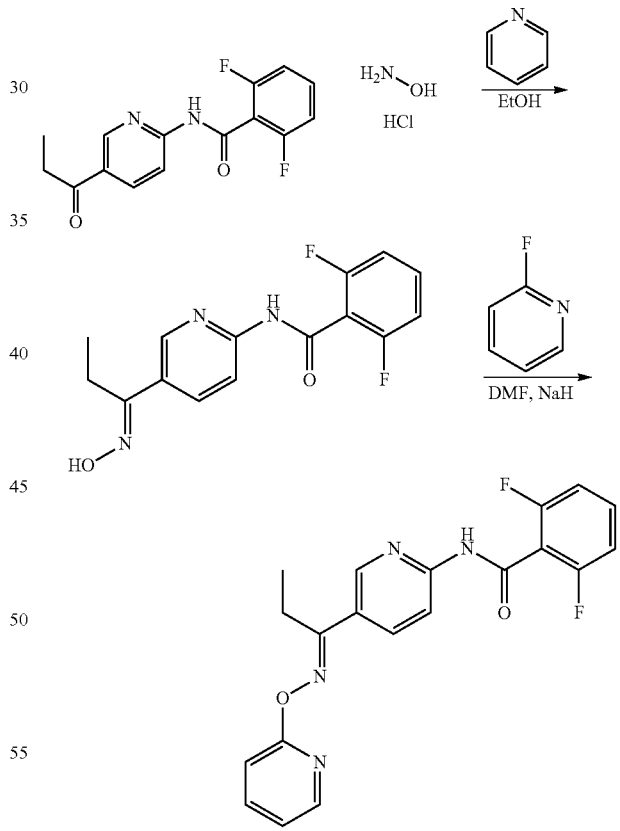

The 2,6-difluoro-N-(5-propionylpyridin-2-yl)benzamide (2.0 g, 6.9 mmol) was then dissolved in ethanol 35 ml and pyridine (3.6 ml, 41.3 mmol). The hydroxylamine hydrochloride (1.4 g, 20.7 mmol) was added to the reaction and allowed stir at room temperature for 2 hours. The reaction was completed and water was added and product crashed out of solution was filtered off giving pure (E)-2,6-difluoro-N-(5-(1-(hydroxyimino)propyl)pyridin-2-yl)benzamide (2.1 g, 99.8%). The oxime was then dissolved in DMF (1 ml) and 2-fluoropyridine (200 mg, 2.1 mmol)) and the reaction was cooled to 0° C. NaH (58 mg, 1.4 mmol) was added to the reaction at a slow pace with regard to the evolution of hydrogen gas. The reaction was then stirred for 2 hours and quenched with water. The reaction was extracted with methylene chloride and the organic layer was separated, dried and rotovaped down to dryness. It was purified by silica gel column using methylene chloride/ethyl acetate gradient. 123 mg was isolated as a 47% yield.

The compounds in Examples 55 through 66, below, were synthesized in a similar way according to the synthetic procedure of Example 54.

Example 55

(E)-N-(5-(1-(((3-chloropyrazin-2-yl)oxy)imino)propyl)pyridin-2-yl)-2,6-difluorobenzamide

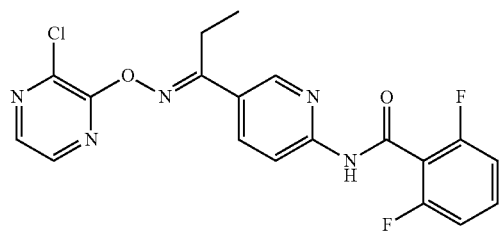 [SMILES: CC/C(=N\Oc1nccnc1Cl)c1ccc(NC(=O)c2c(F)cccc2F)nc1]

$^1$H NMR (400 MHz, CDCl$_3$) δ 8.74 (s, OH), 8.64 (d, J=2.3 Hz, OH), 8.45 (d, J=8.8 Hz, OH), 8.21 (d, J=2.6 Hz, OH), 8.17 (dd, J=8.8, 2.4 Hz, OH), 8.12 (d, J=2.6 Hz, OH), 7.56-7.38 (m, OH), 7.03 (t, J=8.4 Hz, $^1$H), 3.04 (q, J=7.6 Hz, $^1$H), 1.33 (t, J=7.6 Hz, $^1$H). ESMS calc'd. (C$_{19}$H$_{14}$ClF$_2$N$_5$O$_2$) 417.1. found: 418.1 (M+H).

Example 56

(E)-N-(5-(1-(((5-bromopyridin-2-yl)oxy)imino)propyl)pyridin-2-yl)-2,6-difluorobenzamide

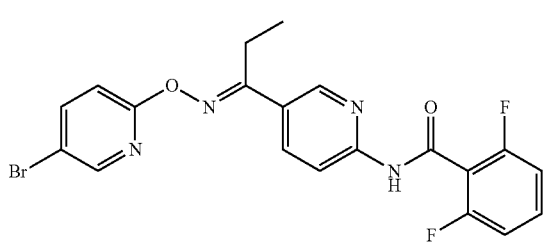

$^1$H NMR (400 MHz, CDCl$_3$) δ 8.67 (s, $^1$H), 8.64 (dd, J=2.4, 0.9 Hz, $^1$H), 8.45 (d, J=8.7 Hz, $^1$H), 8.34 (dd, J=2.5, 0.7 Hz, $^1$H), 8.15 (dd, J=8.7, 2.4 Hz, $^1$H), 7.84 (dd, J=8.8, 2.5 Hz, $^1$H), 7.47 (tt, J=8.5, 6.3 Hz, $^1$H), 7.32 (dd, J=8.9, 0.7 Hz, $^1$H), 7.03 (t, J=8.2 Hz, 2H), 3.01 (q, J=7.6 Hz, 2H), 1.27 (t, J=7.6 Hz, $^3$H). ESMS calc'd. (C$_{20}$H$_{15}$BrF$_2$N$_4$O$_2$) 460.0. found: 461.0 (M+H).

Example 57

(E)-2,6-difluoro-N-(5-(1-((pyrimidin-2-yloxy)imino)propyl)pyridin-2-yl)benzamide

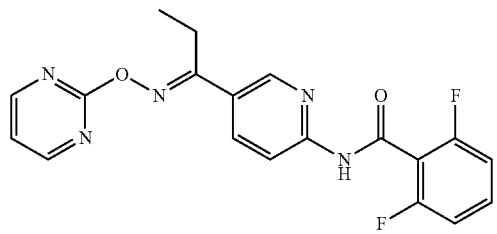 [SMILES: CC/C(=N\Oc1ncccn1)c1ccc(NC(=O)c2c(F)cccc2F)nc1]

$^1$H NMR (400 MHz, CDCl$_3$) δ 8.72-8.65 (m, 2H), 8.56 (s, $^1$H), 8.44 (d, J=8.7 Hz, $^1$H), 8.18 (dd, J=8.7, 2.4 Hz, $^1$H), 7.46 (tt, J=8.5, 6.3 Hz, $^1$H), 7.11 (t, J=4.8 Hz, $^1$H), 7.07-6.94 (m, 2H), 3.05 (q, J=7.6 Hz, 2H), 1.29 (t, J=7.6 Hz, $^3$H). ESMS calc'd. (C$_{19}$H$_{15}$F$_2$N$_3$O$_2$) 383.1. found: 384.1 (M+H).

Example 58

(E)-2,6-difluoro-N-(5-(1-((pyridin-2-yloxy)imino)propyl)pyrazin-2-yl)benzamide

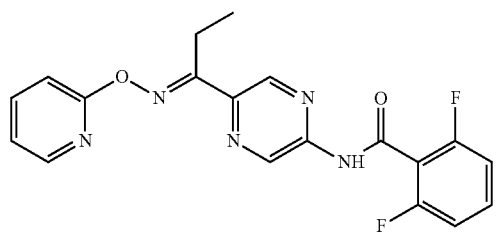 [SMILES: CC/C(=N\Oc1ccccn1)c1cnc(NC(=O)c2c(F)cccc2F)cn1]

$^1$H NMR (400 MHz, CDCl$_3$) δ 9.71 (d, J=1.6 Hz, $^1$H), 8.96 (d, J=1.5 Hz, $^1$H), 8.64 (s, $^1$H), 8.32 (ddd, J=4.9, 2.0, 0.8 Hz, $^1$H), 7.77 (ddd, J=8.4, 7.2, 2.0 Hz, $^1$H), 7.49 (tt, J=8.5, 6.3 Hz, $^1$H), 7.37 (dt, J=8.4, 0.9 Hz, $^1$H), 7.09-6.97 (m, $^3$H), 3.20 (q, J=7.6 Hz, 2H), 1.27 (t, J=7.6 Hz, $^3$H). ESMS calc'd. (C$_{19}$H$_{15}$F$_2$N$_5$O$_2$) 383.1. found: 384.1 (M+H).

Example 59

(E)-2,6-difluoro-N-(5-(1-(((3-fluoropyridin-2-yl)oxy)imino)propyl)pyridin-2-yl)benzamide (STA-12-8260)

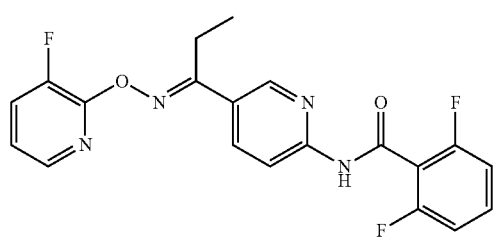 [SMILES: CC/C(=N\Oc1ncccc1F)c1ccc(NC(=O)c2c(F)cccc2F)nc1]

¹H NMR (400 MHz, CDCl₃) δ 8.67 (dd, J=2.4, 0.9 Hz, ¹H), 8.54 (s, ¹H), 8.42 (d, J=8.8 Hz, ¹H), 8.16 (dd, J=8.8, 2.4 Hz, ¹H), 8.12 (dd, J=4.9, 1.5 Hz, ¹H), 7.55-7.38 (m, 2H), 7.10-6.95 (m, ³H), 3.02 (q, J=7.6 Hz, 2H), 1.30 (t, J=7.6 Hz, ³H). ESMS calc'd. (C₂₀H₁₅F₃N₄O₂) 400.1. found: 401.1 (M+H).

Example 60

(E)-2,6-difluoro-N-(5-(1-((pyrazin-2-yloxy)imino)propyl)pyridin-2-yl)benzamide

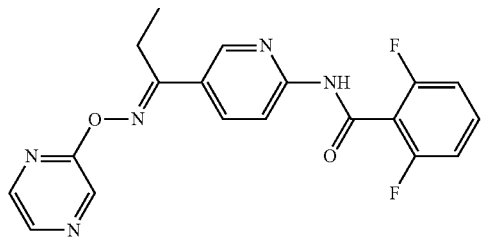 [SMILES: CC/C(=N\Oc1cnccn1)c1ccc(NC(=O)c2c(F)cccc2F)nc1]

¹H NMR (400 MHz, CDCl₃) δ 8.79 (s, ¹H), 8.66 (s, ¹H), 8.47 (d, J=8.8 Hz, ¹H), 8.35 (d, J=2.6 Hz, ¹H), 8.26 (dd, J=2.6, 1.4 Hz, ¹H), 8.16 (dd, J=8.8, 2.4 Hz, ¹H), 7.46 (ddd, J=14.6, 8.5, 6.4 Hz, ¹H), 7.03 (t, J=8.3 Hz, 2H), 3.03 (q, J=7.6 Hz, 2H), 1.34-1.23 (m, ³H). ESMS calc'd. (C₁₉H₁₅F₂N₅O₂) 383.1. found: 384.1 (M+H).

Example 61

(E)-2,6-difluoro-N-(5-(1-((pyridazin-3-yloxy)imino)propyl)pyridin-2-yl)benzamide

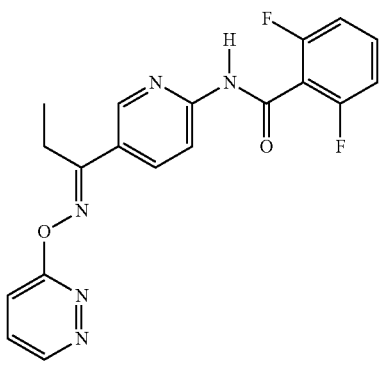 [SMILES: CC/C(=N\Oc1cccnn1)c1ccc(NC(=O)c2c(F)cccc2F)nc1]

¹H NMR (400 MHz, CDCl₃) δ 9.03-8.94 (m, 2H), 8.58 (s, ¹H), 8.47 (d, J=8.7 Hz, ¹H), 8.15 (dd, J=8.7, 2.4 Hz, ¹H), 7.68 (dd, J=9.0, 1.4 Hz, ¹H), 7.55 (dd, J=9.0, 4.5 Hz, ¹H), 7.45 (q, J=7.4 Hz, ¹H), 7.02 (t, J=8.5 Hz, 2H), 3.07 (q, J=7.4 Hz, 2H), 1.30 (t, J=7.6 Hz, ³H). ESMS calc'd. (C₁₉H₁₅F₂N5O₂) 383.1. found: 384.1 (M+H).

Example 62

(E)-2,6-difluoro-N-(5-(1-(((3-methylpyrazin-2-yl)oxy)imino)propyl)pyridin-2-yl)benzamide

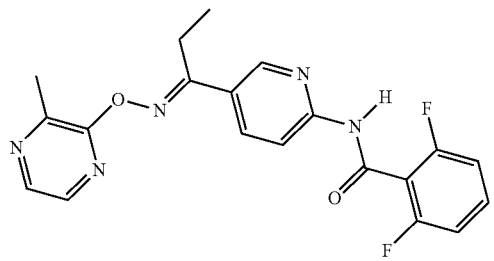 [SMILES: CC/C(=N\Oc1nccnc1C)c1ccc(NC(=O)c2c(F)cccc2F)nc1]

¹H NMR (400 MHz, CDCl₃) δ 9.48 (s, ¹H), 8.50-8.37 (m, 2H), 8.22-8.12 (m, 2H), 8.11 (d, J=2.7 Hz, ¹H), 7.41 (tt, J=8.4, 6.2 Hz, ¹H), 6.98 (t, J=8.2 Hz, 2H), 2.96 (q, J=7.6 Hz, 2H), 2.61 (s, ³H), 1.29 (t, J=7.6 Hz, ³H). ESMS calc'd. (C₂₀H₁₇F₂N₅O₂) 397.1. found: 398.1 (M+H).

Example 63

(E)-N-(5-(1-(((6-cyanopyridin-3-yl)oxy)imino)propyl)pyridin-2-yl)-2,6-difluorobenzamide

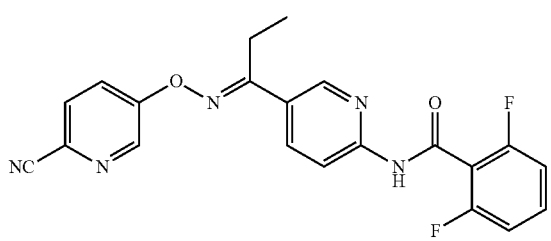 [SMILES: CC/C(=N\Oc1ccc(C#N)nc1)c1ccc(NC(=O)c2c(F)cccc2F)nc1]

¹H NMR (400 MHz, CDCl₃) δ 8.70-8.61 (m, ³H), 8.47 (d, J=8.8 Hz, ¹H), 8.13 (dd, J=8.7, 2.4 Hz, ¹H), 7.76 (dd, J=8.7, 2.7 Hz, ¹H), 7.71 (dd, J=8.7, 0.7 Hz, ¹H), 7.47 (tt, J=8.4, 6.3 Hz, ¹H), 7.04 (t, J=8.3 Hz, 2H), 2.99 (q, J=7.7 Hz, 2H), 1.28 (t, J=7.6 Hz, ³H). ESMS calc'd. (C₂¹H₁₅F₂N₅O₂₂) 407.1. found: 408.1 (M+H).

Example 64

(E)-N-(5-(1-(((2-cyanopyridin-3-yl)oxy)imino)propyl)pyridin-2-yl)-2,6-difluorobenzamide

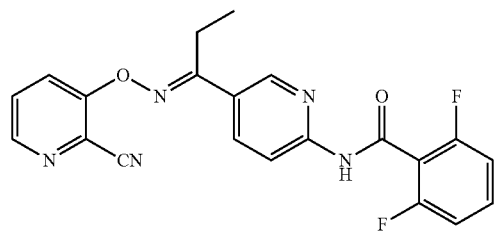 [SMILES: CC/C(=N\Oc1cccnc1C#N)c1ccc(NC(=O)c2c(F)cccc2F)nc1]

¹H NMR (400 MHz, CDCl₃) δ 8.81 (s, ¹H), 8.63-8.57 (m, ¹H), 8.47 (d, J=8.8 Hz, ¹H), 8.39 (dd, J=4.5, 1.4 Hz, ¹H), 8.14 (dd, J=8.8, 2.4 Hz, $^1$H), 8.02 (dd, J=8.7, 1.3 Hz, $^1$H), 7.54 (dd, J=8.7, 4.5 Hz, $^1$H), 7.47 (tt, J=8.4, 6.2 Hz, $^1$H), 7.03 (t, J=8.3 Hz, 2H), 3.05 (q, J=7.6 Hz, 2H), 1.34 (t, J=7.6 Hz, $^3$H). ESMS calc'd. ($C_2{}^1H_{15}F_2N_5O_2$) 407.1. found: 408.1 (M+H).

Example 65

(E)-2,6-difluoro-N-(5-(1-(((6-fluoropyridin-3-yl)oxy)imino)propyl)pyridin-2-yl)benzamide

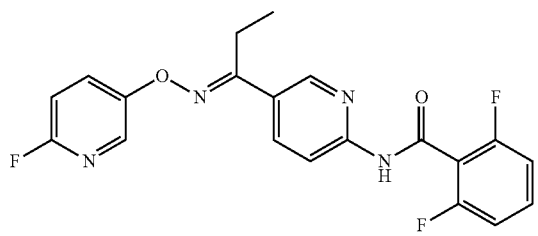 [SMILES: CC/C(=N\Oc1ccc(F)nc1)c1ccc(NC(=O)c2c(F)cccc2F)nc1]

$^1$H NMR (400 MHz, CDCl$_3$) δ 8.78 (s, $^1$H), 8.61 (d, J=1.9 Hz, 2H), 8.51 (d, J=1.2 Hz, $^1$H), 8.40 (dd, J=8.8, 0.9 Hz, $^1$H), 8.17 (dd, J=8.8, 2.4 Hz, $^1$H), 8.12 (dd, J=4.9, 1.5 Hz, $^1$H), 7.49 (ddd, J=9.8, 7.9, 1.5 Hz, $^1$H), 7.08 (ddd, J=8.0, 4.8, 3.2 Hz, $^1$H), 3.02 (q, J=7.6 Hz, $^1$H), 1.30 (t, J=7.6 Hz, 2H). ESMS calc'd. ($C_{20}H_{15}F_3N_4O_2$) 400.1. found: 401.1 (M+H).

Example 66

((E)-2,6-difluoro-N-(5-(1-((pyridin-3-yloxy)imino)propyl)pyridin-2-yl)benzamide

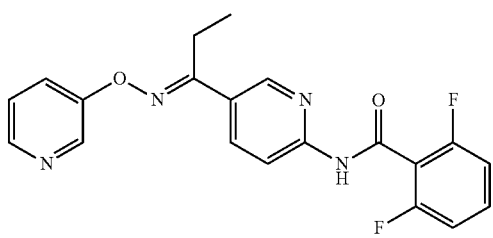 [SMILES: CC/C(=N\Oc1cccnc1)c1ccc(NC(=O)c2c(F)cccc2F)nc1]

ESMS calc'd. ($C_{20}H_{16}F_2N_4O_2$) 382.1. found: 383.1 (M+H).

Example 67

(E)-5-fluoro-4-methyl-N-(5-(1-((pyridin-2-yloxy)imino)propyl)pyridin-2-yl)nicotinamide

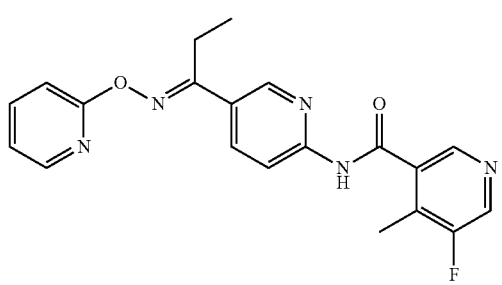 [SMILES: CC/C(=N\Oc1ccccn1)c1ccc(NC(=O)c2cncc(F)c2C)nc1]

$^1$H NMR (400 MHz, CDCl$_3$) δ 8.69-8.65 (m, 2H), 8.63 (s, $^1$H), 8.52 (s, $^1$H), 8.42 (d, J=8.8 Hz, $^1$H), 8.36-8.29 (m, $^1$H), 8.19 (dd, J=8.8, 2.4 Hz, $^1$H), 7.81-7.70 (m, $^1$H), 7.38 (d, J=8.4 Hz, $^1$H), 7.10-6.99 (m, $^1$H), 3.04 (q, J=7.7 Hz, 2H), 2.50 (d, J=2.1 Hz, $^3$H), 1.29 (t, J=7.6 Hz, $^3$H). ESMS calc'd. ($C_{20}H_{18}FN_5O_2$) 379.1. found: 383.1 (M+H).

Procedure:

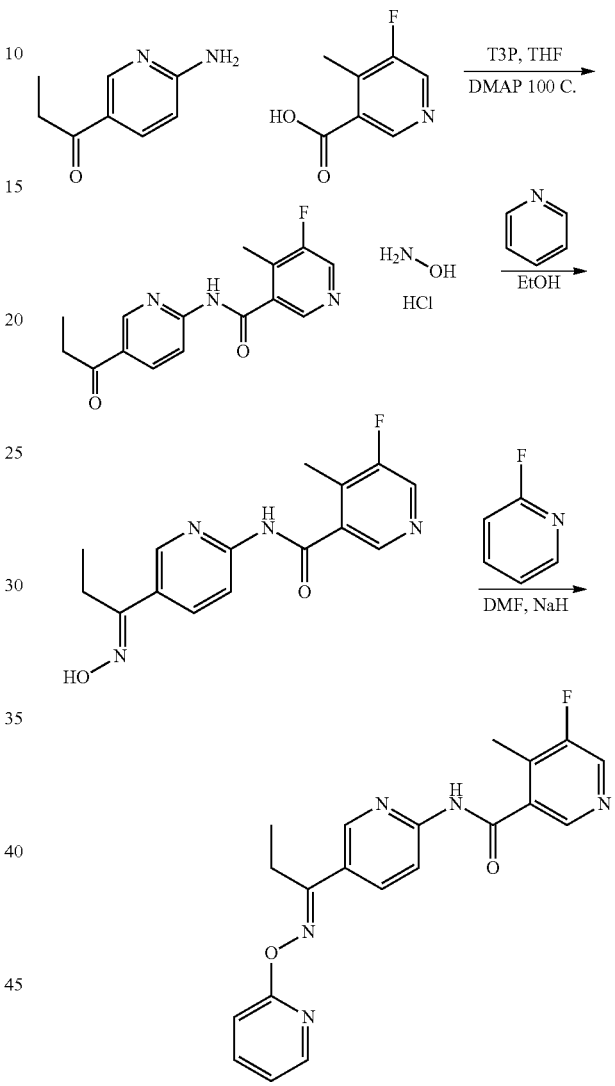

1-(6-aminopyridin-3-yl)propan-1-one (1 g, 6.7 mmol) was dissolved in THF (11 ml) along with DMAP (1.6 g, 13.3 mmol) and T3P 50% in EtOAc (6 g, 13 mmol). The reaction was heated to 100° C. after adding 5-fluoro-4-methylnicotinic acid (1.14 g 7.3 mmol). The reaction was stirred for 3 hours then quenched with a saturated aqueous solution of sodium bicarbonate. The aqueous layer was extracted twice more with ethyl acetate and the organic layer was dried over magnesium sulfate. After column chromatography with ethyl acetate/hexane, 1.4 g of pure amide was isolated in a 73% yield.

The 5-fluoro-4-methyl-N-(5-propionylpyridin-2-yl)nicotinamide was then converted to (E)-5-fluoro-4-methyl-N-(5-(1-((pyridin-2-yloxy)imino)propyl)pyridin-2-yl)nicotinamide in the same fashion as Example 4.

EXAMPLES 68 through 88 were synthesized similarly in accordance with the synthetic procedure in Example 67:

Example 68

(E)-N-(5-(1-(((4-chloropyridin-3-yl)oxy)imino)propyl)pyridin-2-yl)-5-fluoro-4-methylnicotinamide

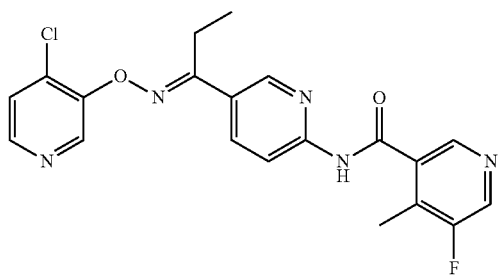 [SMILES: CC/C(=N\Oc1cnccc1Cl)c1ccc(NC(=O)c2cncc(F)c2C)nc1]

¹H NMR (400 MHz, CDCl₃) δ 8.86 (s, ¹H), 8.68-8.65 (m, ¹H), 8.62 (d, J=1.4 Hz, ¹H), 8.51 (d, J=1.3 Hz, ¹H), 8.48-8.40 (m, ¹H), 8.22 (d, J=5.2 Hz, ¹H), 8.17 (dd, J=8.8, 2.4 Hz, ¹H), 7.35 (d, J=5.1 Hz, ¹H), 3.07-2.98 (m, 2H), 2.50 (t, J=1.9 Hz, ³H), 1.40-1.27 (m, ³H). ESMS calc'd. (C₂₀H₁₇ClFN₅O₂) 413.1. found: 414.1 (M+H).

Example 69

(E)-5-fluoro-N-(5-(1-(((3-fluoropyridin-2-yl)oxy)imino)propyl)pyridin-2-yl)-4-methylnicotinamide

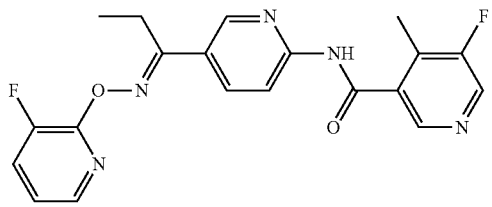 [SMILES: CC/C(=N\Oc1ncccc1F)c1ccc(NC(=O)c2cncc(F)c2C)nc1]

¹H NMR (400 MHz, CDCl₃) δ 9.08-8.99 (m, ¹H), 8.60 (s, ¹H), 8.53 (t, J=2.1 Hz, ¹H), 8.49 (d, J=1.3 Hz, ¹H), 8.40 (d, J=8.6 Hz, ¹H), 8.17 (dd, J=8.7, 2.4 Hz, ¹H), 8.11 (dd, J=4.9, 1.6 Hz, ¹H), 7.48 (ddd, J=9.8, 8.0, 1.6 Hz, ¹H), 7.07 (ddd, J=8.0, 4.8, 3.2 Hz, ¹H), 3.00 (q, J=7.6 Hz, 2H), 2.49 (d, J=2.0 Hz, ³H), 1.30 (t, J=7.6 Hz, ³H). ESMS calc'd. (C₂₀H₁₇F₂N₅O₂) 397.1. found: 398.1 (M+H).

Example 70

(E)-N-(5-(1-(((3-chloropyridin-4-yl)oxy)imino)propyl)pyridin-2-yl)-5-fluoro-4-methylnicotinamide

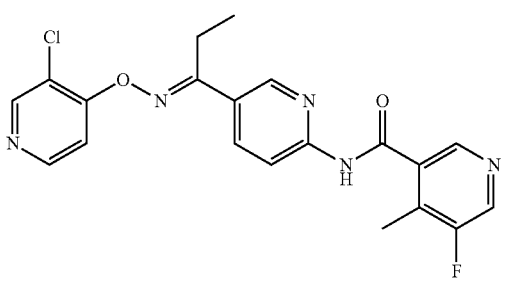 [SMILES: CC/C(=N\Oc1ccncc1Cl)c1ccc(NC(=O)c2cncc(F)c2C)nc1]

¹H NMR (400 MHz, CDCl₃) δ 8.73-8.66 (m, 2H), 8.63 (s, ¹H), 8.53 (d, J=1.4 Hz, 2H), 8.44 (dd, J=8.8, 0.9 Hz, ¹H), 8.42 (d, J=5.6 Hz, ¹H), 8.17 (dd, J=8.8, 2.4 Hz, ¹H), 7.55 (d, J=5.6 Hz, ¹H), 3.04 (q, J=7.6 Hz, 2H), 2.51 (d, J=2.0 Hz, ³H), 1.33 (t, J=7.6 Hz, ³H). ESMS calc'd. (C₂₀H₁₇ClFN₅O₂) 413.1. found: 414.1 (M+H).

Example 71

(E)-N-(5-(1-(((3-chloropyridin-2-yl)oxy)imino)propyl)pyridin-2-yl)-5-fluoro-4-methylnicotinamide

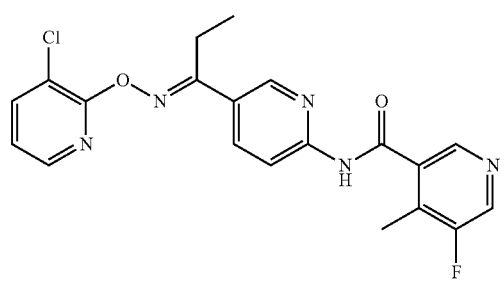 [SMILES: CC/C(=N\Oc1ncccc1Cl)c1ccc(NC(=O)c2cncc(F)c2C)nc1]

¹H NMR (400 MHz, CDCl₃) δ 8.91 (s, ¹H), 8.61 (s, ¹H), 8.59 (d, J=2.2 Hz, ¹H), 8.51 (d, J=1.2 Hz, ¹H), 8.40 (d, J=8.6 Hz, ¹H), 8.24 (dd, J=4.8, 1.7 Hz, ¹H), 8.19 (dd, J=8.8, 2.4 Hz, ¹H), 7.76 (dd, J=7.7, 1.7 Hz, ¹H), 7.03 (dd, J=7.7, 4.8 Hz, ¹H), 3.02 (q, J=7.6 Hz, 2H), 2.49 (d, J=2.0 Hz, ³H), 1.33 (t, J=7.6 Hz, ³H). ESMS calc'd. (C₂₀H₁₇ClFN₅O₂) 413.1. found: 414.1 (M+H).

Example 72

(E)-N-(5-(1-(((3-fluoropyridin-2-yl)oxy)imino)propyl)pyridin-2-yl)-4-methylnicotinamide

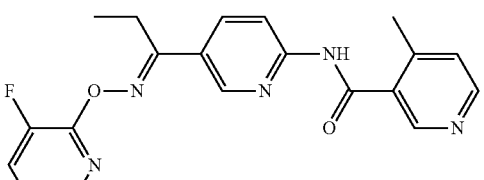

¹H NMR (400 MHz, CDCl₃) δ 8.85 (s, ¹H), 8.78 (s, ¹H), 8.67-8.52 (m, 2H), 8.48-8.36 (m, ¹H), 8.24-8.14 (m, ¹H), 8.14-8.03 (m, ¹H), 7.56-7.41 (m, ¹H), 7.25-7.20 (m, ¹H), 7.14-7.01 (m, ¹H), 3.10-2.94 (m, 2H), 2.57 (s, ³H), 1.30 (t, J=7.4 Hz, ³H). ESMS calc'd. (C₂₀H₁₈FN₅O₂) 379.1. found: 380.1 (M+H).

Example 73

(E)-5-fluoro-4-methyl-N-(5-(1-(((3-methyl-1,2,4-thiadiazol-5-yl)oxy)imino)propyl)pyridin-2-yl)nicotinamide

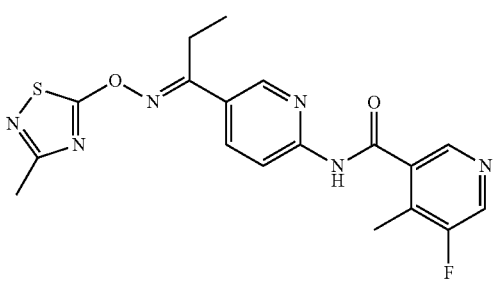 [SMILES: CC/C(=N\Oc1nc(C)ns1)c1ccc(NC(=O)c2cncc(F)c2C)nc1]

$^1$H NMR (400 MHz, CDCl$_3$) δ 8.68-8.61 (m, $^3$H), 8.53 (d, J=1.2 Hz, $^1$H), 8.46 (dd, J=8.8, 0.9 Hz, $^1$H), 8.13 (dd, J=8.8, 2.4 Hz, $^1$H), 3.02 (q, J=7.7 Hz, 2H), 2.54 (s, $^3$H), 2.50 (d, J=2.0 Hz, $^3$H), 1.30 (t, J=7.6 Hz, $^3$H). ESMS calc'd. (C$_{18}$H$_{17}$FN$_6$O$_2$S) 400.1. found: 401.1 (M+H).

Example 74

(E)-5-fluoro-4-methyl-N-(5-((pyridin-2-yloxy)imino)-6,7,8,9-tetrahydro-5H-benzo[7]annulen-2-yl)nicotinamide

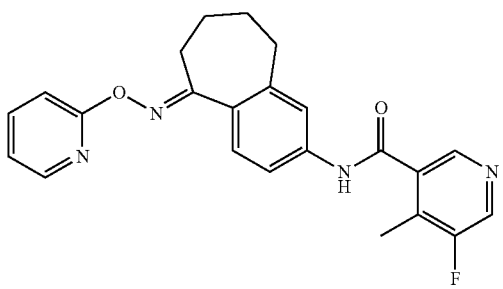 [SMILES: Cc1c(F)cncc1C(=O)Nc1ccc2c(c1)CCCC/C2=N\Oc1ccccn1]

$^1$H NMR (400 MHz, CDCl$_3$) δ 8.56 (s, $^1$H), 8.48 (s, $^1$H), 8.26 (d, J=4.8 Hz, $^1$H), 7.90-7.76 (m, $^1$H), 7.71 (ddd, J=8.7, 7.2, 2.0 Hz, $^1$H), 7.62-7.55 (m, 2H), 7.45 (d, J=8.0 Hz, $^1$H), 7.34 (d, J=8.5 Hz, $^1$H), 7.00 (dd, J=7.2, 4.9 Hz, $^1$H), 3.06-2.96 (m, 2H), 2.82 (t, J=6.6 Hz, 2H), 2.48 (d, J=2.1 Hz, $^3$H), 1.89-1.78 (m, 2H), 1.72 (p, J=6.3 Hz, 2H). ESMS calc'd. (C$_2^3$H$_{21}$FN$_4$O$_2$) 404.2. found: 405.2 (M+H).

Example 75

(E)-N-(5-(1-(((3-chloropyridin-2-yl)oxy)imino)propyl)pyridin-2-yl)-4-methylnicotinamide

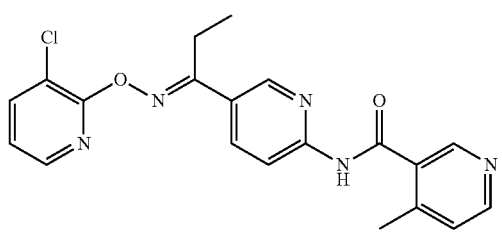 [SMILES: CC/C(=N\Oc1ncccc1Cl)c1ccc(NC(=O)c2cnccc2C)nc1]

ESMS calc'd. (C$_{20}$H$_{17}$ClN$_5$O$_2$) 395.1. found: 396.1 (M+H).

Example 76

(E)-N-(5-(1-(((5,6-difluoropyridin-3-yl)oxy)imino)propyl)pyridin-2-yl)-4-methylnicotinamide

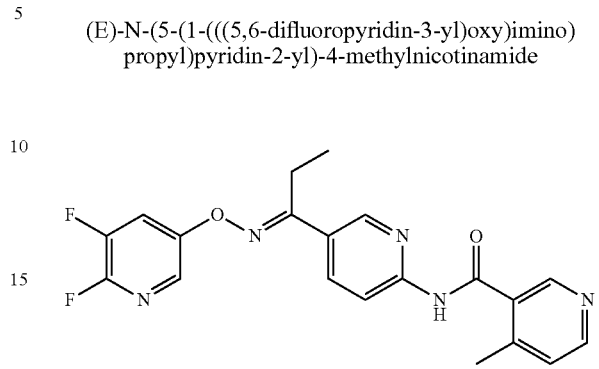

$^1$H NMR (400 MHz, CDCl$_3$) δ 8.79 (s, $^1$H), 8.76 (s, $^1$H), 8.64-8.55 (m, 2H), 8.46 (dd, J=8.8, 0.9 Hz, $^1$H), 8.14 (dd, J=8.7, 2.4 Hz, $^1$H), 7.75 (ddd, J=8.6, 7.4, 2.8 Hz, $^1$H), 7.69 (t, J=2.5 Hz, $^1$H), 7.29-7.23 (m, $^1$H), 3.00 (q, J=7.6 Hz, 2H), 2.58 (s, $^3$H), 1.29 (t, J=7.6 Hz, $^3$H). ESMS calc'd. (C$_{20}$H$_{17}$F$_2$N$_5$O$_2$) 397.1. found: 398.1 (M+H).

Example 77

(E)-N-(5-(1-(((3,5-difluoropyridin-2-yl)oxy)imino)propyl)pyridin-2-yl)-4-methylnicotinamide

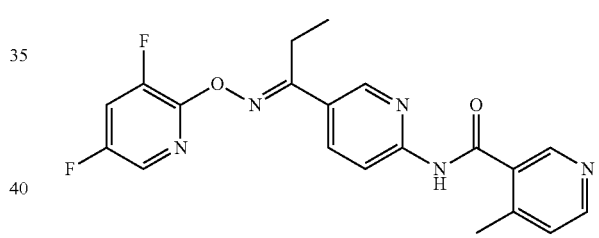

$^1$H NMR (400 MHz, CDCl$_3$) δ 8.78 (s, $^1$H), 8.68 (d, J=2.5 Hz, $^1$H), 8.62-8.55 (m, 2H), 8.41 (dd, J=8.8, 0.9 Hz, $^1$H), 8.14 (dd, J=8.7, 2.4 Hz, $^1$H), 8.03 (d, J=2.6 Hz, $^1$H), 7.34 (ddd, J=9.3, 7.4, 2.6 Hz, $^1$H), 7.24 (dd, J=5.1, 0.8 Hz, $^1$H), 3.00 (q, J=7.6 Hz, 2H), 2.57 (s, $^3$H), 1.30 (t, J=7.6 Hz, $^3$H). ESMS calc'd. (C$_{20}$H$_{17}$F$_2$N$_5$O$_2$) 397.1. found: 398.1 (M+H).

Example 78

(E)-N-(5-(1-(((3-cyanopyridin-2-yl)oxy)imino)propyl)pyridin-2-yl)-4-methylnicotinamide

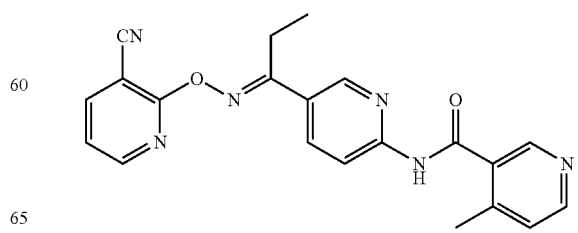

ESMS calc'd. (C₂¹H₁₈N₆O₂₂) 386.15. found: 387.1 (M+H).

Example 79

(E)-N-(5-(1-((cyclopentyloxy)imino)propyl)pyridin-2-yl)-5-fluoro-4-methylnicotinamide

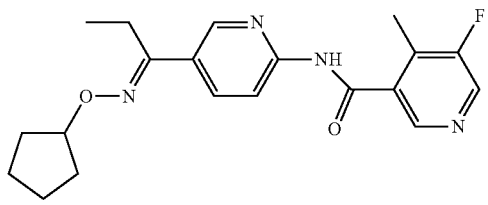 [SMILES: CC/C(=N\OC1CCCC1)c1ccc(NC(=O)c2cncc(F)c2C)nc1]

¹H NMR (400 MHz, CDCl₃) δ 9.63 (s, ¹H), 8.58 (s, ¹H), 8.48 (d, J=1.2 Hz, ¹H), 8.35 (d, J=8.7 Hz, ¹H), 8.25-8.20 (m, ¹H), 8.03 (dd, J=8.7, 2.4 Hz, ¹H), 4.80 (tt, J=5.6, 2.9 Hz, ¹H), 2.67 (q, J=7.6 Hz, 2H), 2.48 (d, J=2.0 Hz, ³H), 1.92-1.54 (m, 8H), 1.10 (t, J=7.6 Hz, ³H). ESMS calc'd. (C₂₀H₂₃FN₄O₂) 370.2. found: 371.2 (M+H).

Example 80

(E)-5-fluoro-4-methyl-N-(5-(1-((oxetan-3-yloxy)imino)propyl)pyridin-2-yl)nicotinamide

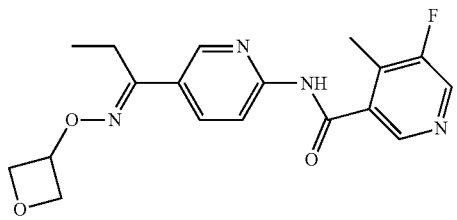 [SMILES: CC/C(=N\OC1COC1)c1ccc(NC(=O)c2cncc(F)c2C)nc1]

¹H NMR (400 MHz, CDCl₃) δ 8.88 (s, ¹H), 8.60 (s, ¹H), 8.50 (d, J=1.2 Hz, ¹H), 8.43 (dd, J=2.4, 0.8 Hz, ¹H), 8.34 (s, ¹H), 8.03 (dd, J=8.8, 2.4 Hz, ¹H), 5.35 (tt, J=6.3, 5.0 Hz, ¹H), 4.93 (ddd, J=7.3, 6.2, 0.9 Hz, 2H), 4.78 (ddd, J=7.3, 4.9, 0.9 Hz, 2H), 2.81 (q, J=7.6 Hz, 2H), 2.48 (d, J=2.0 Hz, ³H), 1.18 (t, J=7.6 Hz, ³H). ESMS calc'd. (C₁₈H₁₉FN₄O₃) 358.1. found: 359.4 (M+H).

Example 81

(E)-N-(5-(1-(sec-butoxyimino)propyl)pyridin-2-yl)-5-fluoro-4-methylnicotinamide

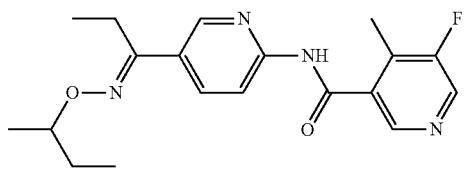 [SMILES: CC/C(=N\OC(C)CC)c1ccc(NC(=O)c2cncc(F)c2C)nc1]

¹H NMR (400 MHz, CDCl₃) δ 8.92 (s, ¹H), 8.60 (s, ¹H), 8.49 (d, J=1.2 Hz, ¹H), 8.41 (dd, J=2.3, 0.9 Hz, ¹H), 8.37-8.30 (m, ¹H), 8.05 (dd, J=8.8, 2.4 Hz, ¹H), 4.26 (h, J=6.3 Hz, ¹H), 2.79-2.63 (m, 2H), 2.48 (d, J=2.0 Hz, ³H), 1.81-1.67 (m, ¹H), 1.64-1.53 (m, ¹H), 1.29 (d, J=6.3 Hz, ³H), 1.13 (t, J=7.6 Hz, ³H), 0.97 (t, J=7.5 Hz, ³H). ESMS calc'd. (C₁₉H₂₃FN₄O₂) 358.2. found: 359.1 (M+H).

Example 82

(E)-N-(5-(cyclopropyl((oxetan-3-yloxy)imino)methyl)pyrazin-2-yl)-5-fluoro-4-methylnicotinamide

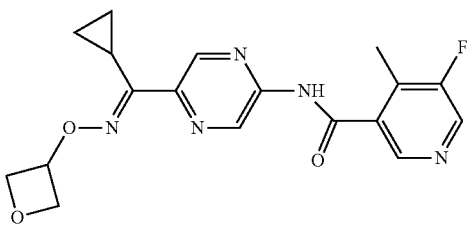 [SMILES: Cc1c(F)cncc1C(=O)Nc1cnc(/C(=N/OC2COC2)C2CC2)cn1]

ESMS calc'd. (C₁₈H₁₈FN₅O₃) 371.1. found: 372.1 (M+H).

Example 83

(E)-N-(5-(1-(((2,5-difluoropyridin-3-yl)oxy)imino)propyl)pyridin-2-yl)-5-fluoro-4-methylnicotinamide

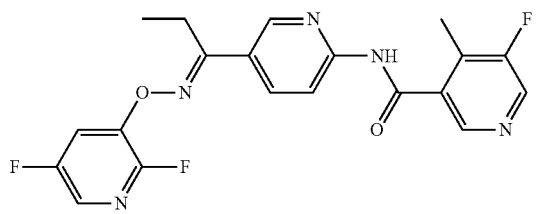 [SMILES: CC/C(=N\Oc1cc(F)cnc1F)c1ccc(NC(=O)c2cncc(F)c2C)nc1]

¹H NMR (400 MHz, CDCl₃) δ 8.68 (s, ¹H), 8.64 (dd, J=2.4, 0.8 Hz, ¹H), 8.63 (s, ¹H), 8.53 (d, J=1.2 Hz, ¹H), 8.44 (dd, J=8.8, 0.9 Hz, ¹H), 8.15 (dd, J=8.7, 2.4 Hz, ¹H), 7.75 (ddd, J=8.5, 7.4, 2.8 Hz, ¹H), 7.70 (t, J=2.5 Hz, ¹H), 3.00 (q, J=7.7 Hz, 2H), 2.51 (d, J=2.0 Hz, ³H), 1.29 (t, J=7.6 Hz, ³H). ESMS calc'd. (C₂₀H₁₆F₃N₃O₂) 415.1. found: 416.1 (M+H).

Example 84

(E)-N-(5-(1-(((3,5-difluoropyridin-2-yl)oxy)imino)propyl)pyridin-2-yl)-5-fluoro-4-methylnicotinamide

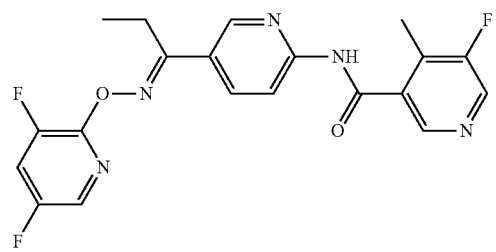 [SMILES: CC/C(=N\Oc1ncc(F)cc1F)c1ccc(NC(=O)c2cncc(F)c2C)nc1]

¹H NMR (400 MHz, CDCl₃) δ 8.72 (s, ¹H), 8.63-8.55 (m, 2H), 8.51 (d, J=1.3 Hz, ¹H), 8.40 (d, J=8.7 Hz, ¹H), 8.15 (dd, J=8.7, 2.4 Hz, ¹H), 8.03 (d, J=2.6 Hz, ¹H), 7.34 (ddd, J=9.7, 7.4, 2.6 Hz, $^1$H), 3.01 (q, J=7.6 Hz, 2H), 2.49 (d, J=2.0 Hz, 4H), 1.30 (t, J=7.6 Hz, $^3$H). SMS calc'd. ($C_{20}H_{16}F_3N_5O_2$) 415.1. found: 416.1 (M+H).

Example 85

(E)-N-(5-(1-(cyclobutoxyimino)propyl)pyridin-2-yl)-5-fluoro-4-methylnicotinamide

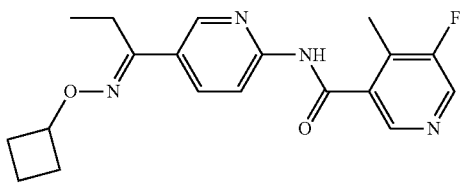 [SMILES: CC/C(=N\OC1CCC1)c1ccc(NC(=O)c2cncc(F)c2C)nc1]

$^1$H NMR (400 MHz, CDCl$_3$) δ 8.61 (s, $^1$H), 8.55 (dd, J=2.4, 0.9 Hz, $^1$H), 8.51 (d, J=1.3 Hz, $^1$H), 8.42 (s, $^1$H), 8.32 (d, J=8.7 Hz, $^1$H), 8.04 (dd, J=8.7, 2.3 Hz, $^1$H), 4.78 (q, J=7.4 Hz, $^1$H), 2.76 (q, J=7.5 Hz, 2H), 2.49 (d, J=2.0 Hz, $^3$H), 2.40-2.29 (m, $^1$H), 2.24-2.08 (m, $^1$H), 1.87-1.74 (m, $^1$H), 1.71-1.61 (m, $^1$H), 1.15 (t, J=7.6 Hz, $^3$H). ESMS calc'd. ($C_{19}H_{21}FN_4O_2$) 356.2. found: 357.2 (M+H).

Example 86

(E)-4-methyl-N-(5-(1-((oxetan-3-yloxy)imino)propyl)pyridin-2-yl)nicotinamide

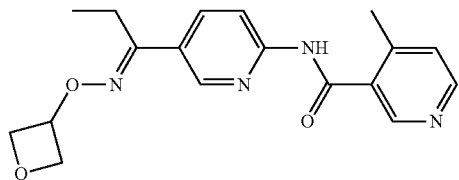 [SMILES: CC/C(=N\OC1COC1)c1ccc(NC(=O)c2cnccc2C)nc1]

$^1$H NMR (400 MHz, CDCl$_3$) δ 9.00 (s, $^1$H), 8.76 (s, $^1$H), 8.55 (d, J=5.0 Hz, $^1$H), 8.41 (dd, J=2.4, 0.9 Hz, $^1$H), 8.37 (dd, J=8.8, 0.9 Hz, $^1$H), 8.02 (dd, J=8.7, 2.3 Hz, $^1$H), 7.22 (dt, J=5.0, 0.8 Hz, $^1$H), 5.41-5.29 (m, $^1$H), 4.93 (ddd, J=7.2, 6.2, 1.0 Hz, 2H), 4.78 (ddd, J=7.4, 5.0, 1.0 Hz, 2H), 2.80 (q, J=7.6 Hz, 2H), 2.55 (s, $^3$H), 1.18 (t, J=7.6 Hz, $^3$H). ESMS calc'd. ($C_{18}H_{20}N_4O_3$) 340.2. found: 341.2 (M+H).

Example 87

(E)-5-fluoro-4-methyl-N-(5-(1-((pyridin-3-ylmethoxy)imino)propyl)pyridin-2-yl)nicotinamide

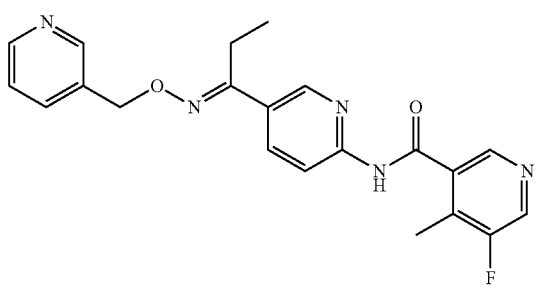 [SMILES: CC/C(=N\OCc1cccnc1)c1ccc(NC(=O)c2cncc(F)c2C)nc1]

$^1$H NMR (400 MHz, CDCl$_3$) δ 8.79 (s, $^1$H), 8.67 (d, J=2.3 Hz, $^1$H), 8.62-8.54 (m, 2H), 8.50 (d, J=1.5 Hz, $^1$H), 8.45 (d, J=2.4 Hz, $^1$H), 8.34 (d, J=8.6 Hz, $^1$H), 8.02 (dd, J=8.7, 2.4 Hz, $^1$H), 7.74 (d, J=7.7 Hz, OH), 7.31 (dd, J=7.7, 4.9 Hz, $^1$H), 5.25 (s, 2H), 2.76 (q, J=7.6 Hz, 2H), 2.48 (d, J=2.1 Hz, $^3$H), 1.14 (t, J=7.5 Hz, $^3$H). ESMS calc'd. ($C_{21}H_{20}FN_5O_2$) 393.2. found: 394.1 (M+H).

Example 88

(E)-N-(5-(1-(cyclopropoxyimino)propyl)pyridin-2-yl)-5-fluoro-4-methylnicotinamide

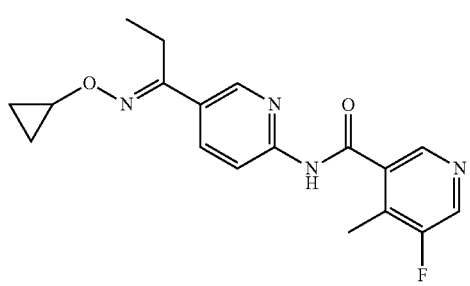

$^1$H NMR (400 MHz, CDCl$_3$) δ 8.61 (s, $^1$H), 8.55 (dd, J=2.4, 0.9 Hz, $^1$H), 8.51 (d, J=1.2 Hz, $^1$H), 8.50-8.45 (m, $^1$H), 8.34 (d, J=8.6 Hz, $^1$H), 8.06 (dd, J=8.7, 2.4 Hz, $^1$H), 4.11 (td, J=6.3, 3.1 Hz, $^1$H), 2.70 (q, J=7.6 Hz, 2H), 2.49 (d, J=2.1 Hz, 4H), 1.11 (t, J=7.6 Hz, $^3$H), 0.85-0.76 (m, 2H), 0.75-0.67 (m, 2H). ESMS calc'd. ($C_{18}H_{19}FN_4O_2$) 342.1. found: 343.1 (M+H).

Example 89

(E)-N-(5-(cyclopropyl(((3-fluoropyridin-2-yl)oxy)imino)methyl)pyridin-2-yl)-2,6-difluorobenzamide

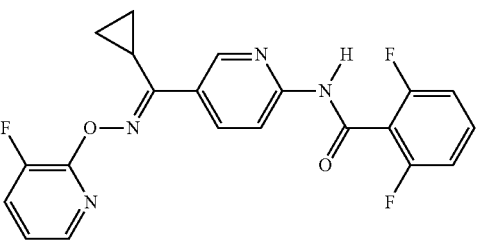 [SMILES: O=C(Nc1ccc(/C(=N/Oc2ncccc2F)C2CC2)cn1)c1c(F)cccc1F]

$^1$H NMR (400 MHz, CDCl$_3$) δ 8.66 (s, $^1$H), 8.49-8.31 (m, 2H), 8.09 (dd, J=4.8, 1.5 Hz, $^1$H), 7.91 (dd, J=8.7, 2.3 Hz, $^1$H), 7.55-7.39 (m, 2H), 7.11-6.96 (m, 2H), 2.55 (tt, J=8.6, 5.4 Hz, $^1$H), 1.17-1.08 (m, 2H), 0.84-0.76 (m, 2H). ESMS calc'd. ($C_{21}H_{15}F_3N_4O_2$) 412.1. found: 413.1 (M+H).

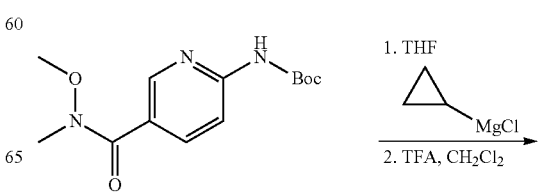

225
-continued

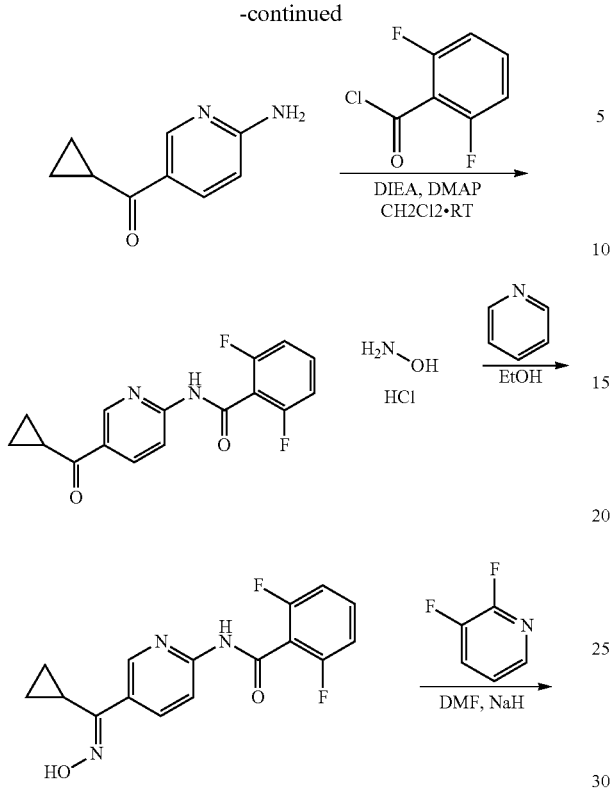

Procedure: The Weinreb amide (600 mg, 2.13 mmol) was dissolved in THF (10 ml) at room temperature. The cyclopropyl Grignard (21 ml, 0.5M)) was then added slowly to the solution and allowed to stir for 3 hours. Once the reaction was complete, water was added to the reaction solution followed by 1N HCl in order to bring the pH to neutral. The reaction was extracted with methylene chloride 2× and then dried over magnesium sulfate. After evaporating to dryness, the residue (560 mg) was dissolved in methylene chloride 2 ml and TFA 2 ml was added. The reaction was stirred for another 3 hours at room temperature then quenched with sat sodium bicarbonate solution. It was then extracted with methylene chloride and dried over sodium sulfate. Purified by column chromatography with silica gel and a ethyl acetate/hexane gradient providing 243 mg in a 70% yield.

The remaining synthesis was completed according to the synthesis of Example 54.

EXAMPLES 90 through 101 were synthesized according to the synthetic procedure of Example 99:

226

Example 90

(E)-N-(5-(cyclopropyl(((3-fluoropyridin-2-yl)oxy)imino)methyl)pyridin-2-yl)-5-fluoro-4-methylnicotinamide

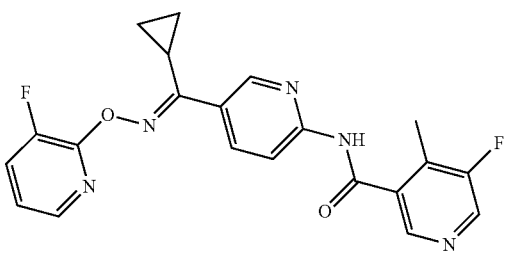 [SMILES: Cc1c(F)cncc1C(=O)Nc1ccc(/C(=N/Oc2ncccc2F)C2CC2)cn1]

$^1$H NMR (400 MHz, CDCl$_3$) δ 8.61 (s, $^1$H), 8.51 (d, J=1.2 Hz, $^1$H), 8.46-8.43 (m, 2H), 8.36 (dd, J=8.5, 0.9 Hz, $^1$H), 8.09 (dd, J=4.9, 1.5 Hz, $^1$H), 7.93 (dd, J=8.6, 2.3 Hz, $^1$H), 7.47 (ddd, J=10.1, 8.0, 1.6 Hz, $^1$H), 7.04 (ddd, J=8.0, 4.9, 3.2 Hz, $^1$H), 2.57 (tt, J=8.5, 5.5 Hz, $^1$H), 2.49 (d, J=2.0 Hz, $^3$H), 1.19-1.11 (m, 2H), 0.84-0.77 (m, 2H). ESMS calc'd. (C$_2$$^1$H$_{18}$F$_2$N$_4$O$_2$) 409.1. found: 410.1 (M+H).

Example 91

(E)-2,6-difluoro-N-(5-(2-methyl-1-((pyridin-2-yloxy)imino)propyl)pyridin-2-yl)benzamide

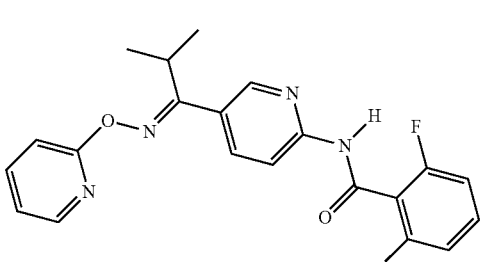

ESMS calc'd. (C$_2$$^1$H$_{18}$F$_2$N$_4$O$_2$) 396.1. found: 397.1 (M+H).

Example 92

(E)-5-fluoro-N-(5-(1-(((3-fluoropyridin-2-yl)oxy)imino)butyl)pyridin-2-yl)-4-methylnicotinamide

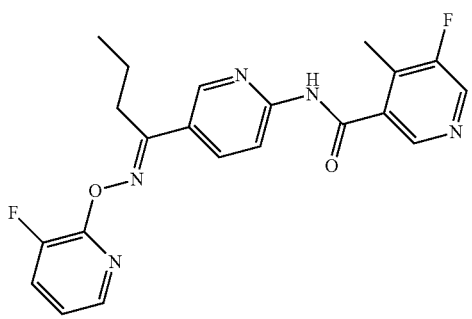 [SMILES: CCC/C(=N\Oc1ncccc1F)c1ccc(NC(=O)c2cncc(F)c2C)nc1]

¹H NMR (400 MHz, CDCl₃) δ 8.94 (s, ¹H), 8.60 (d, J=1.2 Hz, ¹H), 8.56 (s, ¹H), 8.50 (d, J=1.4 Hz, ¹H), 8.40 (d, J=8.7 Hz, ¹H), 8.16 (dd, J=8.8, 2.3 Hz, ¹H), 8.11 (dd, J=4.9, 1.5 Hz, ¹H), 7.48 (ddd, J=9.9, 8.0, 1.5 Hz, ¹H), 7.07 (ddd, J=8.0, 4.8, 3.2 Hz, ¹H), 3.04-2.91 (m, 2H), 2.49 (d, J=1.9 Hz, ³H), 1.72 (q, J=7.7 Hz, 2H), 1.06 (t, J=7.4 Hz, ³H). ESMS calc'd. ($C_{21}H_{18}F_2N_4O_2$) 411.2. found: 412.2 (M+H).

Example 93

(Z)—N-(5-(cyclopropyl(((3-fluoropyridin-2-yl)oxy)imino)methyl)pyridin-2-yl)-5-fluoro-4-methylnicotinamide

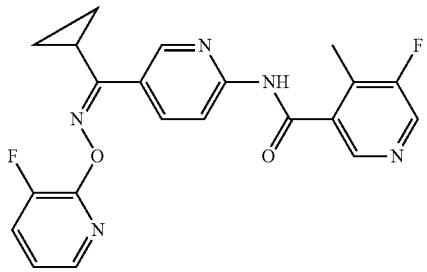 [SMILES: Cc1c(F)cncc1C(=O)Nc1ccc(/C(=N\Oc2ncccc2F)C2CC2)cn1]

ESMS calc'd. ($C_{21}H_{18}F_2N_4O_2$) 382.1. found: 383.1 (M+H).

Example 94

(E)-N-(5-(cyclopropyl(((3-fluoropyridin-2-yl)oxy)imino)methyl)pyrazin-2-yl)-5-fluoro-4-methylnicotinamide

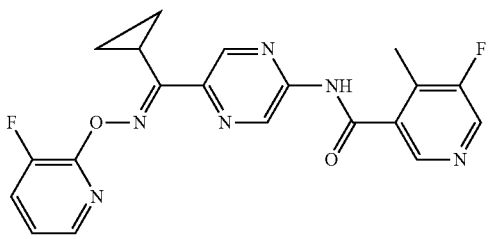 [SMILES: Cc1c(F)cncc1C(=O)Nc1cnc(/C(=N/Oc2ncccc2F)C2CC2)cn1]

¹H NMR (400 MHz, CDCl₃) δ 9.76 (d, J=1.5 Hz, ¹H), 8.81 (d, J=1.5 Hz, ¹H), 8.65 (s, ¹H), 8.55 (d, J=1.2 Hz, ¹H), 8.38 (s, ¹H), 8.11 (dd, J=4.9, 1.5 Hz, ¹H), 7.41 (ddd, J=9.7, 7.9, 1.5 Hz, ¹H), 7.07-7.01 (m, ¹H), 2.52 (d, J=2.0 Hz, ³H), 2.34-2.23 (m, ¹H), 1.14-1.07 (m, 2H), 1.05-0.96 (m, 2H). ESMS calc'd. ($C_{21}H_{18}F_2N_4O_2$) 410.1. found: 411.1 (M+H).

Example 95

(E)-2,6-difluoro-N-(5-((methoxyimino)(6-methoxypyridin-3-yl)methyl)pyridin-2-yl)benzamide

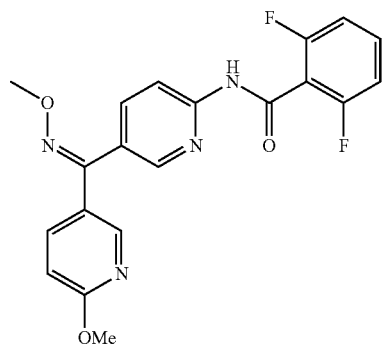 [SMILES: CO/N=C(\c1ccc(NC(=O)c2c(F)cccc2F)nc1)c1ccc(OC)nc1]

SMS calc'd. ($C_{20}H_{16}F_2N_4O_3$) 398.1. found: 399.11 (M+H).

Example 96

(Z)-methyl 4-((4-(2,6-difluorobenzamido)phenyl)(methoxyimino)methyl) piperidine-1-carboxylate

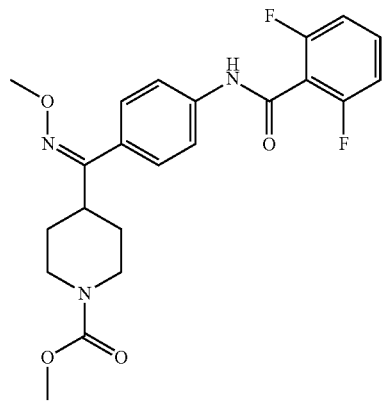 [SMILES: CO/N=C(\c1ccc(NC(=O)c2c(F)cccc2F)cc1)C1CCN(C(=O)OC)CC1]

ESMS calc'd. ($C_{22}H_{23}F_2N_3O_4$) 431.2. found: 432.1 (M+H).

Example 97

2,3-difluoro-N-(5-((methoxyimino) (4-methoxyphenyl)methyl)pyridin-2-yl)benzamide

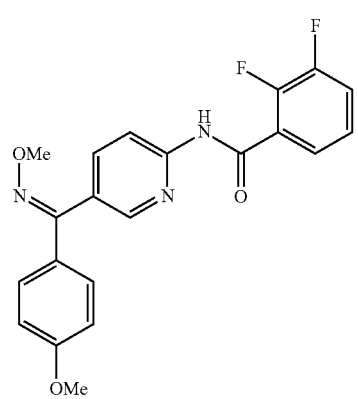 [SMILES: CO/N=C(/c1ccc(OC)cc1)c1ccc(NC(=O)c2cccc(F)c2F)nc1]

ESMS calc'd. (C2¹H17F2N3O3) 397.1. found: 398.1 (M+H).

Example 98

5-fluoro-N-(5-((methoxyimino) (4-methoxyphenyl)methyl)pyridin-2-yl)-4-methylnicotinamide

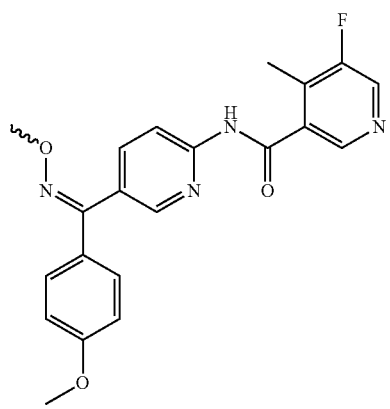

$^1$H NMR (400 MHz, CDCl$_3$) major isomer: δ 9.04 (s, $^1$H), 8.59 (s, $^1$H), 8.47 (br s, $^1$H), 8.41 (d, J=8.6 Hz, $^1$H), 8.12 (dd, J=2.0, 0.7 Hz, $^1$H), 7.80 (dd, J=8.6, 2.0 Hz, $^1$H), 7.41 (d, J=8.6 Hz, 2H), 6.89 (d, J=8.6 Hz, 2H), 3.97 (s, $^3$H), 3.84 (s, $^3$H), 2.48 (d, J=2.0 Hz, $^3$H). ESMS calc'd. (C$_2$$^1$H$_{19}$FN$_4$O$_3$) 394.1. found: 395.1 (M+H).

Procedure:

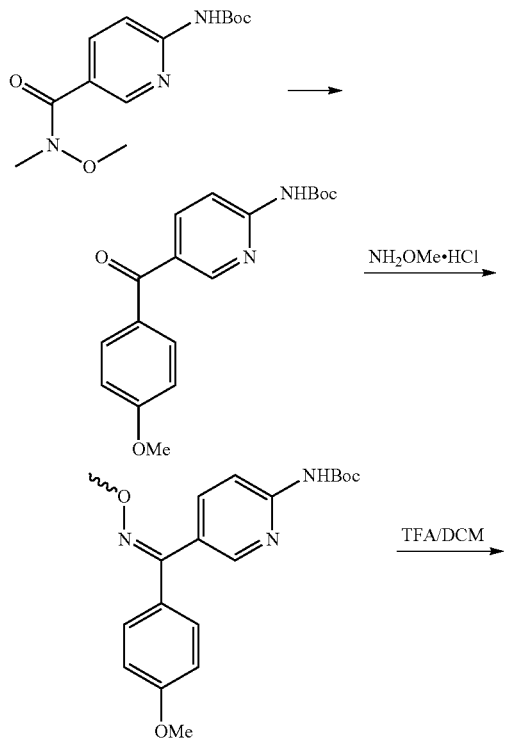

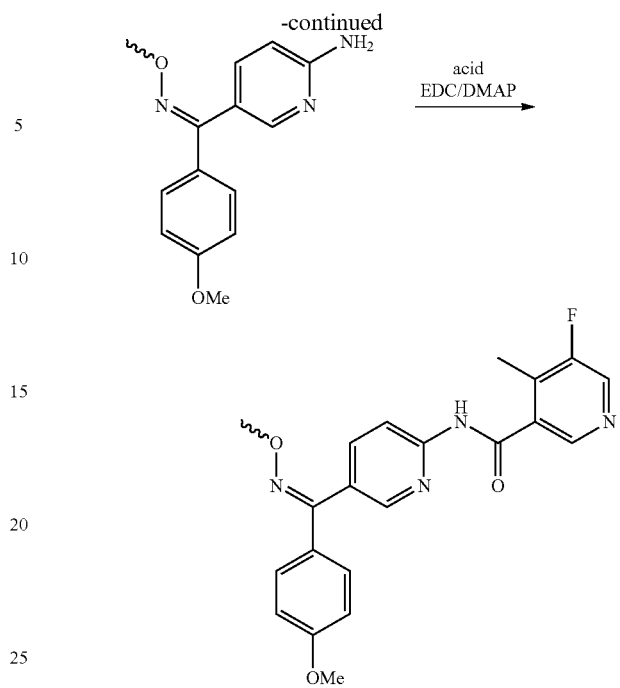

To a solution of tert-butyl (5-(methoxy(methyl)carbamoyl)pyridin-2-yl)carbamate (281 mg, 1.0 mmol) in 10 mL of anhydrous THF at 0° C. was added dropwise a solution of (4-methoxyphenyl)magnesium bromide in THF (0.5 M, 5 mL, 2.5 mmol) over 5 minutes. The solution was warmed room temperature and stirred sealed under N$_2$ for overnight. The reaction solution was quenched with saturated NaHCO$_3$ and extracted with EtOAc. The organic phases were combined, washed with brine, dried over anhydrous sodium sulfate and concentrated. The residue was purified by flash column chromatography on silica gel (eluted with 0-100% EtOAc/hexanes) to give 250 mg of tert-butyl (5-(4-methoxybenzoyl)pyridin-2-yl)carbamate as a white solid. ESMS calc'd. (C$_{18}$H$_{20}$N$_2$O$_4$) 328.1. found: 329.1 (M+H).

To a solution of tert-butyl (5-(4-methoxybenzoyl)pyridin-2-yl)carbamate (130 mg, 0.4 mmol) in 2 mL of MeOH and 2 mL of THF was added O-methylhydroxylamine hydrochloride (620 mg, 8 mmol), NaOAc.H$_2$O (1.09 g, 8 mmol). The mixture was stirred at room temperature for overnight. The reaction was basified with 10% NaOH solution and extracted with DCM. The organic phase was dried over anhydrous sodium sulfate and concentrated under reduced pressure. The residue was purified by flash column chromatography on silica gel to give tert-butyl (5-((methoxyimino)(4-methoxyphenyl)methyl)pyridin-2-yl)carbamate as a mixture of Z/E isomers. ESMS calc'd. (C$_{19}$H$_{23}$N$_3$O$_4$) 357.1. found: 358.2 (M+H).

To a solution of (6-aminopyridin-3-yl)(4-methoxyphenyl)methanone O-methyl oxime (120 mg, 0.336 mmol) in 2 mL of DCM was added 2 mL of trifluoroacetic acid. The solution was stirred at room temperature for 2 hours. The solvent was removed. The residue was taken into 10 mL of EtOAc. The solution was washed with 10% NaOH and brine, dried, concentrated to give 90 mg of (6-aminopyridin-3-yl)(4-methoxyphenyl)methanone O-methyl oxime as a mixture of Z/E isomers. ESMS calc'd. (C$_4$H$_{15}$N$_3$O$_2$) 257.1. found: 258.1 (M+H).

To a solution of (6-aminopyridin-3-yl)(4-methoxyphenyl)methanone O-methyl oxime (20 mg)) in 2 mL of CH$_2$Cl$_2$ at room temperature was added 5-fluoro-4-methylnicotinic acid (30 mg), EDC (40 mg) and DMAP (28 mg). The solution was stirred at room temperature for overnight. The solvent was removed and the residue was treated with K$_2$CO$_3$ (50 mg) and heated in 5 mL of methanol at 65° C. for 10 minutes. The solvent was removed under reduced pressure and the residue was taken into ethyl acetate. The solution was washed with brine, dried over anhydrous sodium sulfate and concentrated. The residue was purified on silica gel by flash column chromatography (eluted with 0-100% EtOAc/hexanes) to give 5-fluoro-N-(5-((methoxyimino)(4-methoxyphenyl)methyl)pyridin-2-yl)-4-methylnicotinamide (15 mg) as a 3:2 mixture of cis/trans isomers.

Example 99

2,3-difluoro-N-(5-((methoxyimino) (4-methoxyphenyl)methyl)pyridin-2-yl)benzamide

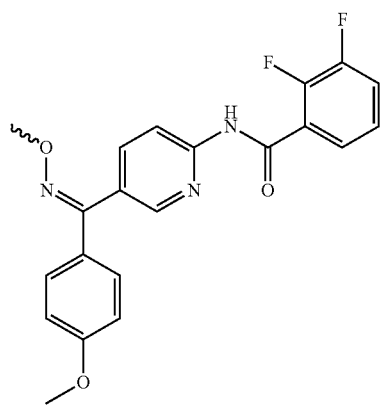

ESMS calc'd. (C$_2{}^1$H$_{17}$F$_2$N$_3$O$_3$) 397.1. found: 398.1 (M+H).

To a solution of (6-aminopyridin-3-yl)(4-methoxyphenyl)methanone O-methyl oxime (20 mg) in 2 mL of CH$_2$Cl$_2$ was added iPrNEt$_2$ (20 mg) and 2,3-difluorobenzoyl chloride (20 mg). The mixture was stirred at room temperature overnight, concentrated under reduced pressure. The residue was purified by on silica gel by flash column chromatography (eluted with 0-100% EtOAc/hexanes) to give 2,3-difluoro-N-(5-((methoxyimino)(4-methoxyphenyl)methyl)pyridin-2-yl)benzamide (12 mg) as a 3:2 mixture of cis/trans isomers.

Representative procedure of N-(5-(2-chloro-5-cyclopropoxyphenyl)pyrazin-2-yl)-4-methylnicotinamide hydrochloride (f)

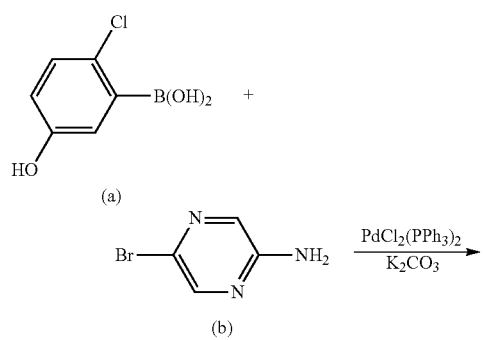

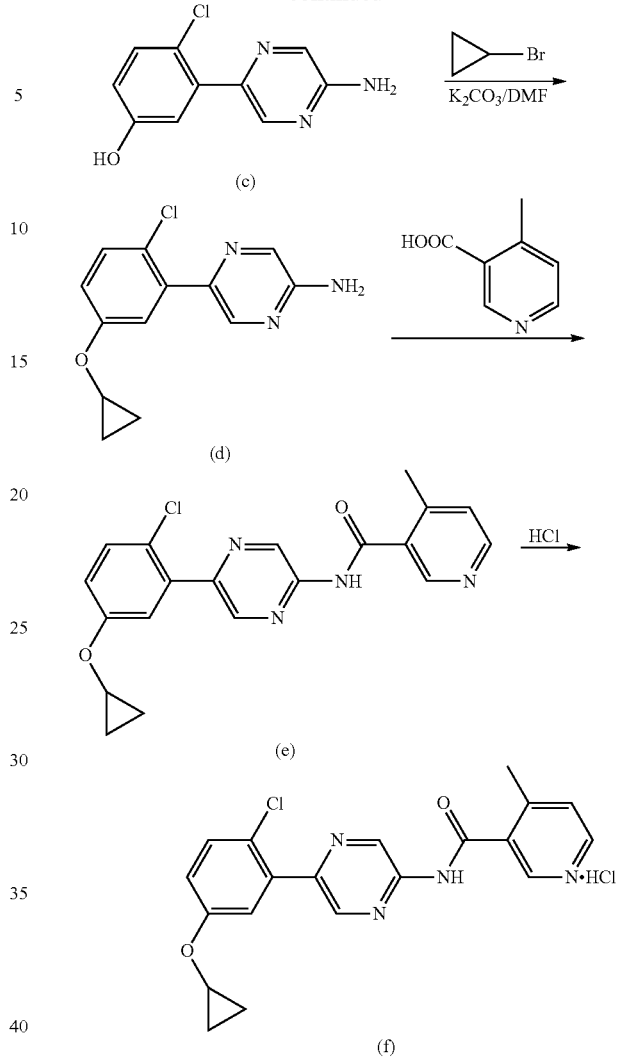

A mixture of 20 mmol each of boric acid a and bromide b and 1 mmol PdCl$_2$(PPh$_3$)$_2$ in dioxane (100 mL)/water (10 mL) was heated at 100° C. for 6 h. The organic layer was dried, concentrated and crystallized from 50% EA/Hexanes to give product c as grayish solid (17 mmol, 85% yields).

5 mmol of the above solid c and 7.5 mmol of cyclopropyl bromide was dissolved in DMF (20 mL), K$_2$CO$_3$ (6.5 mmol) was added and mixture was heated in microwave reactor at 180° C. for 10 h. The reaction mixture was quenched with water (100 mL) and extracted with EA (2×100 mL). The combined EA layer was concentrated and purified by column to give product d as brownish solid (2.5 mmol, 50% yields).

The free amine d (2 mmol) was treated with 3 mmol 4-methylnicotinic acid, 3 mmol TEA and 3 mmol T3P in EA (50 mL) and the mixture was refluxed for 16 h. The reaction mixture was washed with water (2×50 mL) and purified by column to give e as white solid (0.65 mmol, 33% yields).

0.20 g of free form e was dissolved in EA (20 mL) and added HCl in ether (0.5 mL×2M) and stirred for 30 min. The mixture was concentrated and triturated with 30% EA/Hexanes) to give 0.11 g salt form f. $^1$H-NMR (DMSO-d$_6$) δ11.62 (br, $^1$H), 9.54 (d, $^1$H, J=1.6), 8.88 (s, $^1$H), 8.76 (d, $^1$H, J=1.6), 8.7 (d, $^1$H, J=6), 7.6 (d, $^1$H, J=6), 7.5 (d, $^1$H, J=9), 7.3 (d, $^1$H, J=3), 7.2 (dd, $^1$H, J$_1$=9, J$_2$=3), 4.0 (m, $^1$H), 2.55 (s, $^3$H), 0.9 (m, 4H) ppm; ESMS calc'd for C$_{20}$H$_{17}$ClN$_4$O$_2$: 380.1. found: 381.1 (M+H$^+$).

Example 100

N-(5-(2-bromo-5-cyclopropoxyphenyl)pyrazin-2-yl)-2,3-difluorobenzamide

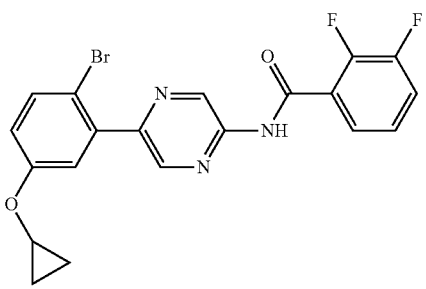 [SMILES: O=C(Nc1cnc(-c2cc(OC3CC3)ccc2Br)cn1)c1cccc(F)c1F]

$^1$H-NMR (CDCl$_3$) δ 9.7 (d, $^1$H, J=2), 9.0 (d, $^1$H, J=12), 8.7 (d, $^1$H, J=2), 8.0 (m, $^1$H), 7.6 (d, $^1$H, J=9), 7.4 (m, $^1$H), 7.3 (m, 2H), 7.0 (dd, $^1$H, J$_1$=9, J$_2$=3), 3.8 (m, $^1$H), 0.8 (m, 4H) ppm; ESMS calc'd for C$_{20}$H$_{14}$BrF$_2$N$_3$O$_2$: 445.0. found: 445.8 (M+H$^+$).

Example 101

N-(5-(2-chloro-5-(oxetan-3-yloxy)phenyl)pyrazin-2-yl)-5-fluoro-4-methylnicotinamide

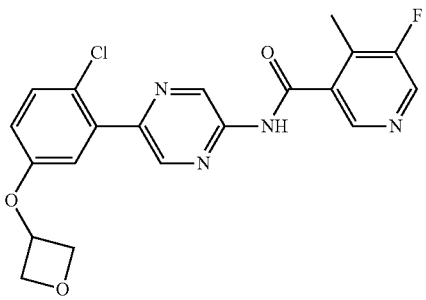 [SMILES: Cc1c(F)cncc1C(=O)Nc1cnc(-c2cc(OC3COC3)ccc2Cl)cn1]

$^1$H-NMR (CDCl$_3$) δ 9.7 (d, $^1$H, J=2), 8.71 (s, $^1$H), 8.65 (s, $^1$H), 8.5 (m, 2H), 7.4 (d, $^1$H, J=9), 7.0 (d, $^1$H, J=3), 6.8 (dd, $^1$H, J$_1$=9, J$_2$=3), 5.3 (m, $^1$H), 5.0 (m, 2H), 4.8 (m, 2H), 2.52 (s, $^3$H) ppm; ESMS calc'd for C$_{20}$H$_{16}$ClFN$_4$O$_2$: 414.1. found: 414.9 (M+H$^+$).

Example 102

N-(5-(5-cyclopropoxy-2-fluorophenyl)-4-methyl-pyridin-2-yl)-5-fluoro-4-methylnicotinamide

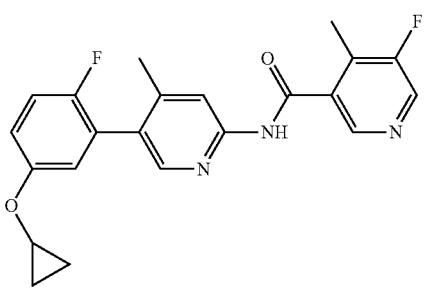 [SMILES: Cc1cc(NC(=O)c2cncc(F)c2C)ncc1-c1cc(OC2CC2)ccc1F]

$^1$H-NMR (CDCl$_3$) δ 9.7 (s, $^1$H), 8.3-8.6 (m, $^3$H), 7.67 (s, $^1$H), 7.1 (m, 2H), 6.8 (dd, $^1$H, J$_1$=6, J$_2$=3), 3.7 (m, $^1$H), 2.46 (s, $^3$H), 2.31 (s, $^3$H), 0.8 (m, 4H) ppm; ESMS calc'd for C$_{22}$H$_{19}$F$_2$N$_3$O$_2$: 395.1. found: 396.0 (M+H$^+$).

Example 103

N-(5-(2-chloro-5-cyclobutoxyphenyl)pyrazin-2-yl)-5-fluoro-4-methylnicotinamide

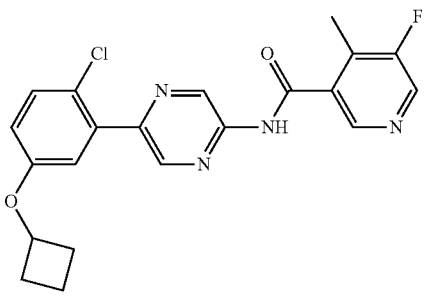 [SMILES: Cc1c(F)cncc1C(=O)Nc1cnc(-c2cc(OC3CCC3)ccc2Cl)cn1]

$^1$H-NMR (CDCl$_3$) δ 9.7 (s, $^1$H), 8.8 (dd, $^1$H, J$_1$=2, J$_2$=9), 8.7 (d, $^1$H, J=2), 8.6 (m, $^1$H), 8.59 (s, $^1$H), 8.53 (s, $^1$H), 8.41 (s, $^1$H), 7.4 (m, $^1$H), 7.1 (d, $^1$H, J=3), 6.8 (dd, $^1$H, J$_1$=9, J$_2$=3), 4.7 (m, $^1$H), 2.52 (s, $^3$H), 2.4 (m, 4H) ppm; ESMS calc'd for C$_2$$^1$H$_{18}$ClFN$_4$O$_2$: 412.1. found: 412.9 (M+H$^+$).

Example 104

5-chloro-N-(5-(5-cyclopropoxy-2-methylphenyl)pyrazin-2-yl)-4-methylnicotinamide

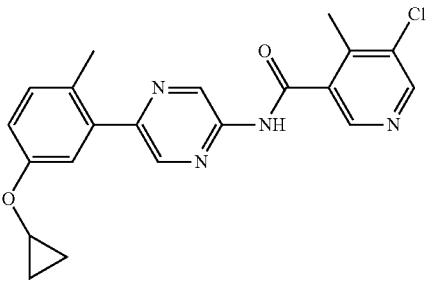 [SMILES: Cc1ccc(OC2CC2)cc1-c1cnc(NC(=O)c2cncc(Cl)c2C)cn1]

$^1$H-NMR (CDCl$_3$) δ 9.72 (s, $^1$H), 8.6 (m, $^3$H), 8.37 (s, $^1$H), 7.2 (d, $^1$H, J=8), 7.1 (d, $^1$H, J=3), 7.0 (dd, $^1$H, J$_1$=8, J$_2$=3), 3.8 (m, $^1$H), 2.60 (s, $^3$H), 2.34 (s, $^3$H), 0.8 (m, 4H) ppm; ESMS calc'd for C$_2$$^1$H$_{19}$ClN$_4$O$_2$: 394.1. found: 394.9 (M+H$^+$).

Example 105

N-(5-(2-chloro-5-(cyclohexyloxy)phenyl)pyrazin-2-yl)-5-fluoro-4-methylnicotinamide

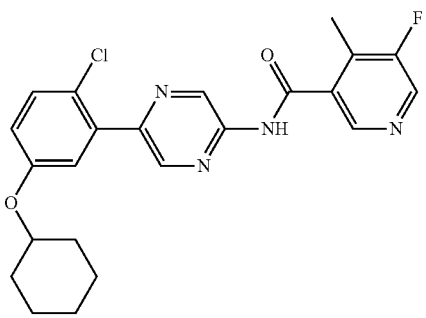 [SMILES: Cc1c(F)cncc1C(=O)Nc1cnc(-c2cc(OC3CCCCC3)ccc2Cl)cn1]

$^1$H-NMR (CDCl$_3$) δ 9.7 (d, $^1$H, J=2), 8.5-8.6 (m, 4H), 7.4 (d, $^1$H, J=9), 7.2 (d, $^1$H, J=3), 7.0 (dd, $^1$H, J$_1$=9, J$_2$=3), 4.3 (m, $^1$H), 2.52 (s, $^3$H), 0.8-2.0 (m, 10H) ppm; ESMS calc'd for C$_2$$^3$H$^{22}$ClFN$_4$O$_2$: 440.1. found: 441.0 (M+H$^+$).

Example 106

N-(5-(2-cyano-5-cyclopropoxyphenyl)pyrazin-2-yl)-5-fluoro-4-methylnicotinamide

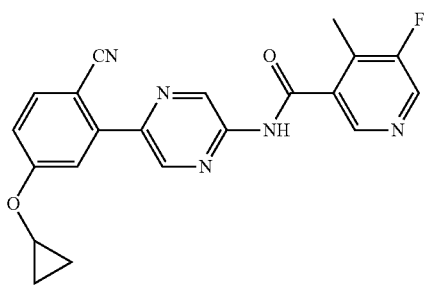 [SMILES: Cc1c(F)cncc1C(=O)Nc1cnc(-c2cc(OC3CC3)ccc2C#N)cn1]

$^1$H-NMR (CDCl$_3$) δ 9.8 (d, $^1$H, J=2), 8.8 (d, $^1$H, J=2), 8.5-8.6 (m, 4H), 7.7 (d, $^1$H, J=9), 7.5 (d, $^1$H, J=3), 7.2 (dd, $^1$H, J$_1$=9, J$_2$=3), 3.9 (m, $^1$H), 2.52 (s, $^3$H), 0.8 (m, 4H) ppm; ESMS calc'd for C$_2$$^1$H$_{16}$FN$_5$O$_2$: 389.1. found: 390.0 (M+H$^+$).

Example 107

N-(5-(2-chloro-5-(cyclopropylmethoxy)phenyl)pyrazin-2-yl)-4-methylnicotinamide

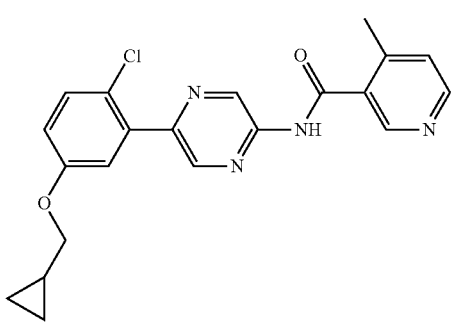 [SMILES: Cc1ccncc1C(=O)Nc1cnc(-c2cc(OCC3CC3)ccc2Cl)cn1]

$^1$H-NMR (CDCl$_3$) δ 9.8 (d, $^1$H, J=2), 8.83 (s, $^1$H), 8.7 (d, $^1$H, J=2), 8.6 (d, $^1$H, J=2), 8.35 (s, $^1$H), 7.4 (d, $^1$H, J=9), 7.3 (m, $^1$H), 7.2 (d, $^1$H, J=3), 6.9 (dd, $^1$H, J$_1$=9, J$_2$=3), 3.8 (d, 2H, J=7), 2.60 (s, $^3$H), 0.7 (m, 2H), 0.4 (m, 2H) ppm; ESMS calc'd for C$_2$$^1$H$_{19}$ClN$_4$O$_2$: 394.1. found: 394.9 (M+H$^+$).

Example 108

N-(5-(2-cyano-5-cyclopropoxyphenyl)pyrazin-2-yl)-4-methylnicotinamide

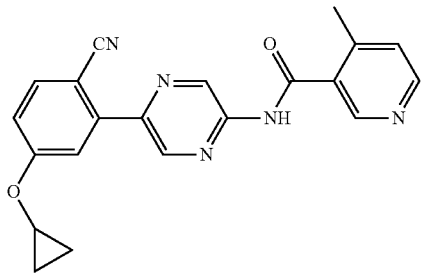 [SMILES: Cc1ccncc1C(=O)Nc1cnc(-c2cc(OC3CC3)ccc2C#N)cn1]

$^1$H-NMR (DMSO-d$_6$) δ11.6 (br, $^1$H), 9.55 (s, $^1$H), 8.9 (d, $^1$H, J=2), 8.7 (d, $^1$H, J=5), 8.6 (d, $^1$H, J=5), 8.0 (d, $^1$H, J=9), 7.3-7.7 (m, $^3$H), 4.0 (m, $^1$H), 2.46 (s, $^3$H), 0.7-0.8 (m, 4H) ppm; ESMS calc'd for C$_2$$^1$H$_{17}$N$_5$O$_2$: 371.1. found: 372.0 (M+H$^+$).

Example 109

N-(5-(2-chloro-5-(cyclopentyloxy)phenyl)pyrazin-2-yl)-4-methylnicotinamide

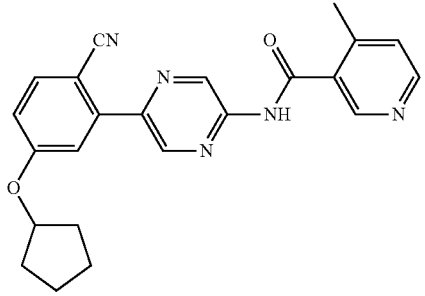 [SMILES: Cc1ccncc1C(=O)Nc1cnc(-c2cc(OC3CCCC3)ccc2C#N)cn1]

$^1$H-NMR (CDCl$_3$) δ 9.8 (d, $^1$H, J=2), 8.81 (s, $^1$H), 8.7 (d, $^1$H, J=2), 8.6 (d, $^1$H, J=5), 8.53 (s, $^1$H), 7.4 (d, $^1$H, J=9), 7.3 (m, $^1$H), 7.2 (d, $^1$H, J=3), 6.9 (dd, $^1$H, J$_1$=9, J$_2$=3), 4.8 (m, $^1$H), 2.60 (s, $^3$H), 1.3-1.8 (m, 8H) ppm; ESMS calc'd for C$_{22}$H$_{21}$ClN$_4$O$_2$: 408.1. found: 408.9 (M+H$^+$).

Example 110

N-(5-(2-chloro-5-cyclopropoxyphenyl)pyrazin-2-yl)-5-fluoro-4-methylnicotinamide

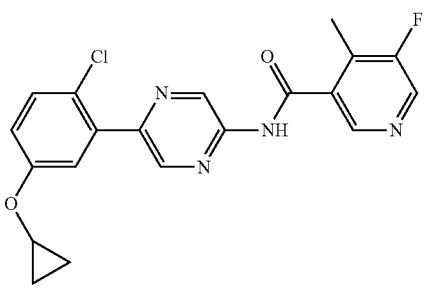 [SMILES: Cc1c(F)cncc1C(=O)Nc1cnc(-c2cc(OC3CC3)ccc2Cl)cn1]

¹H-NMR (CDCl₃) δ 9.7 (d, ¹H, J=2), 8.7 (d, ¹H, J=2), 8.64 (s, ¹H), 8.53 (s, 2H), 7.4 (d, ¹H, J=9), 7.3 (d, ¹H, J=3), 7.1 (dd, ¹H, J₁=9, J₂=3), 3.8 (m, ¹H), 2.53 (s, ³H), 0.8 (m, 4H) ppm; ESMS calc'd for C₂₀H₁₆ClFN₄O₂: 398.1. found: 399.0 (M+H⁺).

Example 111

N-(5-(5-cyclopropoxy-2-ethylphenyl)pyrazin-2-yl)-5-fluoro-4-methylnicotinamide

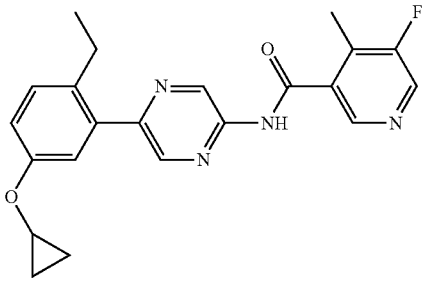 [SMILES: CCc1ccc(OC2CC2)cc1-c1cnc(NC(=O)c2cncc(F)c2C)cn1]

¹H-NMR (CDCl₃) δ 9.7 (d, ¹H, J=2), 8.94 (s, ¹H), 8.61 (s, ¹H), 8.51 (s, ¹H), 8.3 (d, ¹H, J=2), 7.0-7.4 (m, ³H), 3.8 (m, ¹H), 2.7 (q, 2H, J=8), 2.51 (s, ³H), 1.1 (t, ³H, J=8), 0.8 (m, 4H) ppm; ESMS calc'd for C₂₂H₂₁FN₄O₂: 392.1. found: 393.0 (M+H⁺).

Example 112

N-(5-(5-cyclopropoxy-2-ethylphenyl)pyrazin-2-yl)-4-methylnicotinamide

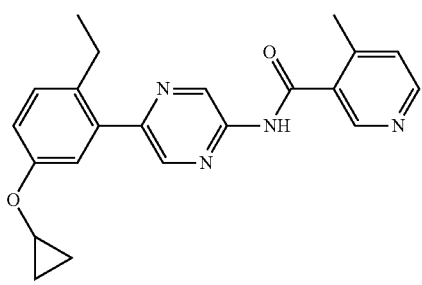 [SMILES: CCc1ccc(OC2CC2)cc1-c1cnc(NC(=O)c2cnccc2C)cn1]

¹H-NMR (CDCl₃) δ 9.7 (d, ¹H, J=2), 8.81 (s, ¹H), 8.6 (d, ¹H, J=5), 8.5 (m, ¹H), 8.4 (d, ¹H, J=2), 7.0-7.4 (m, 4H), 3.8 (m, ¹H), 2.7 (q, 2H, J=8), 2.60 (s, ³H), 1.1 (t, ³H, J=8), 0.8 (m, 4H) ppm; ESMS calc'd for C₂₂H₂₂N₄O₂: 374.2. found: 375.0 (M+H⁺).

Example 113

N-(5-(2-chloro-5-(oxetan-3-yloxy)phenyl)pyrazin-2-yl)-2,3-difluorobenzamide

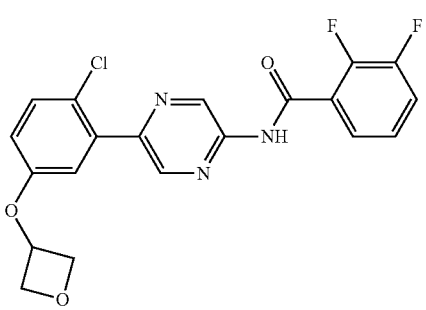 [SMILES: O=C(Nc1cnc(-c2cc(OC3COC3)ccc2Cl)cn1)c1cccc(F)c1F]

¹H-NMR (CDCl₃) δ 9.7 (d, ¹H, J=2), 9.0 (d, ¹H, J=12), 8.7 (d, ¹H, J=2), 8.0 (m, ¹H), 7.6 (d, ¹H, J=9), 7.4 (m, ¹H), 7.3 (m, 2H), 7.0 (dd, ¹H, J₁=9, J₂=3), 5.3 (m, ¹H), 5.0 (m, 2H), 4.8 (m, 2H) ppm; ESMS calc'd for C₂₀H₁₄ClF₂N₃O₂: 417.1. found: 418.0 (M+H⁺).

Example 114

N-(5-(5-cyclopropoxy-2-fluorophenyl)-6-methyl-pyridin-2-yl)-5-fluoro-4-methylnicotinamide

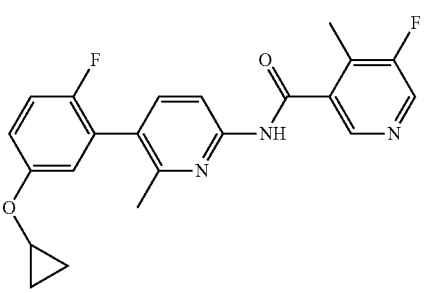 [SMILES: Cc1nc(NC(=O)c2cncc(F)c2C)ccc1-c1cc(OC2CC2)ccc1F]

¹H-NMR (CDCl₃) δ 9.7 (s, ¹H), 8.3-8.6 (m, ³H), 7.67 (s, ¹H), 7.1 (m, 2H), 6.8 (dd, ¹H, J₁=6, J₂=3), 3.8 (m, ¹H), 3.10 (s, ³H), 2.32 (s, ³H), 0.8 (m, 4H) ppm; ESMS calc'd for C₂₂H₁₉F₂N₃O₂: 395.1. found: 396.0 (M+H⁺).

Example 115

N-(5-(2-chloro-5-isopropoxyphenyl)pyrazin-2-yl)-4-methylnicotinamide

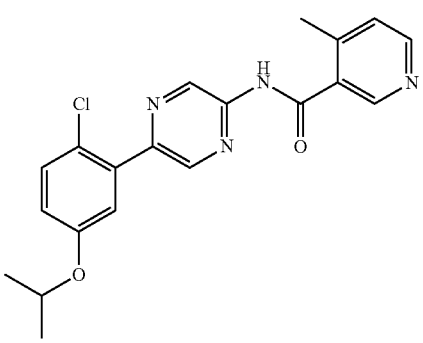 [SMILES: Cc1ccncc1C(=O)Nc1cnc(-c2cc(OC(C)C)ccc2Cl)cn1]

General Procedure of Suzuki Coupling, Alkylation, and Acylation:

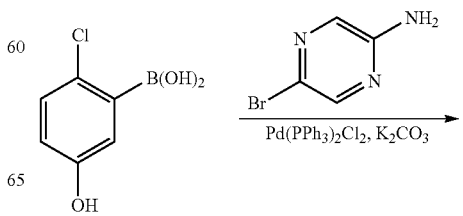

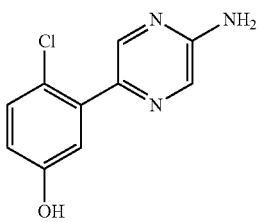

To the solution of (2-chloro-5-hydroxyphenyl)boronic acid (2.1 g, 12.2 mmol) in dioxane/H₂O (30 ml/10 ml) was added 5-bromopyrazin-2-amine (2.2 g, 12.6 mmol), K₂CO₃ (3.1 g, 22.4 mmol), and Pd(PPh₃)₂Cl₂ (0.3 g, 0.42 mmol). The reaction was heated at 90° C. for 12 hr before it was diluted with EtOAc/H₂O (100 ml/100 ml). The organic phase was dried over Na₂SO₄ and concentrated. Column chromatography gave 3-(5-aminopyrazin-2-yl)-4-chlorophenol (2.2 g, 83%) as off-white solid.

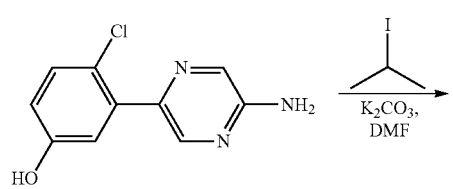

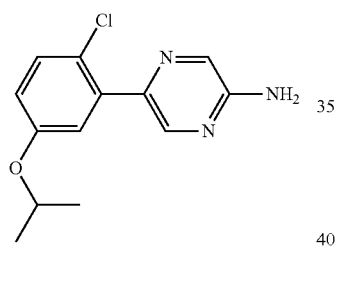

To the solution of 3-(5-aminopyrazin-2-yl)-4-chlorophenol (0.12 g, 0.54 mmol) in DMF (4 mL) was added 2-iodopropane (0.22 mL, 2.17 mmol) and K₂CO₃ (0.3 g, 2.17 mmol). The solution was heated in microwave at 80° C. for 2 hr. The solution was diluted with H₂O (15 mL) and extracted with EtOAc (15 mL). The organic phase was dried over Na₂SO₄ and concentrated. Column chromatography gave 5-(2-chloro-5-isopropoxyphenyl)pyrazin-2-amine (0.09 g, 63%) as colorless oil.

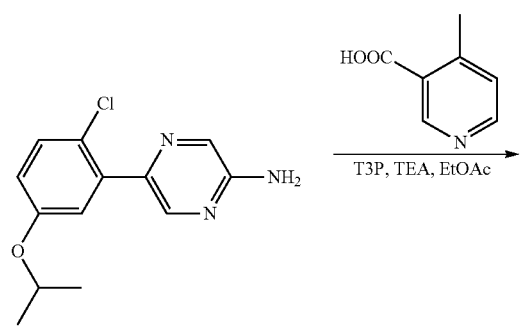

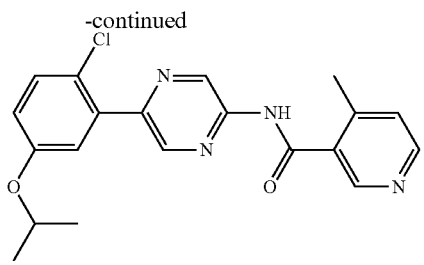

To the solution of 5-(2-chloro-5-isopropoxyphenyl)pyrazin-2-amine (0.05 g, 0.19 mmol) in EtOAc (3 mL) was added 4-methylnicotinic acid (0.05 g, 0.46 mmol), propylphosphonic anhydride (50% wt in EtOAc, 0.34 mL, 0.57 mmol), and TEA (0.1 mL, 0.76 mmol). The solution was heated in microwave at 90° C. for 30 min. The solution was diluted with EtOAc (15 mL) and washed with H₂O (20 mL). The organic phase was dried over Na₂SO₄ and concentrated. Column chromatography gave N-(5-(2-chloro-5-isopropoxyphenyl)pyrazin-2-yl)-4-methylnicotinamide (0.054 g, 75%). ¹H NMR (400 MHz, CDCl₃) δ 9.76 (d, J=1.5, ¹H), 9.08 (s, ¹H), 8.76 (s, ¹H), 8.60 (d, J=1.5, ¹H), 8.57 (d, J=5.1, ¹H), 7.37 (d, J=8.8, ¹H), 7.25 (d, J=5.1, ¹H), 7.17 (d, J=3.0, ¹H), 6.91 (dd, J=3.0, 8.8, ¹H), 4.59 (dt, J=6.1, 12.1, ¹H), 2.58 (s, ³H), 1.35 (d, J=6.1, 7H); ESMS calcd (C₂₀H₁₉ClN₄O₂): 382.1. found: 383.1 (M+H).

EXAMPLES 116 through 117 were synthesized in a similar manner as Example 115:

Example 116

N-(5-(2-chloro-4-((3-fluoropyridin-2-yl)oxy)phenyl)pyridin-2-yl)-4-methylnicotinamide

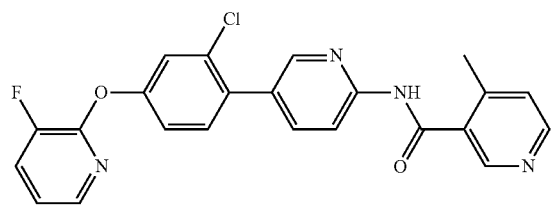 [SMILES: Cc1ccncc1C(=O)Nc1ccc(-c2ccc(Oc3ncccc3F)cc2Cl)cn1]

¹H NMR (400 MHz, CDCl₃) δ 8.79 (s, ¹H), 8.76 (s, ¹H), 8.57 (d, J=5.1 Hz, ¹H), 8.44 (d, J=8.6 Hz, ¹H), 8.27 (d, J=2.3 Hz, ¹H), 7.99 (dd, J=4.9, 1.5 Hz, ¹H), 7.92 (dd, J=8.5, 2.4 Hz, ¹H), 7.53 (ddd, J=9.8, 8.0, 1.5 Hz, ¹H), 7.40-7.34 (m, 2H), 7.24-7.19 (m, 2H), 7.08 (ddd, J=7.9, 4.7, 3.2 Hz, ¹H), 2.57 (s, ³H); ESMS calcd (C₂³H₁₆ClFN₄O₂): 434.1. found: 435.1 (M+H).

Example 117

N-(5-(2-chloro-4-(pyrimidin-2-yloxy)phenyl)pyridin-2-yl)-5-fluoro-4-methylnicotinamide

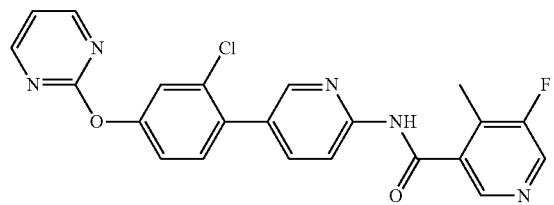 [SMILES: Cc1c(F)cncc1C(=O)Nc1ccc(-c2ccc(Oc3ncccn3)cc2Cl)cn1]

$^1$H NMR (400 MHz, CDCl$_3$) δ 8.62 (d, J=4.6 Hz, $^3$H), 8.55-8.49 (m, 2H), 8.43 (d, J=8.6 Hz, $^1$H), 8.37 (d, J=2.3 Hz, $^1$H), 7.94 (dd, J=8.6, 2.4 Hz, $^1$H), 7.43-7.39 (m, 2H), 7.23 (d, J=2.4 Hz, $^1$H), 7.12 (t, J=4.8 Hz, $^1$H), 2.51 (d, J=2.0 Hz, $^3$H); ESMS calcd (C$_{22}$H$_{15}$ClFN$_5$O$_2$): 435.1. found: 436.1 (M+H).

Example 118

N-(3,5-dichloropyridin-4-yl)-2'-methyl-5'-(oxazol-5-yl)-[1,1'-biphenyl]-4-carboxamide

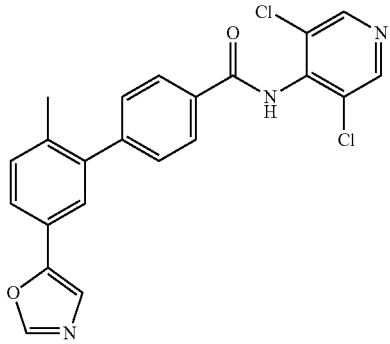 [SMILES: Cc1ccc(-c2cnco2)cc1-c1ccc(C(=O)Nc2c(Cl)cncc2Cl)cc1]

$^1$H NMR (400 MHz, CDCl$_3$) δ 9.72 (d, J=1.4, $^1$H), 8.74 (d, J=8.7, $^1$H), 8.60 (s, $^1$H), 8.51 (d, J=1.0, $^1$H), 8.39 (d, J=1.5, $^1$H), 7.92 (dd, J=1.5, 4.9, $^1$H), 7.47 (ddd, J=1.5, 7.9, 9.7, $^1$H), 7.36 (d, J=8.4, $^1$H), 7.30 (d, J=2.5, $^1$H), 7.18 (dd, J=2.6, 8.3, $^1$H), 6.99 (ddd, J=3.2, 4.9, 8.0, $^1$H), 2.51 (d, J=2.0, $^3$H), 2.44 (d, J=5.1, $^3$H); ESMS calcd (C$_2{}^3$H$_{17}$F$_2$N$_5$O$_2$): 433.1. found: 434.1 (M+H).

Example 119

N-(2'-cyclopropoxy-5'-methyl-[3,4'-bipyridin]-6-yl)-5-fluoro-4-methylnicotinamide

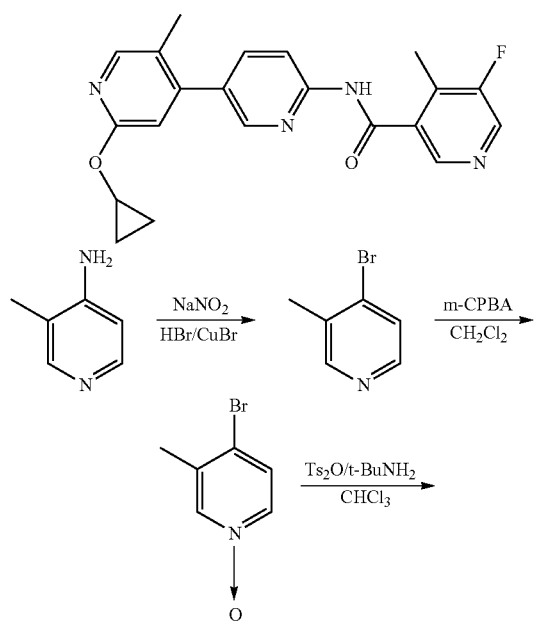

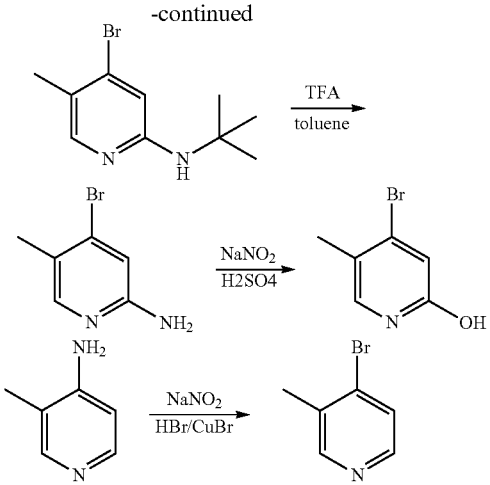

Into a 3000-mL 4-necked round-bottom flask, was placed a solution of 3-methylpyridin-4-amine (120 g, 1.11 mol, 1.00 equiv) in hydrogen bromide (720 mL). This was followed by the addition of a solution of sodium nitrite (153 g, 2.22 mol, 2.00 equiv) in water (500 mL) dropwise with stirring at −15° C. in 2 hour. The resulting solution was stirred for 15 min at −10° C. To this was added copper (I) bromide (80 g, 559.44 mmol, 0.50 equiv) in several batches at −15° C. The resulting solution was allowed to react, with stirring, for an additional 5 h at room temperature. The reaction mixture was cooled to 0 degree C. with a water/ice bath. The pH value of the solution was adjusted to 10 with sodium hydroxide (40%). The solids were filtered out. The resulting solution was extracted with 3×800 mL of dichloromethane and the organic layers combined. The resulting mixture was washed with 1×500 mL of ammonium chloride. The mixture was dried over anhydrous sodium sulfate and concentrated under vacuum. The residue was applied onto a silica gel column with dichloromethane/petroleum ether (1:1). This resulted in 100 g (52%) of 4-bromo-3-methylpyridine as a yellow liquid.

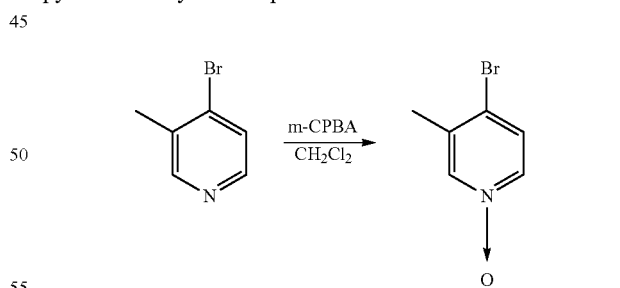

Into a 2000-mL 3-necked round-bottom flask, was placed a solution of 4-bromo-3-methylpyridine (100 g, 581.40 mmol, 1.00 equiv) in dichloromethane (1500 mL), meta-Chloroperbenzoic acid (110 g, 635.84 mmol, 1.09 equiv). The resulting solution was stirred for 15 h at room temperature. The resulting solution was diluted with 500 mL of water. The resulting solution was extracted with 5×300 mL of dichloromethane and the organic layers combined. The resulting mixture was washed with 1×500 mL of saturated sodium bicarbonate. The mixture was dried over sodium sulfate and concentrated under vacuum. The resulting mixture was washed with 200 mL of ethyl acetate/petroleum ether (1:5). This resulted in 95 g (87%) of product as a yellow solid.

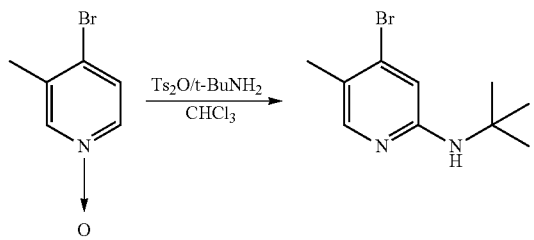

Into a 1000-mL 3-necked round-bottom flask, was placed a solution of 4-bromo-3-methylpyridine N-oxide (30 g, 159.57 mmol, 1.00 equiv) in chloroform (600 mL), 2-methylpropan-2-amine (58.2 g, 797.26 mmol, 5.00 equiv). This was followed by the addition of 4-methylbenzenesulfonic anhydride (105 g, 322.09 mmol, 2.02 equiv) in several batches at 0-5° C. The resulting solution was stirred for 30 min at 0-5° C. in a water/ice bath. The resulting mixture was washed with 1×600 mL of water. The mixture was dried over anhydrous sodium sulfate and concentrated under vacuum. The residue was applied onto a silica gel column with ethyl acetate/petroleum ether (1:20). This resulted in 6 g (15%) of 4-bromo-N-tert-butyl-5-methylpyridin-2-amine as a yellow liquid.

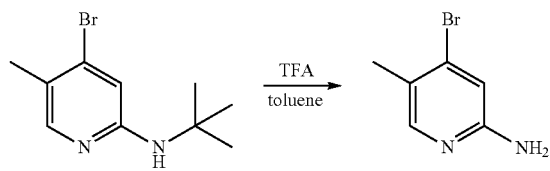

Into a 250-mL 3-necked round-bottom flask, was placed a solution of 4-bromo-N-tert-butyl-5-methylpyridin-2-amine (6 g, 24.69 mmol, 1.00 equiv) in toluene (60 mL), trifluoroacetic acid (20 mL). The resulting solution was stirred for 15 h at 70° C. in an oil bath. The resulting mixture was concentrated under vacuum. The pH value of the solution was adjusted to 7 with saturated sodium bicarbonate. The resulting solution was extracted with 2×100 mL of ethyl acetate and the organic layers combined and dried over anhydrous sodium sulfate and concentrated under vacuum. The resulting mixture was washed with 2×20 mL of ethyl acetate/petroleum ether (1:5). This resulted in 4.3 g (93%) of 4-bromo-5-methylpyridin-2-amine as a light yellow solid.

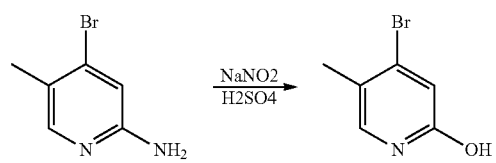

Into a 250-mL 3-necked round-bottom flask, was placed 4-bromo-5-methylpyridin-2-amine (4.5 g, 24.06 mmol, 1.00 equiv), 10% sulfuric acid (60 mL). This was followed by the addition of a solution of NaNO2 (2 g, 28.99 mmol, 1.20 equiv) in water (10 mL) dropwise with stirring at 0-5° C. The resulting solution was stirred for 3 h at room temperature. The pH value of the solution was adjusted to 7 with saturated sodium bicarbonate. The solids were collected by filtration, washed with 2×20 mL of water, 1×10 mL of ethanol and 2×20 mL of hexane. The solid was dried in an oven. This resulted in 3.57 g (77%) of 4-bromo-5-methylpyridin-2-ol as a off-white solid.

N-(2'-cyclopropoxy-5'-methyl-[3,4'-bipyridin]-6-yl)-5-fluoro-4-methylnicotinamide was prepared from 4-bromo-5-methylpyridin-2-ol following general procedures.

$^1$H NMR (400 MHz, CDCl$_3$) δ $^1$H NMR (400 MHz, CDCl$_3$) δ 8.63-8.60 (m, 2H), 8.51 (d, J=0.9, $^1$H), 8.43 (d, J=8.6, $^1$H), 8.22 (d, J=1.6, $^1$H), 8.15 (s, $^1$H), 7.78 (dd, J=2.3, 8.5, $^1$H), 6.66 (s, $^1$H), 4.26-4.14 (m, $^1$H), 2.50 (d, J=2.0, $^3$H), 2.21 (s, $^3$H), 0.84-0.77 (m, 4H); ESMS calcd (C$_2$$^1$H$_{19}$FN$_4$O$_2$): 378.1. found: 379.2 (M+H).

Example 120

N-(5-(2-chloro-5-(pyrimidin-2-yloxy)phenyl)pyridin-2-yl)-3-methylpyrazine-2-carboxamide

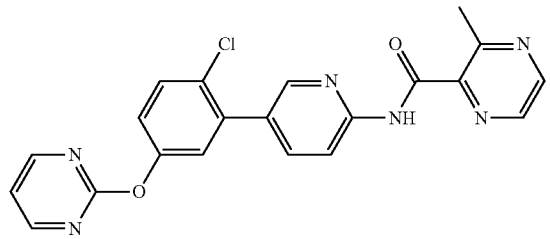 [SMILES: Cc1nccnc1C(=O)Nc1ccc(-c2cc(Oc3ncccn3)ccc2Cl)cn1]

$^1$H NMR (400 MHz, CDCl$_3$) δ 10.53 (s, $^1$H), 8.69 (d, J=2.3 Hz, $^1$H), 8.59 (d, J=4.8 Hz, 2H), 8.50-8.46 (m, $^3$H), 7.93 (dd, J=8.5, 2.4 Hz, $^1$H), 7.56 (d, J=8.6 Hz, $^1$H), 7.25 (d, J=2.8 Hz, $^1$H), 7.20 (dd, J=8.7, 2.8 Hz, $^1$H), 7.09 (t, J=4.8 Hz, $^1$H), 3.08 (s, $^3$H); ESMS calcd (C$_2$$^1$H$_{15}$ClN$_6$O$_2$): 418.1. found: 419.1 (M+H).

Example 121

N-(5-(2-chloro-5-(pyrimidin-2-yloxy)phenyl)pyridin-2-yl)-4-methylpyrimidine-5-carboxamide

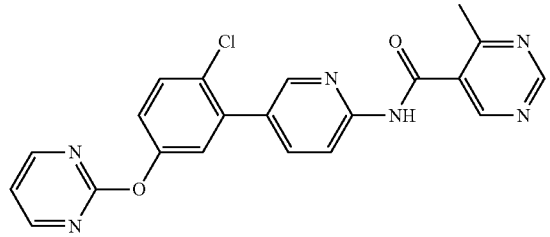

$^1$H NMR (400 MHz, CDCl$_3$) δ 9.18 (s, $^1$H), 8.87 (s, $^1$H), 8.66 (s, $^1$H), 8.59 (dd, J=4.8, 1.2 Hz, 2H), 8.41 (d, J=8.6 Hz, $^1$H), 8.37 (dd, J=2.5, 0.8 Hz, $^1$H), 7.95 (dd, J=8.6, 2.4 Hz, $^1$H), 7.59-7.53 (m, $^1$H), 7.24-7.18 (m, 2H), 7.10 (t, J=4.8 Hz, $^1$H), 2.78 (s, $^3$H); ESMS calcd (C$_2$$^1$H$_{15}$ClN$_6$O$_2$): 418.1. found: 419.1 (M+H).

Example 122

5-fluoro-4-methyl-N-(5-(2-methyl-5-((2-methyl-2H-tetrazol-5-yl)oxy)phenyl)pyridin-2-yl)nicotinamide

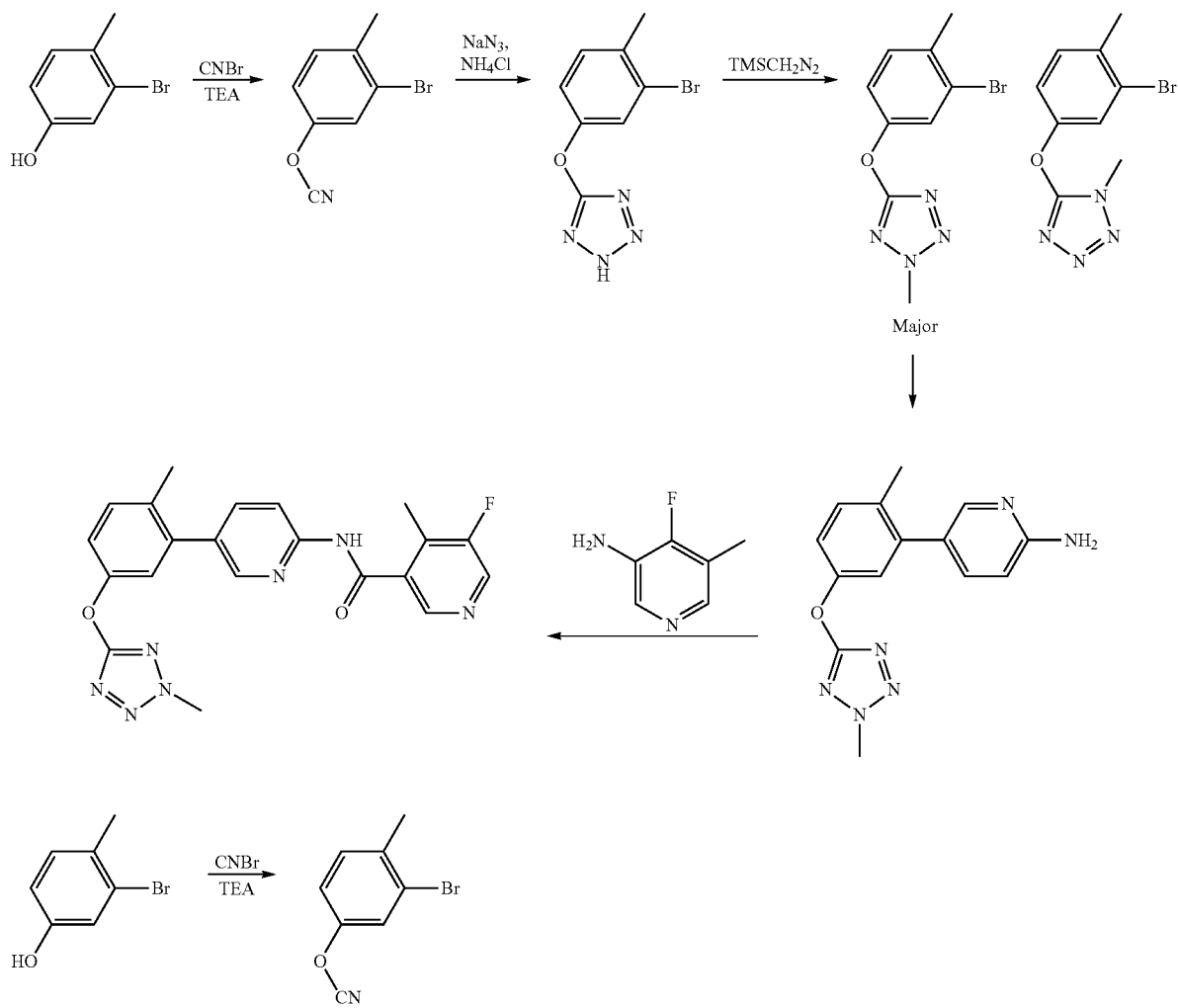

To the solution of 3-bromo-4-methylphenol (0.5 g, 2.67 mmol) in DCM (20 mL) was added CNBr (0.85 g, 8 mmol) and TEA (1.1 mL, 8 mmol) at room temperature. The reaction was stirred at this temperature for 2 hr. The reaction solution was concentrated and column chromatography gave 2-bromo-4-cyanato-1-methylbenzene (0.42 g, 75%).

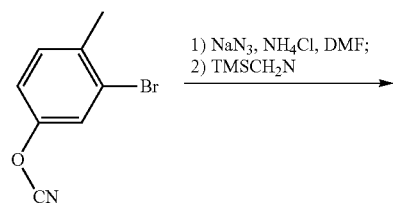

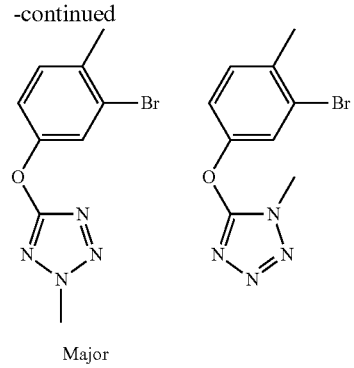

-continued

To the solution of 2-bromo-4-cyanato-1-methylbenzene (0.3 g, 1.42 mmol) in DMF (10 mL) was added $NaN_3$ (0.3 g, 4.62 mmol) and NH$_4$Cl (0.3 g, 5.6 mmol). The reaction was heated at 120° C. in microwave for 2 hr before the reaction was diluted with EtOAc (10 mL) and filtered. To the solution of crude product was added TMSCH$_2$N$_2$ (2 M in hexane, 2 mL). The reaction was stirred at room temperature for 30 min before it was quenched with water (30 mL). The solution was extracted with EtOAc (30 mL). The organic phase was dried over Na$_2$SO$_4$, filtered, and concentrated. Column chromatography gave 5-(3-bromo-4-methylphenoxy)-2-methyl-2H-tetrazole (0.12 g, 31%) and 5-(3-bromo-4-methylphenoxy)-1-methyl-$^1$H-tetrazole (0.06 g, 15%).

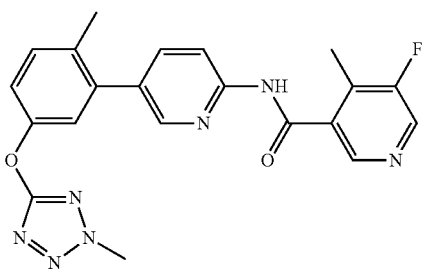 [SMILES: Cc1ccc(Oc2nnn(C)n2)cc1-c1ccc(NC(=O)c2cncc(F)c2C)nc1]

5-fluoro-4-methyl-N-(5-(2-methyl-5-((2-methyl-2H-tetrazol-5-yl)oxy)phenyl)pyridin-2-yl)nicotinamide was prepared following general procedures from 5-(3-bromo-4-methylphenoxy)-2-methyl-2H-tetrazole. $^1$H NMR (400 MHz, CDCl$_3$) δ 8.77 (s, $^1$H), 8.61 (s, $^1$H), 8.49 (d, J=1.2 Hz, $^1$H), 8.41 (d, J=8.5 Hz, $^1$H), 8.16 (dd, J=2.3, 0.9 Hz, $^1$H), 7.78 (dd, J=8.6, 2.3 Hz, $^1$H), 7.34 (d, J=8.4 Hz, $^1$H), 7.23 (dd, J=8.4, 2.6 Hz, $^1$H), 7.13 (d, J=2.6 Hz, $^1$H), 4.27 (s, $^3$H), 2.50 (d, J=2.0 Hz, $^3$H), 2.28 (s, $^3$H); ESMS calcd (C$_2$$^1$H$_{18}$FN$_7$O$_2$): 419.2. found: 420.2 (M+H).

Example 123

5-fluoro-4-methyl-N-(5-(2-methyl-5-((1-methyl-$^1$H-tetrazol-5-yl)oxy)phenyl)pyridin-2-yl)nicotinamide

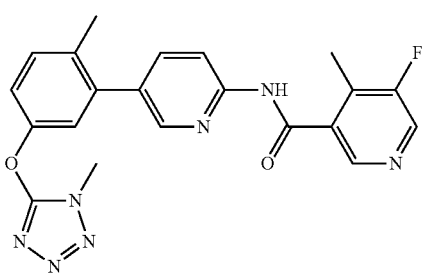 [SMILES: Cc1ccc(Oc2nnnn2C)cc1-c1ccc(NC(=O)c2cncc(F)c2C)nc1]

5-fluoro-4-methyl-N-(5-(2-methyl-5-((1-methyl-$^1$H-tetrazol-5-yl)oxy)phenyl)pyridin-2-yl)nicotinamide was prepared following general procedures from 5-(3-bromo-4-methylphenoxy)-1-methyl-$^1$H-tetrazole. $^1$H NMR (400 MHz, CDCl$_3$) δ 8.74 (s, $^1$H), 8.62 (s, $^1$H), 8.49 (d, J=1.2 Hz, $^1$H), 8.42 (d, J=8.5 Hz, $^1$H), 8.18 (dd, J=2.3, 0.9 Hz, $^1$H), 7.79 (dd, J=8.5, 2.4 Hz, $^1$H), 7.41-7.32 (m, 2H), 7.26 (d, J=2.2 Hz, $^1$H), 4.00 (s, $^3$H), 2.50 (d, J=2.0 Hz, $^3$H), 2.30 (s, $^3$H); ESMS calcd (C$_2$$^1$H$_{18}$FN$_7$O$_2$): 419.2. found: 420.2 (M+H).

Example 124

N-(5-(2-chloro-5-((3-fluoropyridin-2-yl)oxy)phenyl)pyrazin-2-yl)-6-methoxy-4-methylnicotinamide

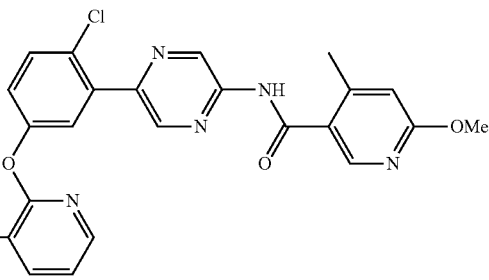

$^1$H NMR (400 MHz, CDCl$_3$) δ 9.71 (d, J=1.5 Hz, $^1$H), 8.69 (d, J=1.5 Hz, $^1$H), 8.45 (s, $^1$H), 8.39 (s, $^1$H), 7.93 (dd, J=4.9, 1.6 Hz, $^1$H), 7.59-7.46 (m, $^3$H), 7.23 (dd, J=8.7, 2.9 Hz, $^1$H), 7.03 (ddd, J=8.0, 4.9, 3.3 Hz, $^1$H), 6.66 (s, $^1$H), 3.97 (s, $^3$H), 2.54 (s, $^3$H); ESMS calcd (C$_2$$^3$H$_{17}$ClFN$_5$O$_3$): 465.9. found: 466.1 (M+H).

Example 125

N-(5-(2-chloro-5-cyclopropoxyphenyl)pyridin-2-yl)-6-methoxy-4-methylnicotinamide

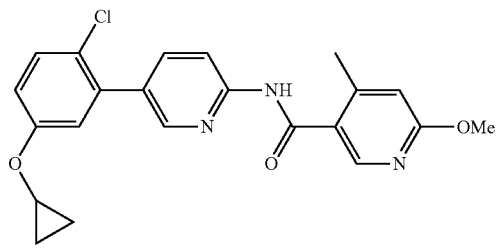 [SMILES: COc1cc(C)c(C(=O)Nc2ccc(-c3cc(OC4CC4)ccc3Cl)cn2)cn1]

$^1$H NMR (400 MHz, CDCl$_3$) δ 8.50 (s, $^1$H), 8.42 (s, $^1$H), 8.40 (dd, J=8.5, 0.8 Hz, $^1$H), 8.32 (dd, J=2.5, 0.8 Hz, $^1$H), 7.88 (dd, J=8.6, 2.4 Hz, $^1$H), 7.39 (d, J=8.6 Hz, $^1$H), 7.07-6.98 (m, 2H), 6.65 (s, $^1$H), 3.96 (s, $^3$H), 3.78-3.71 (m, $^1$H), 2.53 (s, $^3$H), 0.83-0.77 (m, 4H); ESMS calcd (C$_{22}$H$_{20}$ClN$_3$O$_3$): 409.1. found: 410.1 (M+H).

Example 126

5-fluoro-4-methyl-N-(5-(2-methyl-5-((5-methylthiazol-2-yl)oxy)phenyl)pyridin-2-yl)nicotinamide

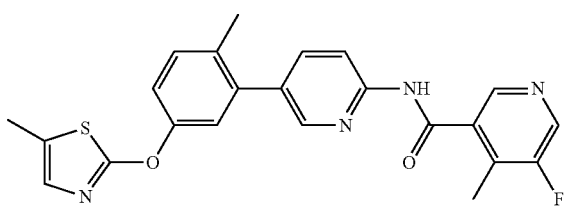 [SMILES: Cc1cnc(Oc2ccc(C)c(-c3ccc(NC(=O)c4cncc(F)c4C)nc3)c2)s1]

¹H NMR (400 MHz, CDCl₃) δ 9.32 (s, ¹H), 8.60 (s, ¹H), 8.46 (d, J=1.2 Hz, ¹H), 8.42 (d, J=8.5 Hz, ¹H), 8.00 (dd, J=2.4, 0.9 Hz, ¹H), 7.78 (dd, J=8.6, 2.3 Hz, ¹H), 7.33 (d, J=8.4 Hz, ¹H), 7.21 (dd, J=8.3, 2.6 Hz, ¹H), 7.09 (d, J=2.6 Hz, ¹H), 6.87 (q, J=1.3 Hz, ¹H), 2.48 (d, J=2.0 Hz, ³H), 2.36 (d, J=1.4 Hz, ³H), 2.26 (s, ³H); ESMS calcd (C₂₃H₁₉FN₄O₂S): 434.1. found: 435.2 (M+H).

Example 127

5-fluoro-4-methyl-N-(5-(2-methyl-5-((5-methylthi-azol-2-yl)oxy)phenyl) pyrazin-2-yl)nicotinamide

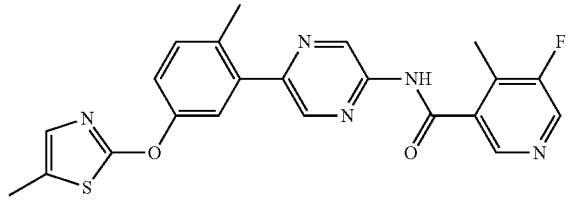 [SMILES: Cc1cnc(Oc2ccc(C)c(-c3cnc(NC(=O)c4cncc(F)c4C)cn3)c2)s1]

¹H NMR (400 MHz, CDCl₃) δ 9.73 (d, J=1.5 Hz, ¹H), 8.84 (s, ¹H), 8.62 (s, ¹H), 8.52 (d, J=1.2 Hz, ¹H), 8.40 (d, J=1.6 Hz, ¹H), 7.37 (d, J=2.6 Hz, ¹H), 7.35 (d, J=8.4 Hz, ¹H), 7.26-7.22 (m, ¹H), 6.86 (q, J=1.3 Hz, ¹H), 2.51 (d, J=2.0 Hz, ³H), 2.42 (s, ³H), 2.35 (d, J=1.4 Hz, ³H); ESMS calcd (C₂₂H₁₈FN₅O₂S): 435.1. found: 436.8 (M+H).

Example 128

2,3-difluoro-N-(5-(2-methyl-5-((5-methylthiazol-2-yl)oxy)phenyl)pyrazin-2-yl)benzamide

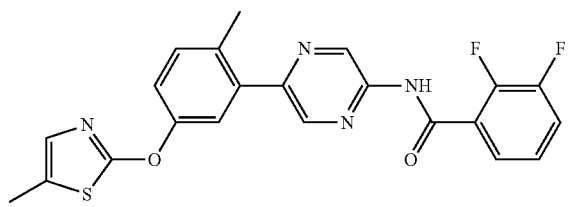 [SMILES: Cc1cnc(Oc2ccc(C)c(-c3cnc(NC(=O)c4cccc(F)c4F)cn3)c2)s1]

¹H NMR (400 MHz, CDCl₃) δ 9.75 (d, J=1.5 Hz, ¹H), 8.95 (d, J=12.6 Hz, ¹H), 8.46 (d, J=1.5 Hz, ¹H), 7.94 (ddt, J=8.1, 6.5, 1.8 Hz, ¹H), 7.45-7.28 (m, 5H), 6.87 (t, J=1.3 Hz, ¹H), 2.42 (s, ³H), 2.35 (d, J=1.3 Hz, ³H); ESMS calcd (C₂₂H₁₆F₂N₄O₂S): 438.1. found: 439.8 (M+H).

Example 129

2,3-difluoro-N-(5-(2-methyl-5-((3-methyl-1,2,4-thiadiazol-5-yl)oxy)phenyl) pyrazin-2-yl)benzamide

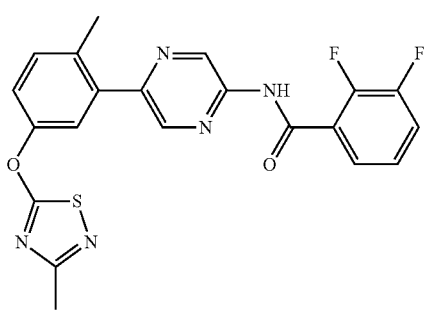 [SMILES: Cc1nsc(Oc2ccc(C)c(-c3cnc(NC(=O)c4cccc(F)c4F)cn3)c2)n1]

¹H NMR (400 MHz, CDCl₃) δ 9.79 (d, J=1.5 Hz, ¹H), 9.10 (d, J=12.0 Hz, ¹H), 8.47 (d, J=1.6 Hz, ¹H), 7.93 (ddd, J=8.3, 5.0, 1.8 Hz, ¹H), 7.46-7.40 (m, 3H), 7.35-7.30 (m, 2H), 2.51 (s, ³H), 2.46 (s, ³H); ESMS calcd (C₂₁H₁₅F₂N₃O₂S): 439.1. found: 440.1 (M+H).

Example 130

4-methyl-N-(5-(2-methyl-5-((3-methyl-1,2,4-thiadiazol-5-yl)oxy)phenyl)pyrazin-2-yl)nicotinamide

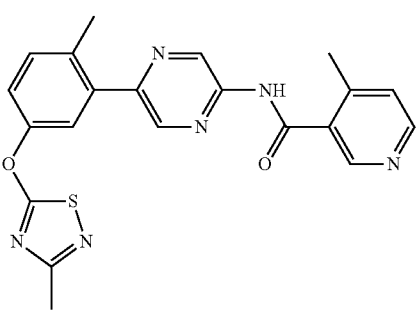 [SMILES: Cc1nsc(Oc2ccc(C)c(-c3cnc(NC(=O)c4cnccc4C)cn3)c2)n1]

¹H NMR (400 MHz, CDCl₃) δ 9.77 (d, J=1.5 Hz, ¹H), 8.81 (s, ¹H), 8.69 (s, ¹H), 8.61 (d, J=5.1 Hz, ¹H), 8.41 (d, J=1.5 Hz, ¹H), 7.45-7.40 (m, 2H), 7.32 (dd, J=8.3, 2.7 Hz, ¹H), 7.29-7.27 (m, ¹H), 2.60 (s, ³H), 2.51 (s, ³H), 2.46 (s, ³H); ESMS calcd (C₂₁H₁₈N₅O₂S): 418.1. found: 419.2 (M+H).

Example 131

5-fluoro-4-methyl-N-(5-(2-methyl-5-((3-methyl-1,2,4-thiadiazol-5-yl)oxy)phenyl)pyrazin-2-yl)nicotinamide

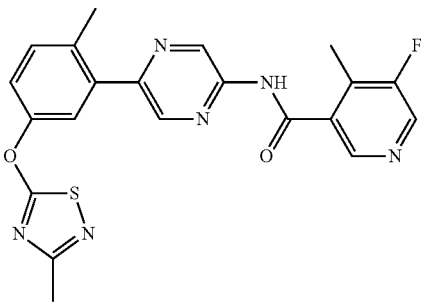 [SMILES: Cc1nsc(Oc2ccc(C)c(-c3cnc(NC(=O)c4cncc(F)c4C)cn3)c2)n1]

¹H NMR (400 MHz, CDCl₃) δ 9.75 (d, J=1.5 Hz, ¹H), 8.65 (s, ¹H), 8.54 (d, J=1.3 Hz, ¹H), 8.49-8.43 (m, 2H), 7.46-7.40 (m, 2H), 7.33 (dd, J=8.3, 2.7 Hz, ¹H), 2.53 (d, J=2.0 Hz, ³H), 2.51 (s, ³H), 2.47 (s, ³H); ESMS calcd (C₂₁H₁₇FN₆O₂S): 436.1. found: 437.2 (M+H).

Example 132

5-fluoro-4-methyl-N-(5-(2-methyl-5-(3-methyl-1,2,4-thiadiazol-5-yl)phenyl)pyridin-2-yl)nicotinamide

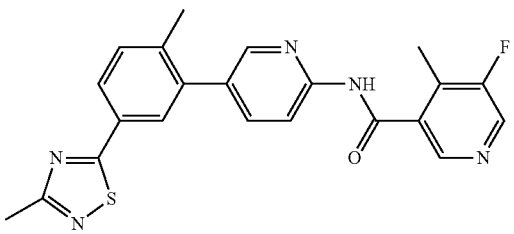 [SMILES: Cc1nsc(-c2ccc(C)c(-c3ccc(NC(=O)c4cncc(F)c4C)nc3)c2)n1]

$^1$H NMR (400 MHz, CDCl$_3$) δ 8.85 (s, $^1$H), 8.63 (s, $^1$H), 8.50 (d, J=1.2 Hz, $^1$H), 8.44 (d, J=8.5 Hz, $^1$H), 8.19 (dd, J=2.3, 0.8 Hz, $^1$H), 7.86 (dd, J=8.0, 2.0 Hz, $^1$H), 7.80 (dd, J=7.7, 2.1 Hz, 2H), 7.43 (d, J=7.9 Hz, $^1$H), 2.73 (s, $^3$H), 2.51 (d, J=2.0 Hz, $^3$H), 2.34 (s, $^3$H); ESMS calcd (C$_{22}$H$_{18}$FN$_5$OS): 419.1. found: 420.8 (M+H).

Example 133

N-(5-(2-chloro-5-(trifluoromethoxy)phenyl)pyrazin-2-yl)-4-methylnicotinamide

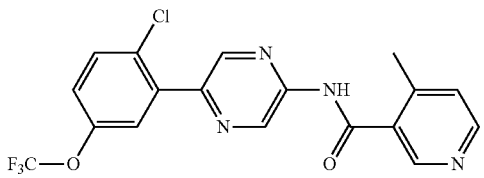 [SMILES: Cc1ccncc1C(=O)Nc1cnc(-c2cc(OC(F)(F)F)ccc2Cl)cn1]

$^1$H NMR (400 MHz, CDCl$_3$) δ 9.79 (d, J=1.5 Hz, $^1$H), 8.82 (s, $^1$H), 8.73 (d, J=1.6 Hz, $^1$H), 8.62 (d, J=5.1 Hz, $^1$H), 8.44 (s, $^1$H), 7.62-7.52 (m, 2H), 7.28 (d, J=5.8 Hz, $^1$H), 2.60 (s, $^3$H); ESMS calcd (C$_{18}$H$_{12}$ClF$_3$N$_4$O$_2$): 408.1. found: 409.1 (M+H).

Example 134

N-(5-(2-ethyl-5-(trifluoromethoxy)phenyl)pyrazin-2-yl)-4-methylnicotinamide

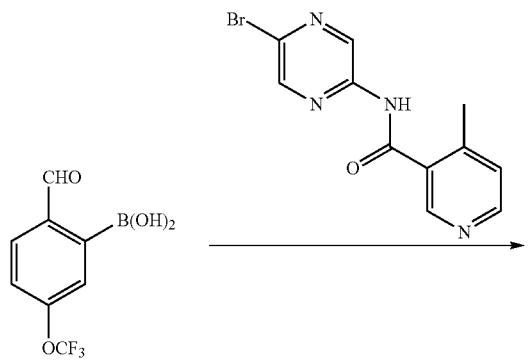

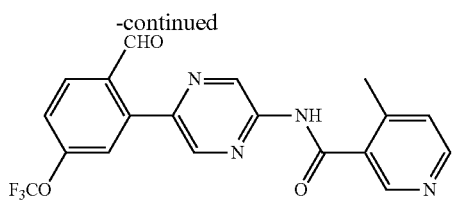

N-(5-(2-formyl-5-(trifluoromethoxy)phenyl)pyrazin-2-yl)-4-methylnicotinamide was prepared following the general Suzuki coupling condition.

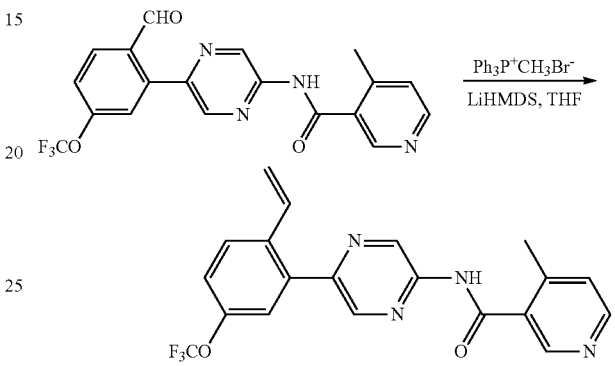

To the solution of methyltriphenylphosphonium bromide (0.11 g, 0.29 mmol) in THF (3 mL) was added LiHMDS (1M, 0.3 mL, 0.3 mmol) at −78° C. After 30 min, the solution of N-(5-(2-formyl-5-(trifluoromethoxy)phenyl)pyrazin-2-yl)-4-methylnicotinamide (0.03 g, 0.075 mmol) in THF (1 mL) was added. The reaction was allowed to warm up to room temperature and stirred for 4 hr before it was quenched with NH$_4$Cl (10 mL). The reaction solution was diluted with EtOAc (20 mL). The organic layer was collected, dried, and concentrated. Column chromatography gave 4-methyl-N-(5-(5-(trifluoromethoxy)-2-vinylphenyl)pyrazin-2-yl)nicotinamide (0.02 g, 66%).

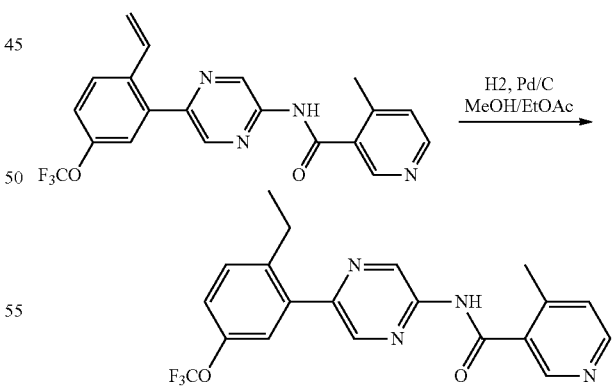

N-(5-(2-ethyl-5-(trifluoromethoxy)phenyl)pyrazin-2-yl)-4-methylnicotinamide was prepared following general hydrogenation condition. $^1$H NMR (400 MHz, CDCl$_3$) δ 9.76 (d, J=1.5 Hz, $^1$H), 8.82 (s, $^1$H), 8.62 (d, J=5.0 Hz, $^1$H), 8.46 (s, $^1$H), 8.38 (d, J=1.5 Hz, $^1$H), 7.39 (d, J=9.3 Hz, $^1$H), 7.29-7.24 (m, $^3$H), 2.76 (q, J=7.5 Hz, 2H), 2.61 (s, $^3$H), 1.16 (t, J=7.5 Hz, $^3$H); ESMS calcd (C$_{20}$H$_{17}$F$_3$N$_4$O$_2$): 402.1. found: 403.2 (M+H).

Example 135

5-fluoro-4-methyl-N-(4-methyl-5-(3-(trifluoromethoxy)phenyl)pyridin-2-yl)nicotinamide

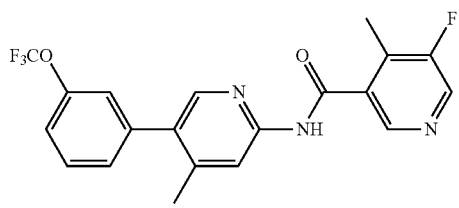 [SMILES: Cc1cc(NC(=O)c2cncc(F)c2C)ncc1-c1cccc(OC(F)(F)F)c1]

$^1$H NMR (400 MHz, CDCl$_3$) δ 9.57 (s, $^1$H), 8.57 (s, $^1$H), 8.39 (d, J=1.2 Hz, $^1$H), 8.32 (s, $^1$H), 7.65 (s, $^1$H), 7.50 (t, J=8.0 Hz, $^1$H), 7.33-7.27 (m, $^1$H), 7.19 (dt, J=7.7, 1.2 Hz, $^1$H), 7.12 (dt, J=2.5, 1.2 Hz, $^1$H), 2.46 (d, J=2.0 Hz, $^3$H), 2.36 (s, $^3$H); ESMS calcd (C$_{20}$H$_{15}$F$_4$N$_3$O$_2$): 405.1. found: 406.2 (M+H).

Example 136

2,3-difluoro-N-(5-(5-((3-fluoropyridin-2-yl)oxy)-2-methylpyridin-3-yl)pyrazin-2-yl)benzamide Preparation of Intermediates:

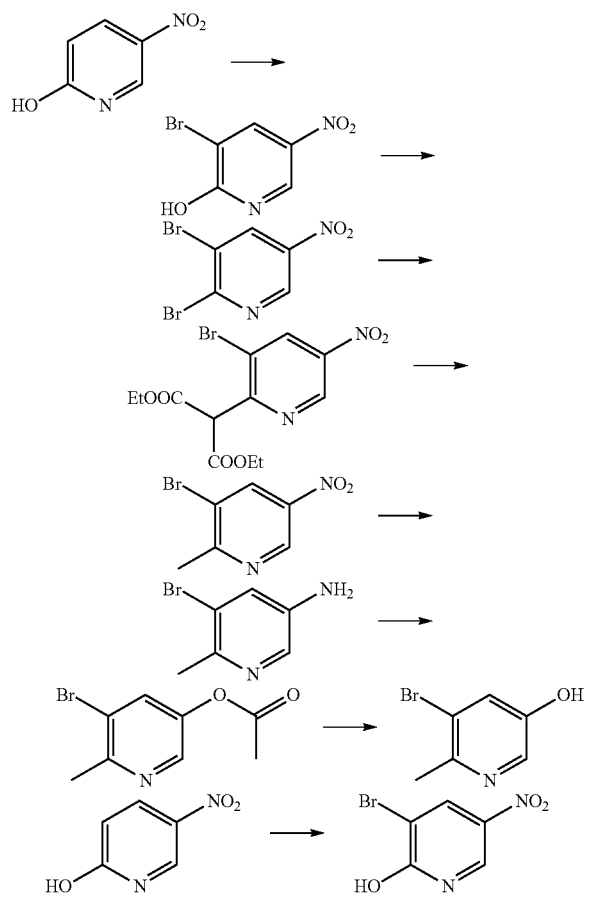

Into a 500 ml 3-necked roundbottom flask, was placed a solution of 5-nitropyridin-2-ol (50 g, 357.14 mmol, 1.00 equiv) in CH3CN (300 ml). To the above was added NBS (64 g) in several batches. The resulting solution was allowed to react, with stirring, overnight while the temperature was maintained at room temperature. A filtration was performed and the filter cake was collected. This resulted in 70 g (85%) of 3-bromo-5-nitropyridin-2-ol as a white solid.

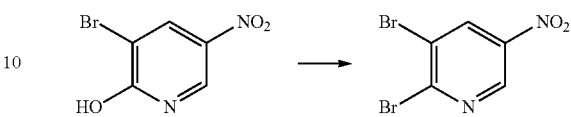

Into a 1000 ml 3-necked round bottom flask, was placed 3-bromo-5-nitropyridin-2-ol (30 g, 137.61 mmol, 1.00 equiv). To this was added POBr3 (50 g). To the mixture was added 1,4-dioxane (500 ml). The resulting solution was allowed to react, with stirring, for 2 hours while the temperature was maintained at 110 degrees C. The reaction progress was monitored by TLC (EtOAc/PE=1:10). The crude was worked up and used for next step.

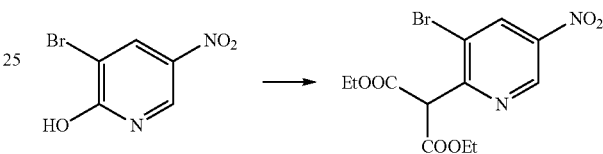

Into a 1000 ml 3-necked roundbottom flask, was placed a solution of 2,3-dibromo-5-nitropyridine (20 g, 70.92 mmol, 1.00 equiv) in THF (300 ml). To this was added diethyl malonate (18 g). To the mixture was added NaH (10 g). The resulting solution was allowed to react, with stirring, for 1 hour while the temperature was maintained at 25 C.°. The reaction mixture was then quenched by the adding 500 ml of H$_2$O. The resulting solution was extracted one time with 500 ml of EtOAc and the organic layers combined and concentrated by evaporation under vacuum using a rotary evaporator. This resulted in 30 g (crude) of diethyl 2-(3-bromo-5-nitropyridin-2-yl)malonate as a red solid.

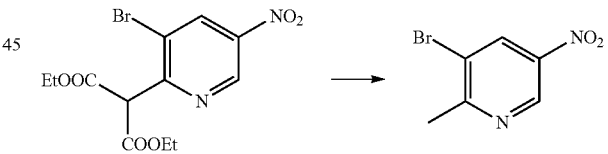

Into a 500 ml 3-necked round bottom flask, was placed a solution of diethyl 2-(3-bromo-5-nitropyridin-2-yl)malonate (30 g, 83.10 mmol, 1.00 equiv) in HCl (200 ml). The resulting solution was allowed to react, with stirring, overnight while the temperature was maintained at 100 degrees C. Adjustment of the pH to 9 was accomplished by the addition of Na$_2$CO$_3$. A filtration was performed and the filter cake was collected. This resulted in 20 g (crude) of 3-bromo-2-methyl-5-nitropyridine as a yellow solid.

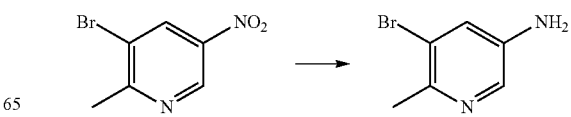

Into a 1000 ml 3-necked round bottom flask, was placed 3-bromo-2-methyl-5-nitropyridine (4 g, 17.59 mmol, 1.00 equiv, 95%). To this was added NH₄Cl (5 g). Addition of MeOH (200 ml) was next. To the mixture was added Fe (2 g). The resulting solution was allowed to react, with stirring, for 1 hour while the temperature was maintained at 90 C.°. The reaction progress was monitored by TLC (EtOAc/PE=1:1). A filtration was performed. The filtrate was concentrated by evaporation under vacuum using a rotary evaporator. The residue was purified by eluting through a column with a 1:3 EtOAc/PE solvent system. This resulted in 3.6 g (99%) of 5-bromo-6-methylpyridin-3-amine as a Yellow solid.

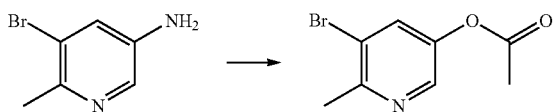

Into a 100 ml 3-necked round bottom flask, was placed a solution of 5-bromo-6-methylpyridin-3-amine (4 g, 2.13 mmol, 1.00 equiv) in HBF₄ (20 ml). This was followed by the addition of a solution of NaNO₂ (1.6 g) in H₂O (5 ml), which was added drop wise with stirring, while cooling to a temperature of 0 C.°. The resulting solution was allowed to react, with stirring, for 1 hour while the temperature was maintained at 0° C. A filtration was performed and the filter cake was collected. The residue was dissolved in 210.8 ml of Ac₂O. This was allowed to react for 1 hour at 80 C.°. The mixture was concentrated by evaporation under vacuum using a rotary evaporator. This resulted in 2.5 g (crude) of 5-bromo-6-methylpyridin-3-yl acetate as yellow oil.

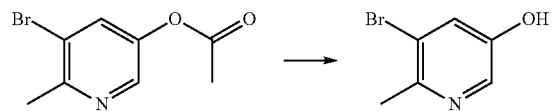

Into a 100 ml 3-necked round bottom flask, was placed a solution of 5-bromo-6-methylpyridin-3-yl acetate (2.6 g, 11.30 mmol, 1.00 equiv) in NaOH (20 ml). The resulting solution was allowed to react, with stirring, overnight while the temperature was maintained at 20 C.°. Adjustment of the pH to 6 was accomplished by the addition of HCl. A filtration was performed and the filter cake was collected. This resulted in 2.1 g (97%) of 5-bromo-6-methylpyridin-3-ol as a yellow solid.

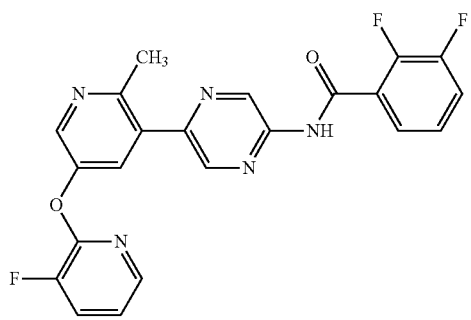 [SMILES: Cc1ncc(Oc2ncccc2F)cc1-c1cnc(NC(=O)c2cccc(F)c2F)cn1]

2,3-difluoro-N-(5-(5-((3-fluoropyridin-2-yl)oxy)-2-methylpyridin-3-yl)pyrazin-2-yl)benzamide was prepared from 5-bromo-6-methylpyridin-3-ol following general procedures. $^1$H NMR (400 MHz, CDCl₃) δ 9.79 (d, J=1.5 Hz, $^1$H), 8.99 (d, J=12.8 Hz, $^1$H), 8.54 (d, J=2.8 Hz, $^1$H), 8.52 (d, J=1.5 Hz, $^1$H), 7.98 (d, J=2.3 Hz, $^1$H), 7.91 (dd, J=4.9, 1.5 Hz, $^1$H), 7.88 (dd, J=4.9, 1.5 Hz, $^1$H), 7.74 (d, J=2.7 Hz, $^1$H), 7.52 (ddd, J=9.6, 8.0, 1.5 Hz, $^1$H), 7.05-7.02 (m, $^1$H), 6.96 (d, J=2.3 Hz, $^1$H), 2.70 (s, $^3$H); ESMS calcd (C₂₂H₁₄F₃N₅O₂): 437.1. found: 438.1 (M+H).

Example 137

N-(5'-cyclopropoxy-2'-methyl-[3,3'-bipyridin]-6-yl)-5-fluoro-4-methylnicotinamide

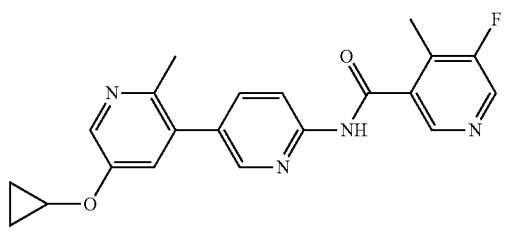 [SMILES: Cc1ncc(OC2CC2)cc1-c1ccc(NC(=O)c2cncc(F)c2C)nc1]

N-(5'-cyclopropoxy-2'-methyl-[3,3'-bipyridin]-6-yl)-5-fluoro-4-methylnicotinamide was prepared from 5-bromo-6-methylpyridin-3-ol following general procedures. $^1$H NMR (400 MHz, CDCl₃) δ 8.88 (s, $^1$H), 8.62 (s, $^1$H), 8.49 (d, J=1.2 Hz, $^1$H), 8.44 (d, J=8.5 Hz, $^1$H), 8.38 (d, J=2.8 Hz, $^1$H), 8.17 (dd, J=2.3, 0.8 Hz, $^1$H), 7.79 (dd, J=8.6, 2.4 Hz, $^1$H), 7.19 (d, J=2.9 Hz, $^1$H), 3.85-3.78 (m, $^1$H), 2.50 (d, J=2.0 Hz, $^3$H), 2.45 (s, $^3$H), 0.86-0.79 (m, 4H); ESMS calcd (C₂₁H₁₉FN₄O₂): 378.1. found: 379.0 (M+H).

Example 138

N-(5-(2-chloro-5-cyclopropoxyphenyl)pyrazin-2-yl)-4-methylpyrimidine-5-carboxamide

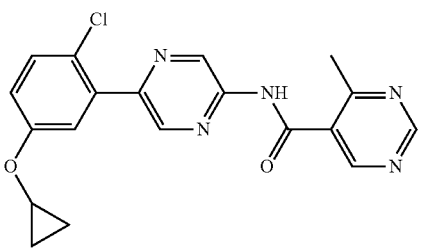 [SMILES: Cc1ncncc1C(=O)Nc1cnc(-c2cc(OC3CC3)ccc2Cl)cn1]

$^1$H NMR (400 MHz, CDCl₃) δ 9.74 (s, $^1$H), 9.21 (s, $^1$H), 8.90 (s, $^1$H), 8.74-8.65 (m, $^1$H), 8.57 (s, $^1$H), 7.40 (dd, J=8.8, 0.7 Hz, $^1$H), 7.35 (d, J=3.0 Hz, $^1$H), 7.07 (ddd, J=9.0, 3.1, 0.8 Hz, $^1$H), 3.83-3.75 (m, $^1$H), 2.80 (s, $^3$H), 0.83-0.78 (m, 4H); ESMS calcd (C₁₉H₁₆ClN₃O₂): 381.1. found: 381.9 (M+H).

Example 139

4-methyl-N-(5-(2-methyl-5-((2-methyl-2H-tetrazol-5-yl)oxy)phenyl)pyridin-2-yl)nicotinamide

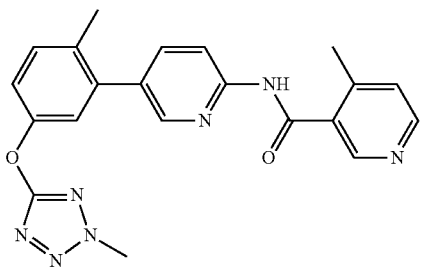 [SMILES: Cc1ccncc1C(=O)Nc1ccc(-c2cc(Oc3nnn(C)n3)ccc2C)cn1]

$^1$H NMR (400 MHz, CDCl$_3$) δ 9.27 (s, $^1$H), 8.76 (s, $^1$H), 8.51 (d, J=5.1 Hz, $^1$H), 8.42 (d, J=8.5 Hz, $^1$H), 7.95 (d, J=2.3 Hz, $^1$H), 7.75 (dd, J=8.5, 2.4 Hz, $^1$H), 7.32 (d, J=8.4 Hz, $^1$H), 7.24-7.17 (m, 2H), 7.09 (d, J=2.6 Hz, $^1$H), 4.26 (d, J=0.7 Hz, $^3$H), 2.55 (s, $^3$H), 2.26 (s, $^3$H); ESMS calcd (C$_{21}$H$_{19}$N$_7$O$_2$): 401.1. found: 402.0 (M+H).

Example 140

2,3-difluoro-N-(5-(2-methyl-5-(2-(pyridin-2-yl)ethyl)phenyl)pyrazin-2-yl)benzamide

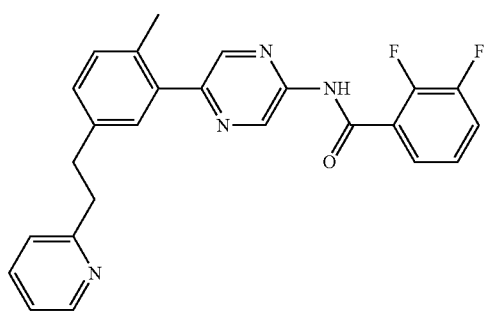 [SMILES: Cc1ccc(CCc2ccccn2)cc1-c1cnc(NC(=O)c2cccc(F)c2F)cn1]

$^1$H NMR (400 MHz, CDCl$_3$) δ 9.74 (d, J=1.5 Hz, $^1$H), 8.96 (d, J=12.4 Hz, $^1$H), 8.60-8.53 (m, $^1$H), 8.39 (d, J=1.5 Hz, $^1$H), 7.94 (ddt, J=8.1, 6.3, 1.7 Hz, $^1$H), 7.58 (td, J=7.6, 1.9 Hz, $^1$H), 7.43 (dtd, J=9.6, 7.9, 1.8 Hz, $^1$H), 7.33-7.27 (m, 2H), 7.25-7.17 (m, 2H), 7.15-7.07 (m, 2H), 3.14-3.07 (m, 4H), 2.38 (s, $^3$H); ESMS calcd (C$_{25}$H$_{20}$F$_2$N$_4$O): 430.1. found: 431.0 (M+H).

Example 141

5-fluoro-4-methyl-N-(5-(2-methyl-5-((trifluoromethyl)sulfonyl)phenyl) pyridin-2-yl)nicotinamide

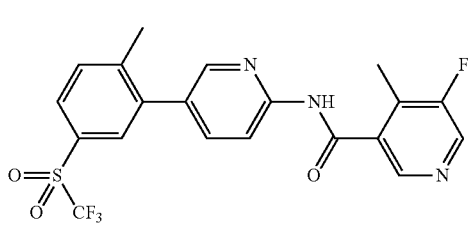 [SMILES: Cc1ccc(S(=O)(=O)C(F)(F)F)cc1-c1ccc(NC(=O)c2cncc(F)c2C)nc1]

$^1$H NMR (400 MHz, CDCl$_3$) δ 9.55 (s, $^1$H), 8.60 (s, $^1$H), 8.50 (d, J=8.6 Hz, $^1$H), 8.47 (d, J=1.2 Hz, $^1$H), 8.04-7.94 (m, 2H), 7.84 (d, J=1.9 Hz, $^1$H), 7.78 (dd, J=8.6, 2.4 Hz, $^1$H), 7.63 (d, J=8.1 Hz, $^1$H), 2.49 (d, J=2.0 Hz, $^3$H), 2.43 (s, $^3$H); ESMS calcd (C$_{20}$H$_{15}$F$_4$N$_3$O$_3$S): 453.1. found: 454.8 (M+H).

Example 142

4-methyl-N-(5-(2-methyl-5-((trifluoromethyl)sulfonyl)phenyl)pyridin-2-yl)nicotinamide

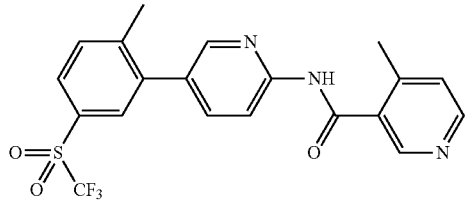 [SMILES: Cc1ccncc1C(=O)Nc1ccc(-c2cc(S(=O)(=O)C(F)(F)F)ccc2C)cn1]

$^1$H NMR (400 MHz, CDCl$_3$) δ 9.24 (s, $^1$H), 8.78 (s, $^1$H), 8.55 (d, J=5.1 Hz, $^1$H), 8.51 (d, J=8.5 Hz, $^1$H), 8.02 (d, J=2.3 Hz, $^1$H), 7.97 (dd, J=8.2, 2.0 Hz, $^1$H), 7.84 (d, J=2.0 Hz, $^1$H), 7.76 (dd, J=8.6, 2.4 Hz, $^1$H), 7.62 (d, J=8.2 Hz, $^1$H), 7.24 (d, J=5.1 Hz, $^1$H), 2.58 (s, $^3$H), 2.43 (s, $^3$H); ESMS calcd (C$_{20}$H$_{16}$F$_3$N$_3$O$_3$S): 435.1. found: 436.7 (M+H).

Example 143

5-fluoro-4-methyl-N-(5-(2-methyl-5-(pyrimidin-2-yloxy)phenyl)pyrazin-2-yl)nicotinamide

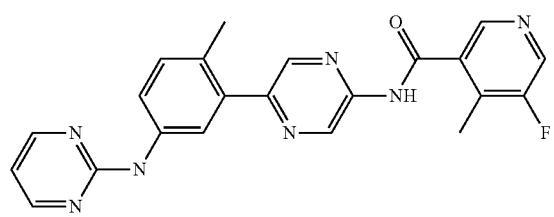

$^1$H NMR (400 MHz, CDCl$_3$) δ 9.73 (d, J=1.5 Hz, $^1$H), 8.68 (s, $^1$H), 8.62 (s, $^1$H), 8.57 (d, J=4.8 Hz, 2H), 8.52 (d, J=1.2 Hz, $^1$H), 8.42 (d, J=1.5 Hz, $^1$H), 7.39 (d, J=8.4 Hz, $^1$H), 7.33 (d, J=2.5 Hz, $^1$H), 7.21 (dd, J=8.3, 2.5 Hz, $^1$H), 7.05 (t, J=4.8 Hz, $^1$H), 2.51 (d, J=2.0 Hz, $^3$H), 2.45 (s, $^3$H); ESMS calcd (C$_{22}$H$_{17}$FN$_6$O$_2$): 416.1. found: 417.0 (M+H).

Example 144

2,3-difluoro-N-(5-(2-methyl-5-((2-methyl-2H-tetrazol-5-yl)oxy)phenyl)pyrazin-2-yl)benzamide

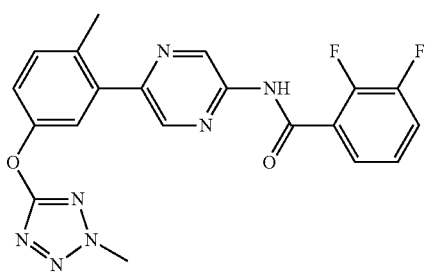

$^1$H NMR (400 MHz, CDCl$_3$) δ 9.75 (d, J=1.5 Hz, $^1$H), 9.00 (d, J=12.2 Hz, $^1$H), 8.45 (d, J=1.5 Hz, $^1$H), 7.93 (ddt, J=8.1, 6.3, 1.8 Hz, $^1$H), 7.47-7.39 (m, 2H), 7.37-7.25 (m, $^3$H), 4.26 (s, $^3$H), 2.43 (s, $^3$H); ESMS calcd (C$_{20}$H$_{15}$F$_2$N$_7$O$_2$): 423.1. found: 424.1 (M+H).

Example 145

N-(5-(2-chloro-5-(pyrimidin-2-yloxy)phenyl) pyrazin-2-yl)-5-fluoro-4-methylnicotinamide

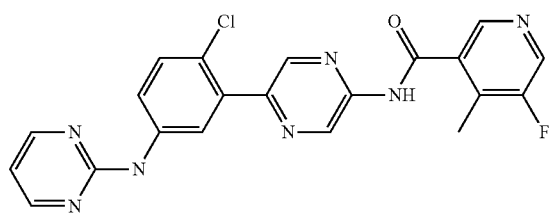

$^1$H NMR (400 MHz, CDCl$_3$) δ 9.74 (d, J=1.5 Hz, $^1$H), 8.79 (d, J=1.5 Hz, $^1$H), 8.66-8.51 (m, 5H), 7.61-7.55 (m, 2H), 7.30-7.25 (m, $^1$H), 7.09 (t, J=4.8 Hz, $^1$H), 2.51 (d, J=2.0 Hz, $^3$H); ESMS calcd (C$_2$$^1$H$_{14}$ClFN$_6$O$_2$): 436.1. found: 437.0 (M+H).

Example 146

Inhibition of IL-2 Production

Jurkat T-cells were placed in a 96 well plate (0.5 million cells per well in 1% FBS medium), and then a test compound of this invention was added at different concentrations. After 10 minutes, the cells were activated with PHA (final concentration 2.5 μg/mL) and incubated for 20 hours at 37° C. under 5% CO$_2$. The final volume was 200 μL. Following incubation, the cells were centrifuged, and the supernatants collected and stored at −70° C. prior to assaying for IL-2 production. A commercial ELISA kit (IL-2 Eli-pair, Diaclone Research, Besancon, France) was used to detect production of IL-2, from which dose response curves were obtained. The IC$_{50}$ value for each compound (shown in Table 1) was calculated as the concentration at which 50% of maximum IL-2 production after stimulation was inhibited versus a non-stimulation control.

Inhibition of other cytokines, such as IL-4, IL-5, IL-13, GM-CSF, TNFα, and IFN-γ, can be tested in a similar manner using a commercially available ELISA kit for each cytokine.

Example 147

Inhibition of Multiple Cytokines in Primary Human PBMCs

Human peripheral blood mononuclear cells (PBMCs) are prepared from heparinized human blood by separation over a Ficoll density gradient.

PBMCs are stimulated with phytohemagglutinin (PHA) in the presence of varying concentrations of compounds of the invention or cyclosporine A (CsA), a known inhibitor of cytokine production. Cytokine production is measured using commercially available human ELISA assay kits (from Cell Science, Inc.) following the manufacturers instructions.

Alternatively, PBMCs with 10% FCS at 1-2×10$^6$/mL are stimulated with pre-coated with anti-CD3 (clone UCHT1) and anti-CD28 (clone ANC28.1/5D10) at 5 μg/mL each, with or without compound or DMSO (maximum concentration: 0.1%). Cell cultures are incubated at 37° C., 5% CO$_2$. Samples of the culture supernatant are collected after 48-72 hrs. incubation for measurement of multiple cytokines. Cytokines present in the supernatants are quantified using BioRad BioPlex assays according to the manufacturer's instructions.

The compounds of the invention are expected to be potent inhibitors of IL-2, IL-4, IL-5, IL-13, GM-CSF, IFN-alpha, and TNF-alpha in primary human PBM cells. In addition, compounds of the invention are not expected to inhibit the anti-inflammatory cytokine, IL-10.

Example 148

Inhibition of Degranulation in RBL Cells

Procedure:

The day before the assay is performed, RBL cells, that have been grown to confluence in a 96 well plate, are incubated at 37° C. for at least 2 hours. The medium is replaced in each well with 100 μL of fresh medium containing 2 μLg/mL of anti-DNP IgE.

On the following day, the cells are washed once with PRS (2.6 mM glucose and 0.1% BSA) and 160 μL of PRS is added to each well. A test compound is added to a well in a 20 μL solution at 10× of the desired concentration and incubated for 20 to 40 minutes at 37° C. 20 μL of 10× mouse anti-IgE (10 μL/mL) is added. Maximum degranulation occurs between 15 to 40 minutes after addition of anti-IgE.

Compounds of the invention are expected to inhibit degranulation.

Example 149

Inhibition of Chemotaxis in T-Cells

T-Cell Isolation:

Twenty mL aliquots of heparinized whole blood (2 pig, 1 human) are subjected to density gradient centrifugation on Ficoll Hypaque. The buffy coat layers representing peripheral blood mononuclear cells (PBMCs) containing lymphocytes and monocytes are washed once, resuspended in 12 mL of incomplete RPMI 1640 and then placed in gelatin-coated T75 culture flasks for 1 hr at 37° C. The non-adherent T-cells, representing peripheral blood lymphocytes (PBLs) depleted of monocytes, are resuspended in complete RPMI media and placed in loosely packed activated nylon wool columns that have been equilibrated with warm media. After 1 hr at 37° C., the non-adherent T-cell populations are eluted by washing of the columns with additional media. The T-cell preparations are centrifuged, resuspended in 5 mL of incomplete RPMI, and counted using a hemocytometer.

Cell Migration Assay:

Aliquots of each T-cell preparation are labeled with Calcien AM (TefLabs) and suspended at a concentration of 2.4×10$^6$/mL in HEPES-buffered Hank's Balanced Salt Solution containing 1.83 mM CaCl$_2$ and 0.8 mM MgCl$_2$, pH 7.4 (HHBSS). An equal volume of HHBSS containing 0, 20 nM, 200 nM or 2000 nM of compound 1 or 20 nM EDTA is then added and the cells incubated for 30 min at 37° C. Fifty µl aliquots of the cell suspensions (60,000 cells) are placed on the membrane (pore size 5 µm) of a Neuroprobe ChemoTx 96 well chemotaxis unit that have been affixed over wells containing 10 ng/mL MIP-1α in HHBSS. The T-cells are allowed to migrate for 2 hr at 37° C., after which the apical surface of the membrane is wiped clean of cells. The chemotaxis units are then placed in a CytoFluor 4000 (PerSeptive BioSystems) and the fluorescence of each well measured (excitation and emission wavelengths of 450 and 530 nm, respectively). The number of migrating cells in each well is determined from a standard curve generated from measuring the fluorescence of serial two-fold dilutions of the labeled cells placed in the lower wells of the chemotaxis unit prior to affixing the membrane.

Compounds of the invention are expected to inhibit chemotactic response of T-cells.

All publications, patent applications, patents, and other documents cited herein are incorporated by reference in their entirety. In case of conflict, the present specification, including definitions, will control. In addition, the materials, methods, and examples are illustrative only and not intended to be limiting in any way.

The invention claimed is:

1. A compound selected from the group consisting of:

| Number | Structure | Compound Name |
|---|---|---|
| 1. | 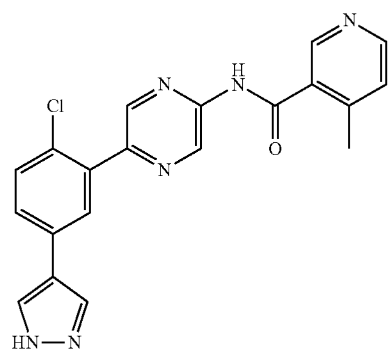 [SMILES: Cc1ccncc1C(=O)Nc1cnc(-c2cc(-c3cn[nH]c3)ccc2Cl)cn1] | N-(5-(2-chloro-5-($^1$H-pyrazol-4-yl)phenyl)pyrazin-2-yl)-4-methylnicotinamide |
| 2. | 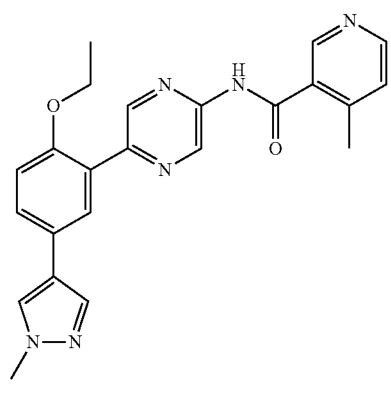 [SMILES: CCOc1ccc(-c2cnn(C)c2)cc1-c1cnc(NC(=O)c2cnccc2C)cn1] | N-(5-(2-ethoxy-5-(1-methyl-$^1$H-pyrazol-4-yl)phenyl)pyrazin-2-yl)-4-methylnicotinamide |
| 3. | 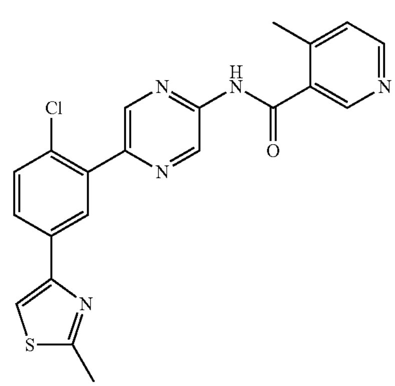 [SMILES: Cc1nc(-c2ccc(Cl)c(-c3cnc(NC(=O)c4cnccc4C)cn3)c2)cs1] | N-(5-(2-chloro-5-(2-methylthiazol-4-yl)phenyl)pyrazin-2-yl)-4-methylnicotinamide |

-continued

| Number | Structure | Compound Name |
|---|---|---|
| 6. | 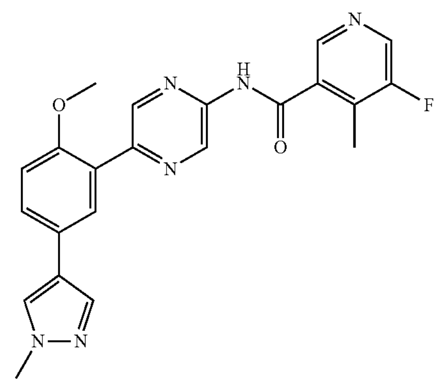 [SMILES: COc1ccc(-c2cnn(C)c2)cc1-c1cnc(NC(=O)c2cncc(F)c2C)cn1] | 5-fluoro-N-(5-(2-methoxy-5-(1-methyl-¹H-pyrazol-4-yl)phenyl)pyrazin-2-yl)-4-methylnicotinamide |
| 8. | 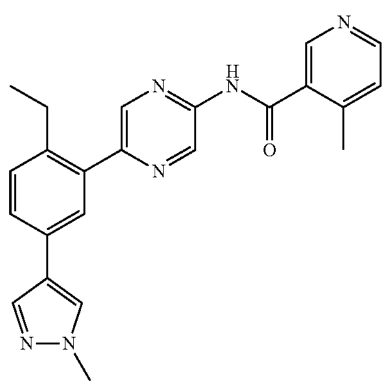 [SMILES: CCc1ccc(-c2cnn(C)c2)cc1-c1cnc(NC(=O)c2cnccc2C)cn1] | N-(5-(2-ethyl-5-(1-methyl-¹H-pyrazol-4-yl)phenyl)pyrazin-2-yl)-4-methylnicotinamide |
| 14. | 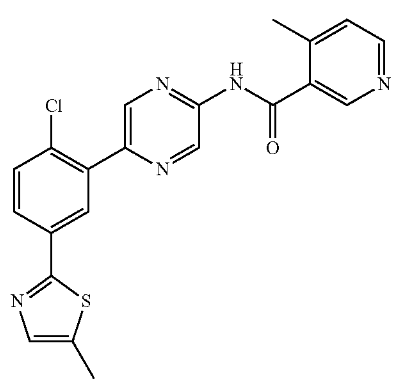 [SMILES: Cc1cnc(-c2ccc(Cl)c(-c3cnc(NC(=O)c4cnccc4C)cn3)c2)s1] | N-(5-(2-chloro-5-(5-methylthiazol-2-yl)phenyl)pyrazin-2-yl)-4-methylnicotinamide |
| 16. | 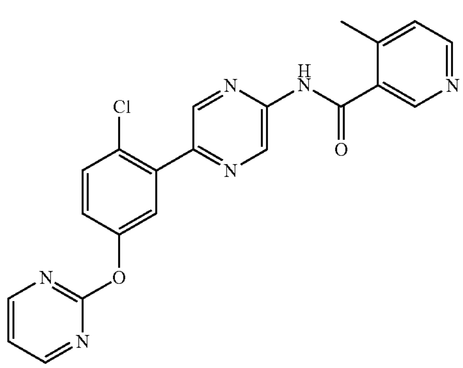 [SMILES: Cc1ccncc1C(=O)Nc1cnc(-c2cc(Oc3ncccn3)ccc2Cl)cn1] | N-(5-(2-chloro-5-(pyrimidin-2-yloxy)phenyl)pyrazin-2-yl)-4-methylnicotinamide |

-continued

| Number | Structure | Compound Name |
|---|---|---|
| 19. | 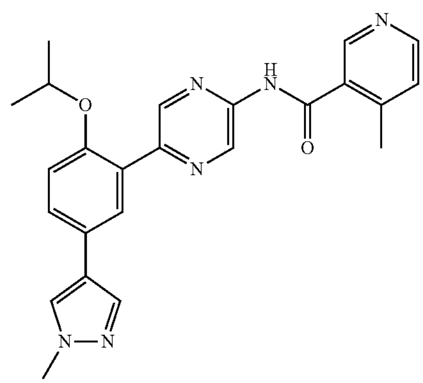 [SMILES: Cc1ccncc1C(=O)Nc1cnc(-c2cc(-c3cnn(C)c3)ccc2OC(C)C)cn1] | N-(5-(2-isopropoxy-5-(1-methyl-1H-pyrazol-4-yl)phenyl)pyrazin-2-yl)-4-methylnicotinamide |
| 22. | 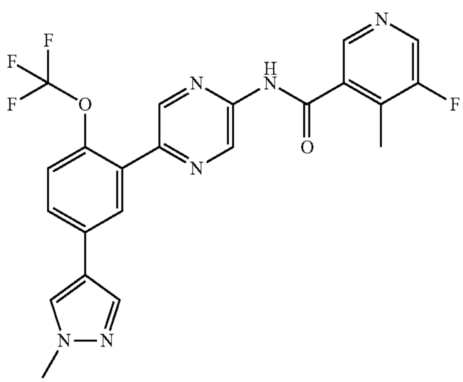 [SMILES: Cc1c(F)cncc1C(=O)Nc1cnc(-c2cc(-c3cnn(C)c3)ccc2OC(F)(F)F)cn1] | 5-fluoro-4-methyl-N-(5-(5-(1-methyl-1H-pyrazol-4-yl)-2-(trifluoromethoxy)phenyl)pyrazin-2-yl)nicotinamide |
| 24. | 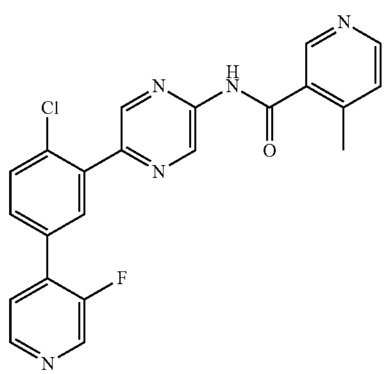 [SMILES: Cc1ccncc1C(=O)Nc1cnc(-c2cc(-c3ccncc3F)ccc2Cl)cn1] | N-(5-(2-chloro-5-(3-fluoropyridin-4-yl)phenyl)pyrazin-2-yl)-4-methylnicotinamide |
| 26. | 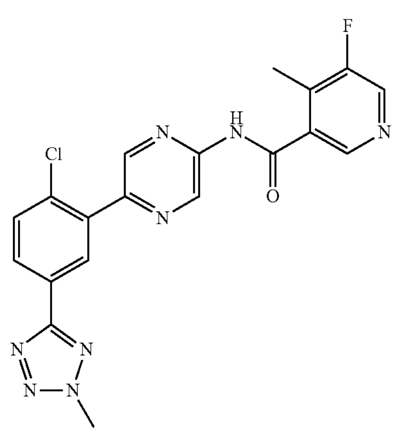 [SMILES: Cc1c(F)cncc1C(=O)Nc1cnc(-c2cc(-c3nnn(C)n3)ccc2Cl)cn1] | N-(5-(2-chloro-5-(2-methyl-2H-tetrazol-5-yl)phenyl)pyrazin-2-yl)-5-fluoro-4-methylnicotinamide |

-continued

| Number | Structure | Compound Name |
|---|---|---|
| 27. | 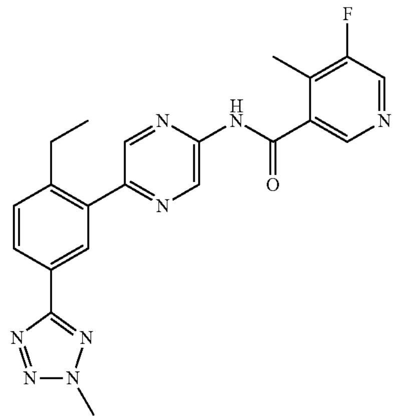 [SMILES: CCc1ccc(-c2nnn(C)n2)cc1-c1cnc(NC(=O)c2cncc(F)c2C)cn1] | N-(5-(2-ethyl-5-(2-methyl-2H-tetrazol-5-yl)phenyl)pyrazin-2-yl)-5-fluoro-4-methylnicotinamide |
| 34. | 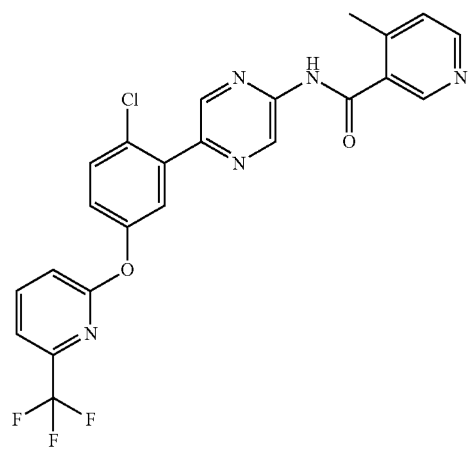 [SMILES: Cc1ccncc1C(=O)Nc1cnc(-c2cc(Oc3cccc(C(F)(F)F)n3)ccc2Cl)cn1] | N-(5-(2-chloro-5-((6-(trifluoromethyl)pyridin-2-yl)oxy)phenyl)pyrazin-2-yl)-4-methylnicotinamide |
| 36. | 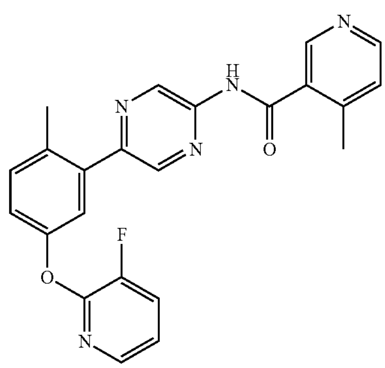 [SMILES: Cc1ccncc1C(=O)Nc1cnc(-c2cc(Oc3ncccc3F)ccc2C)cn1] | N-(5-(5-((3-fluoropyridin-2-yl)oxy)-2-methylphenyl)pyrazin-2-yl)-4-methylnicotinamide |
| 38. | 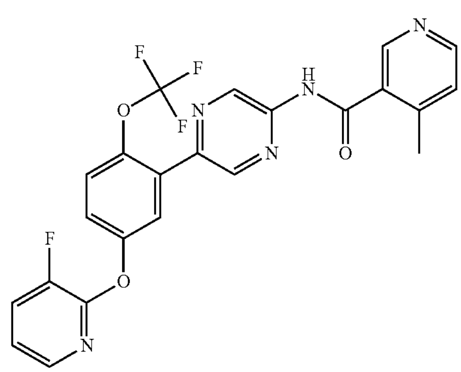 [SMILES: Cc1ccncc1C(=O)Nc1cnc(-c2cc(Oc3ncccc3F)ccc2OC(F)(F)F)cn1] | N-(5-(5-((3-fluoropyridin-2-yl)oxy)-2-(trifluoromethoxy)phenyl)pyrazin-2-yl)-4-methylnicotinamide |

-continued

| Number | Structure | Compound Name |
|---|---|---|
| 39. | 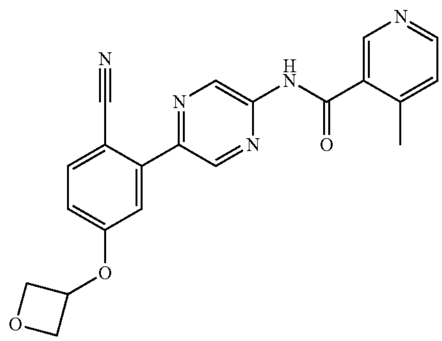 [SMILES: Cc1ccncc1C(=O)Nc1cnc(-c2cc(OC3COC3)ccc2C#N)cn1] | N-(5-(2-cyano-5-(oxetan-3-yloxy)phenyl)pyrazin-2-yl)-4-methylnicotinamide |
| 44. | 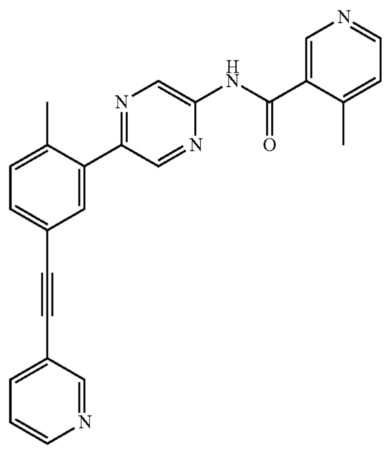 [SMILES: Cc1ccncc1C(=O)Nc1cnc(-c2cc(C#Cc3cccnc3)ccc2C)cn1] | 4-methyl-N-(5-(2-methyl-5-(pyridin-3-ylethynyl)phenyl)pyrazin-2-yl)nicotinamide |
| 45. | 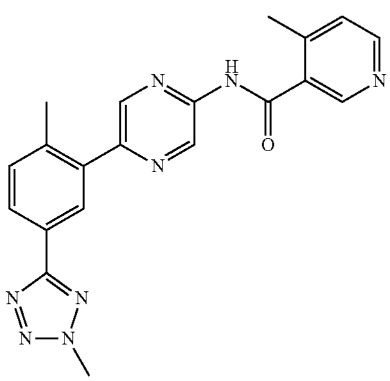 [SMILES: Cc1ccncc1C(=O)Nc1cnc(-c2cc(-c3nnn(C)n3)ccc2C)cn1] | 4-methyl-N-(5-(2-methyl-5-(2-methyl-2H-tetrazol-5-yl)phenyl)pyrazin-2-yl)nicotinamide |
| 49. | 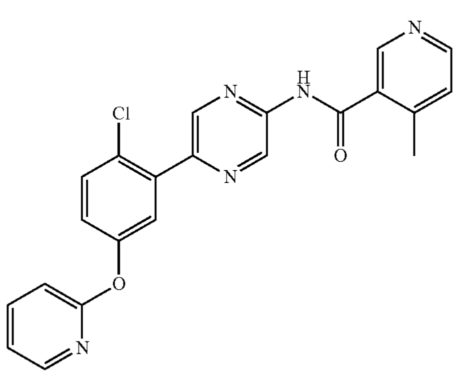 [SMILES: Cc1ccncc1C(=O)Nc1cnc(-c2cc(Oc3ccccn3)ccc2Cl)cn1] | N-(5-(2-chloro-5-(pyridin-2-yloxy)phenyl)pyrazin-2-yl)-4-methylnicotinamide |

| Number | Structure | Compound Name |
|---|---|---|
| 50. | 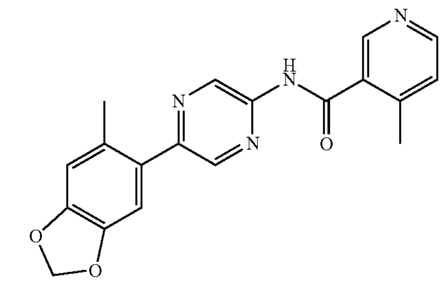 [SMILES: Cc1ccncc1C(=O)Nc1cnc(-c2cc3c(cc2C)OCO3)cn1] | 4-methyl-N-(5-(6-methylbenzo[d][1,3]dioxol-5-yl)pyrazin-2-yl)nicotinamide |
| 51. | 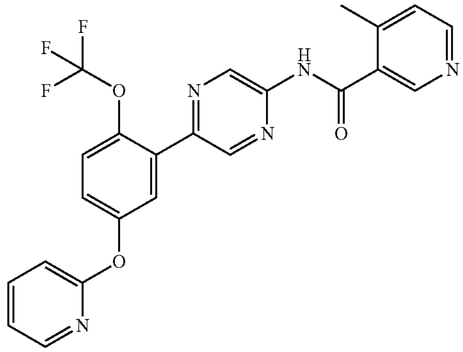 [SMILES: Cc1ccncc1C(=O)Nc1cnc(-c2cc(Oc3ccccn3)ccc2OC(F)(F)F)cn1] | 4-methyl-N-(5-(5-(pyridin-2-yloxy)-2-(trifluoromethoxy)phenyl)pyrazin-2-yl)nicotinamide |
| 52. | 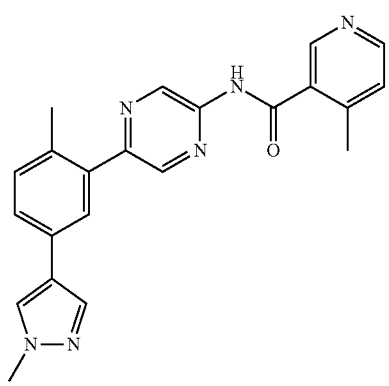 | 4-methyl-N-(5-(2-methyl-5-(1-methyl-1H-pyrazol-4-yl)phenyl)pyrazin-2-yl)nicotinamide |
| 53. | 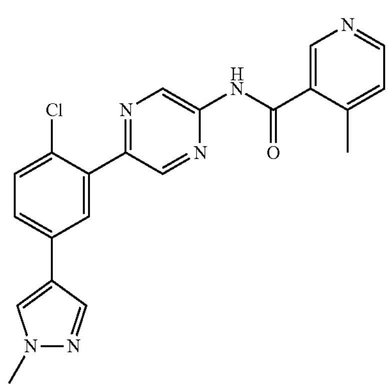 [SMILES: Cc1ccncc1C(=O)Nc1cnc(-c2cc(-c3cnn(C)c3)ccc2Cl)cn1] | N-(5-(2-chloro-5-(1-methyl-1H-pyrazol-4-yl)phenyl)pyrazin-2-yl)-4-methylnicotinamide |

| Number | Structure | Compound Name |
|---|---|---|
| 54. | 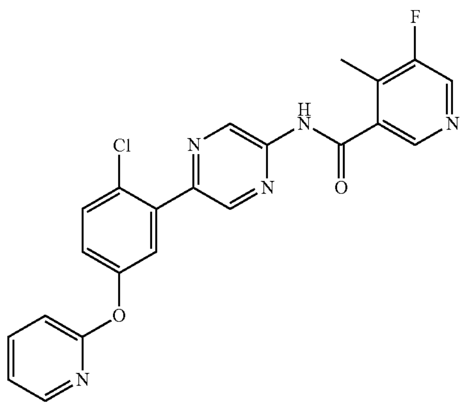 [SMILES: Cc1c(F)cncc1C(=O)Nc1cnc(-c2cc(Oc3ccccn3)ccc2Cl)cn1] | N-(5-(2-chloro-5-(pyridin-2-yloxy)phenyl)pyrazin-2-yl)-5-fluoro-4-methylnicotinamide |
| 56. | 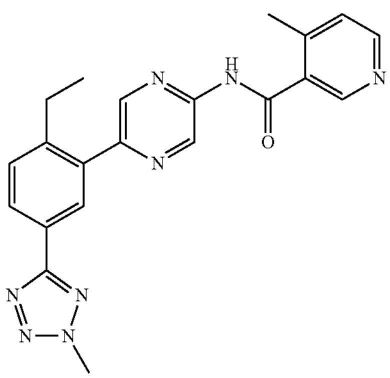 [SMILES: CCc1ccc(-c2nnn(C)n2)cc1-c1cnc(NC(=O)c2cnccc2C)cn1] | N-(5-(2-ethyl-5-(2-methyl-2H-tetrazol-5-yl)phenyl)pyrazin-2-yl)-4-methylnicotinamide |
| 57. | 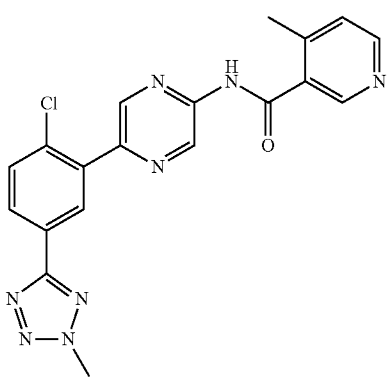 [SMILES: Cc1ccncc1C(=O)Nc1cnc(-c2cc(-c3nnn(C)n3)ccc2Cl)cn1] | N-(5-(2-chloro-5-(2-methyl-2H-tetrazol-5-yl)phenyl)pyrazin-2-yl)-4-methylnicotinamide |
| 61. | 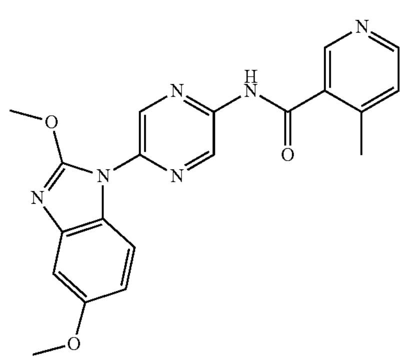 [SMILES: COc1ccc2c(c1)nc(OC)n2-c1cnc(NC(=O)c2cnccc2C)cn1] | N-(5-(2,5-dimethoxy-1H-benzo[d]imidazol-1-yl)pyrazin-2-yl)-4-methylnicotinamide |

-continued

| Number | Structure | Compound Name |
|---|---|---|
| 62. | 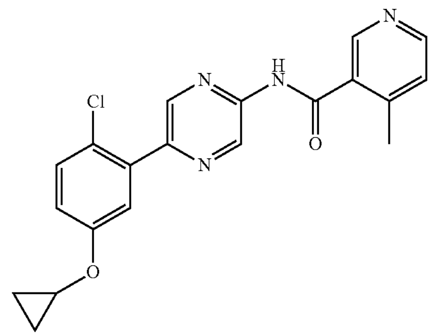 [SMILES: Cc1ccncc1C(=O)Nc1cnc(-c2cc(OC3CC3)ccc2Cl)cn1] | N-(5-(2-chloro-5-cyclopropoxyphenyl)pyrazin-2-yl)-4-methylnicotinamide |
| 65. | 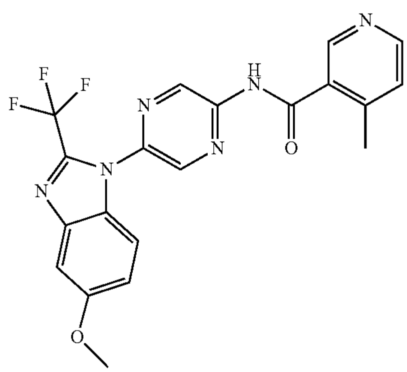 [SMILES: COc1ccc2c(c1)nc(C(F)(F)F)n2-c1cnc(NC(=O)c2cnccc2C)cn1] | N-(5-(5-methoxy-2-(trifluoromethyl)-1H-benzo[d]imidazol-1-yl)pyrazin-2-yl)-4-methylnicotinamide |
| 66. | 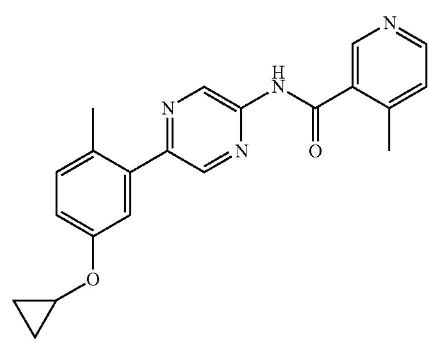 [SMILES: Cc1ccncc1C(=O)Nc1cnc(-c2cc(OC3CC3)ccc2C)cn1] | N-(5-(5-cyclopropoxy-2-methylphenyl)pyrazin-2-yl)-4-methylnicotinamide |
| 68. | 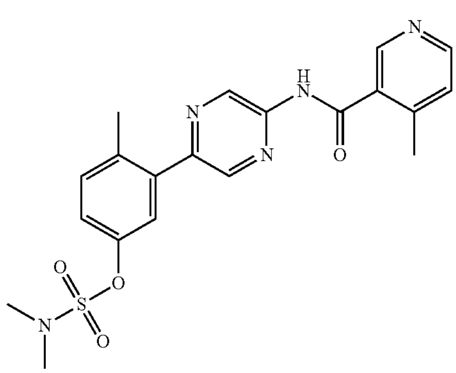 [SMILES: Cc1ccncc1C(=O)Nc1cnc(-c2cc(OS(=O)(=O)N(C)C)ccc2C)cn1] | 4-methyl-3-(5-(4-methylnicotinamido)pyrazin-2-yl)phenyl dimethylsulfamate |

-continued

| Number | Structure | Compound Name |
|---|---|---|
| 69. | 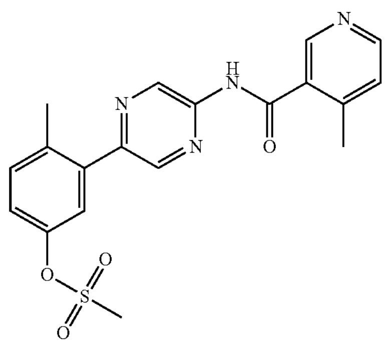 [SMILES: Cc1ccncc1C(=O)Nc1cnc(-c2cc(OS(C)(=O)=O)ccc2C)cn1] | 4-methyl-3-(5-(4-methylnicotinamido)pyrazin-2-yl)phenyl methanesulfonate |
| 79. | 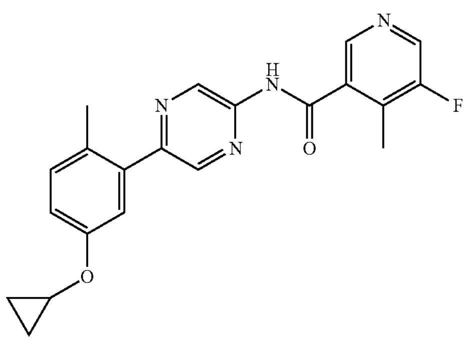 [SMILES: Cc1ccc(OC2CC2)cc1-c1cnc(NC(=O)c2cncc(F)c2C)cn1] | N-(5-(5-cyclopropoxy-2-methylphenyl)pyrazin-2-yl)-5-fluoro-4-methylnicotinamide |
| 80. | 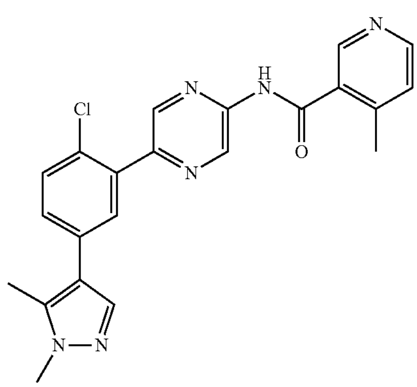 [SMILES: Cc1ccncc1C(=O)Nc1cnc(-c2cc(-c3cnn(C)c3C)ccc2Cl)cn1] | N-(5-(2-chloro-5-(1,5-dimethyl-1H-pyrazol-4-yl)phenyl)pyrazin-2-yl)-4-methylnicotinamide |
| 81. | 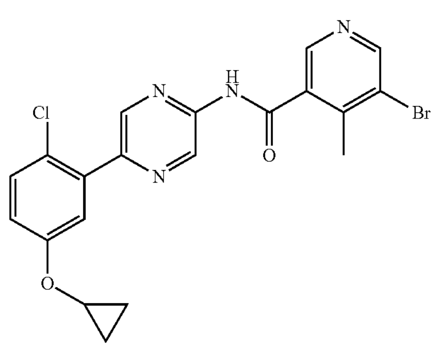 [SMILES: Cc1c(Br)cncc1C(=O)Nc1cnc(-c2cc(OC3CC3)ccc2Cl)cn1] | 5-bromo-N-(5-(2-chloro-5-cyclopropoxyphenyl)pyrazin-2-yl)-4-methylnicotinamide |

| Number | Structure | Compound Name |
|---|---|---|
| 85. | 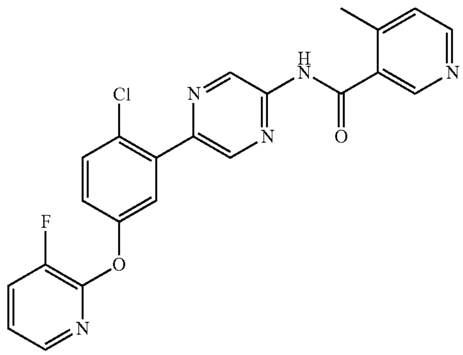 [SMILES: Cc1ccncc1C(=O)Nc1cnc(-c2cc(Oc3ncccc3F)ccc2Cl)cn1] | N-(5-(2-chloro-5-((3-fluoropyridin-2-yl)oxy)phenyl)pyrazin-2-yl)-4-methylnicotinamide |
| 86. | 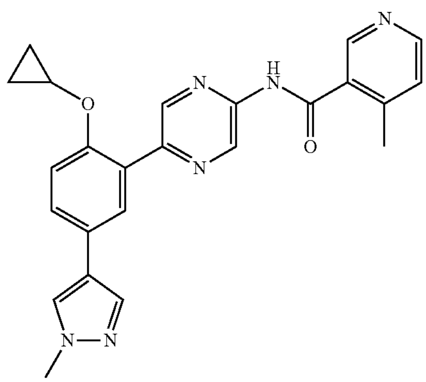 [SMILES: Cc1ccncc1C(=O)Nc1cnc(-c2cc(-c3cnn(C)c3)ccc2OC2CC2)cn1] | N-(5-(2-cyclopropoxy-5-(1-methyl-1H-pyrazol-4-yl)phenyl)pyrazin-2-yl)-4-methylnicotinamide |
| 87. | 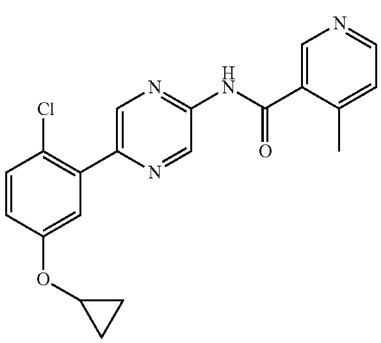 | N-(5-(2-chloro-5-cyclopropoxyphenyl)pyrazin-2-yl)-4-methylnicotinamide hydrochloride |
| 93. | 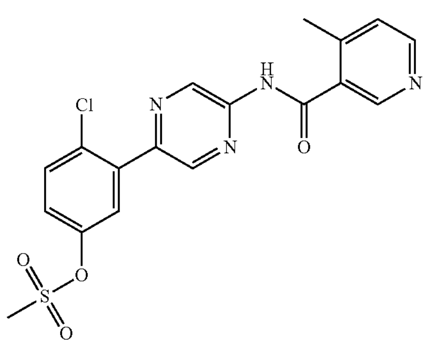 [SMILES: Cc1ccncc1C(=O)Nc1cnc(-c2cc(OS(C)(=O)=O)ccc2Cl)cn1] | 4-chloro-3-(5-(4-methylnicotinamido)pyrazin-2-yl)phenyl methanesulfonate |

| Number | Structure | Compound Name |
|---|---|---|
| 101. | 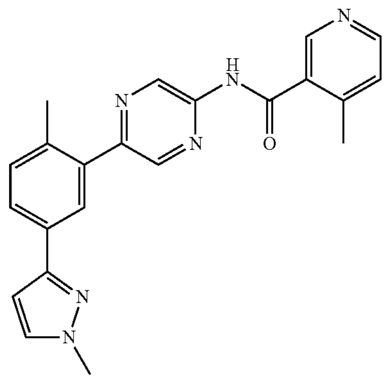 [SMILES: Cc1ccncc1C(=O)Nc1cnc(-c2cc(-c3ccn(C)n3)ccc2C)cn1] | 4-methyl-N-(5-(2-methyl-5-(1-methyl-1H-pyrazol-3-yl)phenyl)pyrazin-2-yl)nicotinamide |
| 110. | 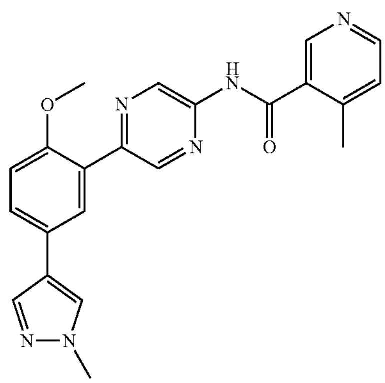 [SMILES: COc1ccc(-c2cnn(C)c2)cc1-c1cnc(NC(=O)c2cnccc2C)cn1] | N-(5-(2-methoxy-5-(1-methyl-1H-pyrazol-4-yl)phenyl)pyrazin-2-yl)-4-methylnicotinamide |
| 114. | 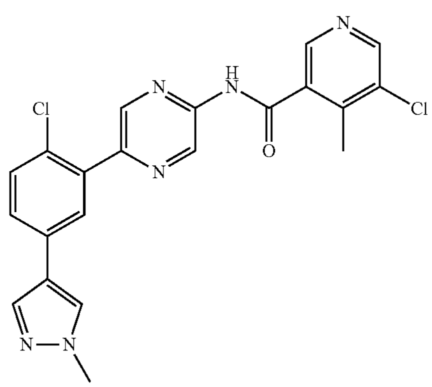 [SMILES: Cc1c(Cl)cncc1C(=O)Nc1cnc(-c2cc(-c3cnn(C)c3)ccc2Cl)cn1] | 5-chloro-N-(5-(2-chloro-5-(1-methyl-1H-pyrazol-4-yl)phenyl)pyrazin-2-yl)-4-methylnicotinamide |
| 121. | 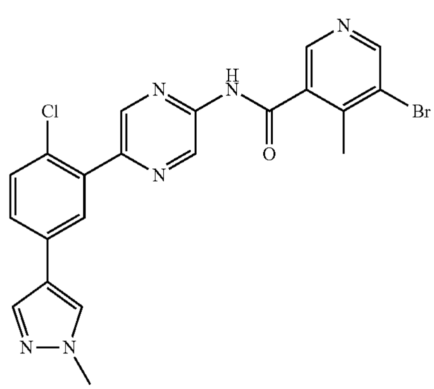 [SMILES: Cc1c(Br)cncc1C(=O)Nc1cnc(-c2cc(-c3cnn(C)c3)ccc2Cl)cn1] | 5-bromo-N-(5-(2-chloro-5-(1-methyl-1H-pyrazol-4-yl)phenyl)pyrazin-2-yl)-4-methylnicotinamide |

| Number | Structure | Compound Name |
|---|---|---|
| 123. | 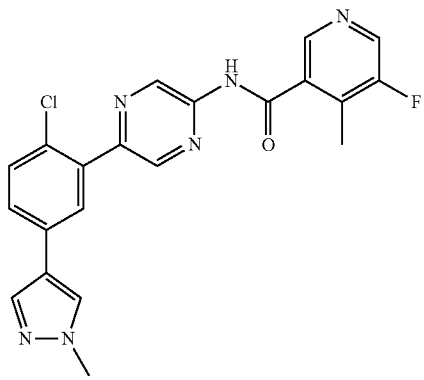 [SMILES: Cc1c(F)cncc1C(=O)Nc1cnc(-c2cc(-c3cnn(C)c3)ccc2Cl)cn1] | N-(5-(2-chloro-5-(1-methyl-¹H-pyrazol-4-yl)phenyl)pyrazin-2-yl)-5-fluoro-4-methylnicotinamide |
| 124. | 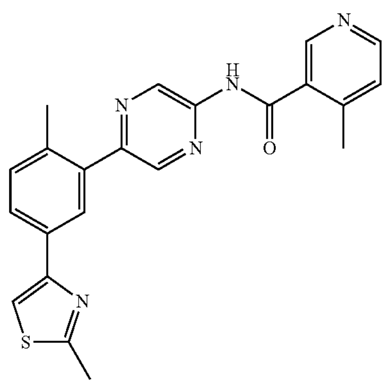 [SMILES: Cc1nc(-c2ccc(C)c(-c3cnc(NC(=O)c4cnccc4C)cn3)c2)cs1] | 4-methyl-N-(5-(2-methyl-5-(2-methylthiazol-4-yl)phenyl)pyrazin-2-yl)nicotinamide |
| 129. | 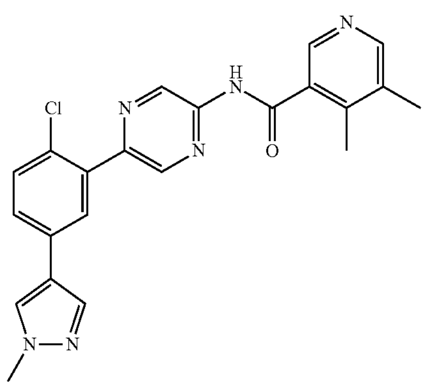 | N-(5-(2-chloro-5-(1-methyl-¹H-pyrazol-4-yl)phenyl)pyrazin-2-yl)-4,5-dimethylnicotinamide |
| 131. | 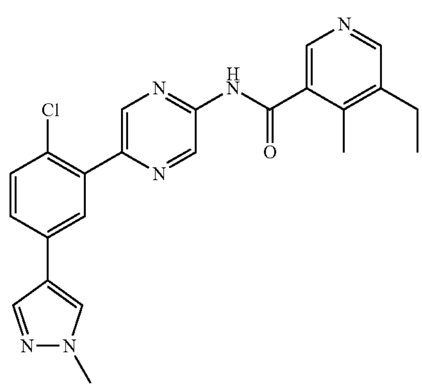 [SMILES: CCc1cncc(C(=O)Nc2cnc(-c3cc(-c4cnn(C)c4)ccc3Cl)cn2)c1C] | N-(5-(2-chloro-5-(1-methyl-¹H-pyrazol-4-yl)phenyl)pyrazin-2-yl)-5-ethyl-4-methylnicotinamide |

| Number | Structure | Compound Name |
|---|---|---|
| 132. | 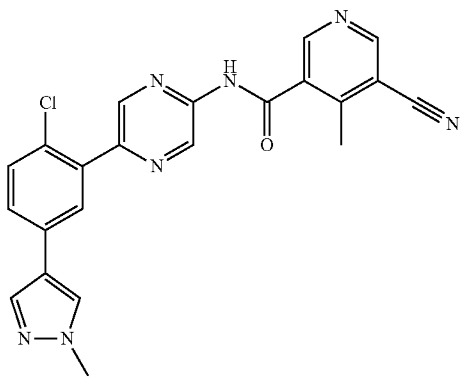 [SMILES: Cc1c(C#N)cncc1C(=O)Nc1cnc(-c2cc(-c3cnn(C)c3)ccc2Cl)cn1] | N-(5-(2-chloro-5-(1-methyl-1H-pyrazol-4-yl)phenyl)pyrazin-2-yl)-5-cyano-4-methylnicotinamide |
| 137. | 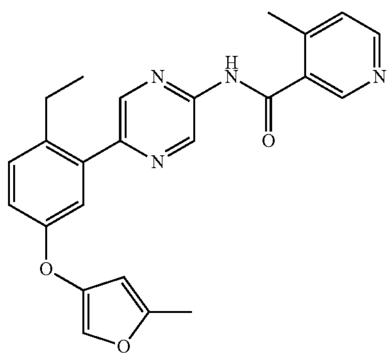 [SMILES: CCc1ccc(Oc2coc(C)c2)cc1-c1cnc(NC(=O)c2cnccc2C)cn1] | N-(5-(2-ethyl-5-((5-methylisoxazol-3-yl)oxy)phenyl)pyrazin-2-yl)-4-methylnicotinamide |
| 142. | 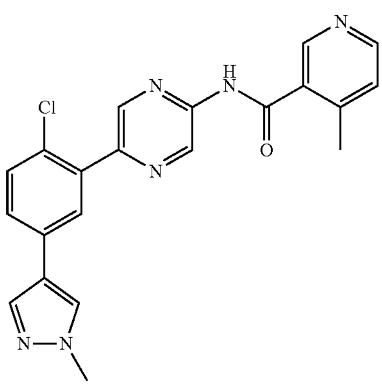 [SMILES: Cc1ccncc1C(=O)Nc1cnc(-c2cc(-c3cnn(C)c3)ccc2Cl)cn1] | N-(5-(2-chloro-5-(1-methyl-1H-pyrazol-4-yl)phenyl)pyrazin-2-yl)-4-methylnicotinamide hydrochloride |
| 143. | 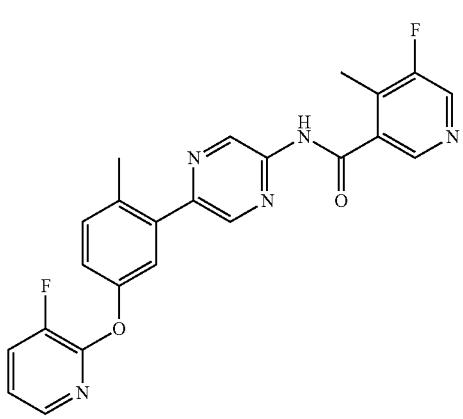 [SMILES: Cc1ccc(Oc2ncccc2F)cc1-c1cnc(NC(=O)c2cncc(F)c2C)cn1] | 5-fluoro-N-(5-(5-((3-fluoropyridin-2-yl)oxy)-2-methylphenyl)pyrazin-2-yl)-4-methylnicotinamide |

| Number | Structure | Compound Name |
| --- | --- | --- |
| 144. | 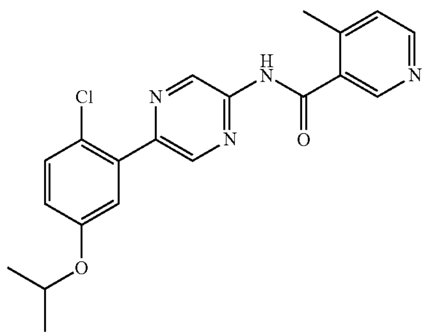 [SMILES: Cc1ccncc1C(=O)Nc1cnc(-c2cc(OC(C)C)ccc2Cl)cn1] | N-(5-(2-chloro-5-isopropoxyphenyl)pyrazin-2-yl)-4-methylnicotinamide |
| 196 | 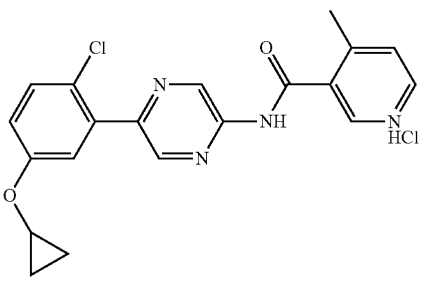 | N-(5-(2-chloro-5-cyclopropoxyphenyl)pyrazin-2-yl)-4-methylnicotinamide hydrochloride |
| 198 | 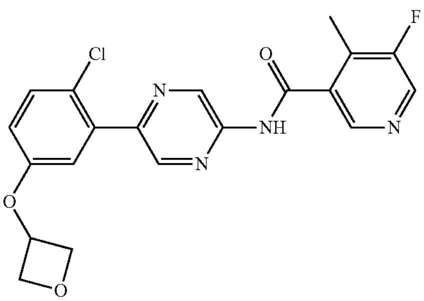 [SMILES: Cc1c(F)cncc1C(=O)Nc1cnc(-c2cc(OC3COC3)ccc2Cl)cn1] | N-(5-(2-chloro-5-(oxetan-3-yloxy)phenyl)pyrazin-2-yl)-5-fluoro-4-methylnicotinamide |
| 200 | 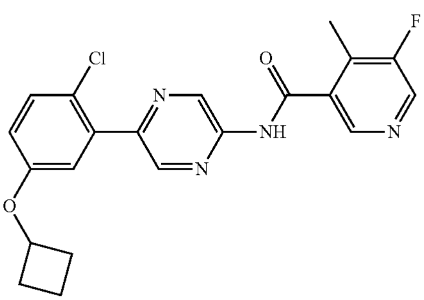 [SMILES: Cc1c(F)cncc1C(=O)Nc1cnc(-c2cc(OC3CCC3)ccc2Cl)cn1] | N-(5-(2-chloro-5-cyclobutoxyphenyl)pyrazin-2-yl)-5-fluoro-4-methylnicotinamide |
| 201 | 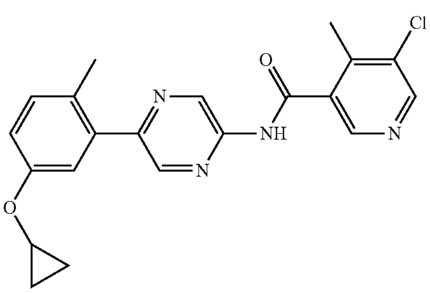 [SMILES: Cc1ccc(OC2CC2)cc1-c1cnc(NC(=O)c2cncc(Cl)c2C)cn1] | 5-chloro-N-(5-(5-cyclopropoxy-2-methylphenyl)pyrazin-2-yl)-4-methylnicotinamide |

| Number | Structure | Compound Name |
|---|---|---|
| 202 | 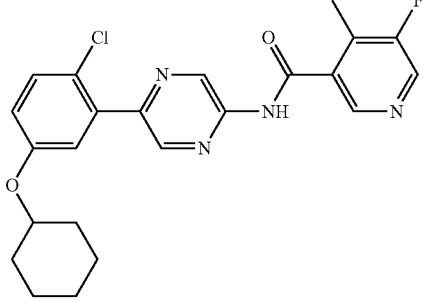 | N-(5-(2-chloro-5-(cyclohexyloxy)phenyl)pyrazin-2-yl)-5-fluoro-4-methylnicotinamide |
| 203 | 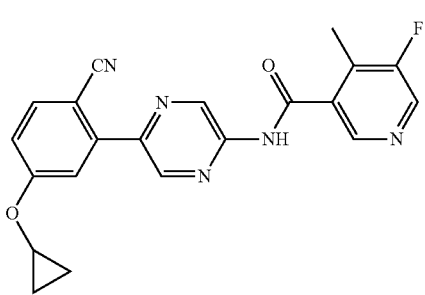 | N-(5-(2-cyano-5-cyclopropoxyphenyl)pyrazin-2-yl)-5-fluoro-4-methylnicotinamide |
| 204 | 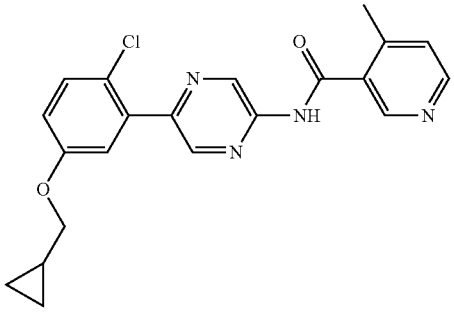 [SMILES: Cc1ccncc1C(=O)Nc1cnc(-c2cc(OCC3CC3)ccc2Cl)cn1] | N-(5-(2-chloro-5-(cyclopropylmethoxy)phenyl)pyrazin-2-yl)-4-methylnicotinamide |
| 205 | 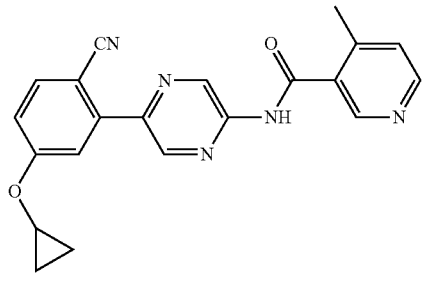 [SMILES: Cc1ccncc1C(=O)Nc1cnc(-c2cc(OC3CC3)ccc2C#N)cn1] | N-(5-(2-cyano-5-cyclopropoxyphenyl)pyrazin-2-yl)-4-methylnicotinamide |
| 206 | 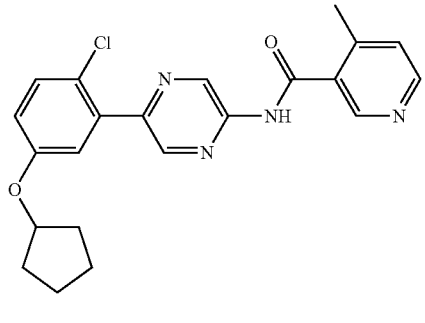 [SMILES: Cc1ccncc1C(=O)Nc1cnc(-c2cc(OC3CCCC3)ccc2Cl)cn1] | N-(5-(2-chloro-5-(cyclopentyloxy)phenyl)pyrazin-2-yl)-4-methylnicotinamide |

| Number | Structure | Compound Name |
|---|---|---|
| 207 | 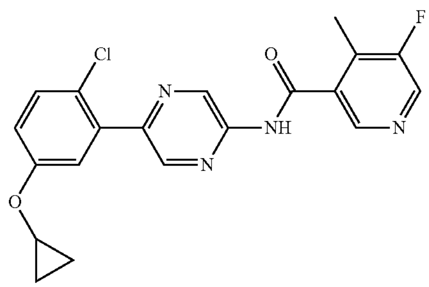 [SMILES: Cc1c(F)cncc1C(=O)Nc1cnc(-c2cc(OC3CC3)ccc2Cl)cn1] | N-(5-(2-chloro-5-cyclopropoxyphenyl)pyrazin-2-yl)-5-fluoro-4-methylnicotinamide |
| 208 | 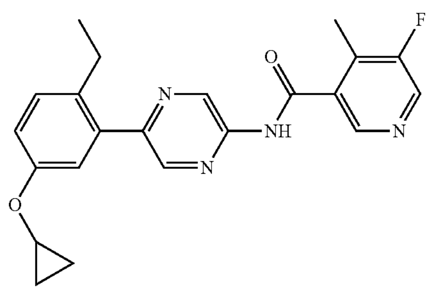 [SMILES: CCc1ccc(OC2CC2)cc1-c1cnc(NC(=O)c2cncc(F)c2C)cn1] | N-(5-(5-cyclopropoxy-2-ethylphenyl)pyrazin-2-yl)-5-fluoro-4-methylnicotinamide |
| 209 | 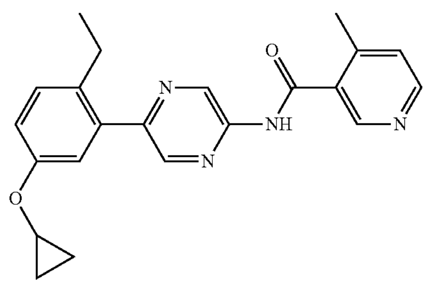 [SMILES: CCc1ccc(OC2CC2)cc1-c1cnc(NC(=O)c2cnccc2C)cn1] | N-(5-(5-cyclopropoxy-2-ethylphenyl)pyrazin-2-yl)-4-methylnicotinamide |
| 212 | 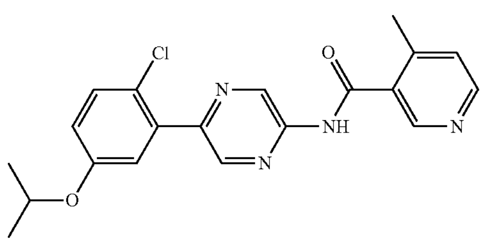 [SMILES: Cc1ccncc1C(=O)Nc1cnc(-c2cc(OC(C)C)ccc2Cl)cn1] | N-(5-(2-chloro-5-isopropoxyphenyl)pyrazin-2-yl)-4-methylnicotinamide |
| 224 | 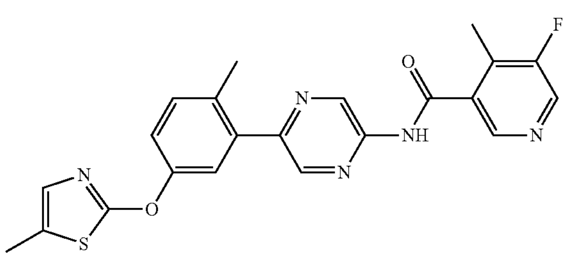 [SMILES: Cc1cnc(Oc2ccc(C)c(-c3cnc(NC(=O)c4cncc(F)c4C)cn3)c2)s1] | 5-fluoro-4-methyl-N-(5-(2-methyl-5-((5-methylthiazol-2-yl)oxy)phenyl)pyrazin-2-yl)nicotinamide |

| Number | Structure | Compound Name |
|---|---|---|
| 227 | 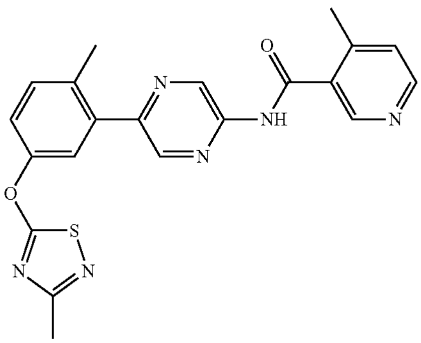 [SMILES: Cc1nsc(Oc2ccc(C)c(-c3cnc(NC(=O)c4cnccc4C)cn3)c2)n1] | 4-methyl-N-(5-(2-methyl-5-((3-methyl-1,2,4-thiadiazol-5-yl)oxy)phenyl)pyrazin-2-yl)nicotinamide |
| 228 | 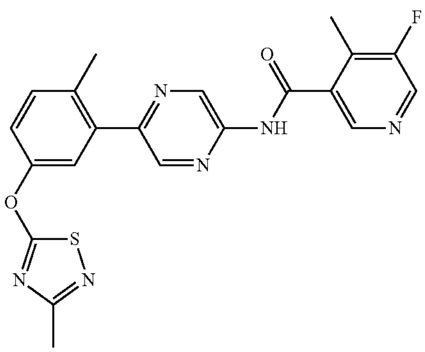 [SMILES: Cc1nsc(Oc2ccc(C)c(-c3cnc(NC(=O)c4cncc(F)c4C)cn3)c2)n1] | 5-fluoro-4-methyl-N-(5-(2-methyl-5-((3-methyl-1,2,4-thiadiazol-5-yl)oxy)phenyl)pyrazin-2-yl)nicotinamide |
| 230 | 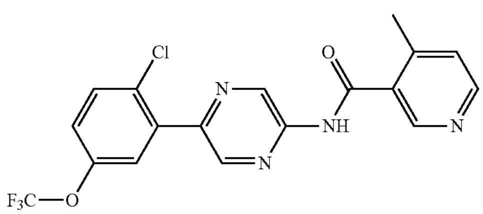 [SMILES: Cc1ccncc1C(=O)Nc1cnc(-c2cc(OC(F)(F)F)ccc2Cl)cn1] | N-(5-(2-chloro-5-(trifluoromethoxy)phenyl)pyrazin-2-yl)-4-methylnicotinamide |
| 231 | 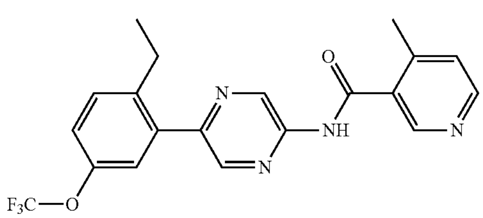 [SMILES: CCc1ccc(OC(F)(F)F)cc1-c1cnc(NC(=O)c2cnccc2C)cn1] | N-(5-(2-ethyl-5-(trifluoromethoxy)phenyl)pyrazin-2-yl)-4-methylnicotinamide |
| 240 | 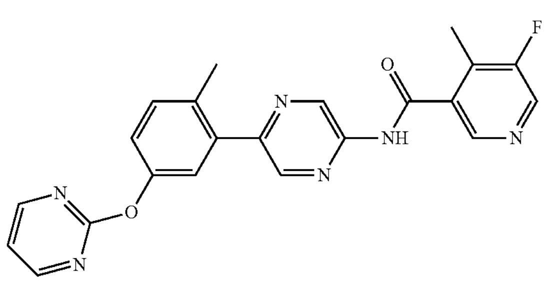 [SMILES: Cc1ccc(Oc2ncccn2)cc1-c1cnc(NC(=O)c2cncc(F)c2C)cn1] | 5-fluoro-4-methyl-N-(5-(2-methyl-5-(pyrimidin-2-yloxy)phenyl)pyrazin-2-yl)nicotinamide |

| Number | Structure | Compound Name |
|---|---|---|
| And | | |
| 242 | | N-(5-(2-chloro-5-(pyrimidin-2-yloxy)phenyl)pyrazin-2-yl)-5-fluoro-4-methylnicotinamide | or a pharmaceutically acceptable salt, or solvate thereof.

2. A pharmaceutical composition comprising the compound of claim 1 or a pharmaceutically acceptable salt or solvate thereof and a pharmaceutically acceptable excipient.

3. The compound of claim 1 of the formula:

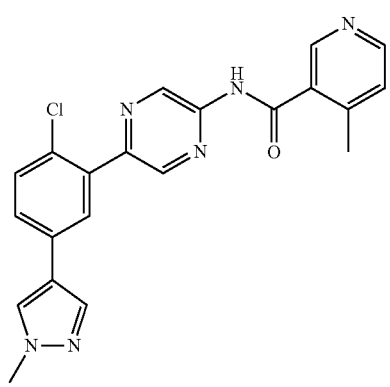

or a pharmaceutically acceptable salt, or solvate thereof.

4. The compound of claim 1 of the formula:

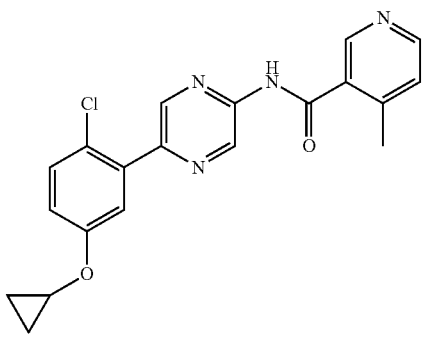 [SMILES: Cc1ccncc1C(=O)Nc1cnc(-c2cc(OC3CC3)ccc2Cl)cn1]

or a pharmaceutically acceptable salt, or solvate thereof.

5. The compound of claim 1 of the formula:

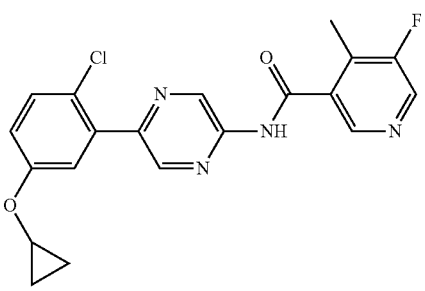 [SMILES: Cc1c(F)cncc1C(=O)Nc1cnc(-c2cc(OC3CC3)ccc2Cl)cn1]

or a pharmaceutically acceptable salt, or solvate thereof.

6. The compound of claim 1 of the formula:

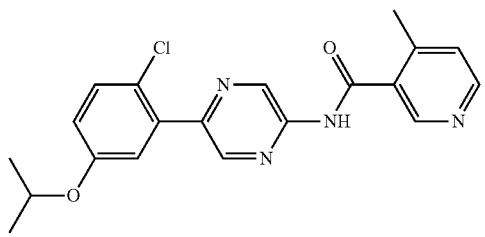 [SMILES: Cc1ccncc1C(=O)Nc1cnc(-c2cc(OC(C)C)ccc2Cl)cn1]

or a pharmaceutically acceptable salt, or solvate thereof.

7. The compound of claim 1 of the formula:

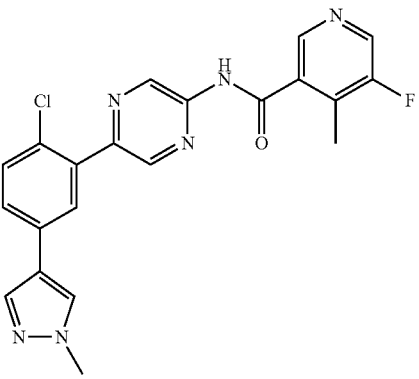 [SMILES: Cc1c(F)cncc1C(=O)Nc1cnc(-c2cc(-c3cnn(C)c3)ccc2Cl)cn1]

or a pharmaceutically acceptable salt, or solvate thereof.

8. The compound of claim 1 of the formula:
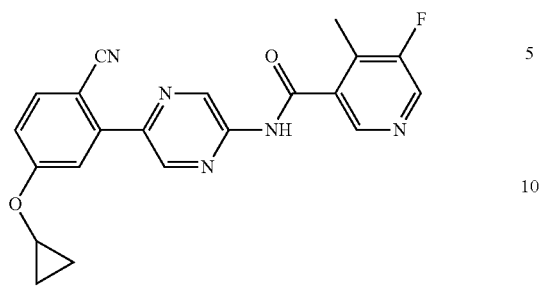
or a pharmaceutically acceptable salt, or solvate thereof.
9. The compound of claim 1 of the formula:
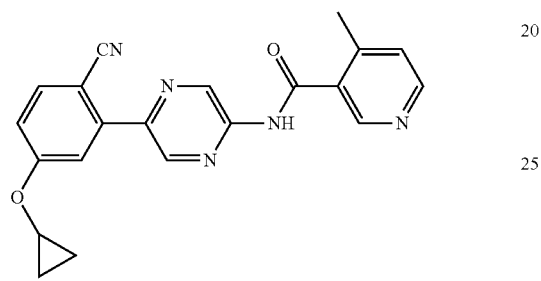
or a pharmaceutically acceptable salt, or solvate thereof.
* * * * *